US010266542B2

(12) United States Patent
Marx et al.

(10) Patent No.: US 10,266,542 B2
(45) Date of Patent: Apr. 23, 2019

(54) EZH2 INHIBITORS

(71) Applicant: Mirati Therapeutics, Inc., San Diego, CA (US)

(72) Inventors: Matthew Arnold Marx, San Diego, CA (US); Matthew Randolph Lee, Del Mar, CA (US); Robert Anthony Galemmo, San Francisco, CA (US); Thomas P. Bobinski, San Diego, CA (US)

(73) Assignee: Mirati Therapeutics, Inc., San Diego, CA (US)

( * ) Notice: Subject to any disclaimer, the term of this patent is extended or adjusted under 35 U.S.C. 154(b) by 0 days.

(21) Appl. No.: 15/921,097

(22) Filed: Mar. 14, 2018

(65) Prior Publication Data

US 2018/0265517 A1 Sep. 20, 2018

Related U.S. Application Data

(60) Provisional application No. 62/471,607, filed on Mar. 15, 2017, provisional application No. 62/533,773, filed on Jul. 18, 2017.

(51) Int. Cl.
| | |
|---|---|
| *C07D 491/048* | (2006.01) |
| *C07D 519/00* | (2006.01) |
| *C07D 471/04* | (2006.01) |
| *C07D 495/04* | (2006.01) |
| *C07D 498/04* | (2006.01) |
| *C07D 513/04* | (2006.01) |
| *A61P 35/00* | (2006.01) |

(52) U.S. Cl.
CPC .......... *C07D 491/048* (2013.01); *A61P 35/00* (2018.01); *C07D 471/04* (2013.01); *C07D 495/04* (2013.01); *C07D 498/04* (2013.01); *C07D 513/04* (2013.01); *C07D 519/00* (2013.01)

(58) Field of Classification Search
CPC .............. C07D 491/048; C07D 519/00; C07D 471/04; C07D 495/04; C07D 498/04; C07D 513/04; A61P 35/00
See application file for complete search history.

(56) References Cited

U.S. PATENT DOCUMENTS

| | | | |
|---|---|---|---|
| 8,410,088 B2 | 4/2013 | Kuntz et al. | |
| 8,536,179 B2 | 9/2013 | Miller et al. | |
| 8,962,620 B2 | 2/2015 | Kuntz et al. | |
| 8,975,291 B2 | 3/2015 | Brackley, III et al. | |
| 9,006,242 B2 | 4/2015 | Kuntz et al. | |
| 9,040,515 B2 | 5/2015 | Edwards et al. | |
| 9,382,234 B2 | 7/2016 | Knight et al. | |
| 9,409,865 B2 | 8/2016 | Albrecht et al. | |
| 9,469,646 B2 | 10/2016 | Albrecht et al. | |
| 9,481,666 B2 | 11/2016 | Kania et al. | |
| 9,505,745 B2 | 11/2016 | Blackledge, Jr. et al. | |
| 9,527,837 B2 | 12/2016 | Yu et al. | |
| 9,549,931 B2 | 1/2017 | Kuntz et al. | |
| 9,556,157 B2 | 1/2017 | Burgess et al. | |
| 9,562,041 B2 | 2/2017 | Burgess et al. | |
| 9,580,437 B2 | 2/2017 | Chan et al. | |
| 9,624,205 B2 | 4/2017 | Campbell | |
| 9,637,472 B2 | 5/2017 | Kuntz et al. | |
| 9,701,666 B2 | 7/2017 | Kuntz et al. | |
| 9,718,838 B2 | 8/2017 | Guo et al. | |
| 9,745,305 B2 | 8/2017 | Albrecht et al. | |
| 9,776,996 B2 | 10/2017 | Campbell et al. | |
| 9,822,103 B2 | 11/2017 | Seitz et al. | |
| 2013/0310379 A1 | 11/2013 | Albrecht et al. | |
| 2014/0142083 A1 | 5/2014 | Kuntz et al. | |
| 2014/0275081 A1 | 9/2014 | Kuntz et al. | |
| 2014/0288123 A1 | 9/2014 | Albrecht et al. | |
| 2014/0296283 A1 | 10/2014 | Campbell et al. | |
| 2014/0303106 A1 | 10/2014 | Zheng et al. | |
| 2014/0315945 A1 | 10/2014 | Campbell et al. | |
| 2014/0315949 A1 | 10/2014 | Albrecht et al. | |
| 2015/0011546 A1 | 1/2015 | Albrecht et al. | |
| 2015/0239842 A1 | 8/2015 | Edwards et al. | |
| 2015/0284370 A1 | 10/2015 | Kuntz et al. | |
| 2015/0344427 A1 | 12/2015 | Kuntz et al. | |
| 2015/0344459 A1 | 12/2015 | Kuntz et al. | |
| 2015/0368229 A1 | 12/2015 | Albrecht et al. | |
| 2016/0024081 A1 | 1/2016 | Campbell et al. | |
| 2016/0031907 A1 | 2/2016 | Campbell et al. | |

(Continued)

FOREIGN PATENT DOCUMENTS

| | | |
|---|---|---|
| WO | 2010/021381 A1 | 2/2010 |
| WO | 2011/140324 A1 | 11/2011 |

(Continued)

OTHER PUBLICATIONS

Lue et al., Emerging EZH2 Inhibitors and Their Application in Lymphoma; Curr. Hematol. Malig. Rep. Oct. 2018, 13(5):369-382.*
Antonysamy et al., "Structural Context of Disease-Associated Mutations and Putative Mechanism of Autoinhibition Revealed by X-Ray Crystallographic Analysis of the EZH2-SET Domain", PLOS One, 2013, 8(12), 1-15.
Broun et al., "Polycomb repressive complex 2 structure with inhibitor reveals a mechanism of activation and drug resistance", Nature Communications, 2016, 1-12.
Broun et al., "Polycomb repressive complex 2 structure with inhibitor reveals a mechanism of activation and drug resistance", Nature Communications, 2016, Supplementary Information, 21 pages.

(Continued)

*Primary Examiner* — Alexander R Pagano
*Assistant Examiner* — Ebenezer O Sackey
(74) *Attorney, Agent, or Firm* — McDonnell Boehnen Hulbert & Berghoff LLP

(57) ABSTRACT

The present invention relates to compounds that inhibit EZH2 activity. In particular, the present invention relates to compounds, pharmaceutical compositions and methods of use, such as methods of treating cancer using the compounds and pharmaceutical compositions of the present invention.

40 Claims, No Drawings

(56) References Cited

U.S. PATENT DOCUMENTS

| | | |
|---|---|---|
| 2016/0130261 A1 | 5/2016 | Burgess et al. |
| 2016/0159782 A1 | 6/2016 | Yu et al. |
| 2016/0176882 A1 | 6/2016 | Chan et al. |
| 2016/0185757 A1 | 6/2016 | Albrecht et al. |
| 2016/0297805 A1 | 10/2016 | Seitz et al. |
| 2016/0297806 A1 | 10/2016 | Kim et al. |
| 2016/0361309 A1 | 12/2016 | McCabe et al. |
| 2017/0015666 A1 | 1/2017 | Miller et al. |
| 2017/0066780 A1 | 3/2017 | Dominguez et al. |
| 2017/0073335 A1 | 3/2017 | Kanno et al. |
| 2017/0152239 A1 | 6/2017 | Edwards et al. |
| 2017/0320880 A1 | 11/2017 | Michaelides et al. |
| 2017/0348306 A1 | 12/2017 | Creasy et al. |

FOREIGN PATENT DOCUMENTS

| | | |
|---|---|---|
| WO | 2011/140325 A1 | 11/2011 |
| WO | 2012/082436 A2 | 6/2012 |
| WO | 2012/142504 A1 | 10/2012 |
| WO | 2012/154760 A1 | 11/2012 |
| WO | 2013/155464 A1 | 11/2013 |
| WO | 2013/173441 A2 | 11/2013 |
| WO | 2014/049488 A1 | 4/2014 |
| WO | 2014/062720 A2 | 4/2014 |
| WO | 2014/097041 A1 | 6/2014 |
| WO | 2014/124418 A1 | 8/2014 |
| WO | 2014/151142 A1 | 9/2014 |
| WO | 2014/177982 A1 | 11/2014 |
| WO | 2014/195919 A1 | 12/2014 |
| WO | 2015/004618 A1 | 1/2015 |
| WO | 2015/010049 A1 | 1/2015 |
| WO | 2015/010078 A2 | 1/2015 |
| WO | 2015/023915 A1 | 2/2015 |
| WO | 2015/077193 A1 | 5/2015 |
| WO | 2015/077194 A1 | 5/2015 |
| WO | 2015/193765 A1 | 12/2015 |
| WO | 2015/193768 A1 | 12/2015 |
| WO | 2016/066697 A1 | 5/2016 |
| WO | 2016/073903 A1 | 5/2016 |
| WO | 2016/073956 A1 | 5/2016 |
| WO | 2016/102493 A1 | 6/2016 |
| WO | 2016/103155 A1 | 6/2016 |
| WO | 2016/123387 A1 | 8/2016 |
| WO | 2016/130396 A1 | 8/2016 |
| WO | 2017/084494 A1 | 5/2017 |
| WO | 2017/100362 A2 | 6/2017 |
| WO | 2017/174023 A1 | 10/2017 |
| WO | 2017/184999 A1 | 10/2017 |
| WO | 2017/191545 A1 | 11/2017 |
| WO | 2017/210395 A1 | 12/2017 |
| WO | 2017/218953 A1 | 12/2017 |

OTHER PUBLICATIONS

Copeland, Robert A., "Epigenetic Medicinal Chemistry", ACS Medicinal Chemistry Letters, 2015, 4 pages.
Campbell et al., "EPZ011989, A Potent, Orally-Available EZH2 Inhibitor with Robust in Vivo Activity", ACS Medicinal Chemistry Letters, 2015, 5 pages.
Knutson et al., "Selective Inhibition of EZH2 by EPZ-6438 Leads to Potent Antitumor Activity in EZH2-Mutant Non-Hodgkin Lymphoma", Molecular Cancer Therapeutics, 2014, 13(4), 842-854.
Knutson et al., "Selective Inhibition of EZH2 by EPZ-6438 Leads to Potent Antitumor Activity in EZH2-Mutant Non-Hodgkin Lymphoma", Molecular Cancer Therapeutics, 2014, Supplemental Information, 6 pages.
Knutson et al., "Selective Inhibition of EZH2 by EPZ-6438 Leads to Potent Antitumor Activity in EZH2-Mutant Non-Hodgkin Lymphoma", Molecular Cancer Therapeutics, 2014, Supplemental Figures, 6 pages.
Garapaty-Rao et al., "Identification of EZH2 and EZH1 Small Molecule Inhibitors with Selective Impace on Diffuse Large B Cell Lymphoma Cell Growth", Chemistry & Biology 20, 2013, 1329-1339.
Horiuchi et al., "Assay Development for Histone Methyltransferases", Assay and Drug Development Technologies, 2013, 11(4), 227-237.
Kung et al., "Design and synthesis of pyridone containing 3,4-dihydroisoquinoline-1(2H)-ones as a novel class of enhancer of zeste homolog 2 (EZH2) inhbitors", Journal of Medicinal Chemistry, 2016, 72 pages.
Kung et al., "Design and synthesis of pyridone containing 3,4-dihydroisoquinoline-1(2H)-ones as a novel class of enhancer of zeste homolog 2 (EZH2) inhbitors", Journal of Medicinal Chemistry, 2016, Supplementary Data, 12 pages.
Kung et al., "Optimization of Orally Bioavailable Enhancer of Zeste Homolog 2 (EZH2) Inhibitors Using Ligand and Property-Based Design Strategies: Identification of Development Candidate (R)-5,8-Dichloro-7-(methoxy)oxetan-3-yl)methyl)-2-((4-methyoxy-6-methyl-2-oxo-1,2-dihydropyridin-3-yl)methyl)-3,4-dihydroisoquinolin-1(2H)-one (PF-06821497)", Journal of Medicinal Chemistry, 2017, 16 pages.
Kuntz et al., "The Importance of Being Me: Magic Methyls, Methyltransferase Inhibitors, and the Discovery of Tazemetostat", Journal of Medicinal Chemistry, 2016, 9 pages.
Kuntz et al., "The Importance of Being Me: Magic Methyls, Methyltransferase Inhibitors, and the Discovery of Tazemetostat", Journal of Medicinal Chemistry, 2016, Supplemental Information, 56 pages.
Souroullas et al., "An oncogenic Ezh2 mutation induces tumors through global redistribution of histone 3 lysine 27 trimethylation", Nature Medicine, 2015, 80 pages.
Stazi et al., "EZH2 inhibitors: a patent review", Expert Opinion on Therapeutic Patents, 2014-2016, 51 pages.
Vaswani et al., "Identification of (R)-N-((4-Methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide (CPI-1205), a Potent and Selective Inhibitor of Histone Methylgransferase EZH12, Suitable for Phase I Clinical Trials for B-Cell Lymphomas", Journal of Medicinal Chemistry, 2016, 47 pages.
Bradley et al., "EZH2 Inhibitor Efficacy in Non-Hodgkin's Lymphoma Does Not Require Suppression of H3K27 Monomethylation", Chemistry & Biology, 2014, vol. 21, 1463-1475.
Nasveschuk et al., "Discovery and Optimization of Tetramethylpiperidinyl Benzamides as Inhibitors of EZH2", ACS Medicinal Chemistry Letters, 2014, vol. 5, 378-383.

* cited by examiner

EZH2 INHIBITORS

CROSS REFERENCE

This application claims benefit of U.S. Provisional Application No. 62/471,607, filed Mar. 15, 2017, and U.S. Provisional Application No. 62/533,773, filed Jul. 18, 2017, the entire content of each application is hereby incorporated by reference in its entirety.

FIELD OF THE INVENTION

The present invention relates to compounds that inhibit EZH2. In particular, the present invention relates to compounds, pharmaceutical compositions comprising the compounds and methods for use therefor.

BACKGROUND OF THE INVENTION

The enhancer of zeste homolog 2 (EZH2) is a mammalian histone methyltransferase that contributes to the epigenetic silencing of target genes and regulates the survival and metastasis of cancer cells. EZH2 is the catalytic subunit of the Polycomb Repressor Complex 2 (PRC2) which functions to silence target genes by tri-methylating lysine 27 of histone H3 (H3K27me3). Histone H3 is one of the five core histone proteins involved in the structure of chromatin in eukaryotic cells. While the precise mechanism by which aberrant EZH2 activity leads to cancer progression is not fully understood, many EZH2 target genes are tumor suppressors suggesting that loss of tumor suppressor function plays an important role.

EZH2 is overexpressed in aggressive solid tumors, including the prostate, breast, skin, bladder, liver, pancreas, and head and neck cancers. For instance, EZH2 transcript and protein were shown to be consistently elevated in invasive breast carcinoma compared with normal breast epithelia. Tissue microarray analysis, which included 917 samples from 280 patients, demonstrated that EZH2 protein levels were strongly associated with breast cancer aggressiveness. Overexpression of EZH2 in immortalized human mammary epithelial cell lines promotes anchorage-independent growth and cell invasion. EZH2-mediated cell invasion required an intact SET domain and histone deacetylase activity (Kleer et al, (2003) Proc. Natl Acad. Sci USA 100(20):11606-11611).

The expression and function of EZH2 in cancer cell lines are inhibited by microRNA-101 (miR-101). An analysis of human prostate tumors revealed that miR-101 expression decreases during cancer progression, paralleling an increase in EZH2 expression. One or both of the two can genomic loci encoding miR-101 were somatically lost in 37.5% of clinically localized prostate cancer cells (6 of 16) and 66.7% of metastatic disease cells (22 of 33). There also is a greater risk of recurrence after prostatectomy in tumors expressing high levels of EZH2 (Varambally et al, (2008) Science 322:1695-1699).

Somatic activating and inactivating mutations of EZH2 have been reported. Somatic activating mutations in EZH2 have been identified in follicular lymphoma and diffuse large B-cell lymphomas that result in increased levels of H3K27me3 (for a review, see Helin and Dhanak (2013) Nature 502:480-488; Pasqualucci et al, (2011) Nature Genet. 43(9):830-837). These mutations taken together with overexpression of EZH2 in various solid tumors suggests that misregulation of EZH2 can lead to silencing of genes that are important to tumor growth and survival. Interestingly, however, inactivating mutations of EZH2 have been identified in myleodysplastic syndrome (MDS) suggesting a potential tumor suppressor role of EZH2 as well.

Thus, enhanced EZH2 activity contributes to undesired cellular proliferation and invasiveness of tumor cells, in part, through trimethylation of H3K27. Since increased H3K27me3 levels appear to contribute to cancer aggressiveness in many tumor types, the inhibition of EZH2 activity may provide therapeutic benefit for a wide range of cancers. The compounds of the present invention offer potential therapeutic benefit as inhibitors of EZH2 activity that may be useful for negatively modulating the activity of EZH2 in a cell or for treating various forms of cancer.

SUMMARY OF THE INVENTION

There is a need to develop new EZH2 inhibitors that demonstrate improved cellular potency, efficacy, stability and safety. The compounds and compositions of the present invention advantageously overcome one or more of these shortcomings by providing potent, selective, and orally active EZH2 inhibitors.

In one aspect of the invention, compounds are provided represented by formula (I):

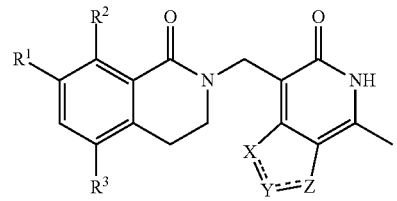

or a pharmaceutically acceptable salt thereof, wherein:

each ----- represents a single or a double bond, wherein only one of the bonds between X—Y and Y—Z is a double bond;

X, Y and Z are each independently selected from O, N, $NR^4$, S, or $CR^5$, wherein when one of X, Y or Z is other than N or $NR^4$, at least one of X, Y or Z is $CR^5$ and only one of X, Y or Z is O or S;

$R^1$ is C1-C6 alkyl, C1-C6 alkoxy, heterocyclyl, aryl, heteroaryl, —$OR^6$; —$NR^4R^6$ or —W—$R^7$; wherein each of the heterocyclyl, aryl, and heteroaryl is optionally substituted with one or more $R^6$;

W is —$(CH_2)_p$—$CR^8R^9$—$(CHR^{10})_q$;

$R^2$ is hydrogen, halogen, haloalkyl, C1-C3 alkyl;

$R^3$ is hydrogen, cyano, halogen, haloalkyl, C1-C4 alkyl, C1-C4 alkoxy, cycloalkyl, heterocyclyl, aryl, heteroaryl or $R^{12}$-L-$R^{13}$, wherein the cycloalkyl, heterocyclyl, aryl, heteroaryl is optionally substituted with one or more C1-C3 alkyl, heteroalkyl or —$NR^4R^{11}$.

each $R^4$ is independently hydrogen or C1-C3 alkyl;

each $R^5$ is independently hydrogen, halogen, C1-C3 alkoxy, cyano, C1-C3 alkyl;

each $R^6$ is independently C1-C3 alkyl, cycloalkyl or heterocyclyl, wherein the heterocyclyl is optionally substituted with one or more C1-C3 alkyl or C1-C3 alkylsulfonyl and the cycloalkyl is optionally substituted with —$NR^4R^{11}$;

$R^7$ is independently cycloalkyl, heterocyclyl, aryl or heteroaryl, wherein each of the cycloalkyl, heterocyclyl, aryl or heteroaryl is optionally substituted with one or more $R^{14}$;

$R^8$ is independently hydrogen, halogen or C1-C4 alkyl;

$R^9$ is hydrogen, —$N(R^4)_2$, hydroxyl, halogen, cyano, hydroxyalkyl, C1-C4 alkyl, or C1-C4 alkoxy;

$R^{10}$ is absent or hydrogen;

$R^{11}$ is hydrogen, acyl, C1-C3 alkyl or C1-C4 alkoxy;

$R^{12}$ is C2-C4 alkynylene, arylene or heteroarylene;

L is a bond or C1-C3 alkylene;

$R^{13}$ is heterocyclyl optionally substituted with one or more acyl or C1-C3 alkyl;

$R^{14}$ is independently selected from oxo, hydroxyl, halogen, cyano, acetyl, hydroxyacetyl, alkyl, alkylsulfonyl, hydroxyalkyl, carbonylalkyl or heterocyclyl; and p and q are each independently zero or one.

In another aspect of the invention, pharmaceutical compositions are provided comprising a therapeutically effective amount of a compound of formula (I) and a pharmaceutically acceptable excipient.

Also provided herein is a compound of formula (I) or a pharmaceutically acceptable salt or solvate thereof, or a pharmaceutical composition thereof as defined herein for use in therapy.

Also provided herein is a compound of formula (I) or a pharmaceutically acceptable salt or solvate thereof or a pharmaceutical composition thereof as defined herein for use in the treatment of cancer.

Also provided herein is a compound of formula (I) or a pharmaceutically acceptable salt or solvate thereof for use in the inhibition of EZH2.

Also provided herein is a compound of formula (I) or a pharmaceutically acceptable salt or solvate thereof or a pharmaceutical composition thereof as defined herein, for use in the treatment of an EZH2-associated disease or disorder.

Also provided herein is the use of a compound of formula (I) or a pharmaceutically acceptable salt or solvate thereof, as defined herein in the manufacture of a medicament for the treatment of cancer.

Also provided herein is a use of a compound of formula (I) or a pharmaceutically acceptable salt or solvate thereof, as defined herein in the manufacture of a medicament for the inhibition of activity of EZH2.

Also provided herein is the use of a compound of formula (I) or a pharmaceutically acceptable salt or solvate thereof, as defined herein, in the manufacture of a medicament for the treatment of an EZH2-associated disease or disorder.

In yet another aspect of the invention, methods for inhibiting EZH2 activity in a cell comprising contacting the cell with a compound of formula (I) are provided. Also provided are methods for treating an EZH2-associated cancer in a patient comprising administering a therapeutically effective amount of a compound of formula (I) or pharmaceutical composition thereof to a patient in need thereof.

DETAILED DESCRIPTION OF THE INVENTION

The present invention relates to EZH2 inhibitors. In particular, the present invention relates to compounds that inhibit the activity of EZH2, pharmaceutical compositions comprising a therapeutically effective amount of the compounds, and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference to the extent they are consistent with the present disclosure. Terms and ranges have their generally defined definition unless expressly defined otherwise.

For simplicity, chemical moieties are defined and referred to throughout primarily as univalent chemical moieties (e.g, alkyl, aryl, etc.). Nevertheless, such terms may also be used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e, 4 for carbon, 3 for N, 2 for O, and 2, 4, or 6 for S, depending on the oxidation state of the S).

As used herein, EZH2 or EZH2 enzyme refers to a mammalian histone methyltransferase, which is the catalytic subunit of the Polycomb Repressor Complex 2 (PRC2), and functions to silence target genes by tri-methylating lysine 27 of histone H3 (H3K27me3).

As used herein, an "EZH2 inhibitor" refers to compounds of the present invention that are represented by formula (I) as described herein. These compounds are capable of negatively modulating or inhibiting all or a portion of the enzymatic activity of the EZH2 enzyme. While not wanting to be bound by any theory, the EZH2 inhibitors of the present invention may inhibit enzymatic activity reversibly or irreversibly, in a competitive or non-competitive manner for substrates, such as binding sites for histones, S-adenosyl methionine and/or S-adenosylhomocyteine.

An "EZH2-associated disease or disorder" as used herein refers to diseases or disorders associated with or mediated by or having a EZH2 mutation or abberant expression of EZH2. A non-limiting example of an EZH2-associated disease or disorder is as EZH2-associated cancer.

The term "amino" refers to —$NH_2$.

The term "acetyl" refers to "—C(O)$CH_3$.

As used herein, the term "hydroxyacetyl" refers to —C(O)CH2OH.

As herein employed, the term "acyl" refers to an alkylcarbonyl or arylcarbonyl substituent wherein the alkyl and aryl portions are as defined herein.

The term "acylamino" refers to an amide group attached at the nitrogen atom (i.e, R—CO—NH—). The term "carbamoyl" refers to an amide group attached at the carbonyl carbon atom (i.e, $NH_2$—CO—).

The term "alkyl" as employed herein refers to straight and branched chain aliphatic groups having from 1 to 12 carbon atoms. As such, "alkyl" encompasses $C_1$, $C_2$, $C_3$, $C_4$, $C_5$, $C_6$, $C_7$, $C_8$, $C_9$, $C_{10}$, $C_{11}$ and $C_{12}$ groups. Examples of alkyl groups include, without limitation, methyl, ethyl, propyl, isopropyl, butyl, isobutyl, sec-butyl, tert-butyl, pentyl, and hexyl.

The term "alkenyl" as used herein means an unsaturated straight or branched chain aliphatic group with one or more carbon-carbon double bonds, having from 2 to 12 carbon atoms. As such, "alkenyl" encompasses $C_2$, $C_3$, $C_4$, $C_5$, $C_6$, $C_7$, $C_8$, $C_9$, $C_{10}$, $C_{11}$ and $C_{12}$ groups. Examples of alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms. As such, "alkynyl" encompasses $C_2$, $C_3$, $C_4$, $C_5$, $C_6$, $C_7$, $C_8$, $C_9$, $C_{10}$, $C_{11}$ and $C_{12}$ groups. Examples of alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Examples of alkylene groups include, without limitation, methylene, ethylene, propylene, and butylene. Exemplary alkenylene groups include, without limitation, ethenylene, propenylene, and butenylene. Exemplary alkynylene groups include, without limitation, ethynylene, propynylene, and butynylene.

The term "alkoxy" refers to —OC1-C6 alkyl.

The term "alkylthio" refers to —S—C1-C6 alkyl.

The term "alkylaminyl" refers to —NR$^4$—C1-C6 alkyl.

The term "sulfonylalkyl" refers to —SO$_2$— C1-C6 alkyl.

The term "cycloalkyl" as employed herein is a saturated and partially unsaturated cyclic hydrocarbon group having 3 to 12 carbons. As such, "cycloalkyl" includes $C_3$, $C_4$, $C_5$, $C_6$, $C_7$, $C_8$, $C_9$, $C_{10}$, $C_{11}$ and $C_{12}$ cyclic hydrocarbon groups. Examples of cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are independently replaced O, S, or NR$^4$ wherein R$^4$ is as defined herein.

An "aryl" group is a $C_6$-$C_{14}$ aromatic moiety comprising one to three aromatic rings. As such, "aryl" includes $C_6$, $C_{10}$, $C_{13}$, and $C_{14}$ cyclic hydrocarbon groups. An exemplary the aryl group is a $C_6$-$C_{10}$ aryl group. Particular aryl groups include, without limitation, phenyl, naphthyl, anthracenyl, and fluorenyl.

An "aralkyl" or "arylalkyl" group comprises an aryl group covalently linked to an alkyl group wherein the moiety is linked to another group via the alkyl moiety. An exemplary aralkyl group is —(C1-C6)alkyl(C6-C10)aryl, including, without limitation, benzyl, phenethyl, and naphthylmethyl.

A "heterocyclyl" or "heterocyclic" group is a mono- or bicyclic (fused or spiro) ring structure having from 3 to 12 atoms, (3, 4, 5, 6, 7, 8, 9, 10, 11 or 12 atoms), for example 4 to 8 atoms, wherein one or more ring atoms are independently —C(O)—, N, NR$^4$, O, or S, and the remainder of the ring atoms are quaternary or carbonyl carbons. Examples of heterocyclic groups include, without limitation, epoxy, oxiranyl, oxetanyl, azetidinyl, aziridinyl, tetrahydrofuranyl, tetrahydropyranyl, tetrahydrothiophenyl, pyrrolidinyl, piperidinyl, piperazinyl, imidazolidinyl, thiazolidinyl, thiatanyl, dithianyl, trithianyl, azathianyl, oxathianyl, dioxolanyl, oxazolidinyl, oxazolidinonyl, decahydroquinolinyl, piperidonyl, 4-piperidonyl, thiomorpholinyl, dimethyl-morpholinyl, and morpholinyl. Specifically excluded from the scope of this term are compounds having adjacent ring O and/or S atoms.

The term "heterocyclylalkyl" refers to a heterocyclyl group as defined herein linked to the remaining portion of the molecule via an alkyl linker.

As used herein, the term "heteroaryl" refers to a group having 5 to 14 ring atoms, preferably 5, 6, 10, 13 or 14 ring atoms; having 6, 10, or 14 it electrons shared in a cyclic array; and having, in addition to carbon atoms, from one to three heteroatoms that are each independently N, O, or S. "Heteroaryl" also includes fused multicyclic (e.g, bicyclic) ring systems in which one or more of the fused rings is non-aromatic, provided that at least one ring is aromatic and at least one ring contains an N, O, or S ring atom.

Examples of heteroaryl groups include acridinyl, azocinyl, benzimidazolyl, benzofuranyl, benzo[d]oxazol-2(3H)-one, 2H-benzo[b][1,4]oxazin-3(4H)-one, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A "heteroaralkyl" or "heteroarylalkyl" group comprises a heteroaryl group covalently linked to another group via an alkyl linker Examples of heteroalkyl groups comprise a $C_1$-$C_6$ alkyl group and a heteroaryl group having 5, 6, 9, or 10 ring atoms. Examples of heteroaralkyl groups include pyridylmethyl, pyridylethyl, pyrrolylmethyl, pyrrolylethyl, imidazolylmethyl, imidazolylethyl, thiazolylmethyl, thiazolylethyl, benzimidazolylmethyl, benzimidazolylethyl quinazolinylmethyl, quinolinylmethyl, quinolinylethyl, benzofuranylmethyl, indolinylethyl isoquinolinylmethyl, isoinodylmethyl, cinnolinylmethyl, and benzothiophenylethyl. Specifically excluded from the scope of this term are compounds having adjacent ring O and/or S atoms.

An "arylene," "heteroarylene," or "heterocyclylene" group is an bivalent aryl, heteroaryl, or heterocyclyl group, respectively, as defined hereinabove, that is positioned between and serves to connect two other chemical groups.

As employed herein, when a moiety (e.g, cycloalkyl, hydrocarbyl, aryl, heteroaryl, heterocyclic, urea, etc.) is described as "optionally substituted" without expressly stating the substitutents it is meant that the group optionally has from one to four, preferably from one to three, more preferably one or two, non-hydrogen substituents.

The term "halogen" or "halo" as employed herein refers to chlorine, bromine, fluorine, or iodine.

The term "haloalkyl" refers to an alkyl chain in which one or more hydrogens have been replaced by a halogen. Exemplary haloalkyls are trifluoromethyl, difluoromethyl, flurochloromethyl, and fluoromethyl.

The term "hydroxyalkyl" refers to -alkylene-OH.

The term "sulfonamido" refers to a sulfonamide substituent attached by either the sulfur or the nitrogen atom.

As used herein, "an effective amount" of a compound is an amount that is sufficient to negatively modulate or inhibit the activity of EZH2.

As used herein, a "therapeutically effective amount" of a compound is an amount that is sufficient to ameliorate or in some manner reduce a symptom or stop or reverse progression of a condition, or negatively modulate or inhibit the activity of EZH2. Such amount may be administered as a single dosage or may be administered according to a regimen, whereby it is effective.

As used herein, "treatment" means any manner in which the symptoms or pathology of a condition, disorder or disease in a patient are ameliorated or otherwise beneficially altered.

As used herein, "amelioration of the symptoms of a particular disorder by administration of a particular compound or pharmaceutical composition" refers to any lessening, whether permanent or temporary, lasting or transient, that can be attributed to or associated with administration of the composition.

Compounds

In one aspect of the invention, compounds are provided represented by formula (I):

Formula (I)

or a pharmaceutically acceptable salt thereof:
wherein:

each ===== represents a single or a double bond, wherein only one of the bonds between X—Y and Y—Z is a double bond;

X, Y and Z are each independently O, N, $NR^4$, S, or $CR^5$, wherein when one of X, Y or Z is other than N or $NR^4$, at least one of X, Y or Z is $CR^5$ and only one of X, Y or Z can be O or S;

$R^1$ is C1-C6 alkyl, C1-C6 alkoxy, heterocyclyl, aryl, heteroaryl, —$OR^6$; —$NR^4R^6$ or —W—$R^7$; wherein each of the heterocyclyl, aryl, or heteroaryl is optionally substituted with one or more $R^6$;

W is —$(CH_2)_p$—$CR^8R^9$—$(CHR^{10})_q$—;

$R^2$ is hydrogen, halogen, haloalkyl, or C1-C3 alkyl;

$R^3$ is hydrogen, cyano, halogen, haloalkyl, C1-C4 alkyl, C1-C4 alkoxy, cycloalkyl, heterocyclyl, aryl, heteroaryl or $R^{12}$-L-$R^{13}$, wherein the cycloalkyl, heterocyclyl, aryl, heteroaryl is optionally substituted with one or more C1-C3 alkyl, heteroalkyl, or —$NR^4R^{11}$.

each $R^4$ is independently hydrogen or C1-C3 alkyl;

each $R^5$ is independently hydrogen, halogen, C1-C3 alkoxy, cyano, or C1-C3 alkyl;

each $R^6$ is independently C1-C3 alkyl, cycloalkyl or heterocyclyl, wherein the heterocyclyl is optionally substituted with one or more C1-C3 alkyl or sulfonyl C1-C3 alkyl and the cycloalkyl is optionally substituted with —$NR^4R^{11}$;

$R^7$ is cycloalkyl, heterocyclyl, aryl or heteroaryl, wherein each of the cycloalkyl, heterocyclyl, aryl or heteroaryl is optionally substituted with one or more $R^{14}$;

$R^8$ is hydrogen, halogen or C1-C4 alkyl;

$R^9$ is hydrogen, —$N(R^4)_2$, hydroxyl, halogen, cyano, hydroxyalkyl, C1-C4 alkyl, or C1-C4 alkoxy;

$R^{10}$ is absent or hydrogen;

$R^{11}$ is hydrogen, acyl, C1-C3 alkyl or C1-C4 alkoxy;

$R^{12}$ is C2-C4 alkynylene, arylene or heteroarylene;

L is a bond or C1-C3 alkylene;

$R^{13}$ is heterocyclyl optionally substituted with one or more acyl or C1-C3 alkyl;

$R^{14}$ is oxo, hydroxyl, halogen, cyano, acetyl, hydroxyacetyl, alkyl, alkylsulfonyl, hydroxyalkyl, carbonylalkyl or heterocyclyl; and p and q are each independently zero or one.

In one embodiment, compounds of formula (I) are provided wherein: X is O and Y and Z are each $CR^5$; Z is O and X and Y are each $CR^5$; X and Y are each $CR^5$ and Z is $NR^4$; X is $NR^4$ and Y and Z are each $CR^5$; X is $NR^4$, Y is $CR^5$ and Z is N; X is N, Y is $CR^5$ and Z is $NR^4$; X is N, Y is $CR^5$ and Z is S; X is S, Y is $CR^5$ and Z is N; X is $NR^4$, Y is N and Z is $CR^5$; X is $CR^5$, Y is N and Z is $NR^4$; X is O, Y is N and Z is $CR^5$; X is $CR^5$, Y is N and Z is O; The compound of claim 1, wherein X is S and Y and Z are each $CR^5$; Z is S and X and Y are each $CR^5$; X is O, Y is $CR^5$ and Z is N; X is N, Y is $CR^5$ and Z is O; X is S, Y is N and Z is $CR^5$; X is $CR^5$, Y is N and Z is S; X is N, Y is N and Z is $NR^4$, and X is $NR^4$, Y is N and Z is N, wherein $R^4$ and $R^5$ are defined as in formula (I).

In one embodiment, compounds of formula (I) are provided wherein $R^1$ is —$OR^6$. In one embodiment, $R^6$ is independently selected from C1-C4 alkyl, hydroxyalkyl or heterocyclyl. In one embodiment, the C1-C4 alkyl is isopropyl.

In another embodiment, compounds of formula (I) are provided wherein $R^1$ is heterocyclyl. In one embodiment, the heterocyclyl is an 8-10 membered spirocycle comprising 1-4 heteroatoms selected from O, N or S. In one embodiment, the spirocycle is 7-oxa-2-azaspiro[3.5]nonan-2-yl.

In one embodiment, compounds of formula (I) are provided wherein $R^1$ is heteroaryl. In one embodiment, the heteroaryl is independently oxazolyl, 1,4-dimethyl-oxazolyl, triazinyl or 1,4-dimethyl-1H-1,2,3-triazinyl.

In a further embodiment, compounds of formula (I) are provided wherein $R^1$ is —$NR^4R^6$. In one embodiment, $R^4$ is C1-C3 alkyl and $R^6$ is heterocyclyl. The one embodiment, the heterocyclyl is tetrahydropyranyl, piperidinyl or methylsulfonylpiperdinyl.

In another embodiment wherein $R^1$ is —$NR^4R^6$, $R^4$ is C1-C3 alkyl and $R^6$ is cycloalkyl optionally substituted with —$NR^4R^{10}$. In one embodiment, the cycloalkyl is substituted with —$NR^4R^{10}$, wherein $R^{10}$ is independently selected from hydrogen, acyl, C1-C3 alkyl or C1-C4 alkoxy.

In another embodiment, compounds of formula (I) are provided $R^1$ is —W—$R^7$. In one embodiment for W, p and q are each zero, $R^8$ is C1-C4 alkoxy; $R^9$ is hydrogen; and $R^7$ is heterocyclyl optionally substituted with acyl or one or more oxo or C1-C3 alkyl. In certain of these embodiments, the $R^7$ heterocyclyl is independently selected from azetidinyl, 1-methyl-azetidinyl, oxetanyl, thietane 1,1-dioxide, furanyl, tetrahydrofuranyl, tetrahydropyranyl, pyrrolidinyl, piperdinyl, 4-methyl-piperdinyl, 4-acyl-piperdinyl, piperazinyl, 4-methyl-piperazinyl, 4-acyl-piperazinyl, dioxidothiopyranyl, or morpholinyl. In another embodiment for W, p and q are each zero, $R^8$ is C1-C4 alkyl; $R^9$ is hydrogen; and $R^7$ is heterocyclyl optionally substituted with acyl or one or more oxo or C1-C3 alkyl. In certain of these embodiments, the $R^7$ heterocyclyl is independently selected from azetidinyl, 1-methyl-azetidinyl, oxetanyl, thietane 1,1-dioxide, furanyl, tetrahydrofuranyl, tetrahydropyranyl, pyrrolidinyl, piperdinyl, 4-methyl-piperdinyl, 4-acyl-piperdinyl, piperazinyl, 4-methyl-piperazinyl, 4-acyl-piperazinyl, dioxidothiopyranyl, or morpholinyl.

In one embodiment, compounds of formula (I) are provided wherein $R^2$ is halogen. In one embodiment, the halogen is chlorine. In one embodiment, compounds of formula (I) are provided, wherein $R^3$ is halogen. In one embodiment, the halogen is chlorine or bromine. In one embodiment, compounds of formula (I) are provided $R^2$ and $R^3$ are each halogen.

In another embodiment, compounds of formula (I) are provided wherein $R^3$ is $R^{12}$-L-$R^{13}$. In one embodiment, $R^{12}$ is heteroarylene. In certain embodiments, the heteroarylene is independently selected from pyrazolylene, pyrimidinylene or triazolylene.

In another embodiment, $R^{12}$ is heteroarylene, L is a bond and $R^{13}$ is independently selected from azetidinyl, 1-methylazetidinyl, piperidinyl, 1-methylpiperdinyl, 4-acyl-piperdinyl, piperazinyl, 4-methylpiperazinyl, 4-acyl-piperazinyl, oxetanyl or morpholinyl.

In one embodiment, compounds of formula (I) are provided wherein $R^3$ is $R^{12}$-L-$R^{13}$. In one embodiment, $R^{12}$ is arylene. In certain embodiments, the arylene is phenylene. In another embodiment, the arylene is phenylene, L is C1 alkylene and $R^{13}$ is morpholinyl.

In one embodiment, compounds of formula (I) are provided wherein $R^3$ is $R^{12}$-L-$R^{13}$. In one embodiment, $R^{12}$ is C2-C4 alkynylene. In one embodiment, the C2-C4 alkynylene is ethynylene. In another embodiment, the C2-C4 alkynylene is ethynylene, L is a bond, and $R^{13}$ is morpholinyl or oxetanyl.

In one embodiment, compounds of formula (I) are independently selected from:

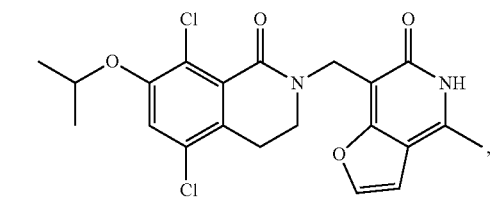

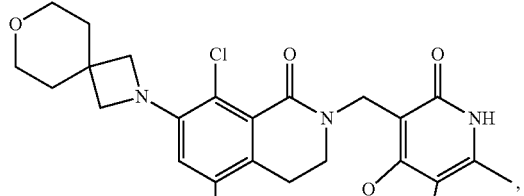

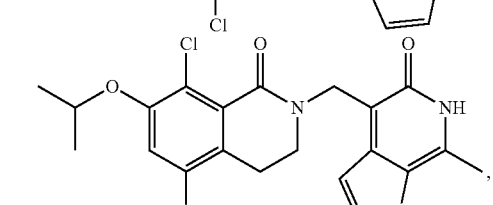

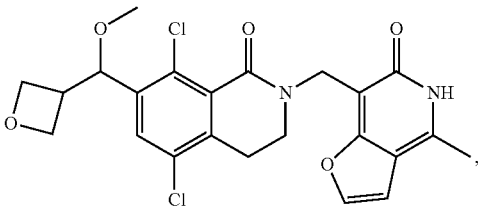

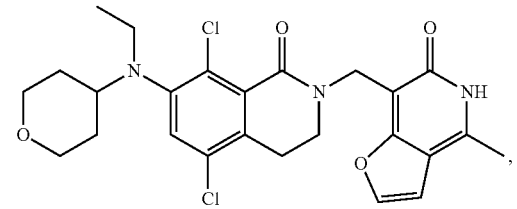

-continued

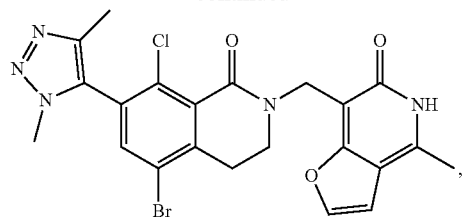

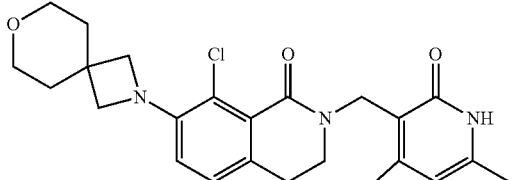

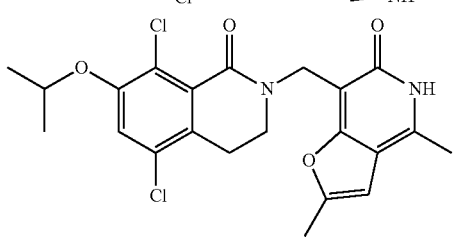

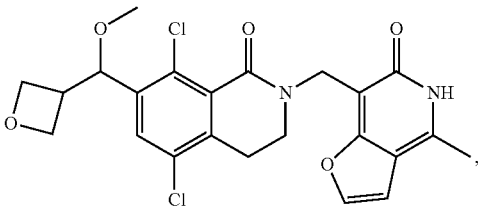

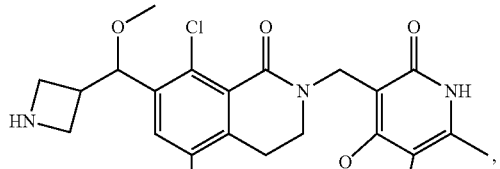

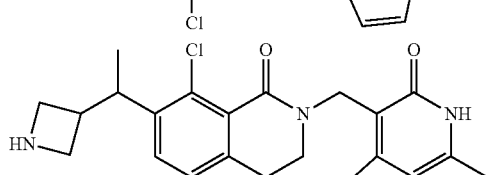

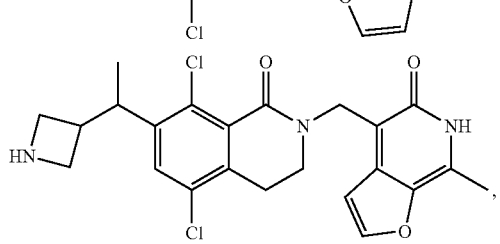

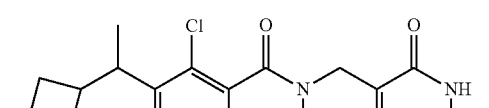

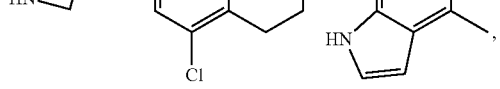

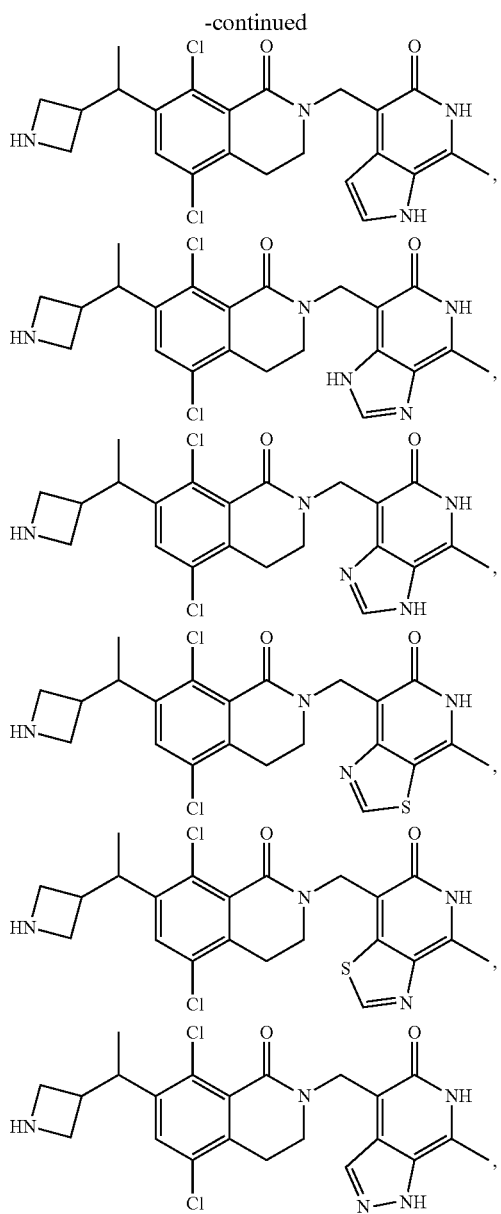
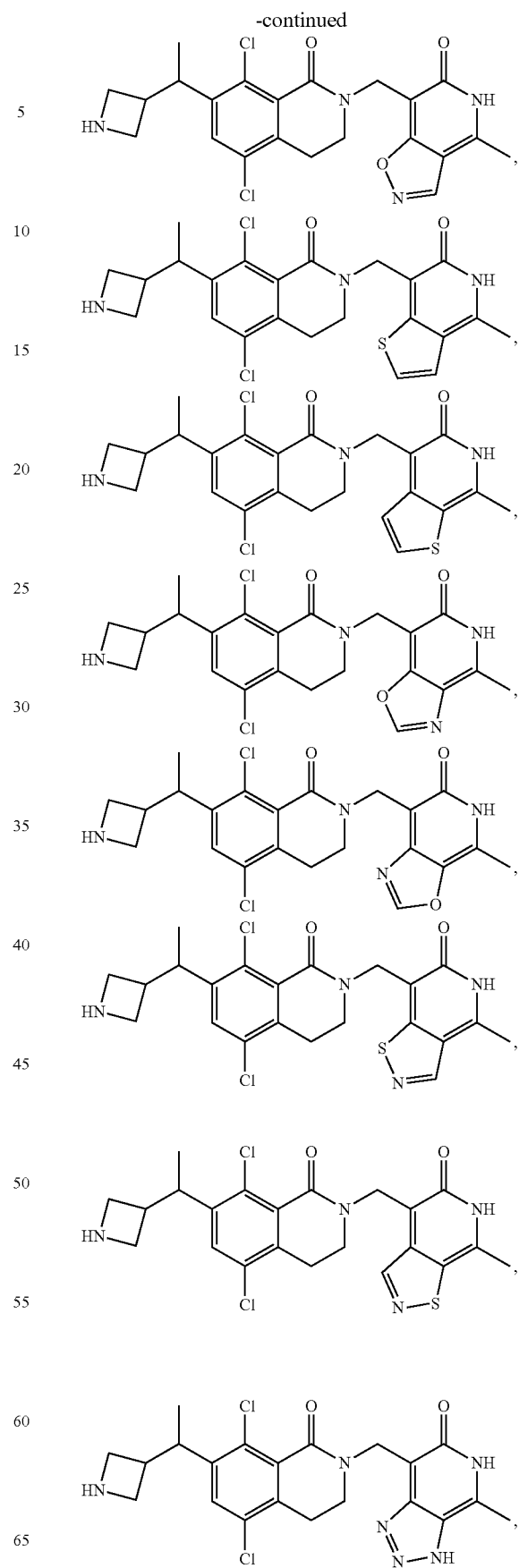

-continued
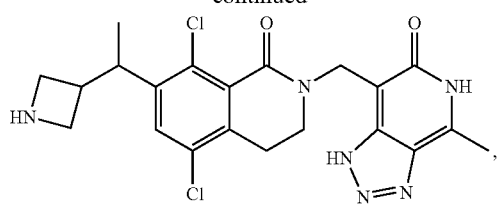
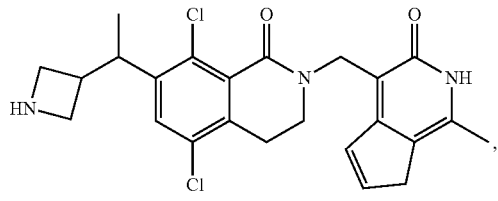
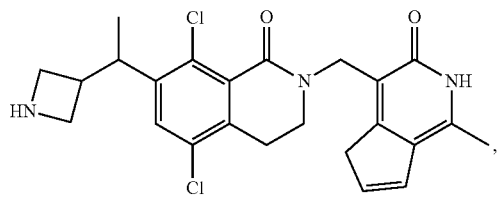
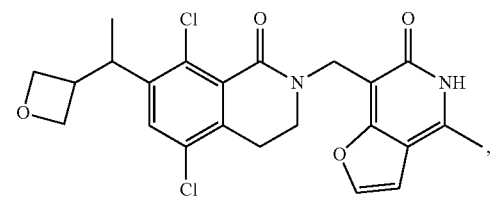
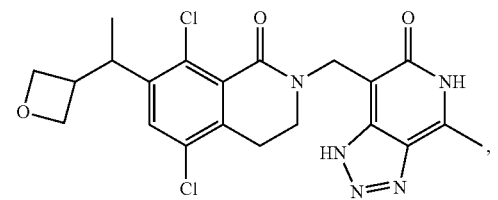
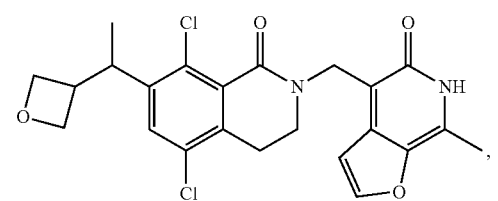
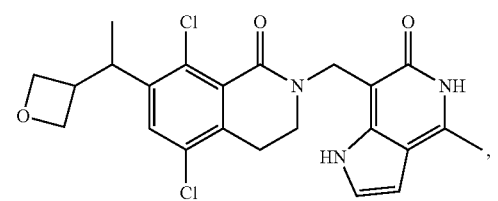
-continued
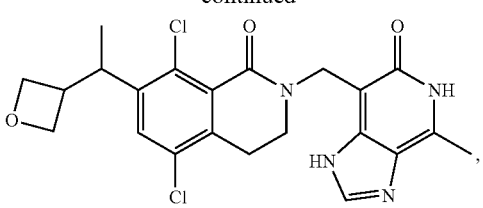
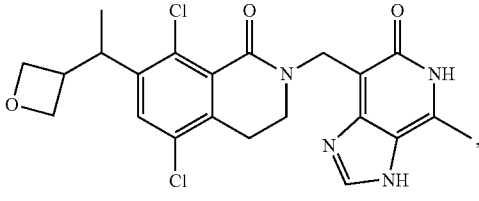
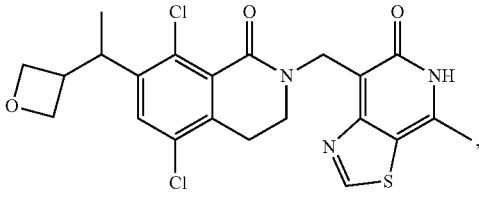
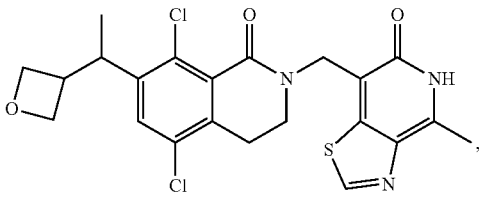
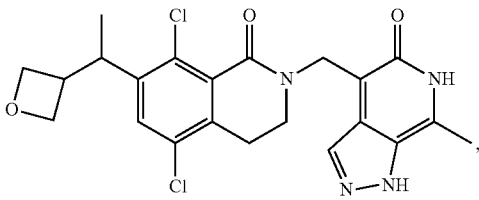
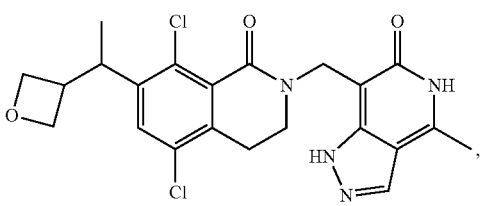
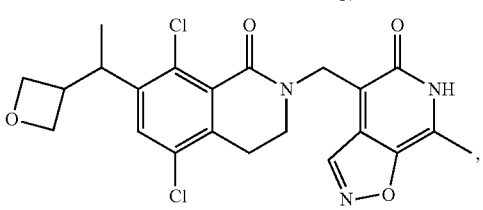
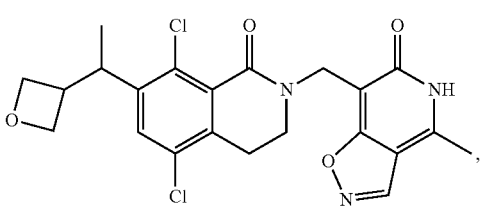

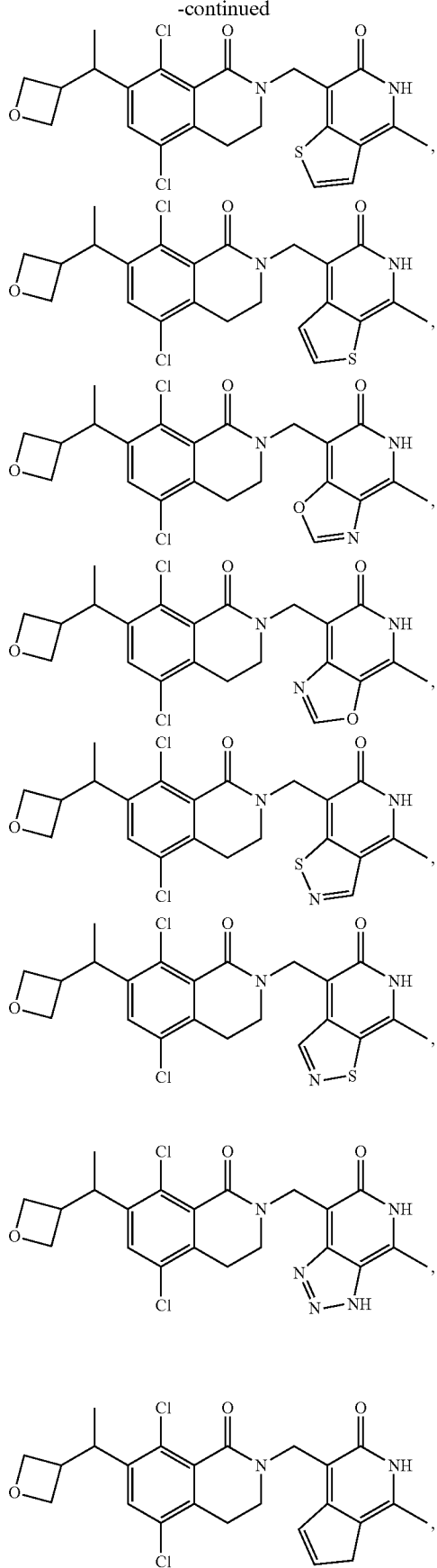
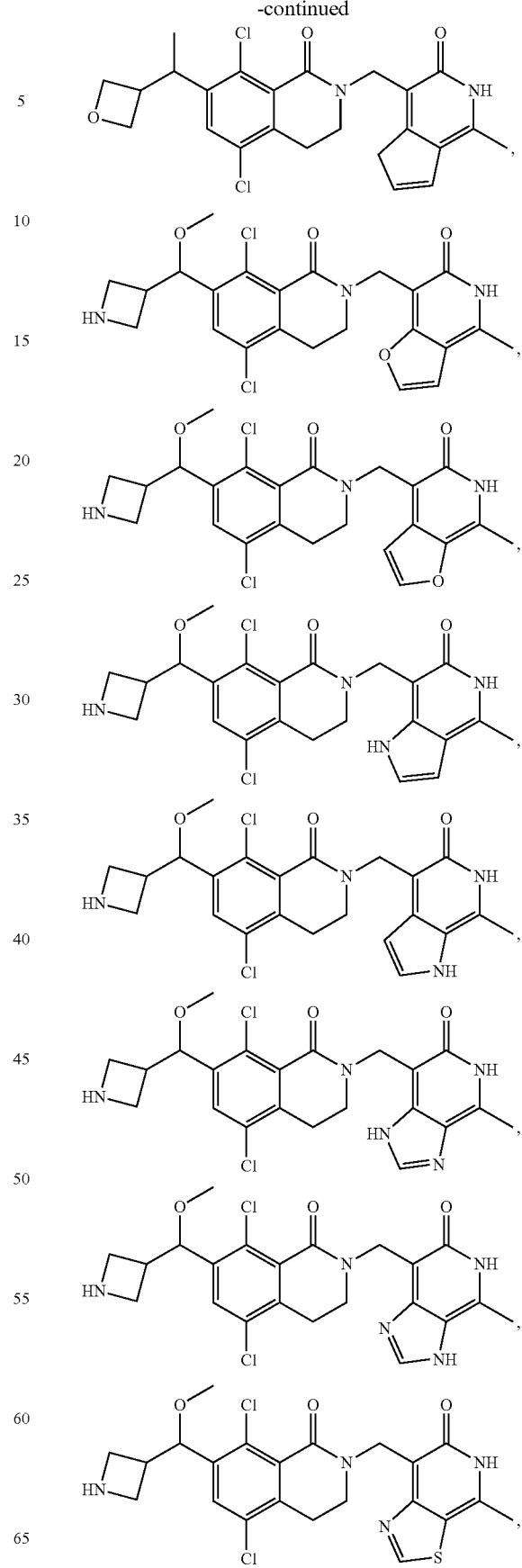

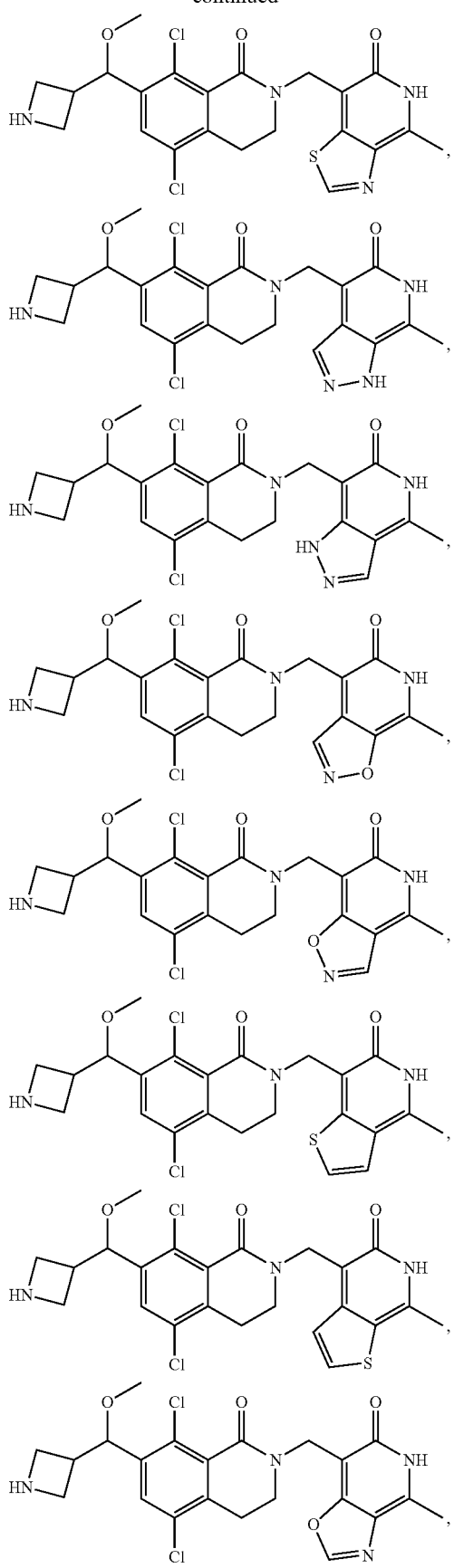
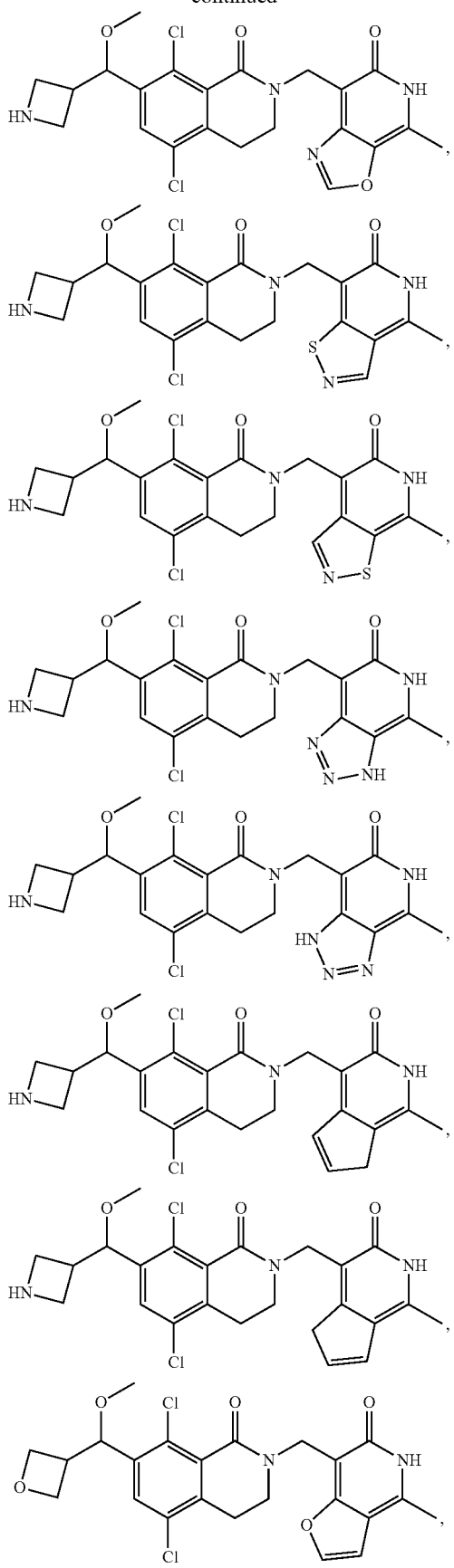

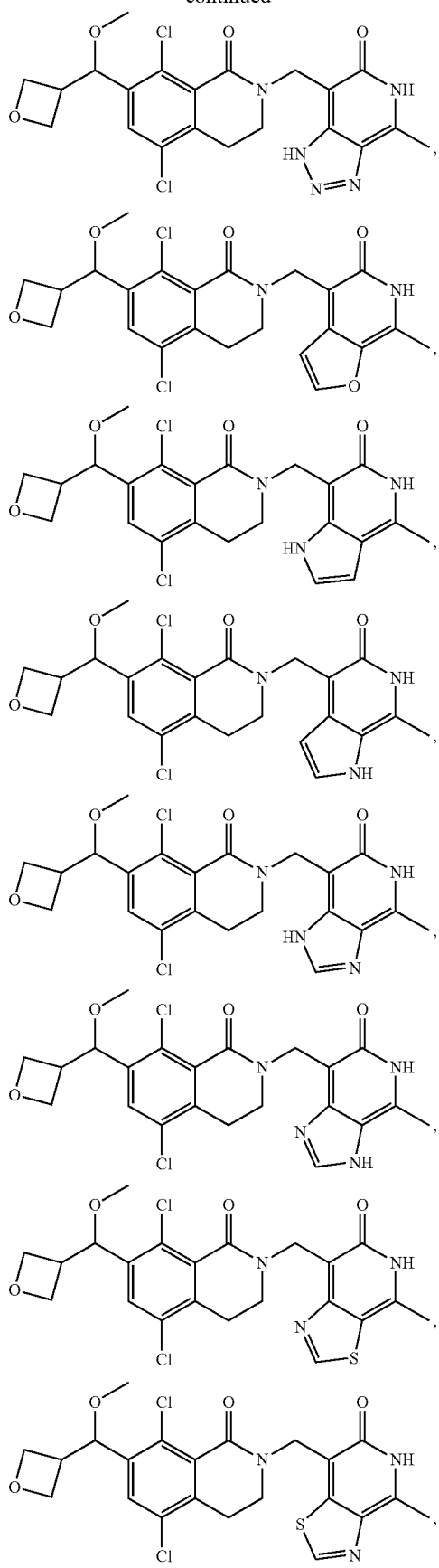
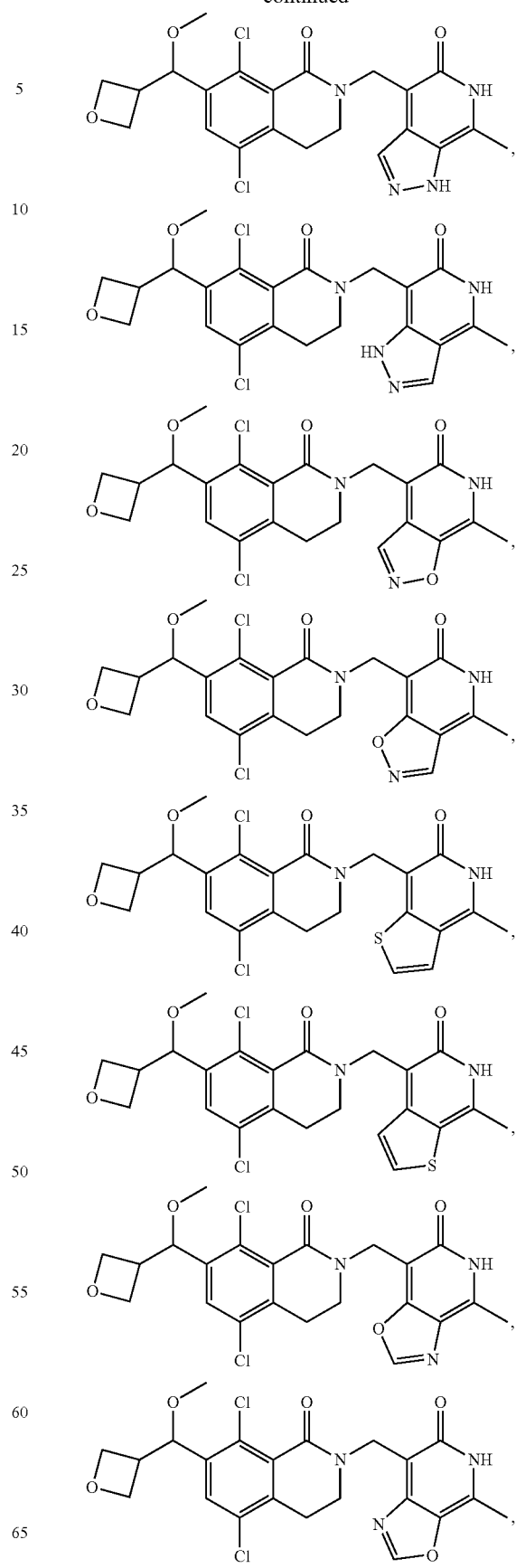

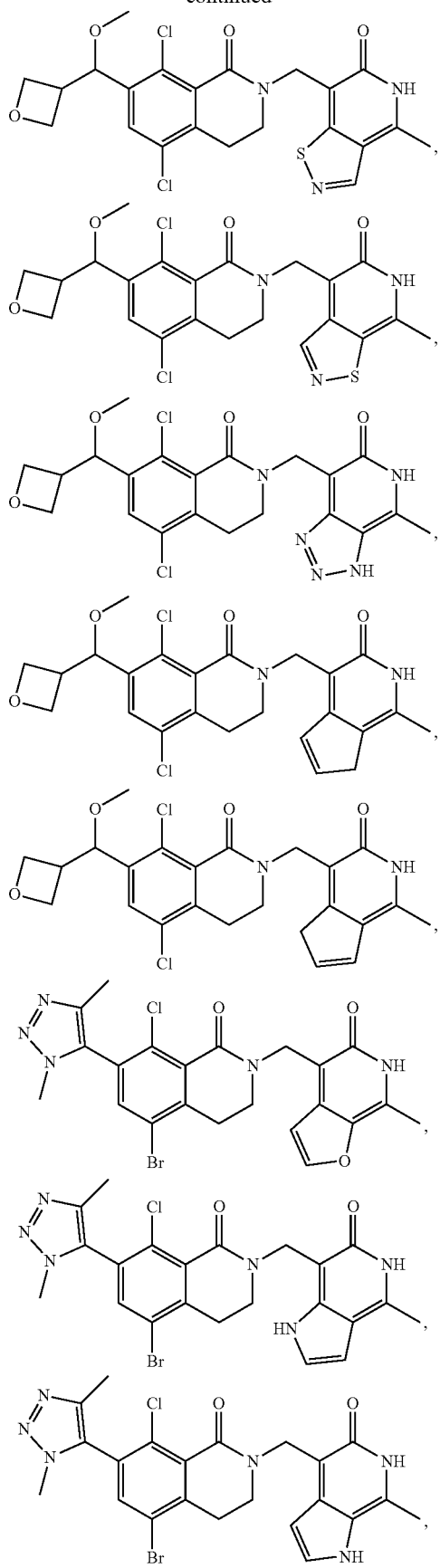
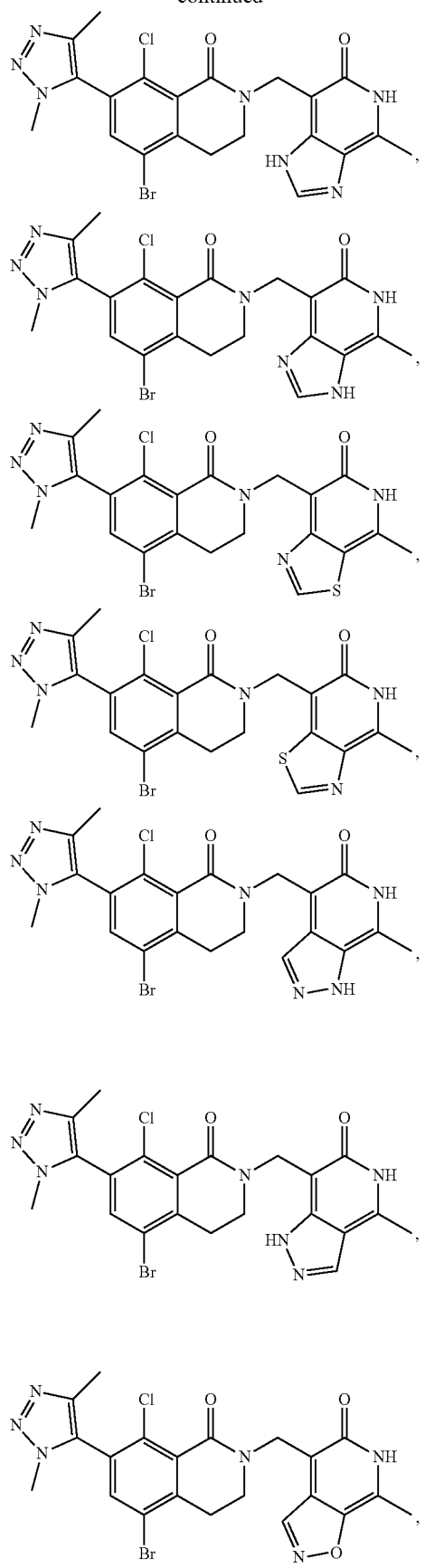

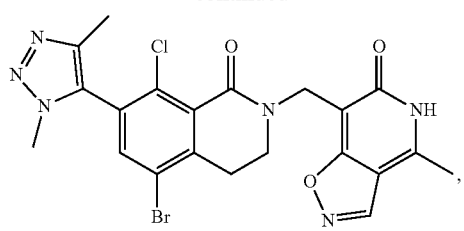
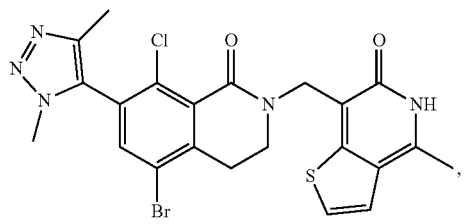
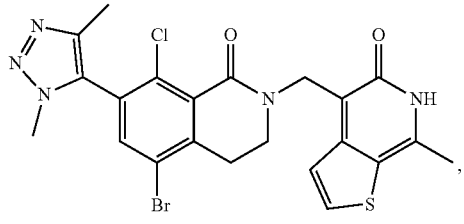
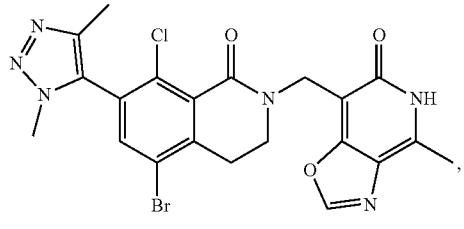
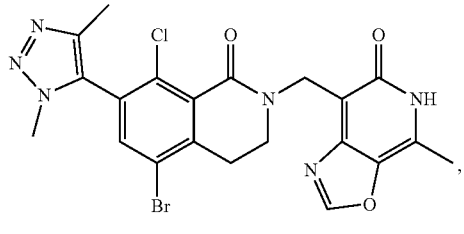
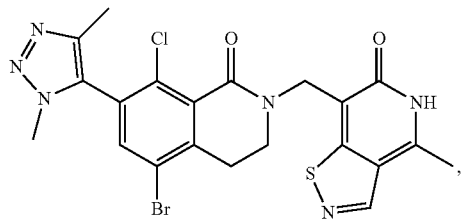
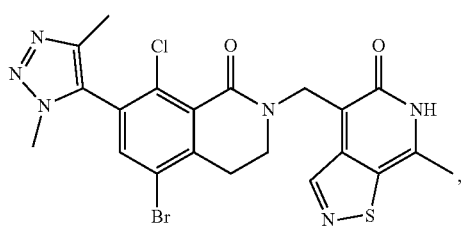
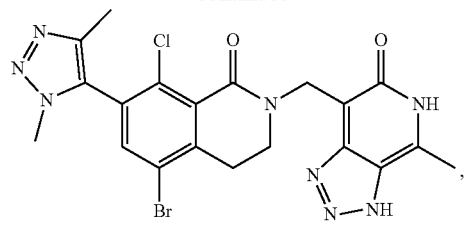
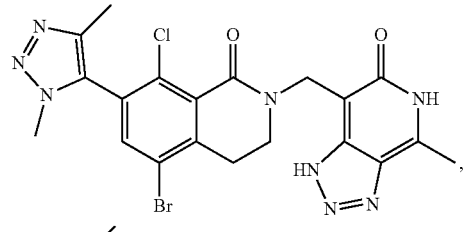
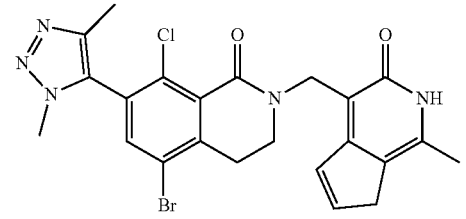
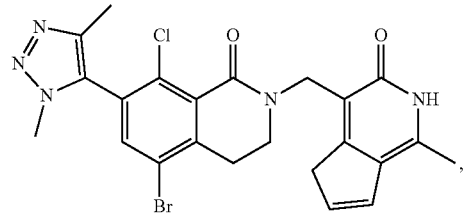
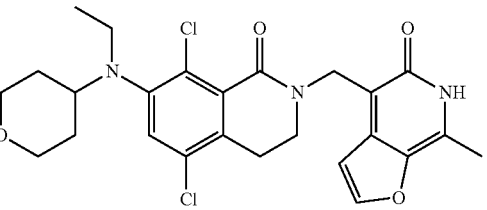
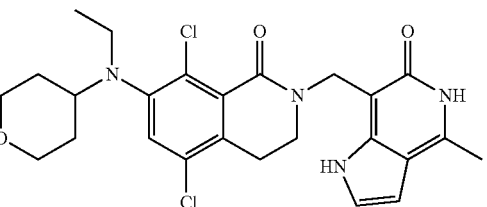
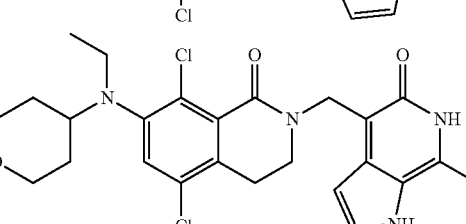
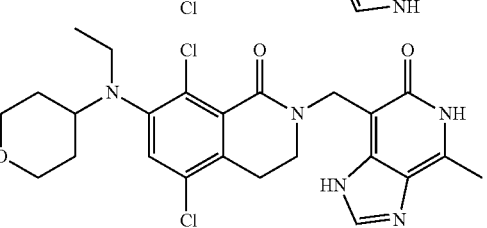

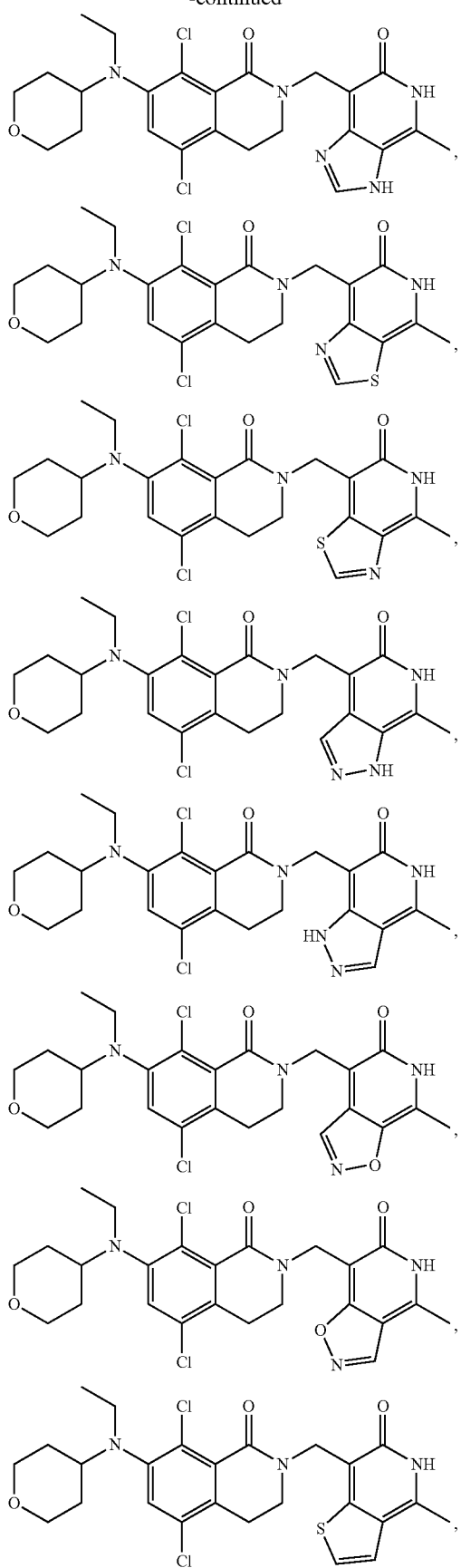
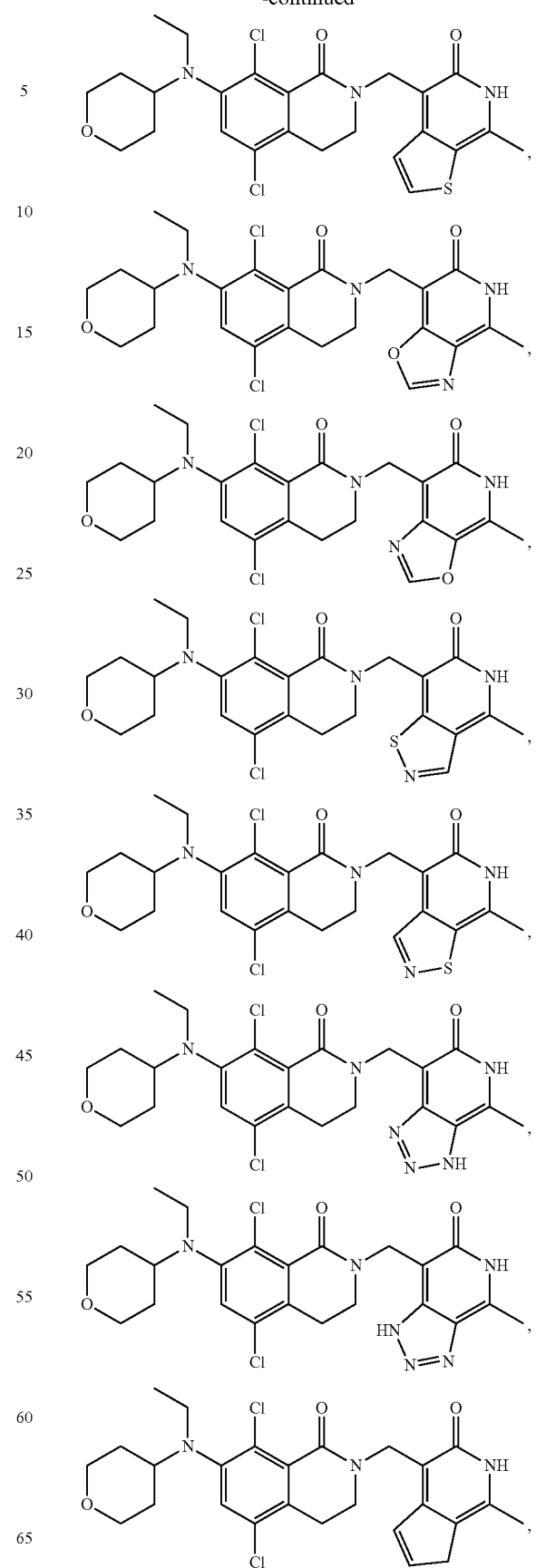

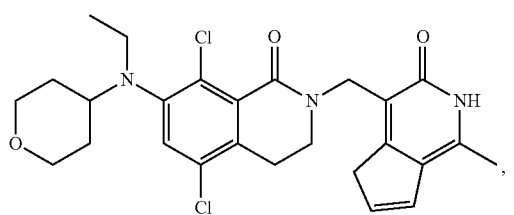
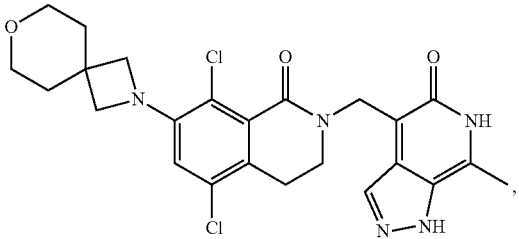
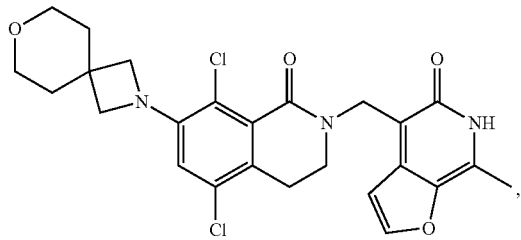
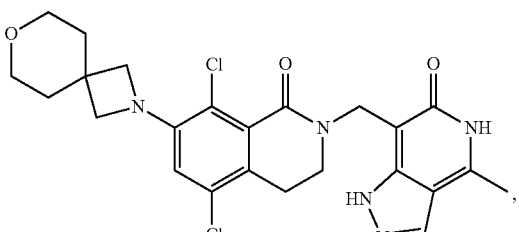
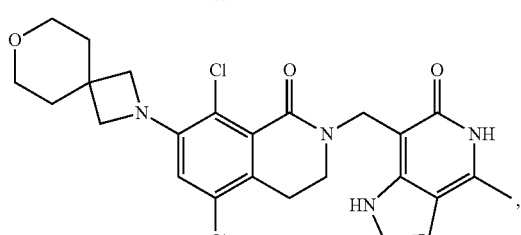
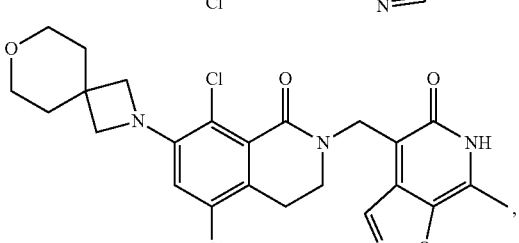
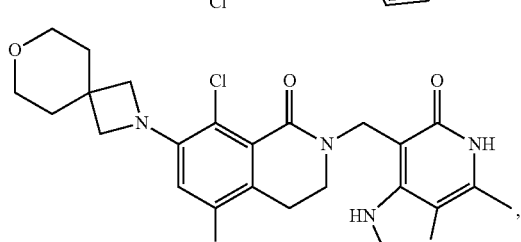
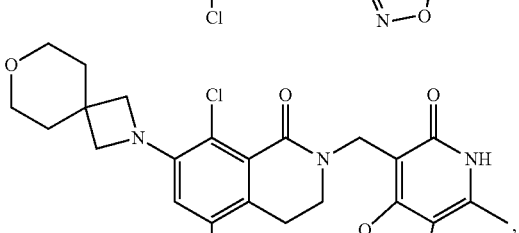
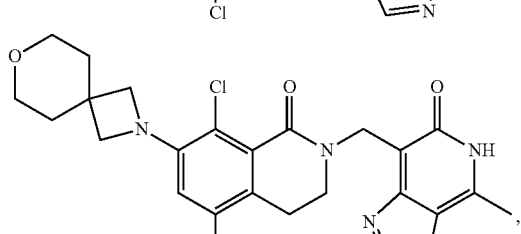
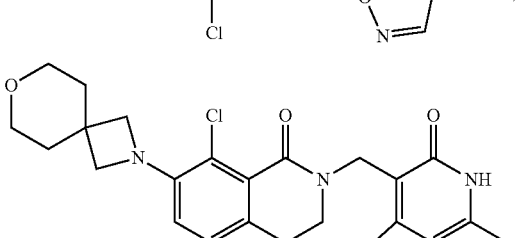
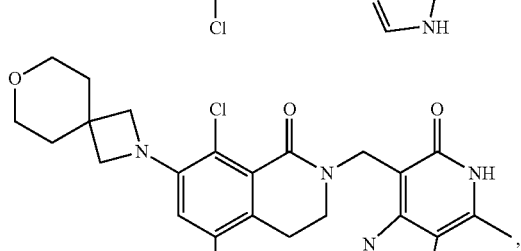
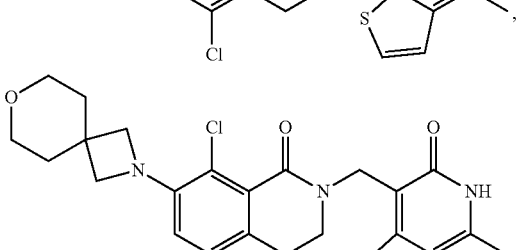
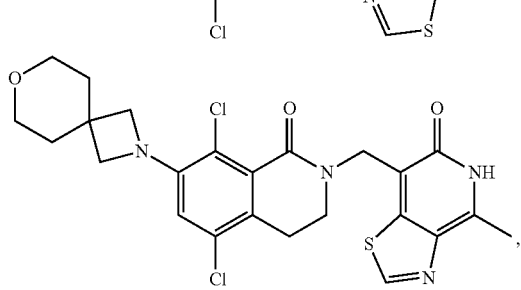
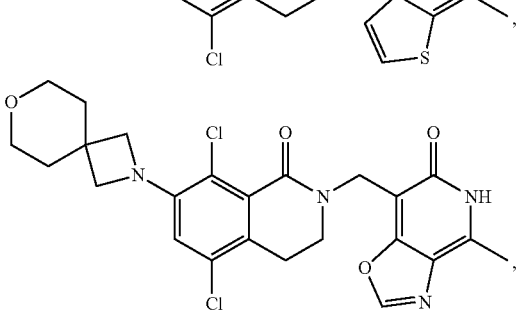

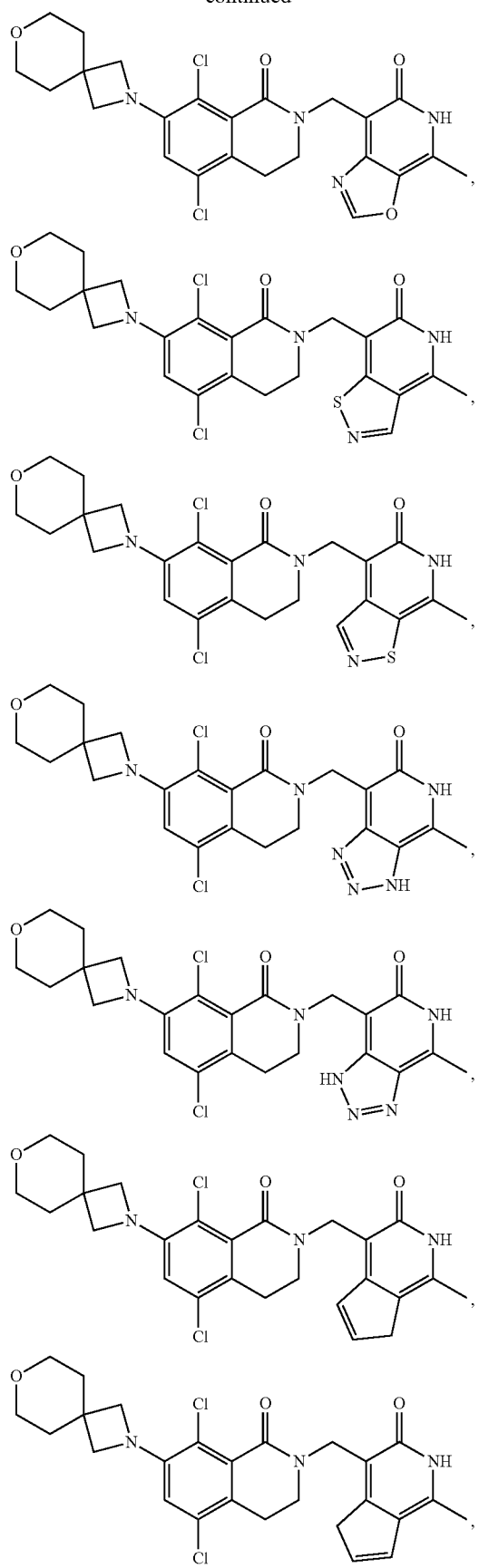
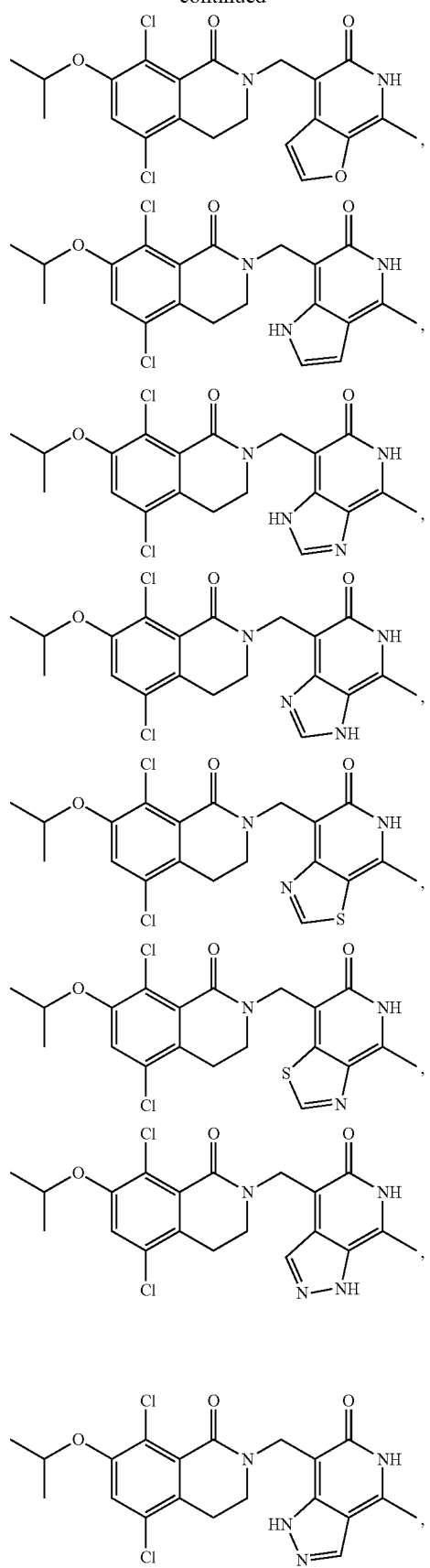

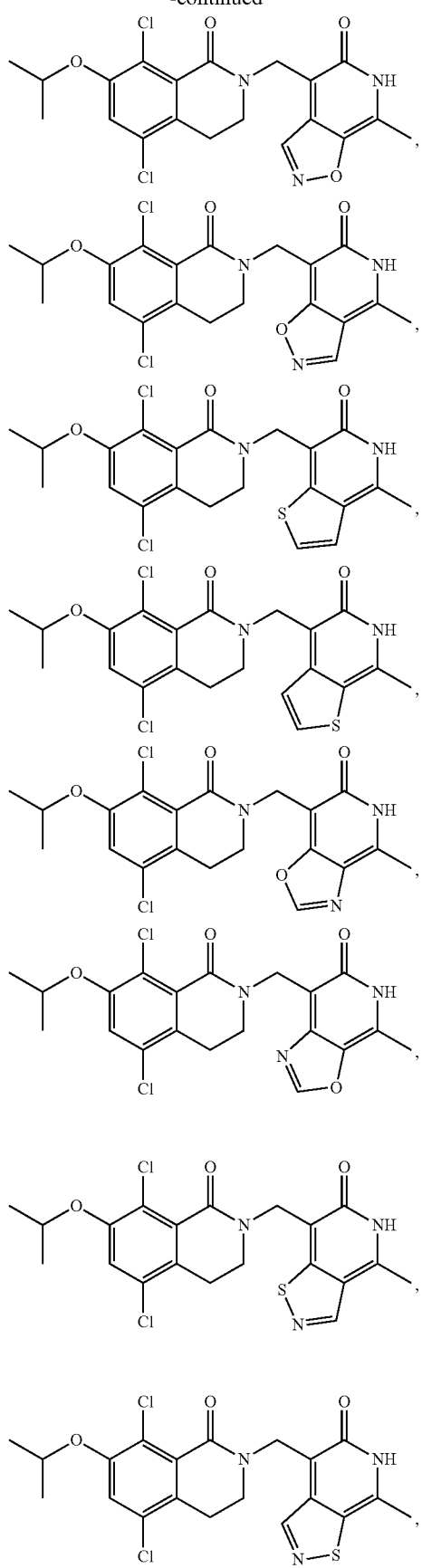
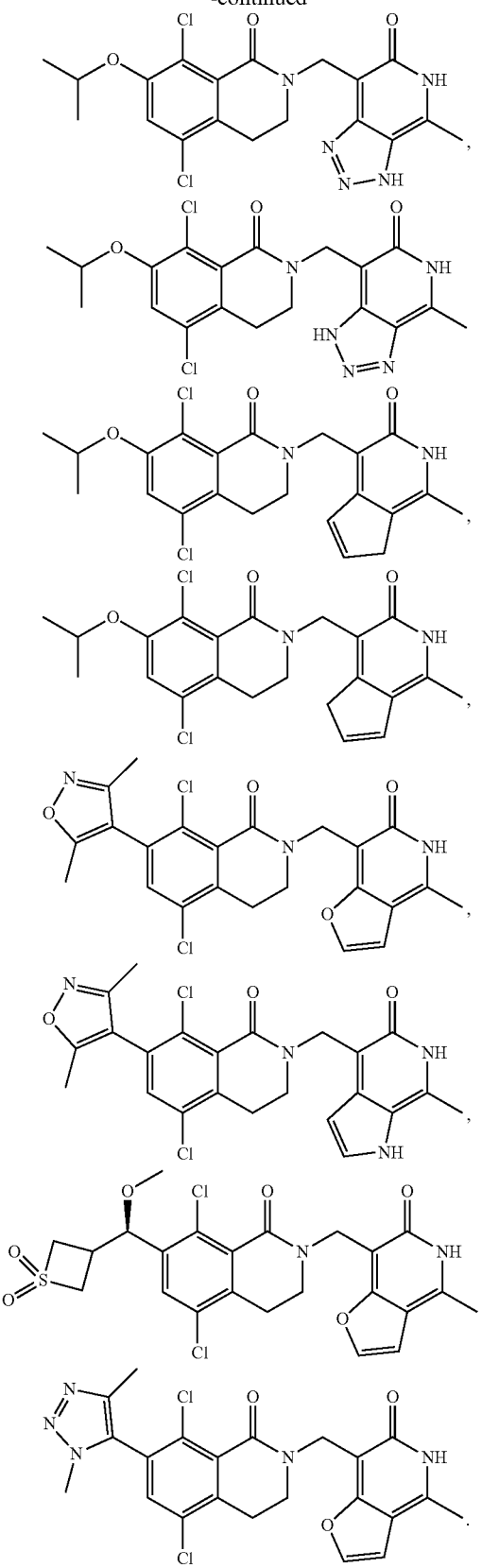
The compounds of formula (I) may be formulated into pharmaceutical compositions.

Pharmaceutical Compositions

In another aspect, the invention provides pharmaceutical compositions comprising a EZH2 inhibitor according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain embodiments, compounds of the invention are administered intravenously in a hospital setting. In certain other embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g, Remington's Pharmaceutical Sciences, 18th Edition, ed. A. Gennaro, Mack Publishing Co, Easton, Pa., 1990.

As used herein, the term "pharmaceutically acceptable salts" refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. A dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods described herein.

Methods of Use

In yet another aspect, the invention provides for methods for inhibiting LSD1 activity in a cell, comprising contacting the cell in which inhibition of LSD1 activity is desired with a therapeutically effective amount of a compound of formula (I), pharmaceutically acceptable salts thereof or pharmaceutical compositions containing the compound or pharmaceutically acceptable salt thereof.

The compositions and methods provided herein are particularly deemed useful for inhibiting EZH2 activity in a cell. In one embodiment, a cell in which inhibition of EZH2 activity is desired is contacted with a therapeutically effective amount of a compound of formula (I) to negatively modulate the activity of EZH2. In other embodiments, a therapeutically effective amount of pharmaceutically acceptable salt or pharmaceutical compositions containing the compound of formula (I) may be used.

By negatively modulating the activity of EZH2, particularly in cases for cells overexpressing the EZH2 enzyme or somatic mutations that activate the EZH2 enzyme, the methods are designed to restore normal cellular transcription expression patterns, e.g, by altering methylation pattern of H3K27, to inhibition undesired cellular proliferation resulting from enhanced EZH2 activity within the cell. The cells may be contacted in a single dose or multiple doses in accordance with a particular treatment regimen to effect the desired negative modulation of EZH2. The degree of mono- and dimethylation of histone H3K27 may be monitored in the cell using well known methods, including those described in Example A below, to assess the effectiveness of treatment and dosages may be adjusted accordingly by the attending medical practitioner.

In another aspect, methods of treating cancer comprising administering to a patient having cancer a therapeutically effective amount of a compound of formula (I), pharmaceutically acceptable salts thereof or pharmaceutical compositions comprising the compound or pharmaceutically acceptable salts thereof are provided. In one embodiment, the cancer is an EZH2-associated cancer.

The compositions and methods provided herein may be used for the treatment of a wide variety of cancer including tumors such as prostate, breast, brain, skin, cervical carcinomas, testicular carcinomas, etc More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is diffuse large B-cell lymphoma (DLBCL).

The concentration and route of administration to the patient will vary depending on the cancer to be treated. The compounds, pharmaceutically acceptable salts thereof and pharmaceutical compositions comprising such compounds and salts also may be co-administered with other anti-neoplastic compounds, e.g, chemotherapy, or used in combination with other treatments, such as radiation or surgical intervention, either as an adjuvant prior to surgery or post-operatively. The degree of mono- and dimethylation of histone H3K27 may be monitored in the patient using well known methods, including those described in Example A below, to access the effectiveness of treatment, along with other prognostic or biological factors, and dosages may be adjusted accordingly by the attending medical practitioner.

General Reaction Scheme, Intermediates and Examples General Reaction Scheme

The compounds of the present invention may be prepared using commercially available reagents and intermediates in the synthetic methods and reaction schemes described herein, or may be prepared using other reagents and conventional methods well known to those skilled in the art.

For instance, intermediates for compounds of the present invention may be prepared according to General Reaction Scheme I:

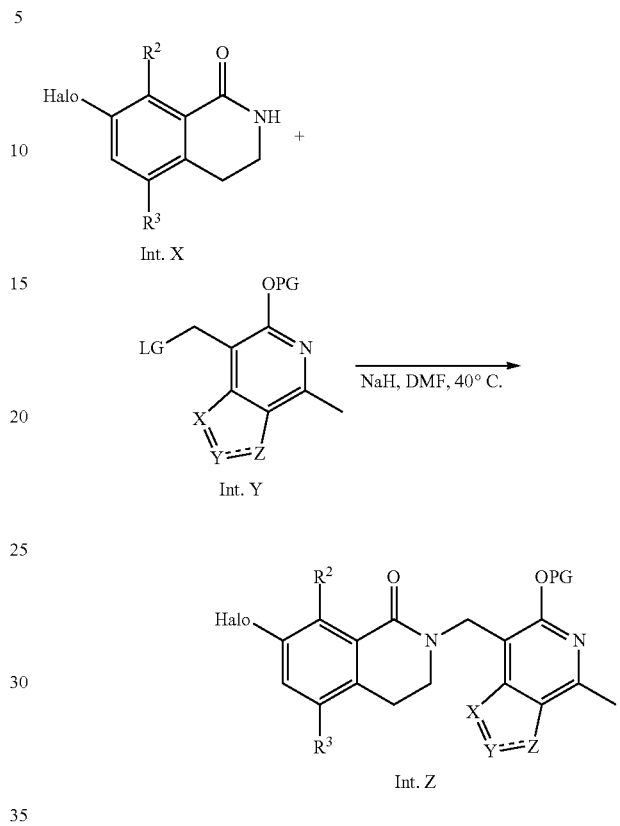

wherein LG is a leaving group; PG is a protecting group; and Halo is halogen.

Intermediates

Intermediates useful for the preparation of compounds of formula (I) may be acquired from commercial suppliers or prepared using reagents, synthetic methods and teachings set forth herein.

A. Intermediate X

Exemplary intermediates that may be used as Intermediate X in General Reaction Scheme I to afford compounds of formula (I) are provided in INTERMEDIATES A-C.

Intermediates A.I and A.II 7-bromo-5,8-dichloro-3,4-dihydroisoquinolin-1(2H)-one and 5,8-dichloro-7-iodo-3,4-dihydroisoquinolin-1(2H)-one

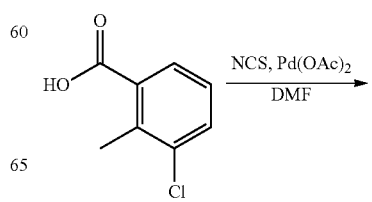

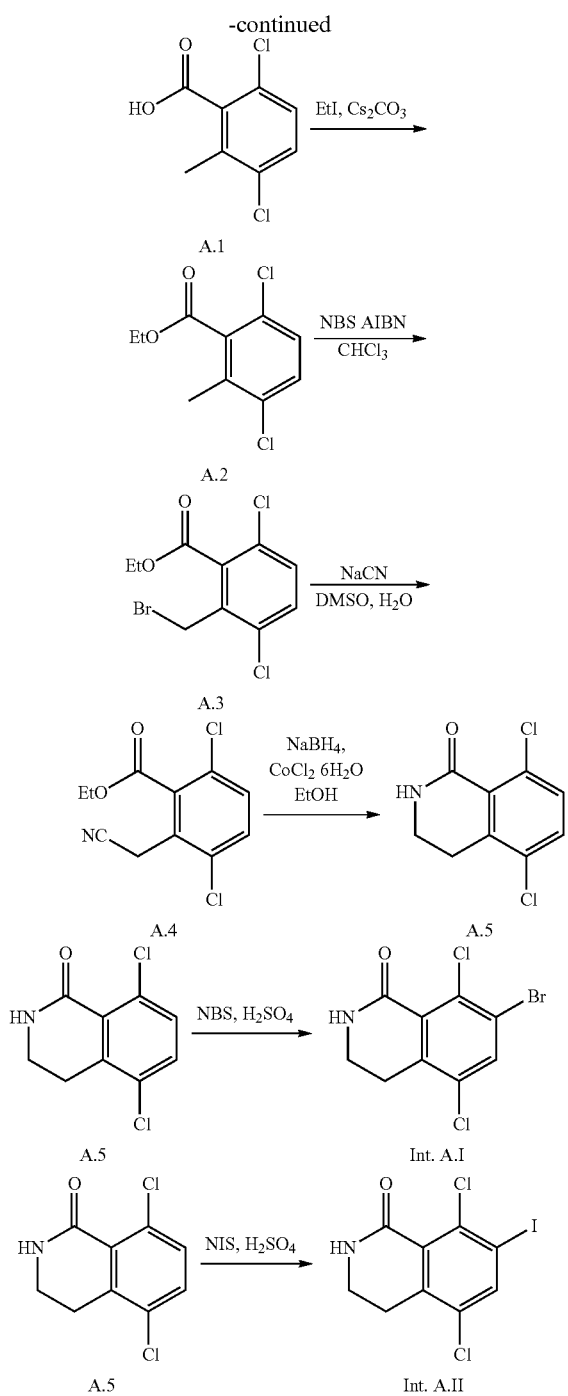

Compound A.1:
A mixture of 3-chloro-2-methyl-benzoic acid (25.0 g, 147 mmol, 1 equivalent), NCS (23.5 g, 176 mmol, 1.2 equivalents) and Pd(OAc)$_2$ (3.62 g, 16.1 mmol, 0.11 equivalent) in DMF (5 mL) was degassed and purged with N$_2$ for 3 times, and then the mixture was stirred at 110° C. for 12 hours under a N$_2$ atmosphere. The mixture was cooled to 20° C. and used in the next step directly.

Compound A.2:
A mixture of 3,6-dichloro-2-methyl-benzoic acid (A.1, 30 g, 146 mmol, 1 equivalent), ethyl iodide (45.6 g, 293 mmol, 2 equivalents) and Cs$_2$CO$_3$ (167 g, 512 mmol, 3.5 equivalents) in DMF (200 mL) was stirred at 25° C. for 1.5 hours under a N$_2$ atmosphere. The reaction mixture was diluted with methyl tert-butylether (500 mL) then washed with water (500 mL) and brine (500 mL). The separated organic layer was dried over sodium sulfate, then was filtered and concentrated under vacuum. The residue was purified by silica gel column chromatography (petroleum ether/ethyl acetate 10/1) to give ethyl 3,6-dichloro-2-methyl-benzoate (A.2, 26.0 g, 112 mmol, 70% purity) as a yellow oil.

$^1$H NMR (400 MHz, CDCl$_3$) δ: 7.34 (d, J=8.4 Hz, 1H), 7.20 (d, J=8.4 Hz, 1H), 4.46 (q, J=7.2 Hz, 2H), 2.36 (s, 3H), 1.42 (t, J=7.2 Hz, 3H).

Compound A.3:
To a solution of ethyl 3,6-dichloro-2-methyl-benzoate (A.2, 26.0 g, 112 mmol, 1 equivalent) and NBS (29.8 g, 167 mmol, 1.5 equivalent) in CHCl$_3$ (250 mL) was added AIBN (5.5 g, 33.5 mmol, 0.3 equivalent). This mixture was stirred at 60° C. for 16 hours. The reaction mixture was diluted with dichloromethane (500 mL) and was washed with water (500 mL) then brine (500 mL). The separated organic layer was dried over sodium sulfate, then was filtered and concentrated under vacuum. Ethyl 2-(bromomethyl)-3,6-dichloro-benzoate (A.3, 30.0 g, crude) was obtained as a yellow oil and was used in the next step without further purification.

Compound A.4:
To a solution of ethyl 2-(bromomethyl)-3,6-dichloro-benzoate (A.3, 30 g, 96.2 mmol, 1 equivalent) in DMSO (50 mL) was added a solution of sodium cyanide (7.07 g, 144 mmol, 1.5 equivalents) in water (50 mL) at 20° C. The mixture was stirred for 1.5 hours then it was diluted with methyl tert-butylether (500 mL), then was washed with water (400 mL) and brine (200 mL). The separated organic layer was dried over sodium sulfate, then was filtered and concentrated under vacuum. The residue was purified by silica gel column chromatography (eluent: petroleum ether/ethyl acetate 10/1). Ethyl 3,6-dichloro-2-(cyanomethyl)benzoate (A.4, 20 g, 77.5 mmol, 80.6% yield, 62% purity) was obtained as a colorless oil.

$^1$H NMR (400 MHz, CDCl$_3$) δ: 7.50-7.45 (m, 1H), 7.43-7.39 (m, 1H), 4.52 (q, J=7.2 Hz, 2H), 3.86 (s, 2H), 1.51-1.42 (m, 3H).

Compound A.5:
To a solution of ethyl 3,6-dichloro-2-(cyanomethyl)benzoate (A.4, 10 g, 38.7 mmol, 1 equivalent) in EtOH (50 mL) was added CoCl$_2$ 6H$_2$O (18.4 g, 77.5 mmol, 2 equivalents) followed by NaBH$_4$ (7.33 g, 193 mmol, 5 equivalents) at 0° C. The reaction mixture was stirred at 25° C. for 1 hour, then it was heated at 80° C. for 16 hours. After this time, it was diluted with water (100 mL) and ethyl acetate (500 mL). The separated organic layer was washed with water (500 mL), then brine (500 mL), and was dried over sodium sulfate. The dried solution was filtered and concentrated under vacuum. The resulting crude product was purified further by silica gel column chromatography with 3/1 petroleum ether/ethyl acetate as an eluent, to give 5,8-dichloro-3,4-dihydro-2H-isoquinolin-1-one (A.5, 3.0 g, 13.9 mmol, 35.8% yield) as a white solid; LCMS [M+1]: 216.

$^1$H NMR (400 MHz, CDCl$_3$) δ: 7.43-7.38 (d, J=8.6 Hz, 1H), 7.37-7.31 (d, J=8.6 Hz, 1H), 6.81 (s, 1H), 3.55-3.47 (t, J=6.4 Hz, 2H), 3.09 (t, J=6.4 Hz, 2H).

Intermediate A.I. 7-bromo-5,8-dichloro-3,4-dihydroisoquinolin-1(2H)-one

To a solution of 5,8-dichloro-3,4-dihydro-2H-isoquinolin-1-one (A.5, 9.82 g, 45.5 mmol, 1 equivalent) in concentrated sulfuric acid (25 mL) at 60° C. was added NBS (13.6 g, 76.4 mmol, 1.68 equivalents) in portions. After the mixture was stirred at 60° C. for 1 hour, then it was poured into ice water and the pH was adjusted to 7 with aqueous saturated sodium bicarbonate solution. The aqueous layer was extracted with dichloromethane (3×200 mL). The combined organic layer was washed with water (300 mL) followed by brine (300 mL) then was dried over sodium sulfate, filtered and concentrated under vacuum. The residue was purified by preparative scale HPLC [column: Kromasil 150×25 mm×10 um; mobile phase, A: water with 0.1% TFA added, B: acetonitrile, B %: 35%-65%, over a 12 minute elution gradient]. INTERMEDIATE A.I, 7-bromo-5,8-dichloro-3,4-dihydro-2H-isoquinolin-1-one (3.90 g, 13.2 mmol, 29.1% yield) was obtained as a white solid; LCMS [M+1]: 296.

$^1$H NMR (400 MHz, chloroform-d) δ: 7.82 (s, 1H), 6.72 (br. s, 1H), 3.51 (dt, J=4.0, 6.4 Hz, 2H), 3.05 (t, J=6.4 Hz, 2H).

Intermediate A.II. 5,8-dichloro-7-iodo-3,4-dihydroisoquinolin-1(2H)-one

To a solution of 5,8-dichloro-3,4-dihydro-2H-isoquinolin-1-one (A.5, 1.20 g, 5.55 mmol, 1 equivalent) in concentrated sulfuric acid (20 mL) was added N-iodosuccinimide (3.75 g, 16.6 mmol, 3 equivalents) at 0° C. After stirring at 15° C. for 12 hours, the reaction mixture was poured into ice-water (100 mL) and the pH adjusted to 7 with aqueous saturated sodium bicarbonate solution. The resulting mixture was extracted with ethyl acetate (50 mL×2), then the organic phase was washed with saturated sodium sulfite aqueous solution (50 mL) and brine (50 mL×3); this organic solution was dried over sodium sulfate, then was filtered and concentrated under vacuum. The residual oil was dispersed into 7/3 petroleum ether/ethyl acetate (5 mL) and stirred for 30 min, whereupon this substance solidified. The solid was collected by filtration and dried in vacuo to give INTERMEDIATE A.II, 5,8-dichloro-7-iodo-3,4-dihydro-2H-isoquinolin-1-one (1.50 g, 4.39 mmol, 79% yield) as a yellow solid; LCMS [M+1]: 341.8.

$^1$H NMR (400 MHz, CD$_3$OD) δ: 8.16 (s, 1H), 3.42 (t, J=6.4 Hz, 2H), 3.02 (t, J=6.4 Hz, 2H).

Intermediate B 7-bromo-5,8-dichloro-3,4-dihydroisoquinolin-1(2H)-one

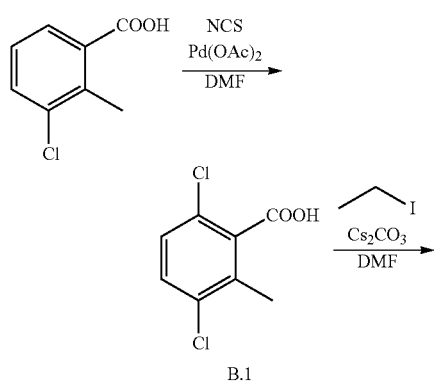

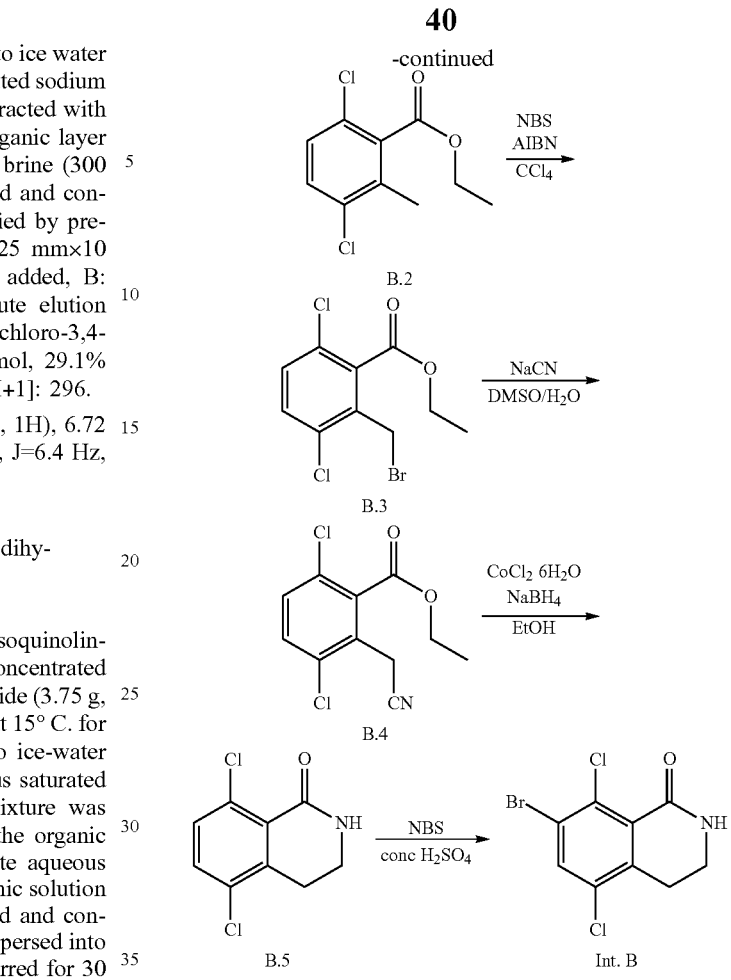

A mixture of 3-chloro-2-methylbenzoic acid, N-chlorosuccinimide and palladium (II) acetate in N,N-dimethylformamide is stirred at 110° C. under a nitrogen atmosphere overnight. After cooling to room temperature, cesium carbonate and iodoethane (317 g, 2.03 mol) are added and stirring continued at room temperature for 1.5 hours. The reaction mixture is poured into a mixture of water and methyl tert-butyl ether. Solids are removed by filtration, and the filtrate layers are separated. The aqueous layer is extracted with more methyl tert-butyl ether. The combined organic extracts are washed with saturated aqueous sodium chloride solution, dried over sodium sulfate, and concentrated in vacuo. The residue may be purified by silica gel chromatography, affording ethyl 3,6-dichloro-2-methylbenzoate (Intermediate B.2) as a yellow oil.

A solution of ethyl 3,6-dichloro-2-methylbenzoate (Intermediate B.2) and N-bromosuccinimide in chloroform is treated with azobisisobutyronitrile and the mixture is refluxed overnight. After cooling to room temperature, the mixture is diluted with dichloromethane and washed with water. The aqueous layer is extracted with dichloromethane. The combined organic extracts are washed with saturated aqueous sodium chloride solution, dried over sodium sulfate, and concentrated in vacuo to give ethyl 2-(bromomethyl)-3,6-dichlorobenzoate (Intermediate B.3) which may be used without further purification.

A solution of sodium cyanide in water is added dropwise to a solution of ethyl 2-(bromomethyl)-3,6-dichlorobenzoate (Intermediate B.3) in dimethysulfoxide at room temperature. The mixture is stirred at room temperature for 1.5 hours. The reaction mixture is poured into a 2:1 mixture of water and methyl tert-butyl ether, and the layers separated. The organic layer is washed with water and with saturated aqueous sodium chloride solution, dried over sodium sulfate, and concentrated in vacuo. The residue may be purified by silica gel chromatography (eluting with 30:1 petroleum ether/ethyl acetate), affording ethyl 3,6-dichloro-2-(cyanomethyl)benzoate (Intermediate B.4) as a yellow oil.

Cobalt (II) chloride hexahydrate is added to a room temperature solution of ethyl 3,6-dichloro-2-(cyanomethyl) benzoate (Intermediate B.4) in ethanol, and the resulting mixture cooled to 0° C. Sodium borohydride is added in portions. The mixture is stirred at room temperature for 1 hour, and then refluxed overnight. The resulting suspension is filtered and the filtrate concentrated in vacuo. The solids in the filter cake are stirred in ethyl acetate, and then filtered again. This procedure may be repeated a second time. The combined filtrates are added to the original filtrate residue, and this organic solution washed with water and saturated aqueous sodium chloride solution, dried over sodium sulfate, and concentrated in vacuo to give 5,8-dichloro-3,4-dihydroisoquinolin-1(2H)-one (Intermediate B.5) as an off-white solid.

To a solution of 5,8-dichloro-3,4-dihydroisoquinolin-1(2H)-one (Intermediate B.5) in concentrated sulfuric acid at 60° C. is added N-bromosuccinimide in portions. Stirring is continued at 60° C. for 2 hours, then more N-bromosuccinimide is added. After stirring at 60° C. for 1 hour more, the mixture is poured onto ice water, then extracted with dichloromethane. The combined organic extracts are washed with saturated aqueous sodium chloride solution, dried over sodium sulfate, and concentrated in vacuo. The residue is stirred in 2:1 ethyl acetate and petroleum ether mixture, and the resulting solids collected by filtration and dried under vacuum to give title compound 7-bromo-5,8-dichloro-3,4-dihydroisoquinolin-1(2H)-one (Intermediate A) as an off-white solid.

Intermediate C 5-bromo-8-chloro-7-iodo-3,4-dihydroisoquinolin-1(2H)-one

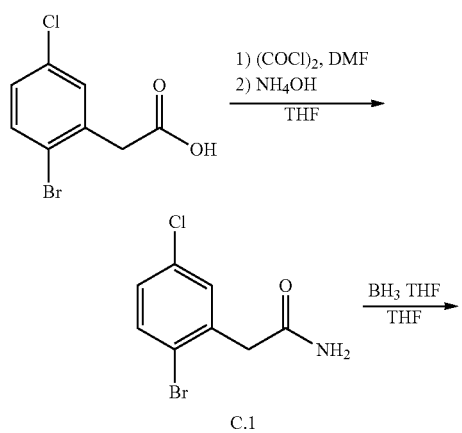

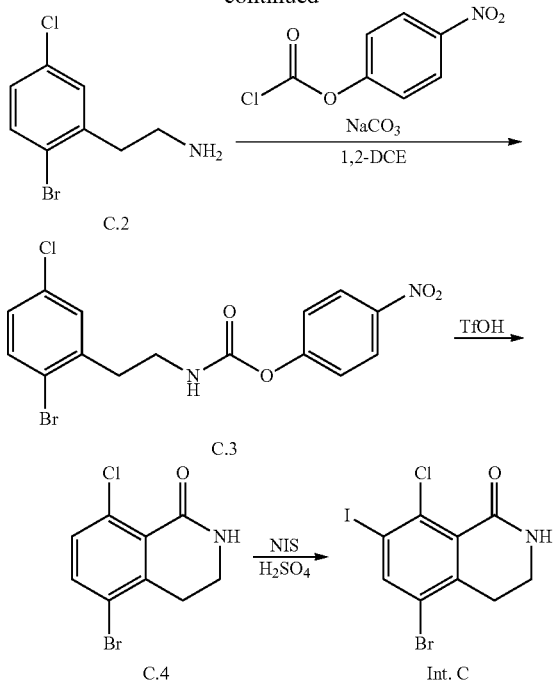

Two batches may be run in parallel under the following conditions, then combined for workup and purification: To a room temperature (15-20° C.) solution of 2-(2-bromo-5-chlorophenyl)acetic acid in anhydrous THF is added oxalyl and DMF, initiating gas evolution. The mixture is stirred at room temperature for two hours, until TLC shows the starting acid is completely consumed. The mixture is cooled to 0° C., and ammonium hydroxide is added in one portion, causing the internal temperature to rise to 40° C. The cooling bath is removed, and the solution stirred vigorously at room temperature for one hour. The two batches are combined, diluted with water, and extracted with ethyl acetate. The combined organic extracts are washed with water, 1N aqueous HCl, and brine, then dried over anhydrous sodium sulfate and concentrated to give crude product as a yellow solid. The crude product is crystallized from 5/1 petroleum ether/ethyl acetate and dried to give 2-(2-bromo-5-chlorophenyl)acetamide (Intermediate C.1) as a white solid.

Two batches are run in parallel under the following conditions, then combined for purification: Borane-THF complex was added dropwise to a cooled (0° C.) suspension of 2-(2-bromo-5-chlorophenyl)acetamide (Intermediate C.1) in anhydrous THF. The clear solution is heated to 80° C. for two hours, then cooled again to 0° C. The mixture is quenched by sequential addition of water and conc. HCl, causing significant gas evolution. Stirring is continued at 10-15° C. for 16 hours, after which the mixture is concentrated to remove THF. The aqueous residue is cooled to 0° C., then 12 N aqueous sodium hydroxide was added to bring the pH to 11. The basified solution is extracted with ethyl acetate. The combined organic extracts are washed with brine, dried over anhydrous sodium sulfate, filtered, and concentrated to give crude product as a yellow oil. Two batches of this crude product are combined, treated with 4N HCl/MeOH, and stirred at 10-15° C. for 16 hours. The mixture is concentrated, and the residue stirred in ethyl acetate for 30 minutes. The resulting white solid is collected by filtration, and the filter cake washed with ethyl acetate.

The solids are dissolved in water, filtered to remove insolubles, and the filtrate extracted with ethyl acetate. The aqueous layer is basified with solid NaOH to pH 10, then extracted with ethyl acetate. The combined organic extracts are washed with brine, dried over anhydrous sodium sulfate, filtered, and concentrated to give 2-(2-bromo-5-chlorophenyl)ethan-1-amine (Intermediate C.2) as a colorless oil.

To a cooled (0° C.) suspension of 2-(2-bromo-5-chlorophenyl)ethan-1-amine (Intermediate C.2) and sodium carbonate in anhydrous 1,2-dichloroethane is added 4-nitrophenyl chloroformate. The mixture is stirred at 0° C. for 30 minutes, then at 10-15° C. for 16 hours. The solution is diluted with water and extracted with dichloromethane. The combined organic extracts are washed with water and brine, dried over anhydrous sodium sulfate, and concentrated. The crude product is crystallized from 5/1 petroleum ether/EtOAc to give 4-nitrophenyl (2-bromo-5-chlorophenethyl)carbamate (Intermediate C.3) as a white solid.

Trifluoromethanesulfonic acid is added dropwise to a cooled (0° C.) suspension of 4-nitrophenyl (2-bromo-5-chlorophenethyl)carbamate (Intermediate C.3) in anhydrous 1,2-dichloroethane. Solids will gradually dissolve over the course of the addition, resulting in a clear yellow solution. The mixture is stirred at 0° C. for 10 minutes, then heated at 60-70° C. for 3 hours. The resulting brown solution is poured into ice-water and stirred until all the ice had melted. The layers are separated, and the aqueous layer extracted with dichloromethane. The combined organic layers are washed with 2N aqueous sodium hydroxide, water, and brine, then dried over anhydrous sodium sulfate and concentrated. The crude product is crystallized from 2/1 petroleum ether/ethyl acetate, to give 5-bromo-8-chloro-3,4-dihydroisoquinolin-1(2H)-one (Intermediate C.4) as a brown solid.

N-iodosuccinimide is added to a cooled (0° C.) solution of 5-bromo-8-chloro-3,4-dihydroisoquinolin-1(2H)-one (Intermediate C.4) in conc. sulfuric acid. The brown suspension is stirred at 10-15° C. for 16 hours, then poured into ice-water and stirred until all the ice had melted. The resulting aqueous suspension is extracted with ethyl acetate. The combined organic extracts are washed with saturated aqueous NaHSO$_3$, 2N aqueous sodium hydroxide, and brine, then dried over anhydrous sodium sulfate and concentrated. The crude product is crystallized with 1/1 petroleum ether/ethyl acetate to give 5-bromo-8-chloro-7-iodo-3,4-dihydroisoquinolin-1(2H)-one (Intermediate C) as an off-white solid.

B. Intermediate Y

Exemplary intermediates that may be used as Intermediate Y in General Reaction Scheme I to afford compounds of formula (I) are provided in INTERMEDIATES D-T.

Intermediate D (5-(benzyloxy)-7-methylfuro[2,3-c]pyridin-4-yl)methanol

An exemplary intermediate for the preparation of compounds of formula (I) wherein Intermediate Y is a substituted furopyridinone is described in INTERMEDIATE D.

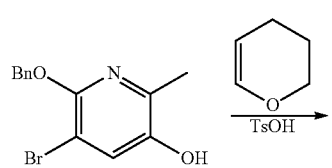

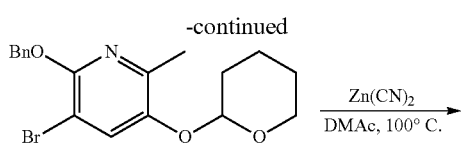

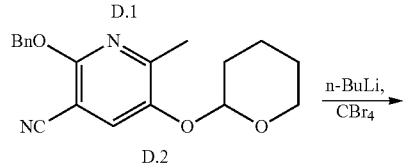

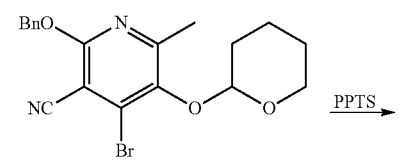

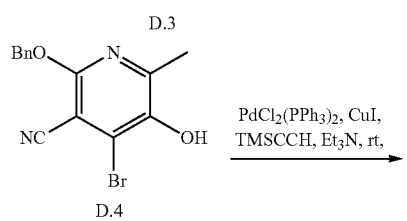

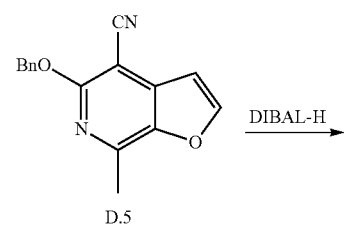

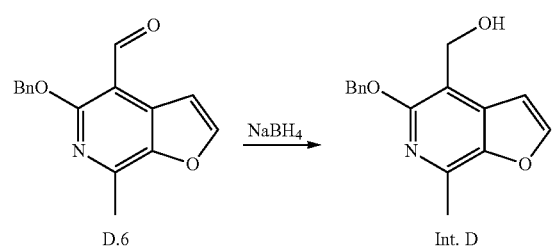

Intermediate D can be prepared from a suitably functionalized pyridine derivative. After protection of the alcohol, for example as the THP ether and metal-catalyzed installation of the nitrile, the remaining site on the pyridine can be brominated with carbon tetrabromide. Removal of the protecting group is followed by formation of the furan ring. Reduction of the nitrile provides Intermediate D.

Intermediate E (4-methyl-1H-imidazo[4,5-c]pyridin-7-yl)methanol

An exemplary intermediate for the preparation of compounds of formula (I) wherein Intermediate Y is a substituted imidazopyridinone is described in INTERMEDIATE E

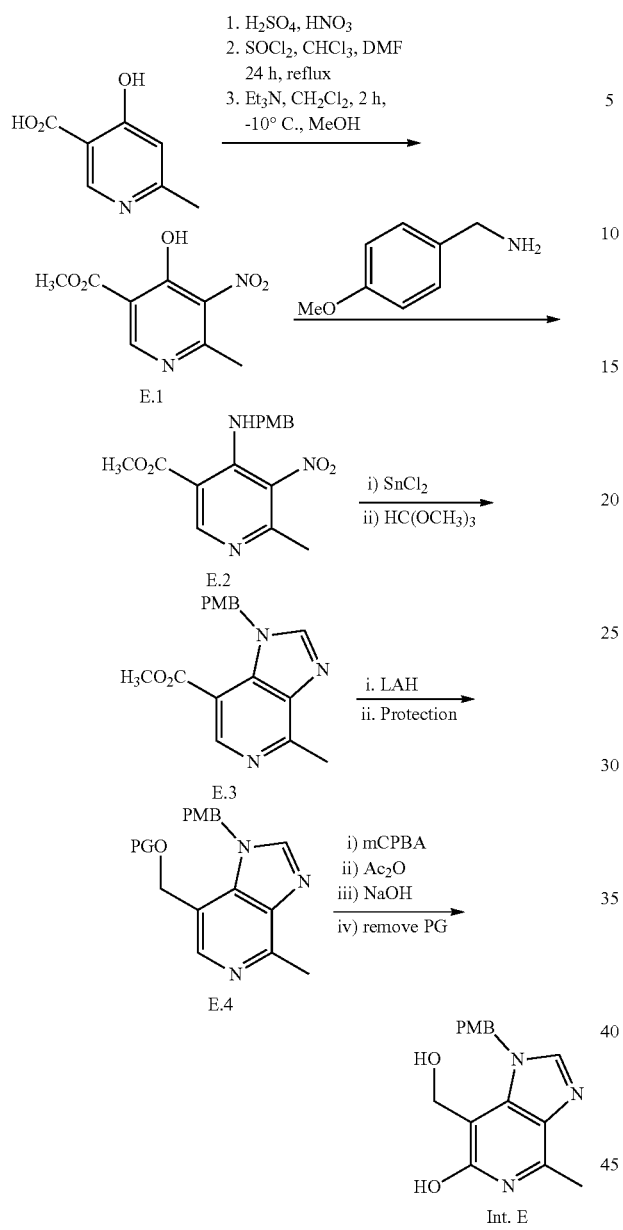
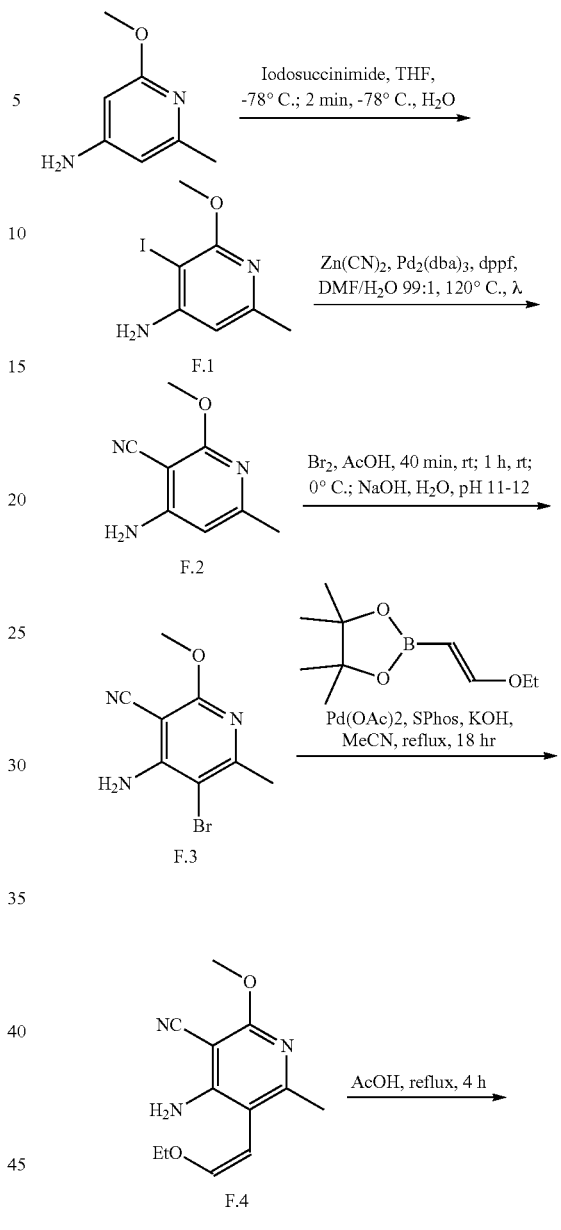

Intermediate E can be prepared from a suitably functionalized pyridine. Nitration of a commercially available material provides intermediate E.1, which can undergo a substitution reaction to provide E.2, with the amine suitably protected. Reduction of the nitro group followed by formation of the imidazole ring is then followed by reduction of the ester and oxidation of the pyridine ring to provide Intermediate E.

Intermediate F (7-(hydroxymethyl)-4-methyl-1,5-dihydro-6H-pyrrolo[3,2-c]pyridin-6-one An exemplary intermediate for the preparation of compounds of formula (I) wherein Intermediate Y is a substituted pyrrolopyridinone is described in INTERMEDIATE F.

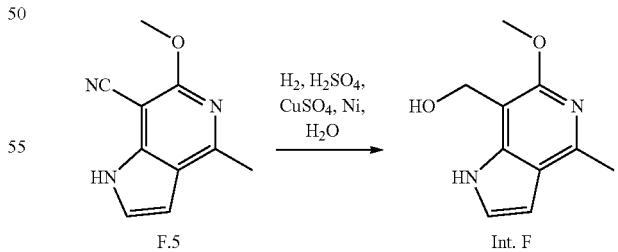

Intermediate F is prepared from a 4-aminopyridine derivative. Iodination of the ring followed by palladium-catalyzed introduction of the nitrile and electrophilic bromination affords intermediate F.3. Introduction of the vinyl ether and ring closure to form the pyrrole is followed by reduction of the nitrile to the alcohol, affording Intermediate F.

Intermediate G

7-(hydroxymethyl)-4-methylthieno[3,2-c]pyridin-6(5H)-one

An exemplary intermediate for the preparation of compounds of formula (I) wherein Intermediate Y is a substituted thienopyridinone is described in INTERMEDIATE G.

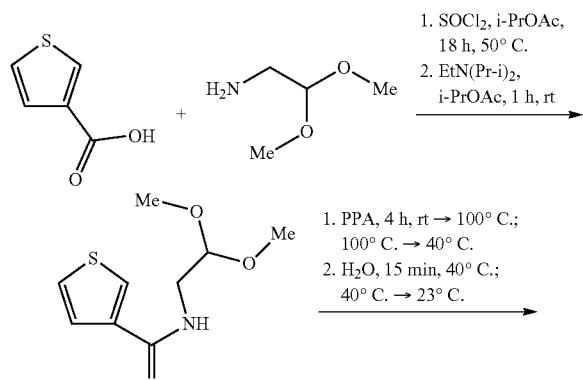

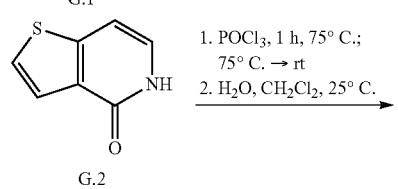

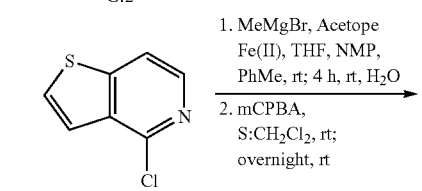

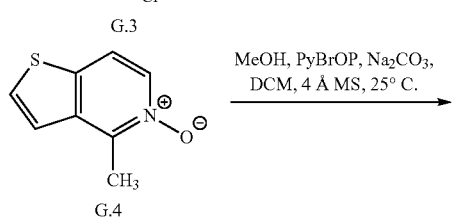

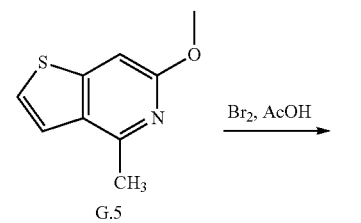

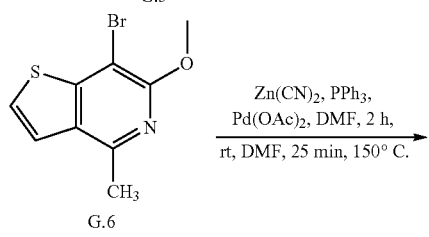

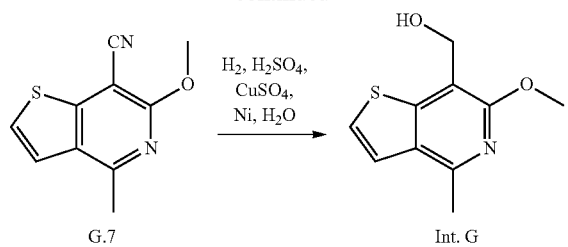

Intermediate G can be prepared from 3-carboxythiophene as described. Amidation with 2-aminoethyl acetal followed by ring closure affords the fused bicyclic system G.2. Chlorination, oxidation, rearrangement and electrophilic bromination will afford intermediate G.6. Metal-catalyzed introduction of the methyl and nitrile groups is followed by reduction of the nitrile to afford Intermediate G.

Intermediate H

4-(hydroxymethyl)-7-methylthieno[2,3-c]pyridin-5(6H)-one

An exemplary intermediate for the preparation of compounds of formula (I) wherein Intermediate Y is a substituted thienopyridinone is described in INTERMEDIATE H.

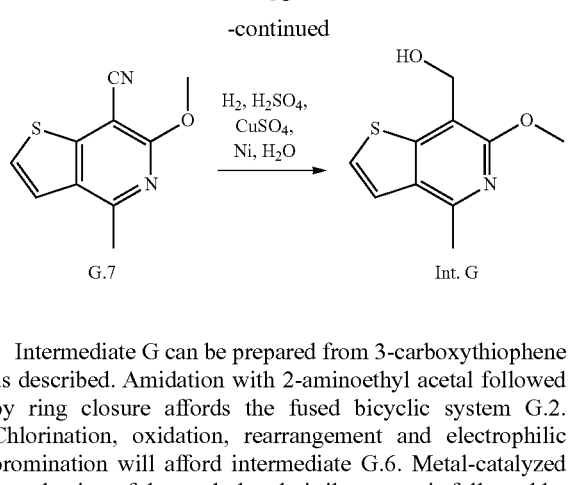

-continued

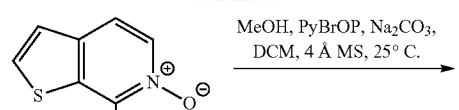
H.4

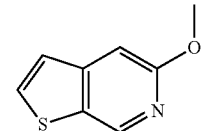
H.5

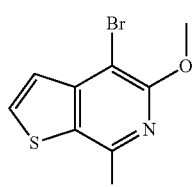
H.6

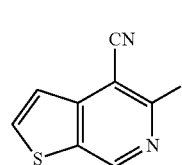 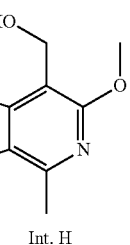
H.7            Int. H

Intermediate H is prepared by a scheme similar to that of Intermediate G, starting from the isomeric thiophene-2-carboxylic acid.

Intermediate I 4-(hydroxymethyl)-1-methyl-2,7-dihydro-3H-cyclopenta[c]pyridin-3-one An exemplary intermediate for the preparation of compounds of formula (I) wherein Intermediate Y is a substituted cyclopentapyridinone is described in INTERMEDIATE I.

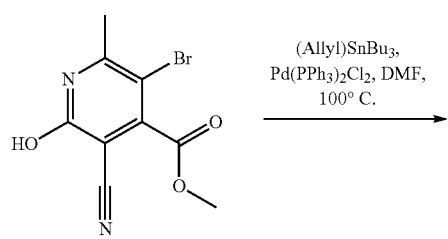

-continued

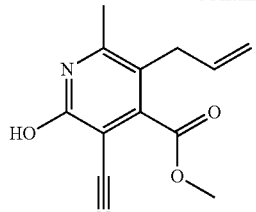
I.1

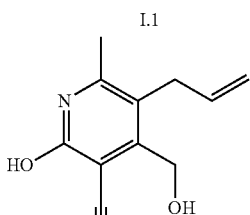
I.2

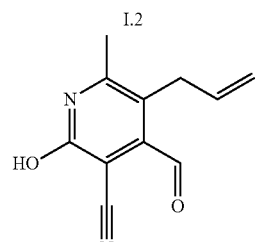
I.3

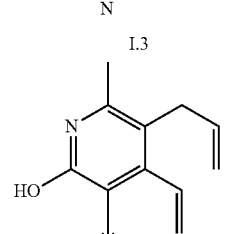
I.4

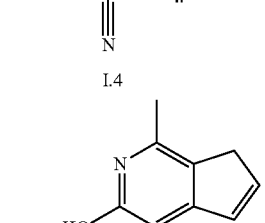
I.5

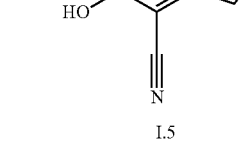

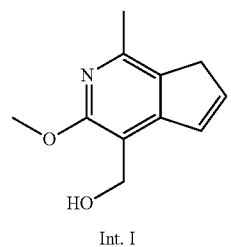
Int. I

A functionalized pyridine derivative can be derivatized to prepare Intermediate I. Palladium-catalyzed allylation of a bromopyridine will afford intermediate I.1. Conversion of the ester to the vinyl group in a series of steps well known to those skilled in the art provides bis-olefin 1.4. A ringclosing metathesis reaction to form the cyclopentene followed by reduction of the nitrile affords Intermediate I.

Intermediate J (6-methoxy-4-methylthiazolo[5,4-c]pyridin-7-yl)methanol

An exemplary intermediate for the preparation of compounds of formula (I) wherein Intermediate Y is a substituted thiazolopyridinone is described in INTERMEDIATE J.

Intermediate J is available from an aminopyridine derivative. Electrophilic iodination and introduction of the nitrile affords intermediate J.2. Protection of the amine, metalation and thiolation afford cyclization precursor J.4. Formation of the thiazole upon heating with formic acid and reduction of the nitrile gives Intermediate J.

Intermediate K (6-(benzyloxy)-4-methylthiazolo[4,5-c]pyridin-7-yl)methanol

An exemplary intermediate for the preparation of compounds of formula (I) wherein Intermediate Y is a substituted thiazolopyridinone is described in INTERMEDIATE K.

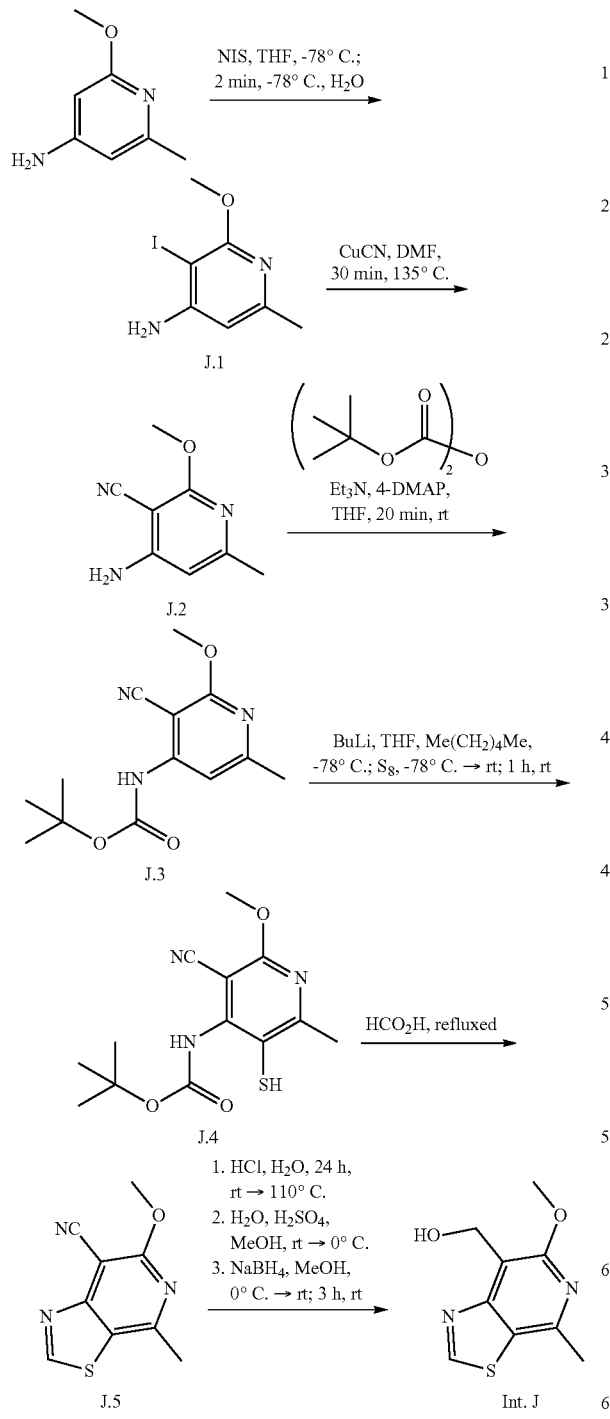

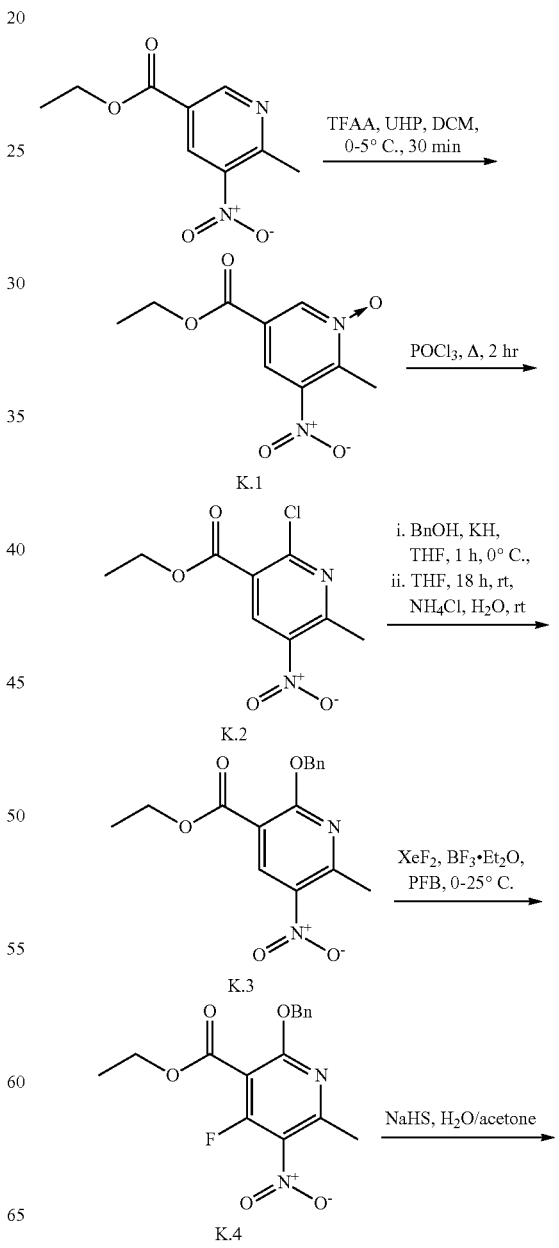

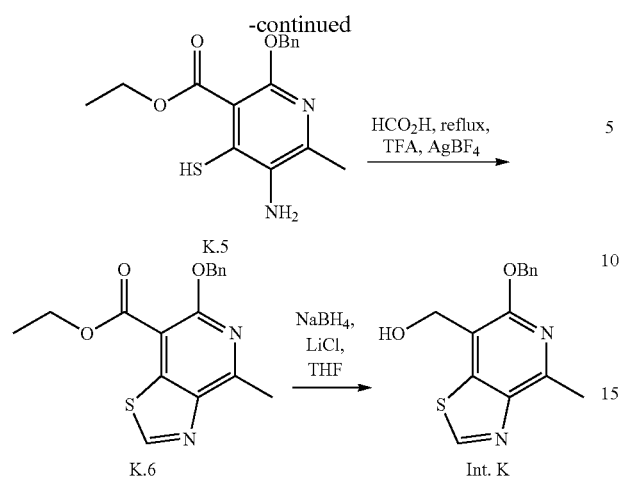

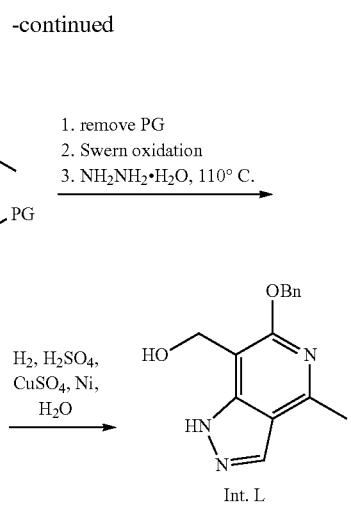

Intermediate K is prepared from a 3-nitropyridine derivative. Oxidation, rearrangement and substitution of the resulting 2-chloropyridine affords protected intermediate K.3. Electrophilic fluorination followed by nucleophilic substitution and reduction gives aminothiol K.5. Formation of the thiazole with formic acid followed by reduction of the carboxylate results in Intermediate K.

Intermediate L (6-(benzyloxy)-4-methyl-1H-pyrazolo[4,3-c]pyridin-7-yl)methanol

An exemplary intermediate for the preparation of compounds of formula (I) wherein Intermediate Y is a substituted pyrazolopyridinone is described in INTERMEDIATE L.

Intermediate L can be prepared from a readily available starting material as shown. Introduction of the benzyloxy substituent at C2 followed by nitration of the remaining unsubstituted position on the ring affords intermediate L.2. Conversion of the nitro group to the cyano group, followed by reduction of the ester to the aldehyde and closure of the pyrazole ring gives intermediate L.4. Reduction of the nitrile then gives final Intermediate L.

Intermediate M (5-(benzyloxy)-7-methyl-1H-pyrazolo[3,4-c]pyridin-4-yl)methanol

An exemplary intermediate for the preparation of compounds of formula (I) wherein Intermediate Y is a substituted pyrazolopyridinone is described in INTERMEDIATE M

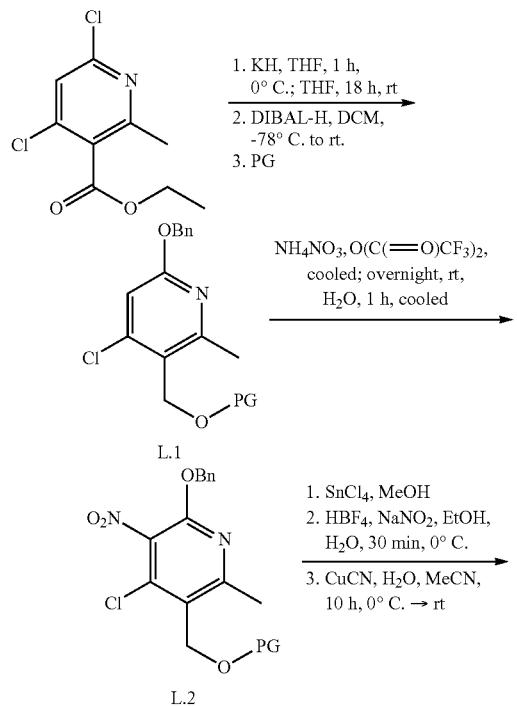

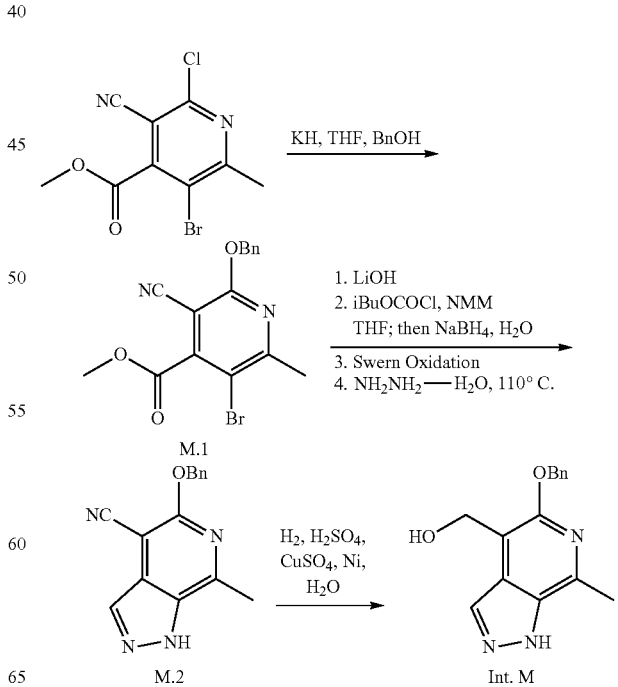

Intermediate M is prepared in a manner similar to Intermediate K. Substitution of a functionalized pyridine derivative with benzyl alcohol provides intermediate M.1. Reduction of the ester to the aldehyde and closure of the ring with hydrazine affords bicycle M.2. Reduction of the nitrile gives alcohol-containing Intermediate M.

Intermediate N (6-(benzyloxy)-4-methylisoxazolo[4,5-c]pyridin-7-yl)methanol

An exemplary intermediate for the preparation of compounds of formula (I) wherein Intermediate Y is a substituted isoxazolopyridinone is described in INTERMEDIATE N.

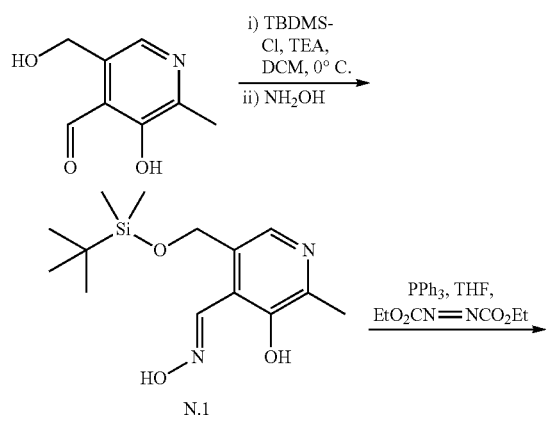

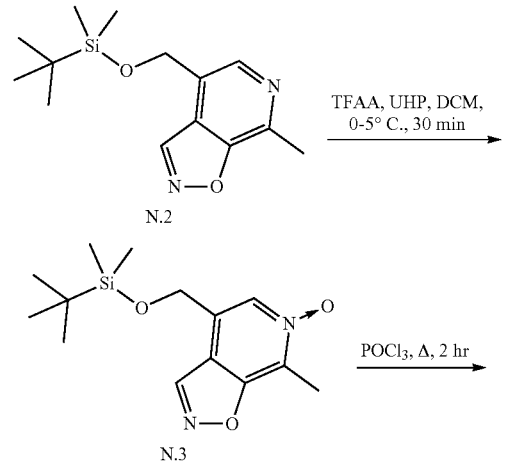

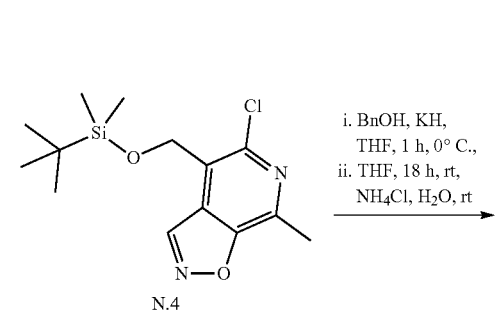
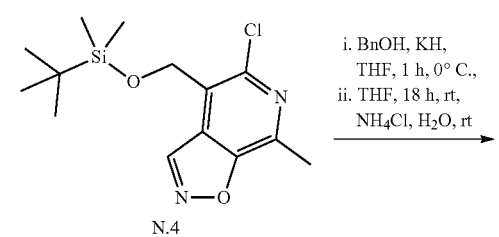

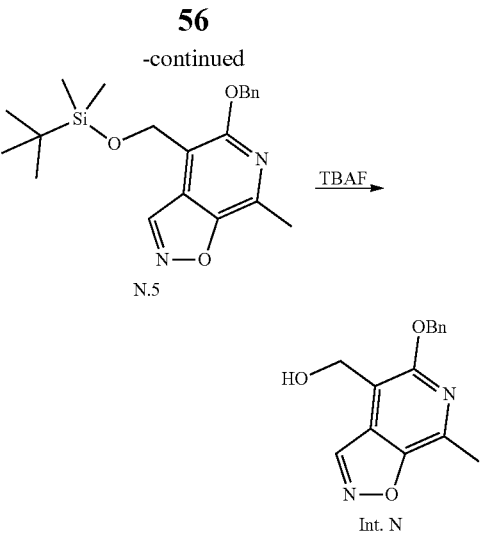

Intermediate N can be prepared from a substituted pyridine as shown. Nitration of a readily available compound followed by ring closure affords bicycle N.2. Conversion of the nitro group to the nitrile followed by oxidation and rearrangement gives chloride N.5. Substitution of the chloride with benzyl alcohol followed by reduction affords Intermediate N.

Intermediate O (6-(benzyloxy)-4-methylisoxazolo[5,4-c]pyridin-7-yl)methanol

An exemplary intermediate for the preparation of compounds of formula (I) wherein Intermediate Y is a substituted isoxazolopyridinone is described in INTERMEDIATE O.

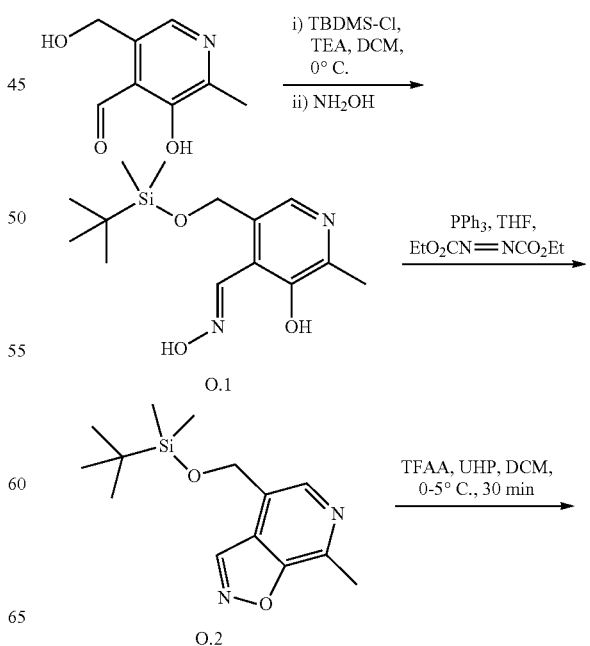

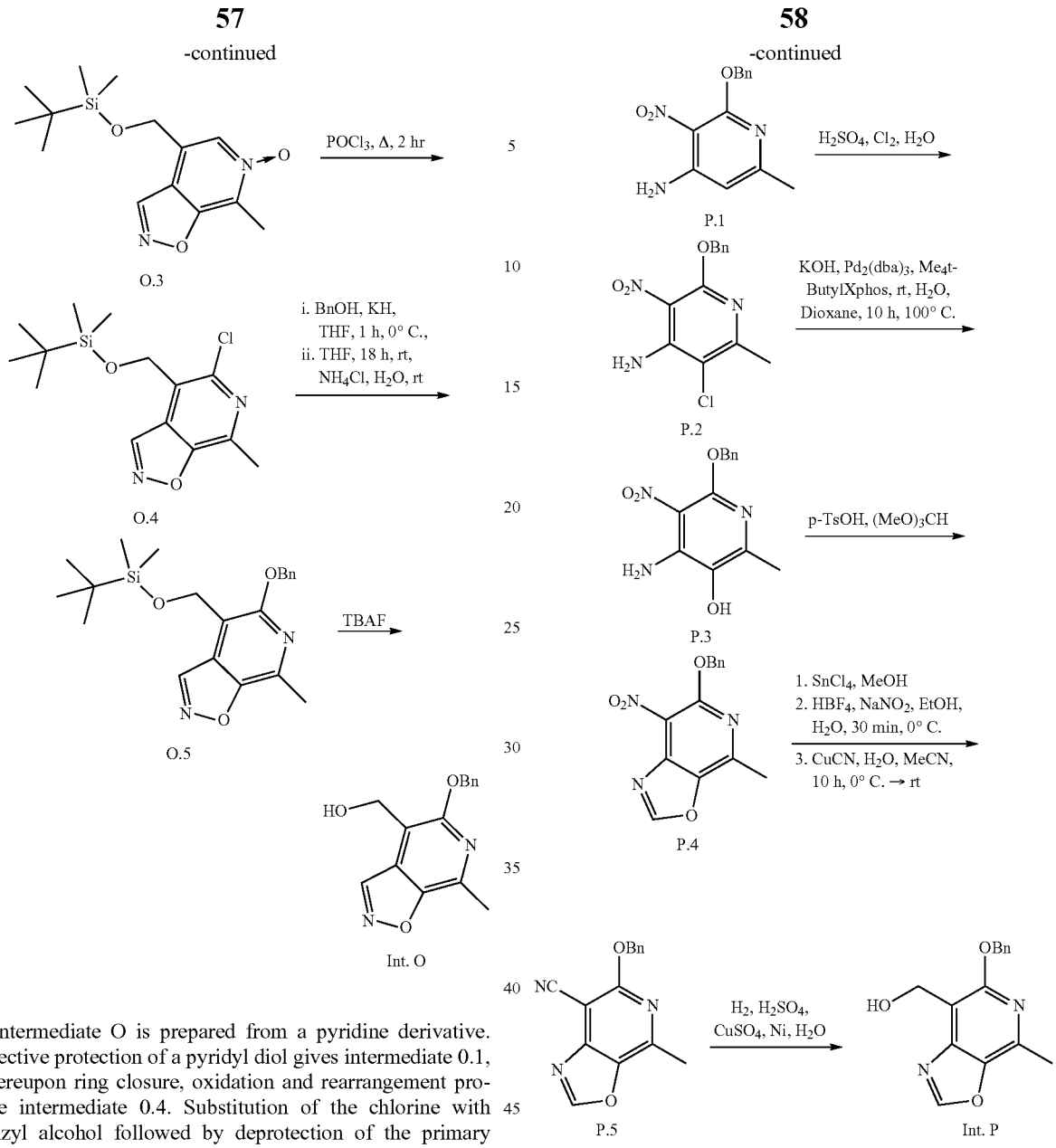

Intermediate O is prepared from a pyridine derivative. Selective protection of a pyridyl diol gives intermediate 0.1, whereupon ring closure, oxidation and rearrangement provide intermediate 0.4. Substitution of the chlorine with benzyl alcohol followed by deprotection of the primary alcohol gives Intermediate O.

Intermediate P (6-(benzyloxy)-4-methyloxazolo[5,4-c]pyridin-7-yl)methanol

An exemplary intermediate for the preparation of compounds of formula (I) wherein Intermediate Y is a substituted oxazolopyridinone is described in INTERMEDIATE P.

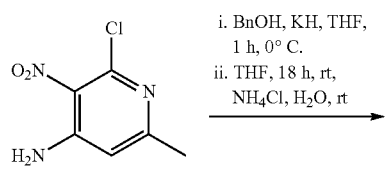

Intermediate P is prepared by substitution of a chloropyridine derivative with benzyl alcohol to give P.1. Chlorination of the resulting compound followed by replacement of the chlorine with a hydroxyl group and conversion of the nitro group to a nitrile provides compound P.4. Cyclization of the amino alcohol and reduction of the nitrile result in Intermediate P.

Intermediate Q (6-(benzyloxy)-4-methylisothiazolo[4,5-c]pyridin-7-yl)methanol

An exemplary intermediate for the preparation of compounds of formula (I) wherein Intermediate Y is a substituted isothiazolopyridinone is described in INTERMEDIATE Q.

Intermediate R

(6-(benzyloxy)-4-methylisothiazolo[5,4-c]pyridin-7-yl)methanol

An exemplary intermediate for the preparation of compounds of formula (I) wherein Intermediate Y is a substituted isothiazolopyridinone is described in INTERMEDIATE R

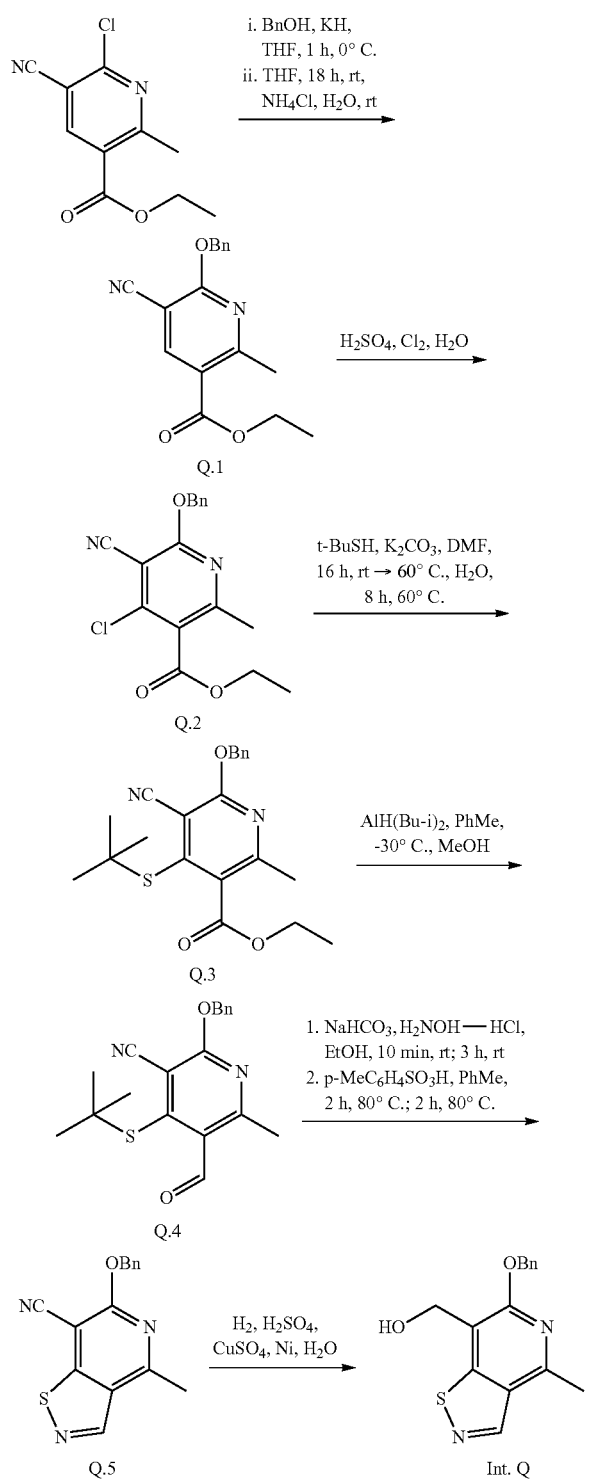
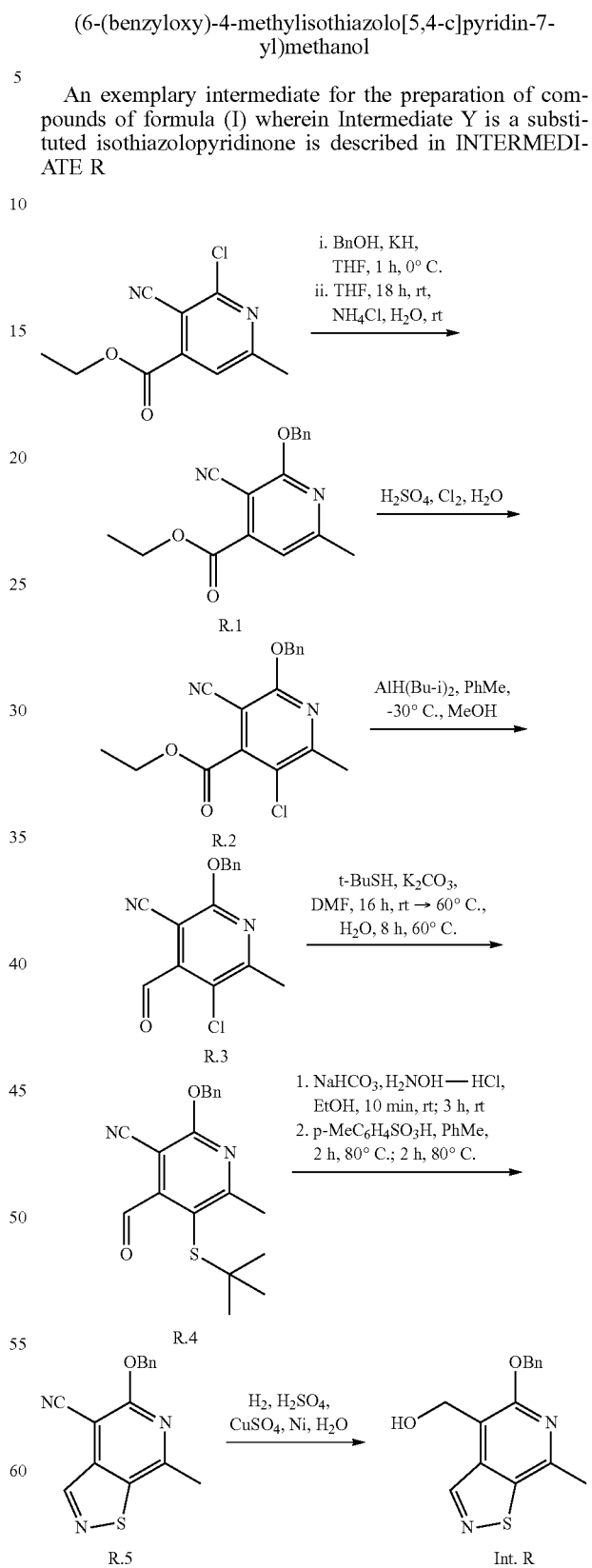

Intermediate Q is prepared from a pyridine derivative as shown. Replacement of the chlorine with benzyl alcohol followed by electrophilic chlorination of the remaining open position of the pyridine give intermediate Q.2. Partial reduction of the ester followed by introduction of tert-butylthiol provides an intermediate that can be cyclized to the isothiazole Q.5. Reduction of the nitrile then gives Intermediate Q.

Preparation of Intermediate R proceeds as shown above. Introduction of the benzyloxyl group by substitution of the chlorine followed by electrophilic chlorination gives intermediate R.2. Partial reduction and substitution gives rise to intermediate R.4, which can then be cyclized to give the bicyclic isothiazole. Reduction of the nitrile group affords Intermediate R.

Intermediate S (6-(benzyloxy)-4-methyl-1H-[1,2,3]triazolo[4,5-c]pyridin-7-yl)methanol An exemplary intermediate for the preparation of compounds of formula (I) wherein Intermediate Y is a substituted triazolopyridinone is described in INTERMEDIATE S.

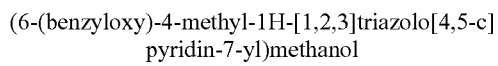

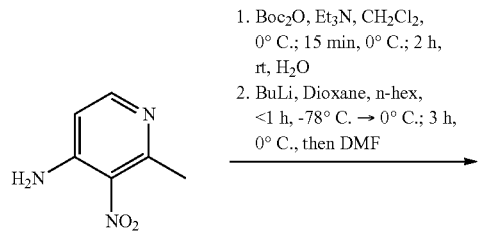

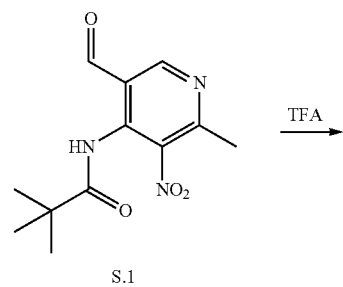

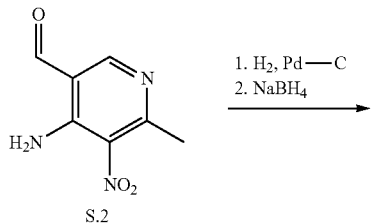

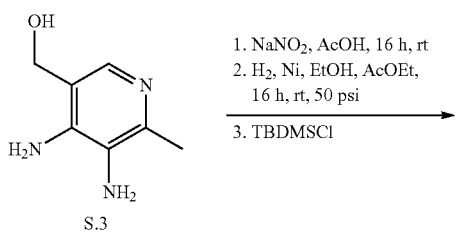

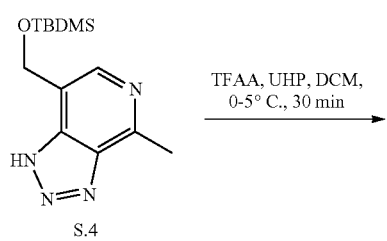

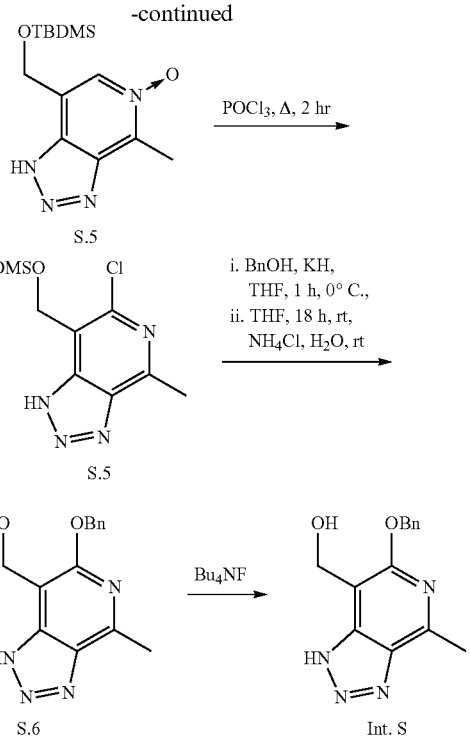

Triazole Intermediate S is prepared as shown. Protection of the amine followed by carbonylation and deprotection provides aldehyde S.2. Reduction to the diamine followed by cyclization gives bicycle S.4. Oxidation, rearrangement and substitution with benzyl alcohol give aldehyde S.6, whereupon reduction provides Intermediate S. In this scheme, protection of the aldehyde and triazole may be necessary.

Intermediate T (5-(benzyloxy)-7-methylisoxazolo[5,4-c]pyridin-4-yl)methanol

An exemplary intermediate for the preparation of compounds of formula (I) wherein Intermediate Y is a substituted isoxazolopyridinone is described in INTERMEDIATE T.

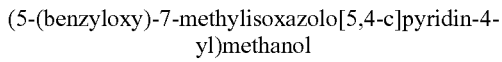

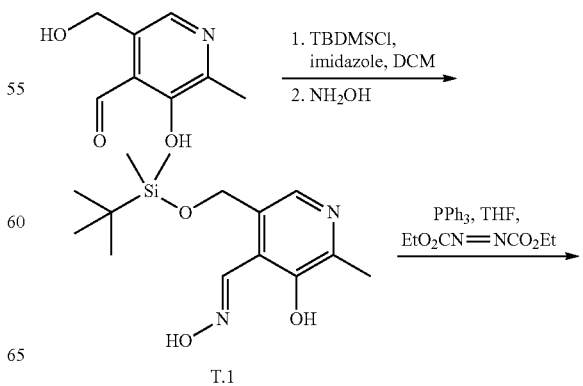

-continued

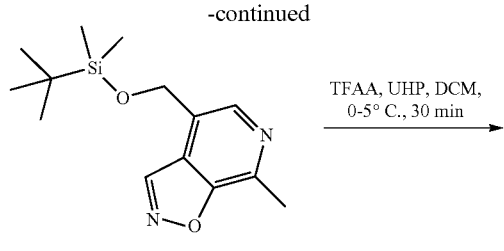
T.2

TFAA, UHP, DCM,
0-5° C., 30 min

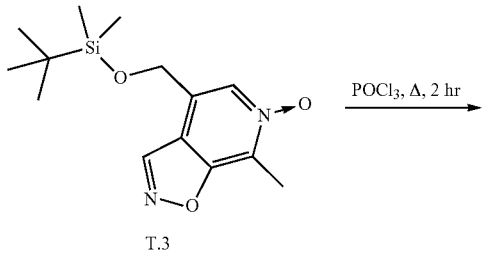
T.3

POCl₃, Δ, 2 hr

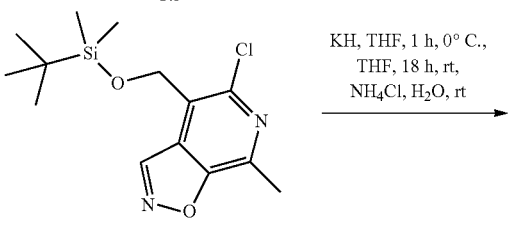
T.4

KH, THF, 1 h, 0° C.,
THF, 18 h, rt,
NH₄Cl, H₂O, rt

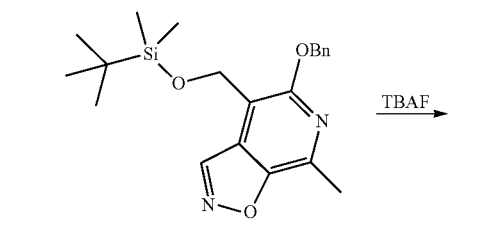
T.5

TBAF

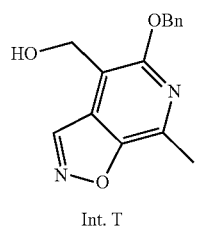
Int. T

Intermediate T is prepared from the pyridine aldehyde shown. Protection of the alcohol followed by ring formation provides isoxazole-containing bicycle T.2. Oxidation of the pyridine, rearrangement and substitution give intermediate T.4, which is deprotected to afford the target Intermediate T.

Alcohols C-T may be converted to Intermediate Y by the addition of a mesylate leaving group ("LG") to afford Intermediate Y prior to coupling to Intermediate X using Procedure A:

Procedure A

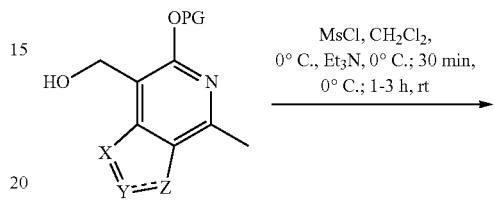

MsCl, CH₂Cl₂,
0° C., Et₃N, 0° C.; 30 min,
0° C.; 1-3 h, rt

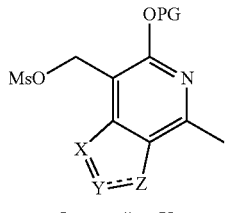
Intermediate Y

Alternatively, Alcohols C-T may be converted to the halide or to the tosylate using methods described in the EXAMPLES herein and other methods well known to those skilled in the art to prepare Intermediate Y.

The following exemplary Intermediate Y intermediates shown in Table 1 may be used for the syntheses of compounds of the present invention in General Reaction Scheme I and following the teachings of preparation of the Procedure A, Schemes I-IV and the EXAMPLES described herein:

TABLE 1

| | | | Intermediate Y |
|---|---|---|---|
| X | Y | Z | INTERMEDIATE |
| O | CR⁵ | CR⁵ | 6-(benzyloxy)-7-(iodomethyl)-4-methylfuro[3,2-c]pyridine; 6-(benzyloxy)-7-(bromomethyl)-4-methylfuro[3,2-c]pyridine; (6-(benzyloxy)-4-methylfuro[3,2-c]pyridin-7-yl)methyl methanesulfonate; and (6-(benzyloxy)-4-methylfuro[3,2-c]pyridin-7-yl)methyl benzenesulfonate |
| CR⁵ | CR⁵ | O | 5-(benzyloxy)-4-(iodomethyl)-7-methylfuro[2,3-c]pyridine; 5-(benzyloxy)-4-(bromomethyl)-7-methylfuro[2,3-c]pyridine; (5-(benzyloxy)-7-methylfuro[2,3-c]pyridin-4-yl)methyl methanesulfonate; and (5-(benzyloxy)-7-methylfuro[2,3-c]pyridin-4-yl)methyl benzenesulfonate |
| NR⁴ | CR⁵ | CR⁵ | 6-(benzyloxy)-7-(iodomethyl)-4-methyl-1H-pyrrolo[3,2-c]pyridine; 6-(benzyloxy)-7-(bromomethyl)-4-methyl-1H-pyrrolo[3,2-c]pyridine; (6-(benzyloxy)-4-methyl-1H-pyrrolo[3,2-c]pyridin-7- |

TABLE 1-continued

Intermediate Y

| X | Y | Z | INTERMEDIATE |
|---|---|---|---|
| CR$^5$ | CR$^5$ | NR$^4$ | yl)methyl methanesulfonate; and (6-(benzyloxy)-4-methyl-1H-pyrrolo[3,2-c]pyridin-7-yl)methyl benzenesulfonate<br>5-(benzyloxy)-4-(iodomethyl)-7-methyl-1H-pyrrolo[2,3-c]pyridine; 5-(benzyloxy)-4-(bromomethyl)-7-methyl-1H-pyrrolo[2,3-c]pyridine; (5-(benzyloxy)-7-methyl-1H-pyrrolo[2,3-c]pyridin-4-yl)methyl methanesulfonate; and (5-(benzyloxy)-7-methyl-1H-pyrrolo[2,3-c]pyridin-4-yl)methyl benzenesulfonate |
| NR$^4$ | CR$^5$ | N | 6-(benzyloxy)-7-(iodomethyl)-4-methyl-3H-imidazo[4,5-c]pyridine; 6-(benzyloxy)-7-(bromomethyl)-4-methyl-3H-imidazo[4,5-c]pyridine; (6-(benzyloxy)-4-methyl-3H-imidazo[4,5-c]pyridin-7-yl)methyl methanesulfonate; and (6-(benzyloxy)-4-methyl-3H-imidazo[4,5-c]pyridin-7-yl)methyl benzenesulfonate |
| N | CR$^5$ | NR$^4$ | 6-(benzyloxy)-7-(iodomethyl)-4-methyl-1H-imidazo[4,5-c]pyridine; 6-(benzyloxy)-7-(bromomethyl)-4-methyl-1H-imidazo[4,5-c]pyridine; (6-(benzyloxy)-4-methyl-1H-imidazo[4,5-c]pyridin-7-yl)methyl methanesulfonate; and (6-(benzyloxy)-4-methyl-1H-imidazo[4,5-c]pyridin-7-yl)methyl benzenesulfonate |
| N | CR$^5$ | S | 6-(benzyloxy)-7-(iodomethyl)-4-methylthiazolo[5,4-c]pyridine; 6-(benzyloxy)-7-(bromomethyl)-4-methylthiazolo[5,4-c]pyridine; (6-(benzyloxy)-4-methylthiazolo[5,4-c]pyridin-7-yl)methyl methanesulfonate; and (6-(benzyloxy)-4-methylthiazolo[5,4-c]pyridin-7-yl)methyl benzenesulfonate |
| S | CR$^5$ | N | 6-(benzyloxy)-7-(iodomethyl)-4-methylthiazolo[4,5-c]pyridine; 6-(benzyloxy)-7-(bromomethyl)-4-methylthiazolo[4,5-c]pyridine; (6-(benzyloxy)-4-methylthiazolo[4,5-c]pyridin-7-yl)methyl methanesulfonate; and (6-(benzyloxy)-4-methylthiazolo[4,5-c]pyridin-7-yl)methyl benzenesulfonate |
| CR$^5$ | N | NR$^4$ | 6-(benzyloxy)-7-(iodomethyl)-4-methyl-1H-pyrazolo[4,3-c]pyridine; 6-(benzyloxy)-7-(bromomethyl)-4-methyl-1H-pyrazolo[4,3-c]pyridine; (6-(benzyloxy)-4-methyl-1H-pyrazolo[4,3-c]pyridin-7-yl)methyl methanesulfonate; and (6-(benzyloxy)-4-methyl-H-pyrazolo[4,3-c]pyridin-7-yl)methyl benzenesulfonate |
| NR$^4$ | N | CR$^5$ | 5-(benzyloxy)-4-(iodomethyl)-7-methyl-1H-pyrazolo[3,4-c]pyridine; 5-(benzyloxy)-4-(bromomethyl)-7-methyl-1H-pyrazolo[3,4-c]pyridine; (5-(benzyloxy)-7-methyl-1H-pyrazolo[3,4-c]pyridin-4-yl)methyl methanesulfonate; and (5-(benzyloxy)-7-methyl-1H-pyrazolo[3,4-c]pyridin-4-yl)methyl benzenesulfonate |
| CR$^5$ | N | O | 5-(benzyloxy)-4-(iodomethyl)-7-methylisoxazolo[5,4-c]pyridine; 5-(benzyloxy)-4-(bromomethyl)-7-methylisoxazolo[5,4-c]pyridine; (5-(benzyloxy)-7-methylisoxazolo[5,4-c]pyridin-4-yl)methyl methanesulfonate; and (5-(benzyloxy)-7-methylisoxazolo[5,4-c]pyridin-4-yl)methyl benzenesulfonate |
| O | N | CR$^5$ | 6-(benzyloxy)-7-(iodomethyl)-4-methylisoxazolo[4,5-c]pyridine; 6-(benzyloxy)-7-(bromomethyl)-4-methylisoxazolo[4,5-c]pyridine; (6-(benzyloxy)-4-methylisoxazolo[4,5-c]pyridin-7-yl)methyl methanesulfonate; and (6-(benzyloxy)-4-methylisoxazolo[4,5-c]pyridin-7-yl)methyl benzenesulfonate |
| S | CR$^5$ | CR$^5$ | 6-(benzyloxy)-7-(iodomethyl)-4-methylthieno[3,2-c]pyridine; 6-(benzyloxy)-7-(bromomethyl)-4-methylthieno[3,2-c]pyridine; (6-(benzyloxy)-4-methylthieno[3,2-c]pyridin-7-yl)methyl methanesulfonate; and (6-(benzyloxy)-4-methylthieno[3,2-c]pyridin-7-yl)methyl benzenesulfonate |
| CR$^5$ | CR$^5$ | S | 5-(benzyloxy)-4-(iodomethyl)-7-methylthieno[2,3-c]pyridine; 5-(benzyloxy)-4-(bromomethyl)-7-methylthieno[2,3-c]pyridine; (5-(benzyloxy)-7-methylthieno[2,3-c]pyridin-4-yl)methyl methanesulfonate; and (5-(benzyloxy)-7-methylthieno[2,3-c]pyridin-4-yl)methyl benzenesulfonate |
| O | CR$^5$ | N | 6-(benzyloxy)-7-(iodomethyl)-4-methyloxazolo[4,5-c]pyridine; 6-(benzyloxy)-7-(bromomethyl)-4-methyloxazolo[4,5-c]pyridine; (6-(benzyloxy)-4-methyloxazolo[4,5-c]pyridin-7-yl)methyl methanesulfonate; and (6-(benzyloxy)-4-methyloxazolo[4,5-c]pyridin-7-yl)methyl benzenesulfonate |
| N | CR$^5$ | O | 6-(benzyloxy)-7-(iodomethyl)-4-methyloxazolo[5,4-c]pyridine; 6-(benzyloxy)-7-(bromomethyl)-4-methyloxazolo[5,4-c]pyridine; (6-(benzyloxy)-4-methyloxazolo[5,4-c]pyridin-7-yl)methyl methanesulfonate; and (6-(benzyloxy)-4-methyloxazolo[5,4-c]pyridin-7-yl)methyl benzenesulfonate |
| S | N | CR$^5$ | 6-(benzyloxy)-7-(iodomethyl)-4-methylisothiazolo[4,5-c]pyridine; 6-(benzyloxy)-7-(bromomethyl)-4-methylisothiazolo[4,5-c]pyridine; (6-(benzyloxy)-4-methylisothiazolo[4,5-c]pyridin-7-yl)methyl methanesulfonate; and (6-(benzyloxy)-4-methylisothiazolo[4,5-c]pyridin-7-yl)methyl benzenesulfonate |

TABLE 1-continued

Intermediate Y

| X | Y | Z | INTERMEDIATE |
|---|---|---|---|
| $CR^5$ | N | S | 5-(benzyloxy)-4-(iodomethyl)-7-methylisothiazolo[5,4-c]pyridine; 5-(benzyloxy)-4-(bromomethyl)-7-methylisothiazolo[5,4-c]pyridine; (5-(benzyloxy)-7-methylisothiazolo[5,4-c]pyridin-4-yl)methyl methanesulfonate; and (5-(benzyloxy)-7-methylisothiazolo[5,4-c]pyridin-4-yl)methyl benzenesulfonate |
| N | N | $NR^4$ | 6-(benzyloxy)-7-(iodomethyl)-4-methyl-3H-[1,2,3]triazolo[4,5-c]pyridine; 6-(benzyloxy)-7-(bromomethyl)-4-methyl-3H-[1,2,3]triazolo[4,5-c]pyridine; (6-(benzyloxy)-4-methyl-3H-[1,2,3]triazolo[4,5-c]pyridin-7-yl)methyl methanesulfonate; and (6-(benzyloxy)-4-methyl-3H-[1,2,3]triazolo[4,5-c]pyridin-7-yl)methyl benzenesulfonate |
| $NR^4$ | N | N | 6-(benzyloxy)-7-(iodomethyl)-4-methyl-3H-[1,2,3]triazolo[4,5-c]pyridine; 6-(benzyloxy)-7-(bromomethyl)-4-methyl-3H-[1,2,3]triazolo[4,5-c]pyridine; (6-(benzyloxy)-4-methyl-1H-[1,2,3]triazolo[4,5-c]pyridin-7-yl)methyl methanesulfonate; and (6-(benzyloxy)-4-methyl-1H-[1,2,3]triazolo[4,5-c]pyridin-7-yl)methyl benzenesulfonate |
| $CH_2$ | CH | CH | 3-(benzyloxy)-4-(iodomethyl)-1-methyl-7H-cyclopenta[c]pyridine; 3-(benzyloxy)-4-(bromomethyl)-1-methyl-7H-cyclopenta[c]pyridine; (3-(benzyloxy)-1-methyl-7H-cyclopenta[c]pyridin-4-yl)methyl methanesulfonate; and (3-(benzyloxy)-1-methyl-7H-cyclopenta[c]pyridin-4-yl)methyl benzenesulfonate |
| CH | CH | $CH_2$ | 3-(benzyloxy)-4-(iodomethyl)-1-methyl-5H-cyclopenta[c]pyridine; 3-(benzyloxy)-4-(bromomethyl)-1-methyl-5H-cyclopenta[c]pyridine; (3-(benzyloxy)-1-methyl-5H-cyclopenta[c]pyridin-4-yl)methyl methanesulfonate; and (3-(benzyloxy)-1-methyl-5H-cyclopenta[c]pyridin-4-yl)methyl benzenesulfonate |

C. $R^1$ Coupling

Intermediate Z of General Reaction Scheme I may be coupled directly to $R^1$ to prepare certain compounds of formula (I) using methods described herein or using alternative methods well known to those of skill in the art.

Alternatively, $R^1$ may be coupled to Intermediate X of General Reaction Scheme I prior to coupling to Intermediate Y to afford compounds of formula (I). Schemes I-IV provide exemplary procedures for the coupling of $R^1$ to Intermediate z for the preparation of compounds of formula (I).

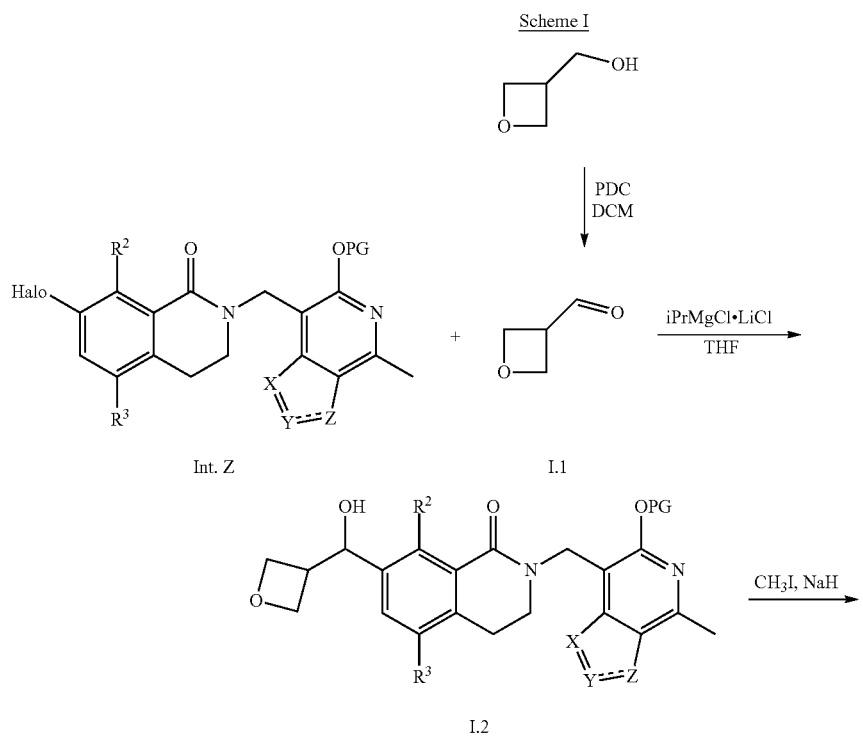

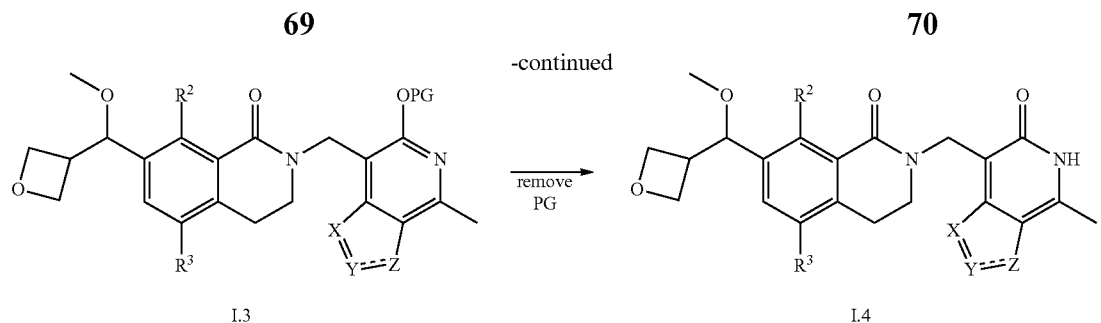

I.3 → I.4

The coupling of $R^1$ to Intermediate Z for the preparation of compounds of formula (I), wherein $R^1$ is W—$R^7$, $R^8$ is hydrogen, $R^9$ is methoxy, p and q are each zero, and $R^7$ is oxetanyl (Compounds ET-FP, Table 2), is described in Scheme I. "PG" refers to a protecting group.

In this preparation, an Intermediate Z is metallated, for example with isopropyl magnesium chloride, and reacted with an aldehyde. Methylation of the resulting alcohol and removal of the protecting group then affords compounds of formula I.4 as shown.

Scheme II

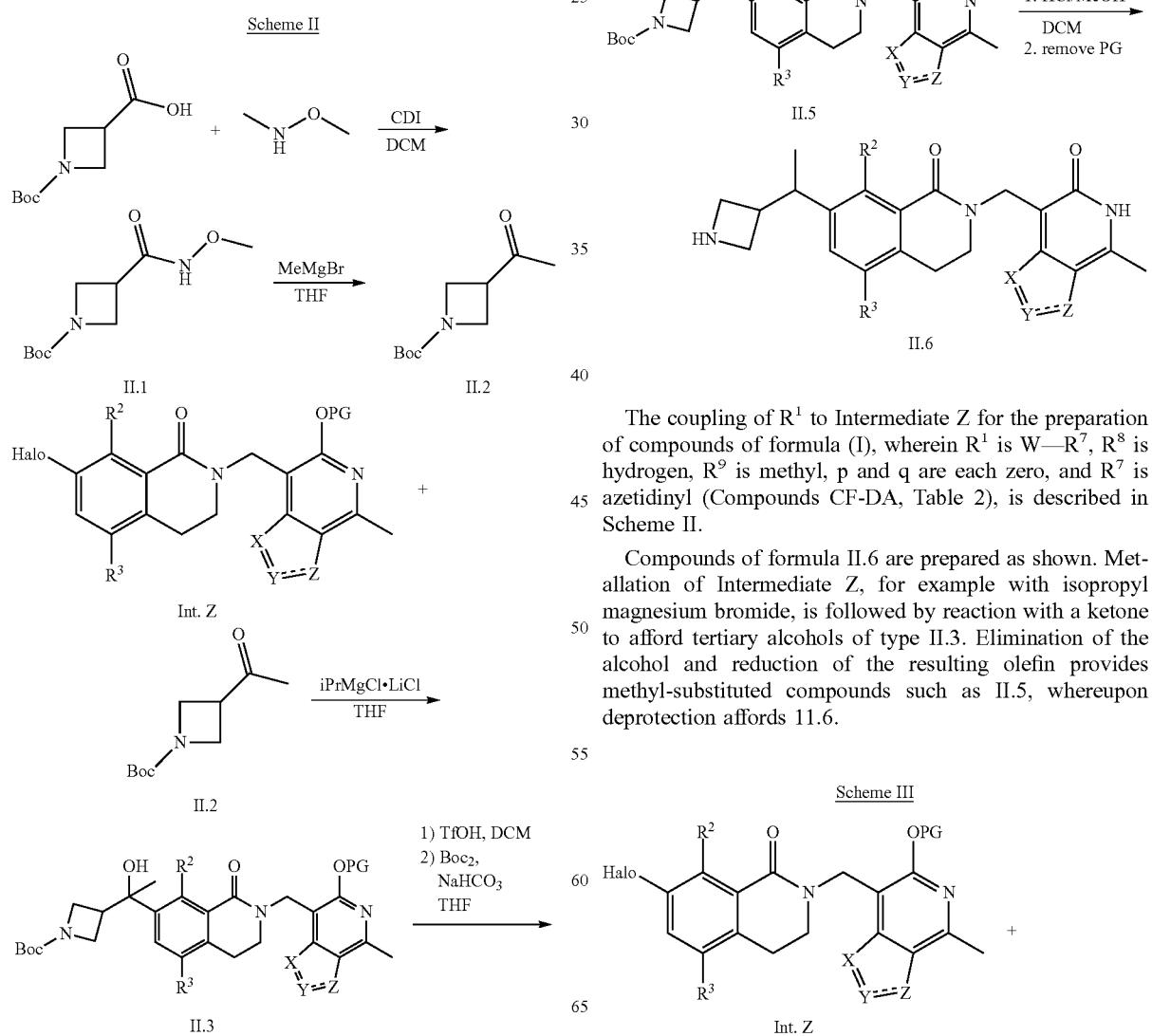

The coupling of $R^1$ to Intermediate Z for the preparation of compounds of formula (I), wherein $R^1$ is W—$R^7$, $R^8$ is hydrogen, $R^9$ is methyl, p and q are each zero, and $R^7$ is azetidinyl (Compounds CF-DA, Table 2), is described in Scheme II.

Compounds of formula II.6 are prepared as shown. Metallation of Intermediate Z, for example with isopropyl magnesium bromide, is followed by reaction with a ketone to afford tertiary alcohols of type II.3. Elimination of the alcohol and reduction of the resulting olefin provides methyl-substituted compounds such as II.5, whereupon deprotection affords 11.6.

Scheme III

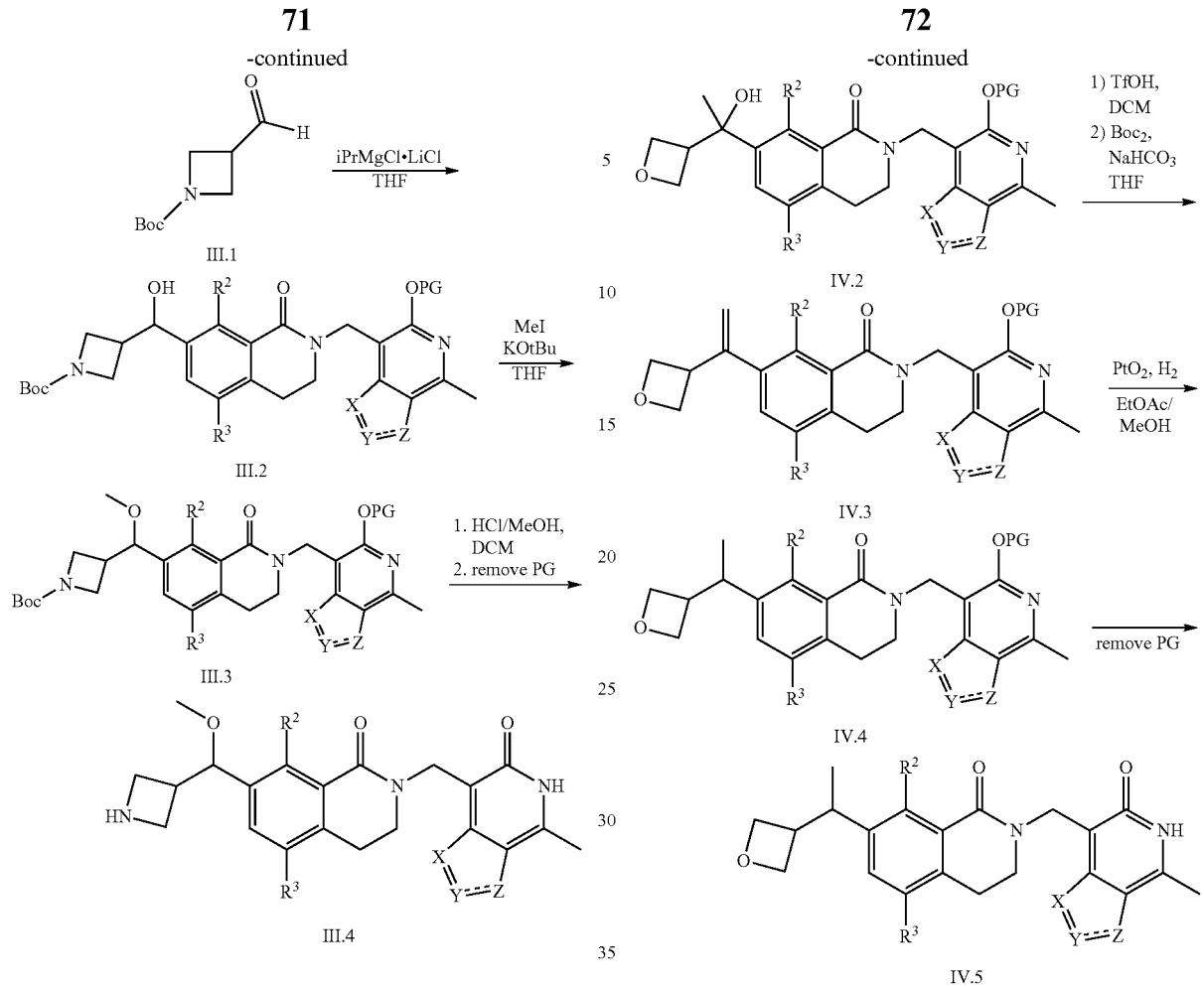

The coupling of $R^1$ to Intermediate Z for the preparation of compounds of formula (I), wherein $R^1$ is W—$R^7$, $R^8$ is hydrogen, $R^9$ is methoxy, p and q are each zero, and $R^7$ is azetidinyl (Compounds DX-ES, Table 2), is described in Scheme III.

In this preparation, an Intermediate Z is metallated, for example with isopropyl magnesium chloride, and reacted with an aldehyde. Methylation of the resulting alcohol and removal of the protecting group then affords compounds of formula III.4 as shown.

Scheme IV

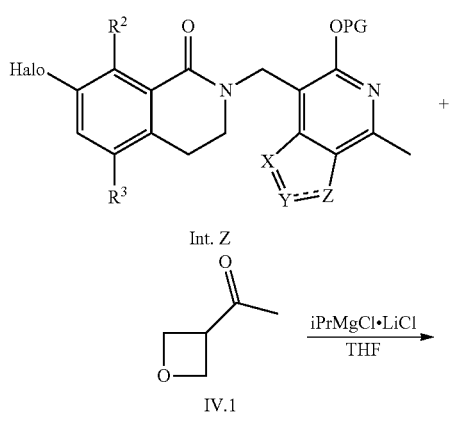

The coupling of $R^1$ to Intermediate Z for the preparation of compounds of formula (I), wherein $R^1$ is W—$R^7$, $R^8$ is hydrogen, $R^9$ is methyl, p and q are each zero, and $R^7$ is oxetanyl (Compounds DB-DW, Table 2), is described in Scheme IV.

Compounds of formula IV.5 are prepared as shown. Metallation of Intermediate Z, for example with isopropyl magnesium bromide, is followed by reaction with a ketone to afford tertiary alcohols of type IV.2. Elimination of the alcohol and reduction of the resulting olefin provides methyl-substituted compounds such as IV.4, whereupon deprotection affords IV.6.

EXAMPLES

The following Examples are intended to illustrate further certain embodiments of the invention and are not intended to limit the scope of the invention.

Exemplary methods for the preparation of compounds of formula (I) wherein $R^1$ is —$OR^6$ are provided in EXAMPLES 1, 4, 6 and 8. In one embodiment, X, Y and Z are O, $CR^5$, and $CR^5$, respectively, and $R^2$ is halogen, $R^3$ is hydrogen and each $R^5$ is hydrogen. In another embodiment, X, Y and Z are O, $CR^5$, and $CR^5$, $R^2$ and $R^3$ are each halogen, and. In another embodiment, X, Y and Z are O, $CR^5$, and $CR^5$, respectively, $R^2$ and $R^3$ are each halogen, and $R^5$ at Y is methyl. In a further embodiment, X, Y and Z are $CR^5$, $CR^5$, and NH, respectively, $R^2$ and $R^3$ are each halogen and each $R^5$ is hydrogen. Additional exemplary compounds of formula (I) wherein $R^1$ is —$OR^6$ are provided as Compounds A-U in Table 2.

Exemplary methods for the preparation of compounds of formula (I) wherein $R^1$ is heterocyclyl are provided in EXAMPLES 2 and 5. In one embodiment, X, Y and Z are O, $CR^5$, and $CR^5$, respectively, and $R^2$ and $R^3$ are each halogen. In a further embodiment, X, Y and Z are $CR^5$, $CR^5$, and NH, respectively, and $R^2$ and $R^3$ are each halogen. Additional exemplary compounds of formula (I) wherein $R^1$ is heterocyclyl are provided as Compounds V-AO in Table 2.

An exemplary method for the preparation of compounds of formula (I) wherein $R^1$ is —$NR^4R^{10}$ is provided in EXAMPLE 3, wherein X, Y and Z are O, $CR^5$, and $CR^5$, respectively, and $R^2$ and $R^3$ are each halogen. Additional exemplary compounds of formula (I) wherein $R^1$ is —$NR^4R^{10}$ are provided as Compounds AP-BJ in Table 2.

An exemplary method for the preparation of compounds of formula (I) wherein $R^1$ is heteroaryl is provided in EXAMPLES 7 and 13-16. In one embodiment, X, Y and Z are O, $CR^5$, and $CR^5$, respectively, $R^2$ and $R^3$ are each halogen and $R^1$ is triazolyl (EXAMPLES 7 & 14) or oxazolyl (EXAMPLE 16). In one embodiment, X, Y and Z are $NR^4$, $CR^5$, and $CR^5$, respectively, $R^2$ and $R^3$ are each halogen and $R^1$ is triazolyl (EXAMPLE 15) or oxazolyl (EXAMPLE 13). Additional exemplary compounds of formula (I) wherein $R^1$ is heteroaryl are provided as Compounds BK-CE in Table 2.

Exemplary methods for the preparation of compounds of formula (I) wherein $R^1$ is or —W—$R^7$ are provided in EXAMPLES 9-12 and 17-19. In one embodiment, X, Y and Z are O, $CR^5$, and $CR^5$, respectively, $R^2$ and $R^3$ are each halogen and W—$R^7$ is methoxy(1-methylazetidin-3-yl)methyl (EXAMPLE 10), methoxy(oxetan-3-yl)methyl (EXAMPLE 9) or 1,1-dioxidothietan-3-yl)(methoxy)methyl (EXAMPLE 18). In a further embodiment, X, Y and Z are $NR^4$, $CR^5$, and $CR^5$, respectively, $R^2$ and $R^3$ are each halogen and W—$R^7$ is methoxy(1-methylazetidin-3-yl)methyl (EXAMPLE 11), methoxy(oxetan-3-yl)methyl (EXAMPLE 17) and oxetan-3-yl)ethyl (EXAMPLE 19). In one embodiment, X, Y and Z are S, $CR^5$, and $CR^5$, respectively, $R^2$ and $R^3$ are each halogen and W—$R^7$ is methoxy(oxetan-3-yl)methyl (EXAMPLE 12). Additional exemplary compounds of formula (I) wherein $R^1$ is W—$R^7$ are provided as Compounds DX-FP in Table 2.

Example 1

7-((5,8-dichloro-7-isopropoxy-1-oxo-3,4-dihydroisoquinolin-2(1H)-yl)methyl)-4-methylfuro[3,2-c]pyridin-6(5H)-one

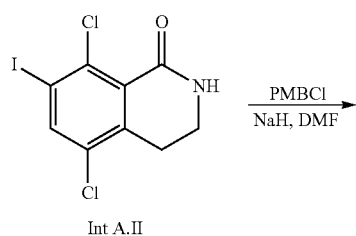

Int A.II

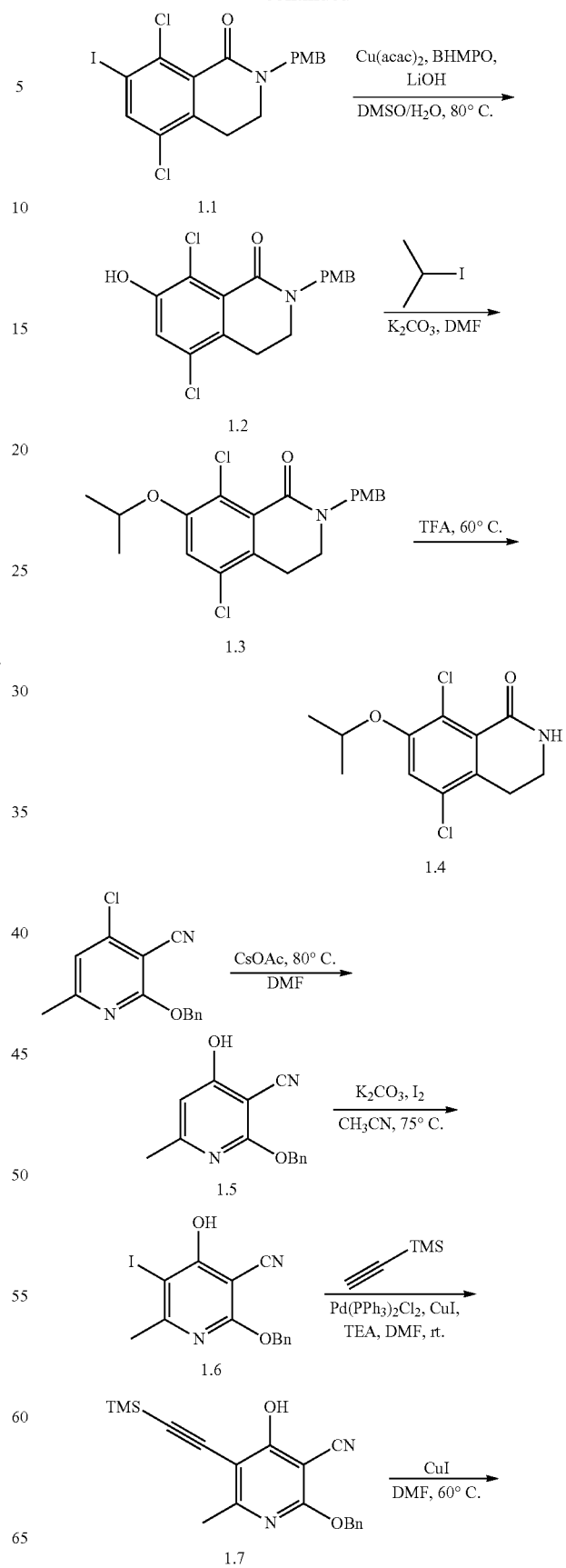

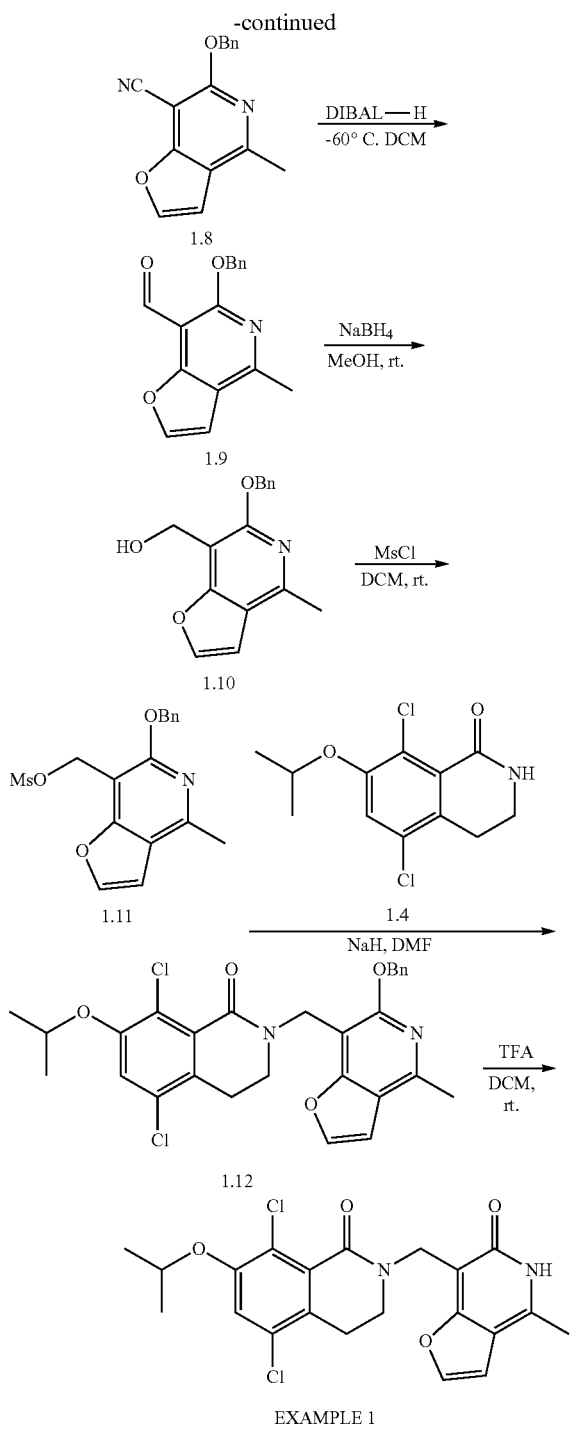

EXAMPLE 1

Compound 1.1:

To a solution of 5,8-dichloro-7-iodo-3,4-dihydro-2H-isoquinolin-1-one (Int. A.II, 1.5 g, 4.39 mmol, 1 equivalent) was added NaH (263 mg, 6.59 mmol, 60% suspension in oil, 1.5 equivalents); this mixture was stirred at 0° C. for 10 min. After gas evolution subsided, 1-(chloromethyl)-4-methoxybenzene (824 mg, 5.27 mmol, 717 μL, 1.2 equivalents) was added and the reaction mixture was stirred at 0° C. for 1 hour. After this time a saturated NH$_4$Cl solution (50 mL) was added to the reaction mixture and a heavy precipitate was formed. This was filtered and the contents of the filter pad were washed with water (20 mL×2). This material was dried under vacuum to afford the desired product 1.1 as a yellow solid (1.5 g, yield=73.9%); LC-MS [M+1]: 242.4.

Compound 1.2:

To 5,8-dichloro-7-iodo-2-[(4-methoxyphenyl)methyl]-3,4-dihydroisoquinolin-1-one (1.1, 1.50 g, 3.25 mmol, 1 equivalent), bis[(Z)-1-methyl-3-oxo-but-1-enoxy]copper (84.9 mg, 325 μmol, 0.1 equivalent) N$_1$,N$_2$-bis(4-hydroxy-2,6-dimethylphenyl)oxalamide (BHMPO, 107 mg, 325 μmol, 0.1 equivalent) in H$_2$O (100 μL) were added LiOH*H$_2$O (409 mg, 9.74 mmol, 3 equivalents) followed by DMSO (400 μL). This mixture was stirred at 80° C. for 5 hours under a nitrogen atmosphere. To the reaction mixture was added 50 mL of saturated NH$_4$Cl solution; the aqueous layer was extracted with ethyl acetate (50 mL×3). The combined organic layers were dried over sodium sulfate and the solvent was removed to give the crude product. This material was purified further by flash chromatography on silica gel (petroleum ether/ethyl acetate 2/1); the desired product 1.2 was isolated as a yellow solid (1.0 g, yield=87.4%); LC-MS [M+1]: 352.0.

$^1$H NMR (400 MHz, chloroform-d) δ=7.38-7.32 (m, 3H), 6.97-6.92 (m, 2H), 6.27 (s, 1H), 4.78 (s, 2H), 3.87 (s, 3H), 3.50 (t, J=6.4 Hz, 2H), 2.95 (t, J=6.4 Hz, 2H).

Compound 1.3:

To a solution of 5,8-dichloro-7-hydroxy-2-[(4-methoxyphenyl) methyl]-3,4-dihydroisoquinolin-1-one (1.2, 750 mg, 2.13 mmol, 1 equivalent) in DMF (4 mL) was added K$_2$CO$_3$ (587 mg, 4.26 mmol, 2 equivalents); this mixture was stirred at 25° C. for 12 hours. The reaction was diluted with water then was extracted with ethyl acetate (25 mL×3). The combined organic layers were washed with brine and dried over sodium sulfate. The solvent was removed to give the desired product 1.3 as a yellow solid (700 mg, yield=83.4%). This material was used in the following reaction without further purification; LC-MS [M+1]: 394.0.

$^1$H NMR (400 MHz, chloroform-d) δ=7.30 (d, J=8.7 Hz, 2H), 7.08 (s, 1H), 6.91-6.86 (m, 2H), 4.72 (s, 2H), 4.54 (td, J=6.0, 12.1 Hz, 1H), 3.82 (s, 3H), 3.43 (t, J=6.4 Hz, 2H), 2.86 (t, J=6.4 Hz, 2H), 1.42 (s, 3H), 1.40 (s, 3H).

Compound 1.4:

5,8-dichloro-7-isopropoxy-2-[(4-methoxyphenyl) methyl]-3,4-dihydroisoquinolin-1-one (1.3, 900 mg, 2.28 mmol, 1 equivalents) in TFA (5 mL) was stirred at 60° C. for 12 hours. The solvent was evaporated to give the crude product; this material was purified by flash chromatography on silica gel (petroleum ether/ethyl acetate 2/1). The desired product 1.4 was obtained as a yellow solid (450 mg, yield=72%); LC-MS [M+1]: 274.0.

$^1$H NMR (400 MHz, chloroform-d) δ=7.10 (s, 1H), 6.30 (br s, 1H), 4.53 (td, J=6.0, 12.2 Hz, 1H), 3.47 (dt, J=4.0, 6.4 Hz, 2H), 3.02 (t, J=6.4 Hz, 2H), 1.41 (s, 3H), 1.39 (s, 3H).

Compound 1.5:

To a solution of 2-benzyloxy-4-chloro-6-methyl-pyridine-3-carbonitrile (1.7 g, 6.57 mmol, 1 equivalent) in DMF (20 mL) was added cesium acetate (3.78 g, 19.7 mmol, 3 equivalents) and H$_2$O (355 mg, 19.71 mmol, 355 μL, 3 equivalents); this mixture was stirred at 80° C. for 24 hours. The reaction mixture was diluted with water (50 mL) then was extracted with ethyl acetate (20 mL×3). The combined organic layers were dried over sodium sulfate and the solvent was removed. There was obtained product 1.5 as a yellow solid (1.4 g, yield=88.7%); LC-MS [M+1]: 263.2.

$^1$H NMR (400 MHz, chloroform-d) δ=7.48 (d, J=7.2 Hz, 2H), 7.41-7.34 (m, 2H), 7.34-7.28 (m, 1H), 6.43 (s, 1H), 5.48 (s, 2H), 2.40 (s, 3H).

Compound 1.6:

To a solution of 2-benzyloxy-4-hydroxy-6-methyl-pyridine-3-carbonitrile (1.5, 1.5 g, 6.24 mmol, 1 equivalent) and $K_2CO_3$ (1.72 g, 12.48 mmol, 2 equivalents) in $CH_3CN$ (30 mL) was added $I_2$ (3.17 g, 12.5 mmol, 2.52 mL, 2 equivalents). This mixture was stirred at 70° C. for 12 hours. The reaction was quenched by saturated $Na_2S_2O_3$ solution then was extracted with ethyl acetate (10 mL×3). The combined organic layers were dried over sodium sulfate and the solvent was removed to give 1.6 as a yellow solid (1.6 g, yield=70.0%). This material was used in the following reaction without further purification; LC-MS [M+1]: 366.9.

$^1$H NMR (400 MHz, methanol-$d_4$) δ=7.44 (d, J=7.6 Hz, 2H), 7.34 (t, J=7.6 Hz, 2H), 7.30-7.24 (m, 1H), 5.33 (s, 2H), 2.52 (s, 3H).

Compound 1.7:

To 2-benzyloxy-4-hydroxy-5-iodo-6-methyl-pyridine-3-carbonitrile (1.6, 500 mg, 1.37 mmol, 1 equivalent), ethynyl(trimethyl)silane (175 mg, 1.78 mmol, 245 μL, 1.3 equivalent), cuprous iodide (52 mg, 273.11 μmol, 0.2 equivalent) and bis(triphenylphosphine)palladium(II)dichloride (95.8 mg, 136 μmol, 0.1 equivalent) in DMF (4 mL) under a nitrogen atmosphere was added TEA (553 mg, 5.46 mmol, 757 μL, 4 equivalents). The reaction mixture was stirred at ambient temperature for 12 hours. The reaction was diluted with water then extracted with ethyl acetate (20 mL×3). The combined organic layers were washed with brine then were dried over sodium sulfate. The solvent was removed to give the product 1.7 as a yellow solid. This material was of sufficient purity to be used in the next step; LC-MS [M+1]: 337.2.

$^1$H NMR (400 MHz, chloroform-d) δ=7.47 (br d, J=7.0 Hz, 2H), 7.40-7.35 (m, 3H), 7.35-7.30 (m, 1H), 5.49 (s, 2H), 2.57 (s, 3H), 0.33-0.24 (m, 9H)

Compound 1.8:

To a solution of 2-benzyloxy-4-hydroxy-6-methyl-5-(2-trimethylsilyl-ethynyl)pyridine-3-carbonitrile (1.7, 440 mg, 1.31 mmol, 1 equivalent) in MeOH (10 mL) was added CuI (249 mg, 1.31 mmol, 1 equivalent). This mixture was stirred at 95° C. for 12 hours. The solvent was removed under vacuum to give crude material; this was applied directly to a silica gel column for purification by flash chromatography (petroleum ether/ethyl acetate 5/1). The product 1.8 was isolated as a yellow solid (210 mg, yield=60.7%); LC-MS [M+1]: 265.2.

$^1$H NMR (400 MHz, chloroform-d) δ=7.58 (d, J=2.4 Hz, 1H), 7.52 (d, J=7.2 Hz, 2H), 7.41-7.36 (m, 2H), 7.35-7.30 (m, 1H), 6.79 (d, J=2.4 Hz, 1H), 5.57 (s, 2H), 2.68 (s, 3H).

Compound 1.9:

6-benzyloxy-4-methyl-furo[3,2-c]pyridine-7-carbonitrile (1.8, 200 mg, 757 μmol, 1 equivalent) in DCM (10 mL) was cooled to −78° C. DIBAL-H solution in DCM (1 M, 832.45 μL, 1.1 equivalents) was added at −78° C. then the reaction mixture was stirred at −60° C. for 2 hours. The reaction was quenched with saturated $NH_4Cl$ solution, then it was extracted with ethyl acetate (2 mL×3) and the combined organic layers were dried over sodium sulfate. The solvent was removed to give 250 mg of the crude product 1.9. This material was of sufficient purity to be used directly in the next step; LC-MS [M+1]: 268.0.

Compound 1.10:

To a solution of 6-benzyloxy-4-methyl-furo[3,2-c]pyridine-7-carbaldehyde (1.9, 90 mg, 337 μmol, 1 equivalent) in MeOH (1 mL) was added $NaBH_4$ (25.5 mg, 673 μmol, 2 equivalents) at 0° C. The reaction mixture was stirred at 25° C. for 1 hour, then it was quenched water $H_2O$. The solvent was removed by evaporation under vacuum. This crude residue was applied to a silica gel column and was purified by flash chromatography (petroleum ether ethyl acetate 5/1). The product 1.10 was obtained as a yellow solid (50 mg, yield=55.1%); LC-MS [M+1]: 270.1.

$^1$H NMR (400 MHz, chloroform-d) δ=7.53-7.46 (m, 3H), 7.42-7.36 (m, 2H), 7.35-7.30 (m, 1H), 6.72 (d, J=2.4 Hz, 1H), 5.52 (s, 2H), 4.95 (d, J=6.4 Hz, 2H), 2.63 (s, 3H).

Compound 1.11:

To a solution of (6-benzyloxy-4-methyl-furo[3,2-c]pyridin-7-yl)methanol (1.10, 100 mg, 371 μmol, 1 equivalent) and TEA (113 mg, 1.11 mmol, 154 μL, 3 equivalents) in DCM (1 mL) was added methanesulfonyl chloride (63.8 mg, 557 μmol, 43.1 μL, 1.5 equivalents) at 0° C. The reaction mixture was stirred at ambient temperature for 1 hour. After this time, it was diluted with water (5 mL) then was extracted with DCM (5 mL×3). The combined organic layers were dried over sodium sulfate and the solvent was removed to give the desired product 1.11 (120 mg, yield=93%). This material was carried on to the next step without further purification.

Compound 1.12:

To 5,8-dichloro-7-isopropoxy-3,4-dihydro-2H-isoquinolin-1-one (1.4, 50.0 mg, 182 μmol, 1.25 equivalents) in DMF (1 mL) was added NaH (11.7 mg, 292 μmol, 60% suspension in oil, 2 equivalents) at 0° C. This mixture was stirred for 15 min, then (6-benzyloxy-4-methyl-furo[3,2-c]pyridin-7-yl)methyl methanesulfonate (1.11, 50.7 mg, 146 μmol, 1 equivalent) in DCM (1 mL) was added. After stirring at ambient temperature for 2 hours, the reaction was quenched with saturated $NH_4Cl$ solution (5 mL) then it was extracted with ethyl acetate (5 mL×3). The combined organic layers were washed with brine and the solvent was removed. The crude material was purified by flash chromatography on silica gel (petroleum ether ethyl acetate 4/1) to give 1.12 as a yellow solid (40 mg, yield=52.2%); LC-MS [M+1]: 525.1.

$^1$H NMR (400 MHz, chloroform-d) δ=7.49 (d, J=2.4 Hz, 1H), 7.48-7.44 (m, 2H), 7.36-7.28 (m, 3H), 7.03 (s, 1H), 7.05-7.02 (m, 1H), 6.68 (d, J=2.4 Hz, 1H), 5.51 (s, 2H), 5.07 (s, 2H), 4.51 (spt, J=6.0 Hz, 1H), 3.32 (t, J=6.4 Hz, 2H), 2.70 (t, J=6.4 Hz, 2H), 2.63 (s, 3H), 1.40 (s, 3H), 1.38 (s, 3H).

EXAMPLE 1. To 2-[(6-benzyloxy-4-methyl-furo[3,2-c]pyridin-7-yl)methyl]-5,8-dichloro-7-isopropoxy-3,4-dihydroisoquinolin-1-one (1.12, 20.0 mg, 38.1 μmol) in DCM (1 mL) was added TFA (1.54 g, 13.51 mmol, 1 mL); this reaction mixture was stirred at 40° C. for 12 hours. The solvent was evaporated to give the crude product. This material was purified by preparative scale HPLC (column: Kromasil 150×25 mm×10 um; mobile phase: [water (0.1% TFA)-ACN]; B %: 35%-65%, 12 min elution gradient). EXAMPLE 1 was obtained as a white solid (10 mg, yield=60.7%, HPLC purity=99.9%); LC-MS [M+1]: 435.1.

$^1$H NMR (400 MHz, methanol-$d_4$) δ=7.56 (d, J=2.4 Hz, 1H), 7.25 (s, 1H), 6.80 (d, J=2.4 Hz, 1H), 4.57-4.66 (m, 1H), 3.59 (t, J=6.4 Hz, 2H), 2.91 (t, J=6.4 Hz, 2H), 2.52 (s, 3H), 1.35 (s, 3H), 1.33 (s, 3H).

Example 2

7-((5,8-dichloro-1-oxo-7-(7-oxa-2-azaspiro[3.5]nonan-2-yl)-3,4-dihydroisoquinolin-2(1H)-yl)methyl)-4-methylfuro[3,2-c]pyridin-6(5H)-one

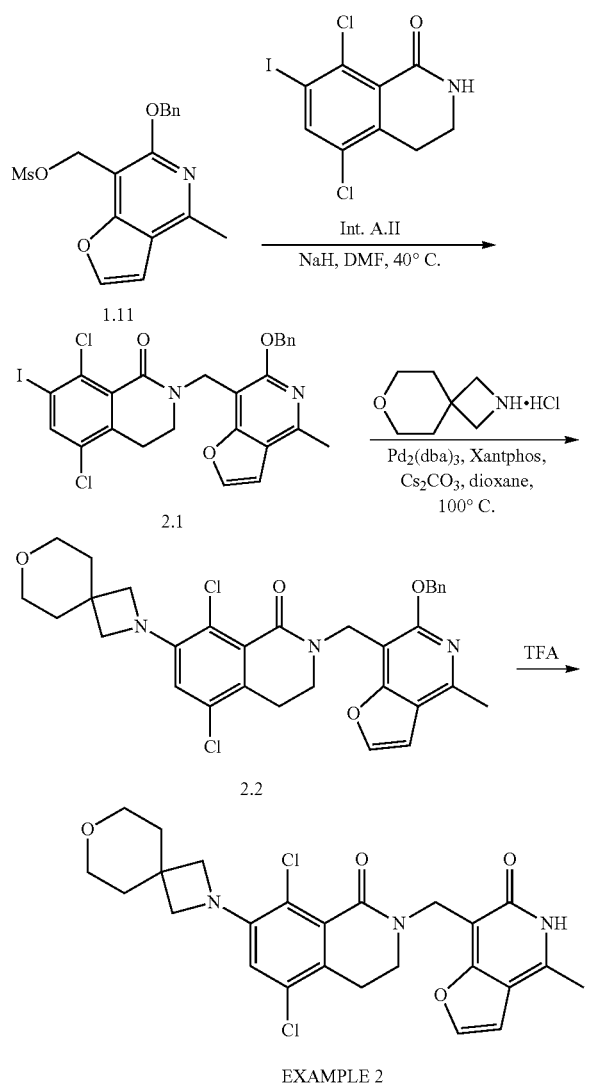

EXAMPLE 2

Compound 2.1:

To a solution of 5,8-dichloro-7-iodo-3,4-dihydro-2H-isoquinolin-1-one (Int A.II, 197 mg, 576 µmol, 2 equivalents) in DMF (2 mL) was added NaH (28.8 mg, 719 mol, 60% suspension in oil, 2.5 equivalents) at 0° C. This mixture was stirred for 15 min, then (6-benzyloxy-4-methyl-furo[3,2-c]pyridin-7-yl)methyl methanesulfonate (1.11, 100 mg, 287 mol, 1 equivalent) was added and stirring was continued at 40° C. for 12 hours. After this time, the reaction was diluted with H₂O (10 mL) then was extracted with ethyl acetate (15 mL×3). The combined organic extracts were washed with brine then dried over Na₂SO₄ and the solvent was removed by evaporation. The resulting crude product was purified with flash chromatography on silica gel (petroleum ether/ethyl acetate 5/1) to give 2.1 as a yellow solid (140 mg, yield=81.9%); LC-MS [M+1]: 593.0.

$^1$H NMR (400 MHz, chloroform-d) δ=7.96 (s, 1H), 7.50 (d, J=2.4 Hz, 1H), 7.47-7.43 (m, 2H), 7.33-7.28 (m, 3H), 6.70 (d, J=2.4 Hz, 1H), 5.50 (s, 2H), 5.06 (s, 2H), 3.34 (t, J=6.4 Hz, 2H), 2.70 (t, J=6.4 Hz, 2H), 2.63 (s, 3H).

Compound 2.2:

To a mixture of 2-[(6-benzyloxy-4-methyl-furo[3,2-c]pyridin-7-yl)methyl]-5,8-dichloro-7-iodo-3,4-dihydroisoquinolin-1-one (2.1, 50.0 mg, 84.3 µmol, 1 equivalent), 7-oxa-2-azaspiro[3.5]nonane (41.4 mg, 253 µmol, 3 equivalents, HCl salt), Xantphos (9.75 mg, 16.8 µmol, 0.2 equivalent) and Cs₂CO₃ (109 mg, 337 µmol, 4 equivalents) in dioxane (2 mL) was added Pd₂(dba)₃ (11.6 mg, 12.6 µmol, 0.15 equivalent). This reaction mixture was stirred at 100° C. under a nitrogen atmosphere for 4 hours. The reaction was filtered and the solvent was evaporated to afford the crude product. 2.2. This material was purified further by flash chromatography on silica gel (petroleum ether/ethyl acetate 2/1); pure 2.2 is a yellow solid (40 mg, yield=80.1%); LC-MS [M+1]: 592.3.

$^1$H NMR (400 MHz, chloroform-d) δ=7.50-7.45 (m, 3H), 7.35-7.29 (m, 3H), 6.68 (d, J=2.4 Hz, 1H), 6.59 (s, 1H), 5.51 (s, 2H), 5.06 (s, 2H), 3.87 (s, 4H), 3.70-3.67 (m, 4H), 3.31 (t, J=6.0 Hz, 2H), 2.67 (t, J=6.0 Hz, 2H), 2.63 (s, 3H), 1.84 (br d, J=5.2 Hz, 4H).

EXAMPLE 2. 7-((5,8-dichloro-1-oxo-7-(7-oxa-2-azaspiro[3.5]nonan-2-yl)-3,4-dihydroisoquinolin-2(1H)-yl)methyl)-4-methylfuro[3,2-c]pyridin-6(5H)-one: A mixture of 2-[(6-benzyloxy-4-methyl-furo[3,2-c]pyridin-7-yl)methyl]-5,8-dichloro-7-(7-oxa-2-azaspiro[3.5]nonan-2-yl)-3,4-dihydroisoquinolin-1-one (2.2, 30 mg, 50.6 µmol, 1 equivalent) and TFA (1.54 g, 13.5 mmol, 1 mL) was stirred at 30° C. for 5 hours. The solvent was removed to give a crude product that was purified further by preparative scale-HPLC (column: Phenomenex Gemini 150×25 mm×10 um; mobile phase: [(water (0.05% ammonia hydroxide v/v)-ACN]; B %: 30%-60%, 10 min). Pure EXAMPLE 2 is a yellow solid (22 mg, yield=86.5%, purity=97.3%); LC-MS [M+1]: 502.1.

$^1$H NMR (400 MHz, chloroform-d) δ=7.68 (br s, 1H), 6.76 (d, J=2.0 Hz, 1H), 6.61 (br s, 1H), 4.90 (br s, 2H), 3.84 (s, 4H), 3.72 (br s, 2H), 3.69-3.65 (m, 4H), 2.95 (br s, 2H), 2.74 (s, 3H), 1.83 (br t, J=5.2 Hz, 4H).

Example 3

7-((5,8-dichloro-7-(ethyl(tetrahydro-2H-pyran-4-yl)amino)-1-oxo-3,4-dihydroisoquinolin-2(1H)-yl)methyl)-4-methylfuro[3,2-c]pyridin-6(5H)-on

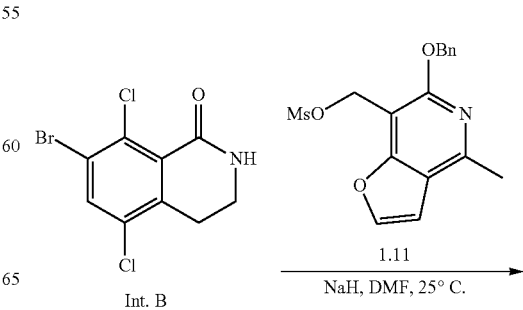

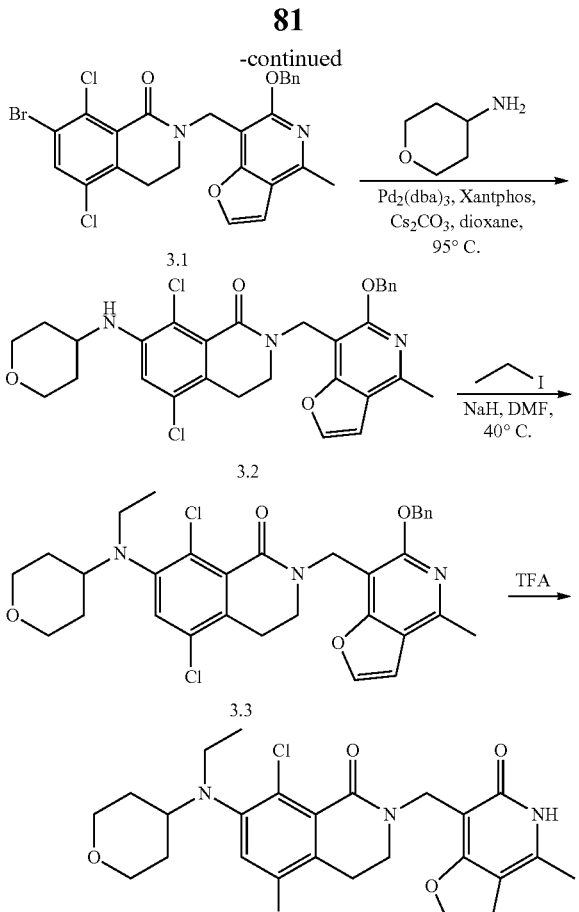

EXAMPLE 3

This material was purified by flash chromatography on silica gel (petroleum ether/ethyl acetate 5/1) to give 3.2 as a yellow solid (50 mg, yield=58.2%); LC-MS [M+1]: 566.4.

$^1$H NMR (400 MHz, chloroform-d) δ=7.49 (d, J=2.4 Hz, 1H), 7.46 (br d, J=6.4 Hz, 2H), 7.34-7.28 (m, 3H), 6.74 (s, 1H), 6.69 (d, J=2.4 Hz, 1H), 5.50 (s, 2H), 5.07 (s, 2H), 4.71 (br d, J=8.0 Hz, 1H), 4.06-4.02 (m, 1H), 4.01 (t, J=3.6 Hz, 1H), 3.60-3.47 (m, 3H), 3.31 (t, J=6.0 Hz, 2H), 2.67 (t, J=6.0 Hz, 2H), 2.63 (s, 3H), 2.06 (s, 2H), 2.02 (br s, 1H).

EXAMPLE 3. To a solution of 2-[(6-benzyloxy-4-methyl-furo[3,2-c]pyridin-7-yl)methyl]-5,8-dichloro-7-(tetrahydro-pyran-4-ylamino)-3,4-dihydroisoquinolin-1-one (3.2, 40 mg, 70.6 µmol, 1 equivalent) in DMF (1 mL) was added NaH (4.24 mg, 106 µmol, 60% suspension in oil, 1.5 equivalents) at 0° C. followed by iodoethane (22 mg, 141 µmol, 11.3 µL, 2 equivalents). The mixture was stirred at 45° C. for 12 hours. After this time, the reaction was quenched with water (5 mL) and was extracted with ethyl acetate (5 mL×3). The combined organic layers were washed with brine then were dried over anhydrous sodium sulfate. The solvent was removed to give the crude product 3.3. Without further handling, 3.3 was taken up in TFA (1 mL) and this mixture was stirred at 30° C. for 4 hours. After this time the reaction was complete and the solvent was removed by evaporation. The resulting residue was purified by preparative scale HPLC (column: Phenomenex Gemini 150×25 mm×10 um; mobile phase: [water (0.05% ammonia hydroxide v/v)-ACN]; B %: 37%-67%, 10 min). Pure EXAMPLE 3 is a white solid (8 mg, yield for the two steps=25.41%, HPLC purity=99.6%); LC-MS [M+1]: 504.3.

$^1$H NMR (400 MHz, chloroform-d) δ=7.40 (d, J=2.4 Hz, 1H), 7.18 (s, 1H), 6.52 (d, J=2.4 Hz, 1H), 4.93 (s, 2H), 3.98 (br d, J=11.2 Hz, 2H), 3.74 (t, J=6.0 Hz, 2H), 3.39-3.30 (m, 2H), 3.29-3.20 (m, 1H), 3.13 (q, J=7.2 Hz, 2H), 2.94 (t, J=6.0 Hz, 2H), 2.56 (s, 3H), 1.84-1.66 (m, 4H), 0.92 (t, J=7.2 Hz, 3H).

Example 4

5,8-dichloro-7-isopropoxy-2-((7-methyl-5-oxo-5,6-dihydro-1H-pyrrolo[2,3-c]pyridin-4-yl)methyl)-3,4-dihydroisoquinolin-1(2H)-one

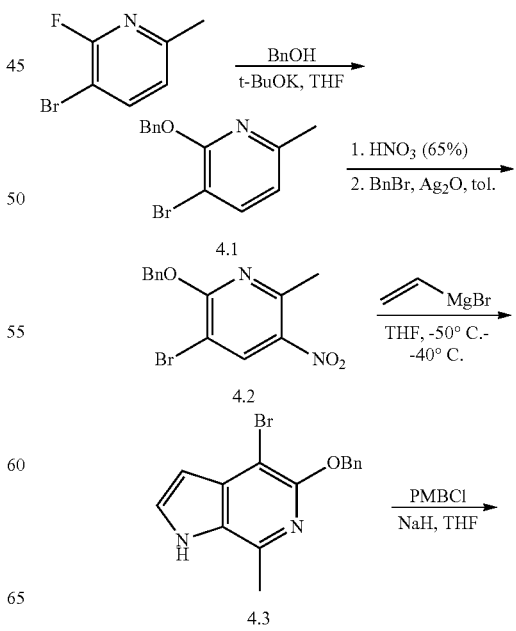

Compound 3.1:

To a solution of 7-bromo-5,8-dichloro-3,4-dihydro-2H-isoquinolin-1-one (Int. B, 106 mg, 360 µmol, 2.5 equivalents) in DMF (4 mL) was added NaH (17.3 mg, 431 mol, 60% suspension in oil, 3 equivalents) at 0° C. When the gas evolution subsided, (6-benzyloxy-4-methyl-furo[3,2-c]pyridin-7-yl)methyl methanesulfonate (1.11, 50 mg, 144 µmol, 1 equivalent) was added and this mixture was stirred at ambient temperature for 2 hours. After this time, the reaction was quenched with 5 mL of water then it was extracted with ethyl acetate (15 mL×3). The combined organic layers were washed with brine then were dried with sodium sulfate and the solvent was removed to give the crude product. The crude product was purified by flash chromatography on silica gel (petroleum ether/ethyl acetate 4/1) to give 3.1 as a yellow solid (45 mg, yield=57.2%); LC-MS [M+1]: 547.0.

$^1$H NMR (400 MHz, chloroform-d) δ=7.73 (s, 1H), 7.50 (d, J=2.2 Hz, 1H), 7.47-7.42 (m, 2H), 7.35-7.28 (m, 3H), 6.70 (d, J=2.0 Hz, 1H), 5.50 (s, 2H), 5.06 (s, 2H), 3.35 (t, J=6.0 Hz, 2H), 2.70 (t, J=6.0 Hz, 2H), 2.64 (s, 3H).

Compound 3.2:

To a solution of 2-[(6-benzyloxy-4-methyl-furo[3,2-c]pyridin-7-yl)methyl]-5,8-dichloro-7-iodo-3,4-dihydroiso-quinolin-1-one (3.1, 90 mg, 152 µmol, 1 equivalent), tetra-hydropyran-4-amine (46 mg, 455 µmol, 3 equivalents), Xantphos (17.6 mg, 30.3 mol, 0.2 equivalent) and Cs$_2$CO$_3$ (98.8 mg, 303 µmol, 2 equivalents) in dioxane (2 mL) was added Pd$_2$(dba)$_3$ (20.8 mg, 22.8 µmol, 0.15 equivalent). This mixture was stirred at 100° C. for 3 hours; then it was filtered and the solvent was evaporated to obtain the crude product.

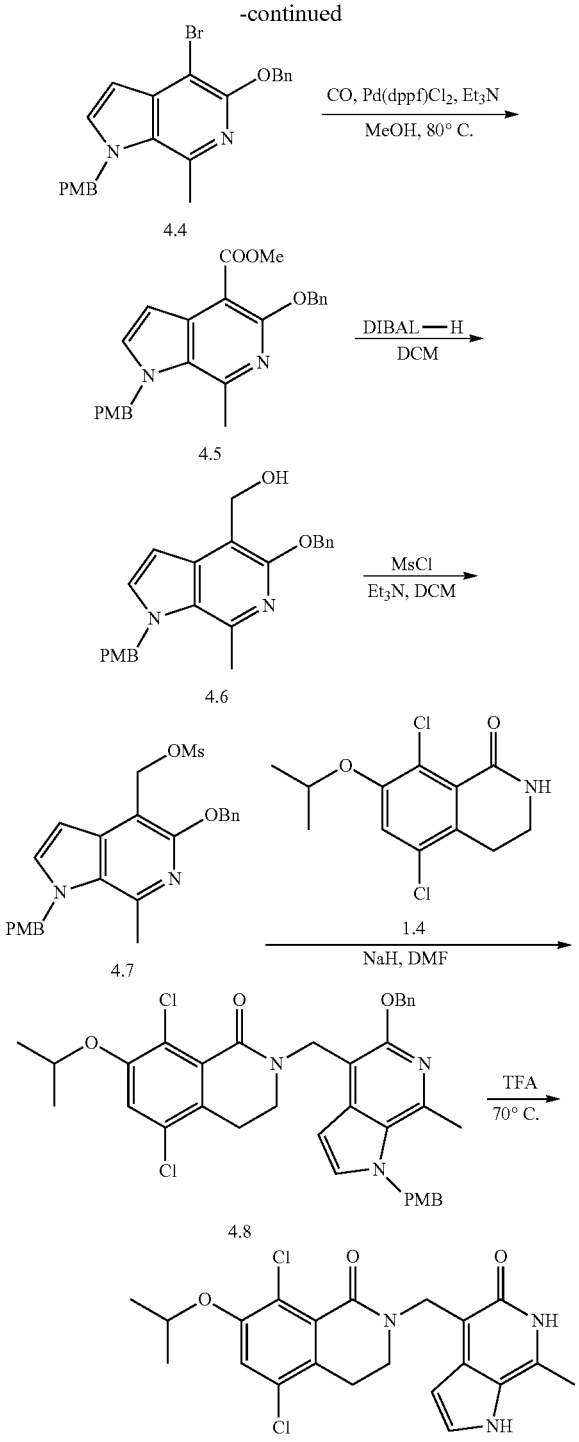

EXAMPLE 4

Compound 4.1:

To a solution of 3-bromo-2-fluoro-6-methyl-pyridine (12.2 g, 64.2 mmol, 1 equivalent) and benzyl alcohol (6.94 g, 64.2 mmol, 6.68 mL, 1 equivalent) in THF (10 mL) was added potassium tert-butoxide (7.2 g, 64.2 mmol, 1 equivalent) in portions at 0° C. This mixture was stirred at 0° C. for 1 hour, then warmed to 25° C. and stirred for 12 hrs. The mixture was filtered and the filtrate was concentrated under vacuum to give the crude product which was purified by silica gel chromatography (Petroleum ether/Ethyl acetate 10/1) to afford 2-benzyloxy-3-bromo-6-methyl-pyridine (4.1, 15 g, 84% yield) as colorless oil.

1H NMR (400 MHz, CDCl$_3$) δ=7.67 (d, J=7.6 Hz, 1H), 7.52 (d, J=7.2 Hz, 2H), 7.41-7.35 (m, 2H), 7.34-7.29 (m, 1H), 6.64 (d, J=7.6 Hz, 1H), 5.46 (s, 2H), 2.42 (s, 3H).

Compound 4.2:

Nitric acid (20 mL) was cooled to 0° C., 2-benzyloxy-3-bromo-6-methyl-pyridine (4.1, 15 g, 53.9 mmol, 1 equivalent) was added dropwise, then the reaction mixture was stirred at 25° C. for 12 hrs. The reaction was quenched with water (50 mL), the pH of the solution was adjusted to 6 with solid sodium bicarbonate (about 5 g). A copious precipitate was formed and the suspension was filtered then the solid was collected and was dried in vacuo. The solid was dispersed in ethyl acetate (5 mL) then stirred for 15 min. This suspension was filtered, the filter cake was collected and was dried in vacuo to give 3-bromo-6-methyl-5-nitro-pyridin-2-ol (7.4 g, 58.9% yield) as a brown solid. It was apparent that the benzyl group was removed under the reaction conditions; this material was carried on to the next step without further manipulation.

To a solution of 3-bromo-6-methyl-5-nitro-pyridin-2-ol (7.4 g, 31.7 mmol, 1 equivalent) in toluene (75 mL) was added silver oxide (8.1 g, 34.9 mmol, 1.1 equivalent) then benzyl bromide (6.52 g, 38.1 mmol, 4.53 mL, 1.2 equivalent). The reaction mixture was stirred at 110° C. under nitrogen for 12 hrs. After the solid precipitate was removed by filtration, the filtrate was concentrated by rotary evaporator under vacuum. The resulting crude material was purified by silica gel chromatography (Petroleum ether/Ethyl acetate 10/1 to 5/1) to give 2-benzyloxy-3-bromo-6-methyl-5-nitro-pyridine (4.2, 7.3 g, 71.1% yield) as a yellow solid.

$^1$H NMR (400 MHz, CDCl$_3$) δ=8.56 (s, 1H), 7.50 (d, J=7.2 Hz, 2H), 7.44-7.32 (m, 3H), 5.56 (s, 2H), 2.81 (s, 3H).

Compound 4.3:

To a solution of 2-benzyloxy-3-bromo-6-methyl-5-nitro-pyridine (4.2, 3.4 g, 10.5 mmol, 1 equivalent) in THF (34 mL) was added bromo(vinyl)magnesium (1 M, 31.5 mL, 3 equivalents) in one portion at −50° C., then the reaction mixture was stirred at −40° C. for an additional hour. After this time the reaction mixture was quenched with saturated ammonium chloride solution (100 mL) and was extracted with ethyl acetate (100 mL×3). The combined organic extracts were washed with brine (100 mL×3) then were dried with anhydrous sodium sulfate, and filtered. The material that was obtained after the solvent was removed, was purified by silica gel chromatography (Petroleum ether/Ethyl acetate 10/1 to 4/1) to afford the 5-benzyloxy-4-bromo-7-methyl-1H-pyrrolo[2,3-c]pyridine (4.3, 700 mg, 21% yield) as a brown oil.

1H NMR (400 MHz, CDCl$_3$) δ=8.05 (br s, 1H), 7.47 (d, J=7.6 Hz, 2H), 7.31-7.25 (m, 3H), 7.23-7.19 (m, 1H), 6.44 (dd, J=2.0, 3.2 Hz, 1H), 5.44 (s, 2H), 2.53 (s, 3H).

Compound 4.4:

To a solution of 5-benzyloxy-4-bromo-7-methyl-1H-pyrrolo[2,3-c]pyridine (4.3, 700 mg, 2.21 mmol, 1 equivalent) in DMF (7 mL) was added NaH (133 mg, 3.32 mmol, 60% suspension in oil, 1.5 equivalents) at 0° C. The reaction mixture was stirred at 0° C. for 30 min; when gas evolution ceased, p-methoxybenzyl chloride (381 mg, 2.43 mmol, 331 µL, 1.1 equivalents) was added dropwise. The reaction mixture was warmed to 25° C. and was stirred for 1 h. The reaction mixture was quenched with water (20 mL) and was extracted with ethyl acetate (20 mL×3). The combined organic phase was washed with brine (20 mL×2), was dried with anhydrous sodium sulfate, then was filtered and concentrated in vacuum. The residue was purified by prep-TLC (Petroleum ether/Ethyl acetate 2/1) to give 5-benzyloxy-4-bromo-1-[(4-methoxyphenyl)methyl]-7-methyl-pyrrolo[2,3-c]pyridine (4.4, 700 mg, 72.4% yield) as a brown oil.

$^1$H NMR (400 MHz, CDCl$_3$) δ=7.53 (d, J=7.2 Hz, 2H), 7.39-7.33 (m, 3H), 7.30-7.26 (m, 1H), 7.20 (d, J=2.8 Hz, 1H), 6.88-6.83 (m, 4H), 6.50 (d, J=3.2 Hz, 1H), 5.50 (s, 2H), 5.45 (s, 2H), 3.78 (s, 3H), 2.62 (s, 3H).

Compound 4.5:

To 5-benzyloxy-4-bromo-1-[(4-methoxyphenyl)methyl]-7-methyl-pyrrolo[2,3-c]pyridine (4.4, 500 mg, 1.14 mmol, 1 equivalent) in methanol (5 mL) was added triethylamine (346 mg, 3.42 mmol, 474 μL, 3 equivalents) and Pd(dppf)Cl$_2$ (83.4 mg, 114 μmol, 0.1 equivalent) under nitrogen. The reaction mixture was purged with carbon monoxide 5 times then was stirred at 80° C. for 12 hours under an atmosphere of carbon monoxide (50 psi). After it was cooled to room temperature, the reaction mixture was filtered and concentrated to give the crude product. This material was purified by preparative-TLC (Petroleum ether/Ethyl acetate 3/1) to give methyl 5-benzyloxy-1-[(4-methoxyphenyl)methyl]-7-methyl-pyrrolo[2,3-c]pyridine-4-carboxylate (4.5, 200 mg, yield=42%) as brown oil; LCMS [M+1]: 417.1.

Compound 4.6:

To a solution of methyl 5-benzyloxy-1-[(4-methoxyphenyl)methyl]-7-methyl-pyrrolo[2,3-c]pyridine-4-carboxylate (4.5, 280 mg, 672 μmol, 1 equivalent) in DCM (3 mL) was added DIBAL-H (1 M DCM solution, 2.02 mL, 3 equivalents) at 0° C. The reaction was stirred at 25° C. for 2 hrs. After this time, the reaction mixture was quenched with saturated ammonium chloride solution (10 mL) then was extracted with DCM (5 mL×3). The combined organic phase was washed with brine (5 mL×2), was dried with anhydrous sodium sulfate then was filtered and concentrated in vacuum. The residue was purified by preparative-TLC (Petroleum ether/Ethyl acetate 2/1) to give 5-benzyloxy-1-[(4-methoxyphenyl)methyl]-7-methyl-pyrrolo[2,3-c]pyridin-4-yl]methanol (4.6, 200 mg, 76.6% yield) as a brown oil.

1H NMR (400 MHz, CDCl$_3$) δ=7.48 (d, J=7.2 Hz, 2H), 7.40-7.34 (m, 2H), 7.33-7.28 (m, 1H), 7.19 (d, J=3.2 Hz, 1H), 6.87-6.82 (m, 4H), 6.53 (d, J=3.2 Hz, 1H), 5.48 (s, H), 4.94 (s, 2H), 3.78 (s, 3H), 2.67 (s, 3H).

Compound 4.7:

To [5-benzyloxy-1-[(4-methoxyphenyl)methyl]pyrrolo[2,3-c]pyridin-4-yl]methanol (4.6, 80.0 mg, 214 μmol, 1 equivalent) and triethylamine (64.9 mg, 641 mol, 88.9 μL, 3 equivalents) in DCM (2 mL) was added methanesulfonyl chloride (49.0 mg, 427 μmol, 33.1 μL, 2 equivalents) at 0° C.; the reaction was stirred at 0° C. for 1 hour. The reaction mixture was quenched with saturated sodium bicarbonate solution (2 mL) and was extracted with DCM (2 mL×3). The combined organic phase was washed with brine (2 mL×2), dried with anhydrous sodium sulfate, filtered and concentrated in vacuum at 25° C. to give [5-benzyloxy-1-[(4-methoxyphenyl)methyl]pyrrolo[2,3-c]pyridin-4-yl]methyl-methanesulfonate (4.7, 96 mg). This material was carried on to the next step without further manipulation.

Compound 4.8:

To a solution of [5-benzyloxy-1-[(4-methoxyphenyl)methyl]-7-methyl-pyrrolo[2,3-c]pyridin-4-yl]methyl methanesulfonate (4.7, 96 mg, 206 μmol, 1 equivalent) in DMF (1 mL) was added NaH (16.5 mg, 412 μmol, 60% suspension in oil, 2 equivalents) at 0° C. The reaction was stirred at 0° C. for 20 min; after gas evolution ceased, 5,8-dichloro-7-isopropoxy-3,4-dihydro-2H-isoquinolin-1-one (1.4, 56.4 mg, 206 μmol, 1 equivalent) was added dropwise. The reaction was warmed to 25° C. and stirred for 1 h. The reaction mixture was quenched with water (5 mL), extracted with ethyl acetate (3 mL×3). The combined organic phase was washed with brine (3 mL×2) then was dried with anhydrous sodium sulfate, filtered and concentrated in vacuum. The crude product was purified by preparative-TLC (Petroleum ether/Ethyl acetate 2/1) to give 2-[[5-benzyloxy-1-[(4-methoxyphenyl)methyl]-7-methyl-pyrrolo[2,3-c]pyridin-4-yl]methyl]-5,8-dichloro-7-isopropoxy-3,4-dihydroisoquinolin-1-one (4.8, 80 mg, 124 μmol, 60.3% yield) as a brown oil; LCMS [M+1]: 644.2.

EXAMPLE 4. A solution of 2-[[5-benzyloxy-1-[(4-methoxyphenyl)methyl]-7-methyl-pyrrolo[2,3-c]pyridin-4-yl]methyl]-5,8-dichloro-7-isopropoxy-3,4-dihydroisoquinolin-1-one (80 mg, 124 μmol, 1 equivalent) in TFA (1 mL) was stirred at 70° C. for 12 hrs. The reaction mixture was concentrated in vacuum then to the residue was added saturated sodium bicarbonate solution (5 mL). The aqueous phase was extracted with ethyl acetate (5 mL×3). The combined organic phase was washed with brine (5 mL×2) then was dried with anhydrous sodium sulfate, filtered and concentrated in vacuum. The residue was purified by preparative-HPLC (column: Kromasil 150×25 mm×10 um; mobile phase: [water (0.1% TFA)-ACN]; B %: 35%-65%, 12 min elution gradient) to give 5,8-dichloro-7-isopropoxy-2-[(7-methyl-5-oxo-1,6-dihydropyrrolo[2,3-c]pyridin-4-yl)methyl]-3,4-dihydroisoquinolin-1-one (EXAMPLE 4, 7.35 mg, 12.4% yield, 90.5% purity) as a gray solid; LC-MS [M+1]: 434.1.

1H NMR (400 MHz, CD$_3$OD) δ=7.97 (d, J=2.8 Hz, 1H), 7.35 (s, 1H), 6.86 (d, J=2.8 Hz, 1H), 5.05 (s, 2H), 4.70-4.64 (m, 1H), 3.72 (t, J=6.4 Hz, 2H), 2.96 (t, J=6.4 Hz, 2H), 2.82 (s, 3H), 1.38 (s, 3H), 1.36 (s, 3H).

Example 5

5,8-dichloro-2-((7-methyl-5-oxo-5,6-dihydro-1H-pyrrolo[2,3-c]pyridin-4-yl)methyl)-7-(7-oxa-2-azaspiro[3.5]nonan-2-yl)-3,4-dihydroisoquinolin-1(2H)-one

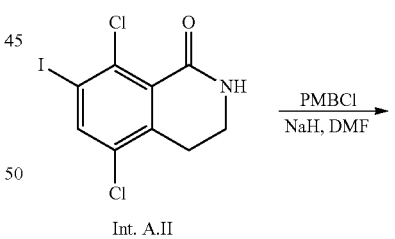

Int. A.II

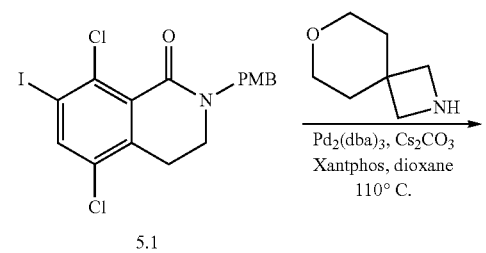

5.1

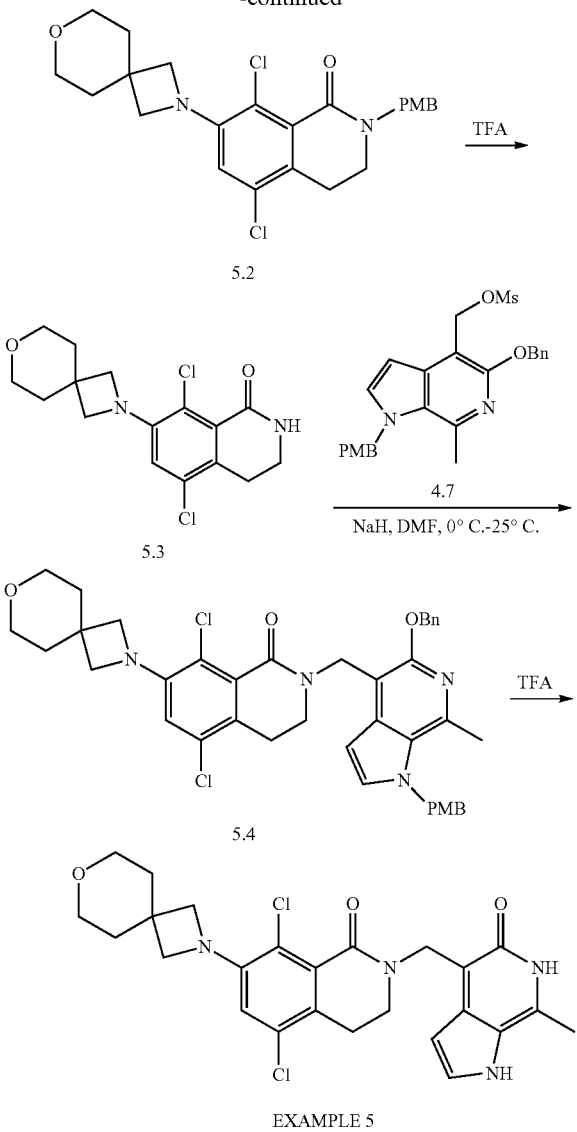

EXAMPLE 5

Compound 5.1:

To a solution of 5,8-dichloro-7-iodo-3,4-dihydro-2H-isoquinolin-1-one (Int. A.II, 950 mg, 2.78 mmol, 1 equivalent) in DMF (9 mL) was added NaH (167 mg, 4.17 mmol, 60% suspension in oil, 1.5 equivalents) at 0° C. After the reaction mixture was stirred at 0° C. for 30 min, the gas evolution subsided and p-methoxybenzyl chloride (479 mg, 3.06 mmol, 416 μL, 1.1 equivalents) was added dropwise, then the mixture was warmed to 25° C. and was stirred for 1 h. The reaction mixture was quenched with water (10 mL) at 0° C.; the resulting precipitate was filtered and the solid was collected. After it was dried under vacuum there was obtained 5,8-dichloro-7-iodo-2-[(4-methoxyphenyl)methyl]-3,4-dihydroisoquinolin-1-one (5.1, 950 mg, 74.0% yield) as a white solid.

$^1$H NMR (400 MHz, DMSO-d$_6$) δ=8.22 (s, 1H), 7.25 (d, J=7.2 Hz, 2H), 6.91 (d, J=7.2 Hz, 2H), 4.62 (s, 2H), 3.74 (s, 3H), 3.45 (t, J=5.2 Hz, 2H), 2.87 (t, J=5.2 Hz, 2H).

Compound 5.2:

To 5,8-dichloro-7-iodo-2-[(4-methoxyphenyl)methyl]-3,4-dihydroisoquinolin-1-one (5.1, 500 mg, 1.08 mmol, 1 equivalent) and 7-oxa-2-azaspiro[3.5]nonane (212 mg, 1.3 mmol, 1.2 equivalents, HCl salt) in dioxane (1 mL) was added Pd$_2$(dba)$_3$ (99.1 mg, 108 μmol, 0.1 equivalent), cesium carbonate (1.06 g, 3.25 mmol, 3 equivalents) and Xantphos (125 mg, 216 μmol, 0.2 equivalent) under nitrogen. The reaction mixture was stirred at 100° C. for 2 hrs. The reaction mixture was cooled to 25° C. then filtered; the filtrate was concentrated in vacuum and the residue was purified by preparative-TLC (Petroleum ether/Ethyl acetate 2/1) to give 5,8-dichloro-2-[(4-methoxyphenyl)methyl]-7-(7-oxa-2-azaspiro[3.5]nonan-2-yl)-3,4-dihydroisoquinolin-1-one as a brown oil (5.2, 400 mg, crude); LC-MS: [M+1] 461.1.

Compound 5.3:

A solution of 5,8-dichloro-2-[(4-methoxyphenyl)methyl]-7-(7-oxa-2-azaspiro[3.5]nonan-2-yl)-3,4-dihydroisoquinolin-1-one (5.2, 390 mg, 845 μmol, 1 equivalent) in TFA (3 mL) was stirred at 70° C. for 12 hrs. The reaction mixture was concentrated in vacuum and the residue was suspended in saturated sodium bicarbonate solution (10 mL). The aqueous mixture was extracted with DCM (20 mL×3) and the combined organic phase was washed with brine (20 mL×2) and dried with anhydrous sodium sulfate. The dried solution was concentrated in vacuum, then the residue was purified by preparative-TLC (Dichloromethane/Methanol 10/1) to give 5,8-dichloro-7-(7-oxa-2-azaspiro[3.5]nonan-2-yl)-3,4-dihydro-2H-isoquinolin-1-one (5.3, 160 mg, crude) as a brown oil.

$^1$H NMR (400 MHz, CDCl$_3$) δ=6.65 (s, 1H), 3.88 (s, 4H), 3.68 (t, J=5.2 Hz, 4H), 3.47-3.42 (m, 2H), 3.01-2.97 (m, 2H), 1.84 (t, J=5.2 Hz, 4H).

Compound 5.4:

To a solution of 5,8-dichloro-7-(7-oxa-2-azaspiro[3.5]nonan-2-yl)-3,4-dihydro-2H-isoquinolin-1-one (5.3, 35.1 mg, 103 μmol, 1 equivalent) in DMF (1 mL) was added NaH (8.23 mg, 206 μmol, 60% suspension in oil, 2 equivalents) at 0° C. After the reaction mixture was stirred at 0° C. for 20 min, gas evolution ceased and [5-benzyloxy-1-[(4-methoxyphenyl)methyl]-7-methyl-pyrrolo[2,3-c]pyridin-4-yl]methylmethanesulfonate (4.7, 48 mg, 103 μmol, 1 equivalent) was added dropwise, then the reaction was warmed to 25° C. and was stirred for 1 h. The reaction mixture was quenched with water (5 mL) and was extracted with ethyl acetate (5 mL×3). The combined organic phase was washed with brine (5 mL×2) then was dried with anhydrous sodium sulfate and concentrated in vacuum. The residue was purified by preparative-TLC (Petroleum ether/Ethyl acetate 2/1) to give 2-[[5-benzyloxy-1-[(4-methoxyphenyl)methyl]-7-methyl-pyrrolo[2,3-c]pyridin-4-yl]methyl]-5,8-dichloro-7-(7-oxa-2-azaspiro[3.5]nonan-2-yl)-3,4-dihydroisoquinolin-1-one (5.4, 50 mg, yield=68.3%) as a brown solid; LCMS: [M+1] 711.2.

EXAMPLE 5. A solution of 2-[[5-benzyloxy-1-[(4-methoxyphenyl)methyl]-7-methyl-pyrrolo[2,3-c]pyridin-4-yl]methyl]-5,8-dichloro-7-(7-oxa-2-azaspiro[3.5]nonan-2-yl)-3,4-dihydroisoquinolin-1-one (5.4, 40 mg, 56.2 μmol, 1 equivalent) in TFA (1 mL) was stirred at 70° C. for 12 hrs. The reaction mixture was concentrated in vacuo and was taken up with aqueous saturated sodium bicarbonate solution (9 mL), then was extracted with ethyl acetate (5 mL×3). The combined organic phase was washed with brine (5 mL×2) then was dried with anhydrous sodium sulfate and was concentrated. The residue was purified by preparative-HPLC (column: Kromasil 150×25 mm×10 um; mobile phase: [water (0.1% TFA)-ACN]; B %: 35%-65%, 12 min elution gradient) to give 5,8-dichloro-2-[(7-methyl-5-oxo-1,6-dihydropyrrolo[2,3-c]pyridin-4-yl)methyl]-7-(7-oxa-2-azaspiro[3.5]nonan-2-yl)-3,4-dihydroisoquinolin-1-one as brown oil (EXAMPLE 5, 9.37 mg, 32.7% yield, 98.8% purity); LC-MS: [M+1] 501.2.

$^1$H NMR (400 MHz, CD$_3$OD) δ=7.90 (d, J=2.8 Hz, 1H), 7.21 (s, 1H), 6.79 (d, J=2.4 Hz, 1H), 5.06-5.01 (m, 2H), 3.96-3.88 (m, 3H), 3.80-3.74 (m, 1H), 3.72-3.61 (m, 4H), 3.55-3.45 (m, 1H), 3.41-3.35 (m, 1H), 2.92-2.84 (m, 2H), 2.79 (s, 3H), 2.07-1.97 (m, 3H), 1.87-1.82 (m, 1H).

Example 6

7-((8-chloro-7-isopropoxy-1-oxo-3,4-dihydroisoquinolin-2(1H)-yl)methyl)-4-methylfuro[3,2-c]pyridin-6(5H)-one

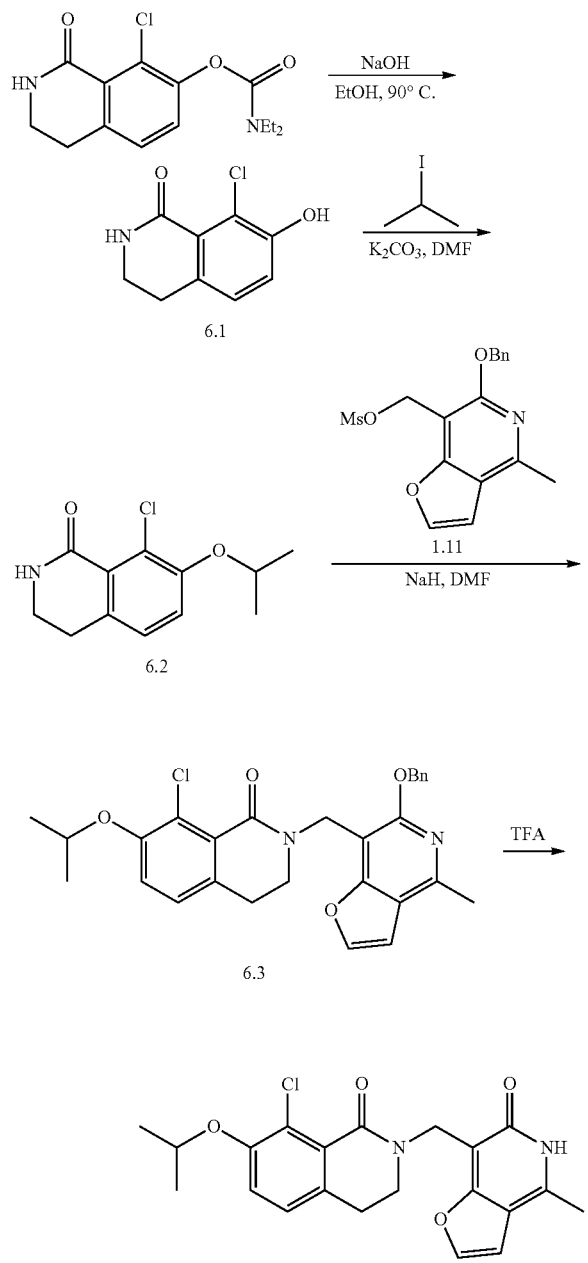

Compound 6.1:

To a solution of (8-chloro-1-oxo-3,4-dihydro-2H-isoquinolin-7-yl) N,N-diethylcarbamate (1 g, 3.37 mmol, 1 equivalent) in EtOH (10 mL) was added NaOH (674 mg, 16.8 mmol, 5 equivalents). The reaction was stirred at 90° C. for 12 hours. Then the reaction mixture was diluted with water (10 mL). The pH of the solution was adjusted the to 4 with AcOH, then the aqueous phase was extracted with ethyl acetate (45 mL×2). The combined organic layers were washed with saturated sodium bicarbonate solution (30 mL×2) and brine (45 mL×2), then was dried over sodium sulfate. The solvent was removed to give the 8-chloro-7-hydroxy-3,4-dihydro-2H-isoquinolin-1-one (6.1, 500 mg, 2.42 mmol, yield=71.7%) as a yellow oil; LC-MS [M+1]: 198.0.

Compound 6.2:

To a solution of 8-chloro-7-hydroxy-3,4-dihydro-2H-isoquinolin-1-one (6.1, 500 mg, 2.53 mmol, 1 equivalent) in DMF (5 mL) was added 2-iodopropane (516 mg, 3.04 mmol, 304 μL, 1.2 equivalents) and K$_2$CO$_3$ (1.05 g, 7.59 mmol, 3 equivalents). The reaction was stirred for 2 hours, then was poured into H$_2$O (50 mL) and extracted with ethyl acetate (50 mL×2). The combined organic phase was washed with brine (50 mL×2) and was dried with anhydrous sodium sulfate. After the solution was dried and filtered it was concentrated. The resulting material was purified by column chromatography (eluent: ethyl acetate) to give the 8-chloro-7-isopropoxy-3,4-dihydro-2H-isoquinolin-1-one (6.2, 480 mg, 2 mmol, 79.2% yield) as a white solid.

$^1$H NMR (400 MHz, chloroform-d) δ=7.09-7.00 (m, 2H), 6.20 (br s, 1H), 4.55-4.48 (m, 1H), 3.46 (dt, J=4.0, 6.4 Hz, 2H), 2.91 (br d, J=6.4 Hz, 2H), 1.39 (s, 3H), 1.37 (s, 3H).

Compound 6.3:

To 8-chloro-7-isopropoxy-3,4-dihydro-2H-isoquinolin-1-one (6.2, 80 mg, 334 μmol, 1 equivalent) in DMF (5 mL) was added NaH (26.7 mg, 667 μmol, 60% suspension in oil, 2 equivalents) at 0° C. The reaction was stirred at 0° C. for 0.5 hour, then (6-benzyloxy-4-methyl-furo[3,2-c]pyridin-7-yl)methyl methanesulfonate (1.11, 60 mg, 167 μmol, 0.5 equivalent) was added to mixture and was stirred at 25° C. for an additional 1 hour. The reaction was quenched with H$_2$O (40 mL) and was extracted with ethyl acetate (20 mL×2). The combined organic phase was washed with brine (50 mL), then was dried over anhydrous sodium sulfate and concentrated. The residue was purified by preparative-TLC (petroleum ether/ethyl acetate 5/1) to give the 2-[(6-benzyloxy-4-methyl-furo[3,2-c]pyridin-7-yl)methyl]-8-chloro-7-isopropoxy-3,4-dihydroisoquinolin-1-one as a white solid (6.3, 88 mg, 176 μmol, 53% yield); LCMS [M+1]: 316.0.

EXAMPLE 6. To 2-[(6-benzyloxy-4-methyl-furo[3,2-c]pyridin-7-yl)methyl]-8-chloro-7-isopropoxy-3,4-dihydroisoquinolin-1-one (6.3, 44 mg, 89.6 μmol, 1 equivalent) in DCM (2.5 mL) was added TFA (135 mg, 1.19 mmol, 88 μL, 13.26 equivalents). The reaction mixture was stirred at 35° C. for 1 hour. After this time, the reaction was concentrated in vacuo to give a solid material which was recrystallized from MeOH (2 mL) to give 7-[(8-chloro-7-isopropoxy-1-oxo-3,4-dihydroisoquinolin-2-yl)methyl]-4-methyl-5H-furo[3,2-c]pyridin-6-one (EXAMPLE 6, 25 mg, yield=67.8%) as a white solid; LC-MS [M+1]: 401.0.

$^1$H NMR (400 MHz, chloroform-d) δ=7.71 (d, J=2.4 Hz, 1H), 7.00 (d, J=1.2 Hz, 2H), 6.76 (d, J=2.4 Hz, 1H), 4.91 (s, 2H), 4.52-4.46 (m, 1H), 3.78-3.74 (m, 2H), 2.91 (t, J=6.4 Hz, 2H), 2.75 (s, 3H), 1.36 (s, 3H), 1.35 (s, 3H).

Example 7
7-[[5-bromo-8-chloro-7-(3,5-dimethyltriazol-4-yl)-1-oxo-3,4-dihydroisoquinolin-2-yl]methyl]-4-methyl-5H-furo[3,2-c]pyridin-6-one
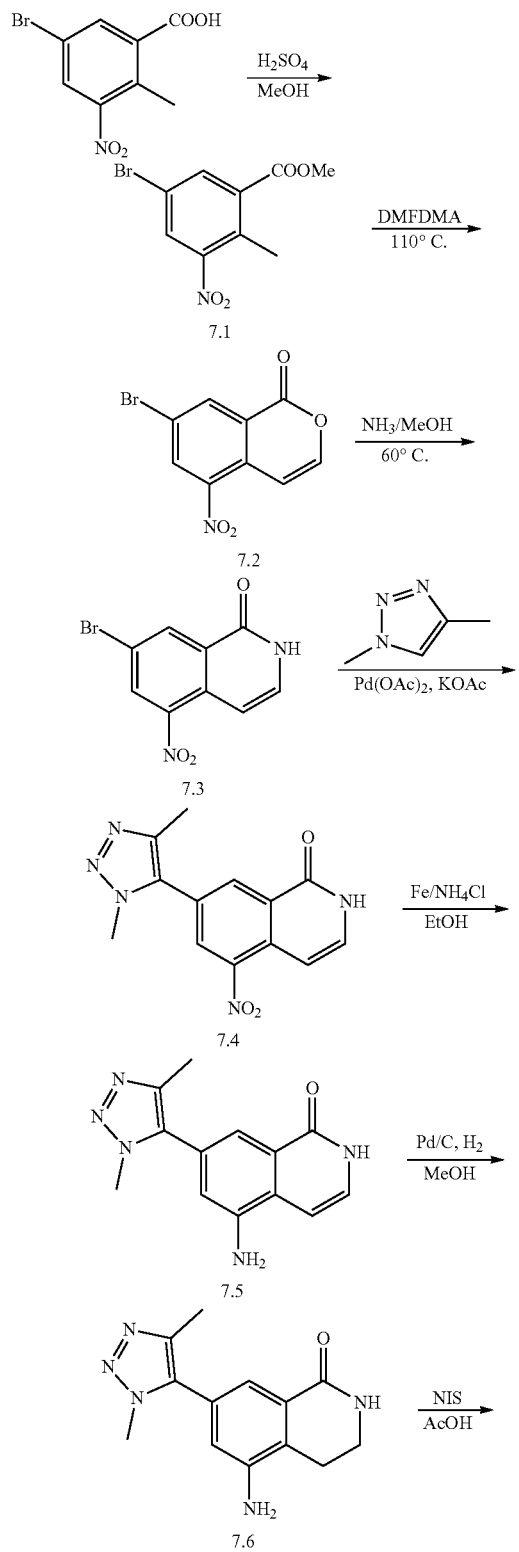
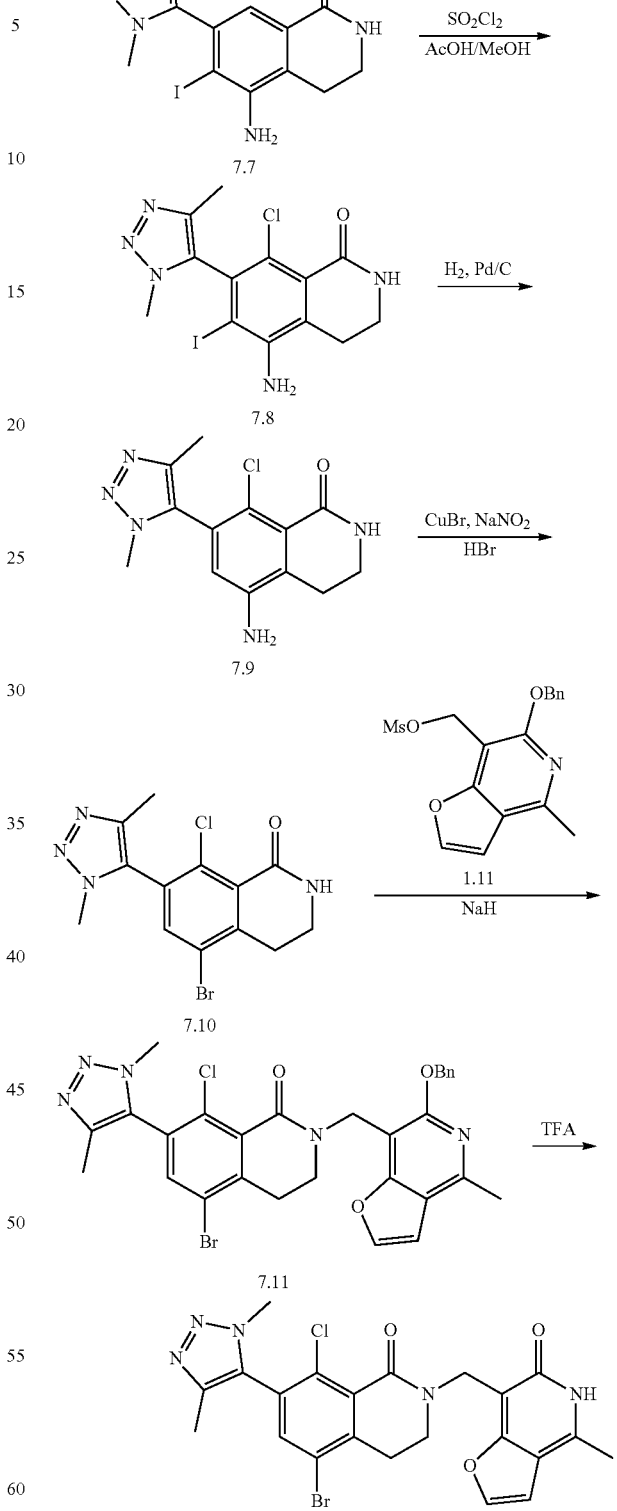
EXAMPLE 7
Compound 7.1:
To a solution of 5-bromo-2-methyl-3-nitro-benzoic acid (1 g, 3.85 mmol, 1 equivalent) in MeOH (20 mL) was added H$_2$SO$_4$ (3.78 g, 38.5 mmol, 2.05 mL, 10 equivalents). The mixture was stirred at 75° C. for 12 hrs. When the reaction was complete, the pH of the mixture was adjusted to 7 with saturated sodium bicarbonate aqueous solution, then extracted with ethyl acetate (20 mL×3). The combined organic phase was dried over sodium sulfate and concentrated to give methyl 5-bromo-2-methyl-3-nitro-benzoate (7.1, 1 g, 3.65 mmol, 94.8% yield) as a light yellow solid.

$^1$H NMR (400 MHz, CDCl$_3$) δ=8.14 (d, J=2.0 Hz, 1H), 7.99 (d, J=2.0 Hz, 1H), 3.96 (s, 3H), 2.58 (s, 3H).

Compound 7.2:

Methyl 5-bromo-2-methyl-3-nitro-benzoate (7.1, 200 mg, 730 µmol, 200 µL, 1 equivalent) in DMFDMA (261 mg, 2.19 mmol, 290 µL, 3 equivalents) was stirred at 110° C. for 12 hrs. The reaction mixture was diluted with ethyl acetate (30 mL) then washed with brine (20 mL×3). The organic phase was dried over sodium sulfate and concentrated in vacuo. The residue was purified by preparative-TLC (SiO$_2$, petroleum ether/ethyl acetate 5/1) to give 7-bromo-5-nitro-isochromen-1-one (7.2, 90.0 mg, 333 µmol, 45.7% yield) as a yellow solid.

$^1$H NMR (400 MHz, CDCl$_3$) δ=8.76 (d, J=2.0 Hz, 1H), 8.61 (d, J=2.0 Hz, 1H), 7.46 (d, J=6.0 Hz, 1H), 7.35 (d, J=6.10 Hz, 1H).

Compound 7.3:

A pressure tube containing 7-bromo-5-nitro-isochromen-1-one (7.2, 2.5 g, 9.26 mmol, 1 equivalent) in MeOH (30 mL) was cooled to 0° C. and the solution was purged with ammonia gas for 15 min. The pressure tube was sealed and then it was stirred at 60° C. for 12 hrs. After this time the reaction mixture was cooled to 0° C., the tube was opened and the resulting precipitate was filtered and washed with cold MeOH (3 mL). The solid was dried under vacuum to give 7-bromo-5-nitro-2H-isoquinolin-1-one (7.3, 1.86 g, 6.91 mmol, 74.7% yield) as a yellow solid.

$^1$H NMR (400 MHz, DMSO-d$_6$) δ=11.79 (br s, 1H), 8.61 (d, J=2.8 Hz, 2H), 7.48 (d, J=7.6 Hz, 1H), 6.89 (d, J=7.6 Hz, 1H).

Compound 7.4:

A mixture of 7-bromo-5-nitro-2H-isoquinolin-1-one (7.3, 1 g, 3.72 mmol, 1 equivalent), 1,4-dimethyltriazole (397 mg, 4.09 mmol, 1.1 equivalents), KOAc (1.82 g, 18.6 mmol, 5 equivalents), Pd(OAc)$_2$ (83.5 mg, 372 µmol, 0.1 equivalent) and bis(1-adamantyl)butylphosphane (267 mg, 743 µmol, 0.2 equivalent) in 2-methylbutan-2-ol (100 mL) was purged with nitrogen 3 times. This reaction mixture was stirred at 120° C. for 12 hours under a nitrogen atmosphere. After this time, the reaction mixture was diluted with ethyl acetate (50 mL) then it was filtered. The filtrate was washed with brine (30 mL×3), dried over sodium sulfate and concentrated. This crude product was purified further by column chromatography (SiO$_2$, dichloromethane/methanol 200/1 to 50/1) to give 7-(3,5-dimethyltriazol-4-yl)-5-nitro-2H-isoquinolin-1-one (7.4, 550 mg, 1.93 mmol, 51.8% yield) as a yellow solid; LCMS [M+1]: 286.2.

$^1$H NMR (400 MHz, DMSO-d$_6$) δ=11.96 (br s, 1H), 8.65-8.48 (m, 2H), 7.54 (br s, 1H), 6.97 (d, J=7.6 Hz, 1H), 3.99 (s, 3H), 2.28 (s, 3H)

Compound 7.5:

To a solution of 7-(3,5-dimethyltriazol-4-yl)-5-nitro-2H-isoquinolin-1-one (7.4, 500 mg, 1.75 mmol, 1 equivalent) in EtOH (40 mL) and H$_2$O (10 mL) was added iron powder (293 mg, 5.25 mmol, 3 equivalents) and NH$_4$Cl (749 mg, 14 mmol, 489 µL, 8 equivalents). This mixture was stirred at 75° C. for 4 hrs. When the reaction was complete, it was filtered to remove the suspended solids. The filtrate was concentrated and the resulting solid was suspended in water (3 mL) and was filtered. The filter cake was air-dried to give 5-amino-7-(3,5-dimethyltriazol-4-yl)-2H-isoquinolin-1-one (7.5, 420 mg, 1.65 mmol, 94% yield) as a light yellow solid.

Compound 7.6:

To a solution of 5-amino-7-(3,5-dimethyltriazol-4-yl)-2H-isoquinolin-1-one (7.5, 300 mg, 1.18 mmol, 1 equivalent) in MeOH (30 mL) was added 10% Pd/C (100 mg, 1.18 mmol, 1 equivalent). This mixture was shaken in a Parr apparatus at 25° C. for 48 hours under a hydrogen atmosphere (50 psi). The reaction vessel was purged repeatedly with nitrogen, then the catalyst was removed by filtration through a pad of diatomaceous earth under a stream of nitrogen. The filtrate was concentrated to give 5-amino-7-(3,5-dimethyltriazol-4-yl)-3,4-dihydro-2H-isoquinolin-1-one (7.6, 200 mg, 777 µmol, 66.1% yield) as a light yellow solid.

$^1$H NMR (400 MHz, DMSO-d$_6$) δ=7.91 (br s, 1H), 7.12 (d, J=1.6 Hz, 1H), 6.83 (d, J=1.6 Hz, 1H), 5.38 (s, 2H), 3.89 (s, 3H), 3.40-3.37 (m, 2H), 2.71-2.67 (m, 2H), 2.20 (s, 3H)

Compound 7.7:

To a solution of 5-amino-7-(3,5-dimethyltriazol-4-yl)-3,4-dihydro-2H-isoquinolin-1-one (7.6, 200 mg, 777 µmol, 1 equivalent) in AcOH (15 mL) was added NIS (175 mg, 777 µmol, 1 equivalent). The mixture was stirred at 25° C. for 2 hrs. After this time, the reaction mixture was quenched with water (1 mL) and concentrated. The crude product was purified further by preparative-TLC (SiO$_2$, dichloromethane/methanol 10/1) to isolate 5-amino-7-(3,5-dimethyltriazol-4-yl)-6-iodo-3,4-dihydro-2H-isoquinolin-1-one (7.7, 280 mg, 731 mol, 94% yield) as a yellow solid; LCMS [M+1]: 383.9.

$^1$H NMR (400 MHz, CD$_3$OD) δ=7.19 (s, 1H), 3.79 (s, 3H), 3.56 (t, J=6.8 Hz, 2H), 2.91 (t, J=6.8 Hz, 2H), 2.13 (s, 3H).

Compound 7.8:

To 5-amino-7-(3,5-dimethyltriazol-4-yl)-6-iodo-3,4-dihydro-2H-isoquinolin-1-one (7.7, 280 mg, 731 µmol, 1 equivalent) in AcOH (20 mL) and MeOH (2 mL) was added sulfuryl chloride (1.13 g, 8.40 mmol, 840 µL, 11.5 equivalents) at 12° C. The reaction mixture was stirred at 12° C. for 3 hours. After the reaction was complete, it was concentrated in vacuo, then was diluted with MeOH (10 mL) and the pH was adjusted to 8 with saturated sodium bicarbonate solution. The remaining solids were removed by filtration and the filtrate was concentrated. The crude product was purified further by preparative-TLC (SiO$_2$, dichloromethane/methanol 10/1) to isolate 5-amino-8-chloro-7-(3,5-dimethyltriazol-4-yl)-6-iodo-3,4-dihydro-2H-isoquinolin-1-one (7.8, 200 mg, 479 µmol, 65.5% yield) as a yellow solid; LCMS [M+1]: 418.0.

Compound 7.9:

To 5-amino-8-chloro-7-(3,5-dimethyltriazol-4-yl)-6-iodo-3,4-dihydro-2H-isoquinolin-1-one (7.8, 380 mg, 910 µmol, 1 equivalent) in AcOH (5 mL) and EtOH (50 mL) was added 5% Pd/C (200 mg, 910 µmol, 1 equivalent). This mixture was purged with hydrogen gas, then was stirred at 20° C. for 12 hours under an atmosphere of hydrogen at ambient pressure. After this time the reaction was complete; it was purged with nitrogen then was filtered and concentrated. The material that was obtained was purified by preparative-TLC (SiO$_2$, dichloromethane/methanol 10/1) to give 5-amino-8-chloro-7-(3,5-dimethyltriazol-4-yl)-3,4-dihydro-2H-isoquinolin-1-one (7.9, 240 mg, 823 µmol, 90.4% yield) as a yellow solid; LCMS [M+1]: 292.0.

Compound 7.10:

To a solution of 5-amino-8-chloro-7-(3,5-dimethyltriazol-4-yl)-3,4-dihydro-2H-isoquinolin-1-one (7.9, 140 mg, 480

µmol, 1 equivalent) in THF (4 mL) was added hydrobromic acid (3.2 g, 15.8 mmol, 2.15 mL, 37% solution in water, 33 equivalents) at 0° C. The mixture was stirred at 12° C. for 3 hours and was cooled to 0° C. To the cold solution was added solid CuBr (207 mg, 1.44 mmol, 43.9 µL, 3 equivalents); this was followed by NaNO$_2$ (49.7 mg, 720 µmol, 39.1 µL, 1.5 equivalents). The mixture was stirred at 0° C. for 2 hrs. After this time, the pH of the reaction mixture was adjusted to 8 by the addition of aqueous saturated sodium bicarbonate solution, then the slightly basic solution was extracted with ethyl acetate (20 mL×2). The combined organic phase was dried over sodium sulfate, then it was filtered and concentrated. The residue was purified by preparative-TLC (SiO$_2$, dichloromethane/methanol 10/1) to isolate the desired product 5-bromo-8-chloro-7-(3,5-dimethyltriazol-4-yl)-3,4-dihydro-2H-isoquinolin-1-one (7.10, 90 mg, 253 µmol, 52.7% yield) as a yellow solid; LCMS [M+1]: 356.9.

Compound 7.11:

To of 5-bromo-8-chloro-7-(3,5-dimethyltriazol-4-yl)-3,4-dihydro-2H-isoquinolin-1-one (7.10, 60 mg, 169 µmol, 1 equivalent) in DMF (2 mL) was added NaH (13.5 mg, 337 µmol, 60% suspension in oil, 2 equivalents). The mixture was stirred at 0° C. for 0.5 hr. After the evolution of gas subsided, (6-benzyloxy-4-methyl-furo[3,2-c]pyridin-7-yl)methyl methanesulfonate (1.11, 93.8 mg, 270 µmol, 1.6 equivalents) was added and the reaction was stirred at 0° C. for 1 hr. After this time the reaction was complete and was quenched by the addition of water (2 mL) at 0° C. The reaction mixture was extracted with ethyl acetate (20 mL×2), the organic phases were combined and washed with brine (25.0 mL×3). The clear organic solution was dried over sodium sulfate, then was filtered and concentrated to give a crude product. The desired compound 7.11, was isolated by purification with preparative scale TLC (SiO$_2$, petroleum ether/ethyl acetate 1/1). 2-[(6-benzyloxy-4-methyl-furo[3,2-c]pyridin-7-yl)methyl]-5-bromo-8-chloro-7-(3,5-dimethyltriazol-4-yl)-3,4-dihydroisoquinolin-1-one (7.11, 45.0 mg, 74.2 µmol, 44% yield) was obtained as a yellow solid; LCMS [M+1]:608.0.

EXAMPLE 7. 7-[[5-bromo-8-chloro-7-(3,5-dimethyltriazol-4-yl)-1-oxo-3,4-dihydroisoquinolin-2-yl]methyl]-4-methyl-5H-furo[3,2-c]pyridin-6-one: A solution of 2-[(6-benzyloxy-4-methyl-furo[3,2-c]pyridin-7-yl)methyl]-5-bromo-8-chloro-7-(3,5-dimethyltriazol-4-yl)-3,4-dihydroisoquinolin-1-one (7.11, 45 mg, 74.2 µmol, 1 equivalent) in DCM (2 mL) and TFA (1 mL) was stirred at 35° C. for 5 hrs. The reaction mixture was concentrated to give the crude product. This material was purified with preparative-HPLC (TFA condition, column: Boston pH-lex 150×25 10 um; mobile phase: [water (0.1% TFA)-ACN]; B %: 26%-56%, 10 min) to give 7-[[5-bromo-8-chloro-7-(3,5-dimethyltriazol-4-yl)-1-oxo-3,4-dihydroisoquinolin-2-yl]methyl]-4-methyl-5H-furo[3,2-c]pyridin-6-one (EXAMPLE 7, 37 mg, 71.5 µmol, 96.5% yield, 99.9% purity) as a pink solid; LCMS [M+1]: 518.2.

$^1$H NMR (400 MHz, CD$_3$OD) δ=7.82 (s, 1H), 7.61 (d, J=2.4 Hz, 1H), 6.84 (d, J=2.4 Hz, 1H), 4.91 (s, 2H), 3.86 (s, 3H), 3.71 (t, J=6.4 Hz, 2H), 3.15-3.09 (m, 2H), 2.55 (s, 3H), 2.18 (s, 3H).

Example 8

7-((5,8-dichloro-7-isopropoxy-1-oxo-3,4-dihydroisoquinolin-2(1H)-yl)methyl)-2,4-dimethylfuro[3,2-c]pyridin-6(5H)-one

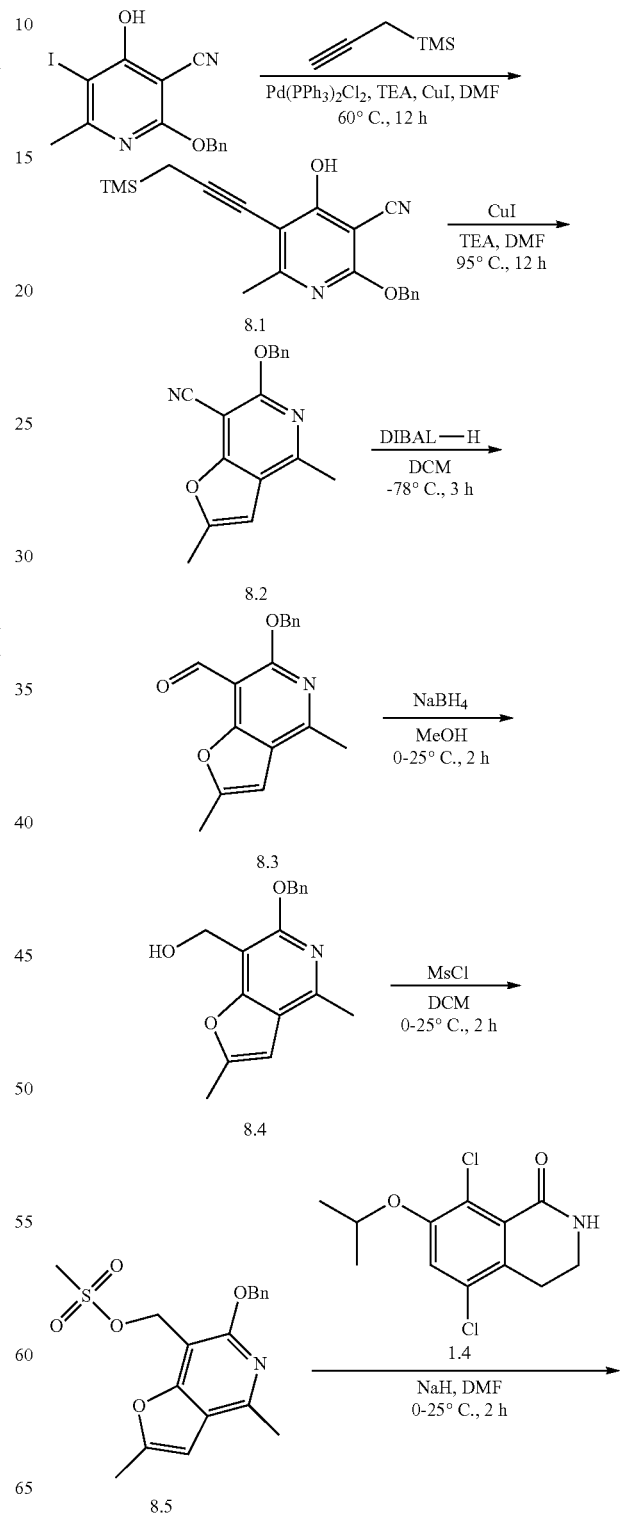

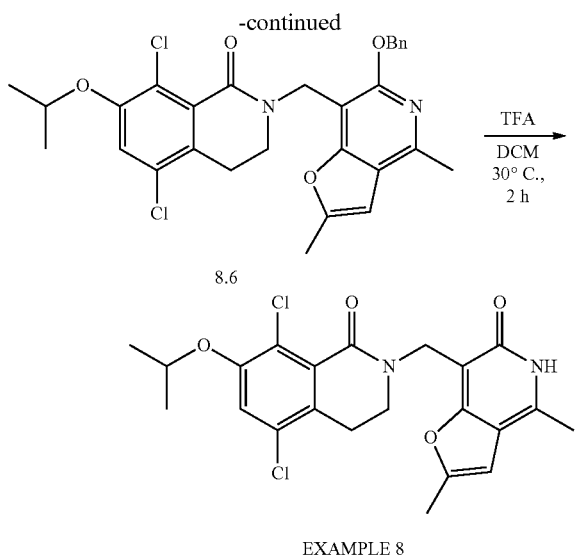

EXAMPLE 8

Compound 8.1.

To a solution of 2-benzyloxy-4-hydroxy-5-iodo-6-methyl-pyridine-3-carbonitrile (600 mg, 1.64 mmol, 1.00 eq.), trimethyl(prop-2-ynyl)silane (239 mg, 2.13 mmol, 319 µL, 1.30 eq.), cuprous iodide (62.4 mg, 328 µmol, 0.20 eq.), bis(triphenylphosphine)palladium(II) dichloride (115 mg, 164 µmol, 0.10 eq) in DMF (6.00 mL) was added TEA (663 mg, 6.55 mmol, 909 µL, 4.00 eq) under nitrogen atmosphere, the mixture was stirred at 25° C. for 3 hours, then stirred at 60° C. for 6 hours. After cooled to room temperature, the reaction solution was filtered, the filtrate was evaporated under reduced pressure to give a brown residue which could be used directly for the next step. LCMS [M+1]: 351.3.

Compound 8.2.

To a solution of 2-benzyloxy-4-hydroxy-6-methyl-5-(3-trimethylsilylprop-1-ynyl)pyridine-3-carbonitrile (574 mg, 1.64 mmol, 1.00 eq.) in DMF (6.00 mL) was added cuprous iodide (249 mg, 1.31 mmol, 1.00 eq.), TEA (497 mg, 4.91 mmol, 681 µL, 3.00 eq.), the mixture was stirred at 95° C. for 12 hours. After cooled to room temperature, the solvent was removed under reduced pressure to give a brown residue which was purified by column chromatography (SiO$_2$, Petroleum ether/Ethyl acetate 20/1), obtained 6-benzyloxy-2,4-dimethyl-furo[3,2-c]pyridine-7-carbonitrile (200 mg, 43.0% yield, 98.0% purity) as a white solid. LCMS [M+1]: 279.3.

$^1$H NMR (400 MHz, chloroform-d) δ=7.52 (d, J=7.2 Hz, 2H), 7.41-7.35 (m, 2H), 7.34-7.29 (m, 1H), 6.36 (d, J=1.2 Hz, 1H), 5.54 (s, 2H), 2.61 (s, 3H), 2.47 (s, 3H).

Compound 8.3.

To a stirred solution of 6-benzyloxy-2,4-dimethyl-furo[3,2-c]pyridine-7-carbonitrile (122 mg, 438 µmol, 1 eq.) in DCM (1.00 mL) was added DIBAL-H (1 M, 614 µL, 1.4 eq.) under −78° C., the mixture was stirred at −78° C. for 3 hours. The reaction was quenched by adding saturated NH$_4$Cl solution (2.00 mL) slowly at 0° C., then extracted by DCM (5.00 mL×3) and washed by brine (5.00 mL×1), dried over sodium sulfate and the solvent was removed to afford 6-benzyloxy-2,4-dimethyl-furo[3,2-c]pyridine-7-carbaldehyde (100 mg, crude) was obtained as a yellow oil. LCMS [M+1]: 279.3.

Compound 8.4.

To a solution of 6-benzyloxy-2,4-dimethyl-furo[3,2-c]pyridine-7-carbaldehyde (95 mg, 337 µmol, 1.0 eq.) in MeOH (1.00 mL) was added NaBH$_4$ (25.6 mg, 675 mol, 2.0 eq.) at 0° C., after stirred at 25° C. for 2 hours, the reaction mixture was quenched by saturated NH$_4$Cl solution (2.00 mL), then extracted by ethyl acetate (10.0 mL×3), dried over sodium sulfate and the solvent was removed to afford the residue which was purified by column chromatography (SiO$_2$, Petroleum ether/Ethyl acetate 10/1) to give (6-benzyloxy-2,4-dimethyl-furo[3,2-c]pyridin-7-yl)methanol (16.0 mg, 45.9 µmol, 13.6% yield, 81.3% purity) as a light yellow solid. LCMS [M+1]: 284.2.

$^1$H NMR (400 MHz, chloroform-d) δ=7.48 (br d, J=7.2 Hz, 2H), 7.41-7.29 (m, 3H), 6.30 (s, 1H), 5.50 (s, 2H), 4.92 (br d, J=3.6 Hz, 2H), 2.57 (s, 3H), 2.43 (s, 3H).

Compound 8.5.

To a solution of (6-benzyloxy-2,4-dimethyl-furo[3,2-c]pyridin-7-yl)methanol (40 mg, 141 µmol, 1.0 eq), TEA (42.86 mg, 424 µmol, 59.0 µL, 3 eq.) in DCM (1.00 mL) was added methanesulfonyl chloride (32.3 mg, 282 ummol, 21.9 µL, 2.0 eq.) at 0° C., the mixture was stirred at 25° C. for 1 hour. The reaction was quenched by adding water (5.00 mL), extracted by ethyl acetate (5.00 mL×3), dried over sodium sulfate and the solvent was removed to afford the crude product. The residue was purified by column chromatography (SiO$_2$, Petroleum ether/Ethyl acetate 20/1) to afford (6-benzyloxy-2,4-dimethyl-furo[3,2-c]pyridin-7-yl)methyl methanesulfonate (25 mg, 69.1 µmol, 49.0% yield, 99.9% purity) as a white solid.

Compound 8.6.

To a solution of 5,8-dichloro-7-isopropoxy-3,4-dihydro-2H-isoquinolin-1-one (18.96 mg, 69.17 µmol, 1.25 eq.) in DMF (1.00 mL) was added NaH (4.43 mg, 110.68 µmol, 60.0% purity, 2.0 eq.) and stirred for 15 min at 0° C., then (6-benzyloxy-2,4-dimethyl-furo[3,2-c]pyridin-7-yl)methyl methanesulfonate (20 mg, 55.3 µmol, 1 eq) in DMF (1.00 mL) was added to the mixture and stirred at 25° C. for 2 hours. The reaction was quenched by adding water (5.00 mL), extracted by ethyl acetate (5.00 mL×3), dried over sodium sulfate and the solvent was removed to afford the crude product, the residue was purified by column chromatography (SiO$_2$, Petroleum ether/Ethyl acetate 30/1) to afford 2-[(6-benzyloxy-2,4-dimethyl-furo[3,2-c]pyridin-7-yl)methyl]-5,8-dichloro-7-isopropoxy-3,4-dihydroisoquinolin-1-one (15.0 mg, 16.7 µmol, 30.2% yield, 60.0% purity) as a yellow solid. LCMS [M+1]: 539.3.

EXAMPLE 8. To a solution of 2-[(6-benzyloxy-2,4-dimethyl-furo[3,2-c]pyridin-7-yl)methyl]-5,8-dichloro-7-isopropoxy-3,4-dihydroisoquinolin-1-one (10 mg, 18.5 µmol, 1.0 eq.) in DCM (500 µL) was added TFA (500 µL), the mixture was stirred at 30° C. for 1 hr. The residue was purified by prep-HPLC (mobile phase: [water (0.1% TFA)-ACN]; B %: 37%-67%, 10 min) to afford 7-[(5,8-dichloro-7-isopropoxy-1-oxo-3,4-dihydroisoquinolin-2-yl)methyl]-2,4-dimethyl-5H-furo[3,2-c]pyridin-6-one (2.89 mg 33.0% yield, 95.0% purity) as a white solid. LCMS [M+1]: 449.1.

$^1$H NMR (400 MHz, methanol-d$_4$) δ=7.29 (s, 1H), 6.39 (d, J=1.2 Hz, 1H), 4.86 (br s, 2H), 4.64 (td, J=6.0, 12.0 Hz, 1H), 3.57 (t, J=6.4 Hz, 2H), 2.96 (t, J=6.4 Hz, 2H), 2.47 (s, 3H), 2.32 (s, 3H), 1.36 (s, 3H), 1.35 (s, 3H).

Example 9

7-((5,8-dichloro-7-(methoxy(oxetan-3-yl)methyl)-1-oxo-3,4-dihydroisoquinolin-2(1H)-yl)methyl)-4-methylfuro[3,2-c]pyridin-6(5H)-on

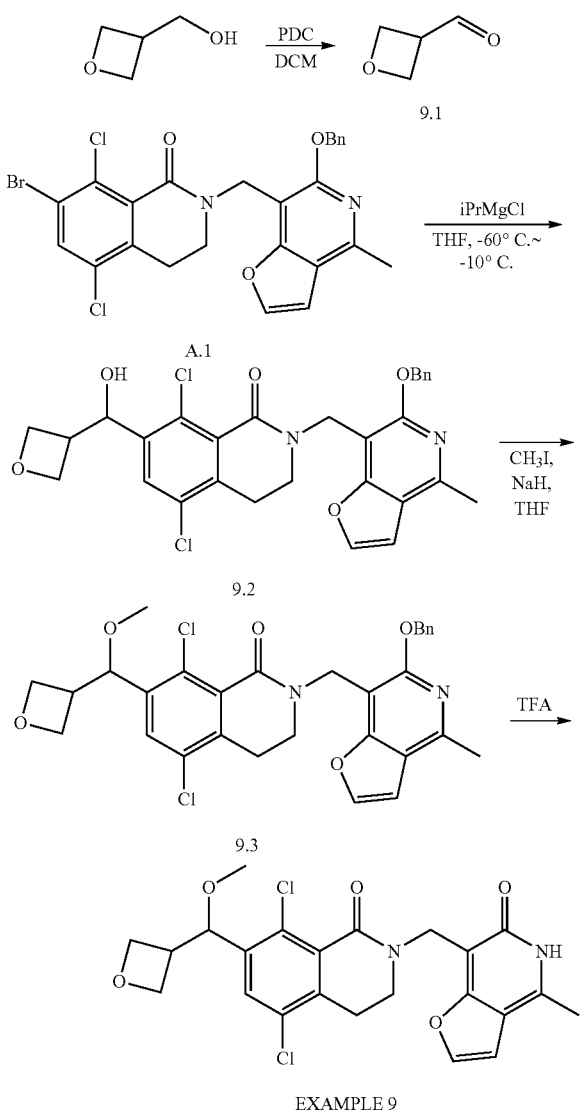

EXAMPLE 9

Compound 9.1:

To a solution of oxetan-3-ylmethanol (0.50 g, 5.68 mmol, 1 equivalent) in DCM (25 mL) was added pyridinium dichromate (1.39 g, 3.69 mmol, 0.65 equivalent) in five portions. After stirred at 25° C. for 16 hours, the resulting black mixture was filtered through a silica gel pad and washed with DCM (8×10 mL), dried over sodium sulfate then concentrated under reduced pressure to give the oxetane-3-carbaldehyde (9.1) as a yellow oil (0.38 g, yield=58.7%). This material was used without further purification.

Compound 9.2:

To a solution of 2-[(6-benzyloxy-4-methyl-furo[3,2-c]pyridin-7-yl)methyl]-7-bromo-5,8-dichloro-3,4-dihydroisoquinolin-1-one (Intermediate A.1, 0.18 g, 330 mol, 1 equivalent) in THF (3 mL) was added isopropylmagnesium chloride (2.0 M solution in THF, 494 μL, 3 equivalents) at −78° C. and was stirred for 1 hour. After this time, oxetane-3-carbaldehyde (142 mg, 1.65 mmol, 5 equivalents) was added to the mixture over 10 minutes, then the mixture was warmed to ambient temperature over 50 minutes. The reaction was quenched with MeOH (5 mL) and the solvent was evaporated to afford the crude product. This material was purified by flash chromatography on silica gel (petroleum ether/ethyl acetate=3/1) to give 2-((6-(benzyloxy)-4-methylfuro[3,2-c]pyridin-7-yl)methyl)-5,8-dichloro-7-(hydroxy(oxetan-3-yl)methyl)-3,4-dihydroisoquinolin-1(2H)-one as a yellow solid (9.2, 0.06 g, yield=31.3%); LC-MS [M+1]$^+$: 553.3.

Compound 9.3:

To a solution of 2-[(6-benzyloxy-4-methyl-furo[3,2-c]pyridin-7-yl)methyl]-5,8-dichloro-7-[hydroxy(oxetan-3-yl)methyl]-3,4-dihydroisoquinolin-1-one (9.2, 0.01 g, 18 μmol, 1 equivalent) in THF (5 mL) was added NaH (2.17 mg, 54.2 μmol, 60% suspension in mineral oil, 3 equivalents) at 0° C. After this was stirred for 5 minutes, iodomethane (5.13 mg, 36.1 μmol, 2.25 μL, 2 equivalents) was added to the mixture and this was stirred at 25° C. for 1 hour. The residue was quenched with MeOH (5 mL), then the solvent was evaporated and was purified by flash chromatography on silica gel (petroleum ether/ethyl acetate=5/1) to give the desired product as a yellow solid (9.3, 8 mg, yield=70.2%); LC-MS [M+1]$^+$: 567.3.

EXAMPLE 9. 7-((5,8-dichloro-7-(methoxy(oxetan-3-yl)methyl)-1-oxo-3,4-dihydroisoquinolin-2(1H)-yl)methyl)-4-methylfuro[3,2-c]pyridin-6(5H)-one: To a solution of 2-[(6-benzyloxy-4-methyl-furo[3,2-c]pyridin-7-yl)methyl]-5,8-dichloro-7-[methoxy(oxetan-3-yl)methyl]-3,4-dihydroisoquinolin-1-one (9.3, 0.03 g, 52.9 μmol, 1 equivalent) in DCM (2 mL) was added TFA (2.05 g, 18.0 mmol, 1.33 mL, 340 equivalents), the mixture was stirred at 25° C. for 8 hours. The solvent was removed under reduced pressure to afford the crude product which was purified by preparative scale HPLC (column: Phenomenex Synergi C18 150×25×10 μm; mobile phase, A: water (0.1% TFA), B: ACN; B %: 20%-50%, 12 minute gradient) to give 7-((5,8-dichloro-7-(methoxy(oxetan-3-yl)methyl)-1-oxo-3,4-dihydroisoquinolin-2(1H)-yl)methyl)-4-methylfuro[3,2-c]pyridin-6(5H)-one as a pink solid (EXAMPLE 9, 5 mg, yield=18.7%, purity=94.5%); LC-MS [M+1]$^+$: 477.3.

$^1$H NMR (400 MHz, CDCl$_3$) δ=7.70 (d, J=2.4 Hz, 1H), 7.53 (s, 1H), 6.77 (d, J=2.4 Hz, 1H), 5.04 (d, J=6.0 Hz, 1H), 4.90 (s, 2H), 4.77-4.70 (m, 1H), 4.69-4.53 (m, 3H), 3.81 (br t, J=6.0 Hz, 2H), 3.41-3.30 (m, 1H), 3.28 (s, 3H), 3.06 (br t, J=6.0 Hz, 2H), 2.74 (s, 3H).

Example 10

7-((5,8-dichloro-7-(methoxy(1-methylazetidin-3-yl)methyl)-1-oxo-3,4-dihydroisoquinolin-2(1H)-yl)methyl)-4-methylfuro[3,2-c]pyridin-6(5H)-one

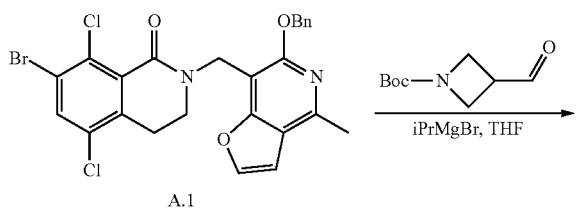

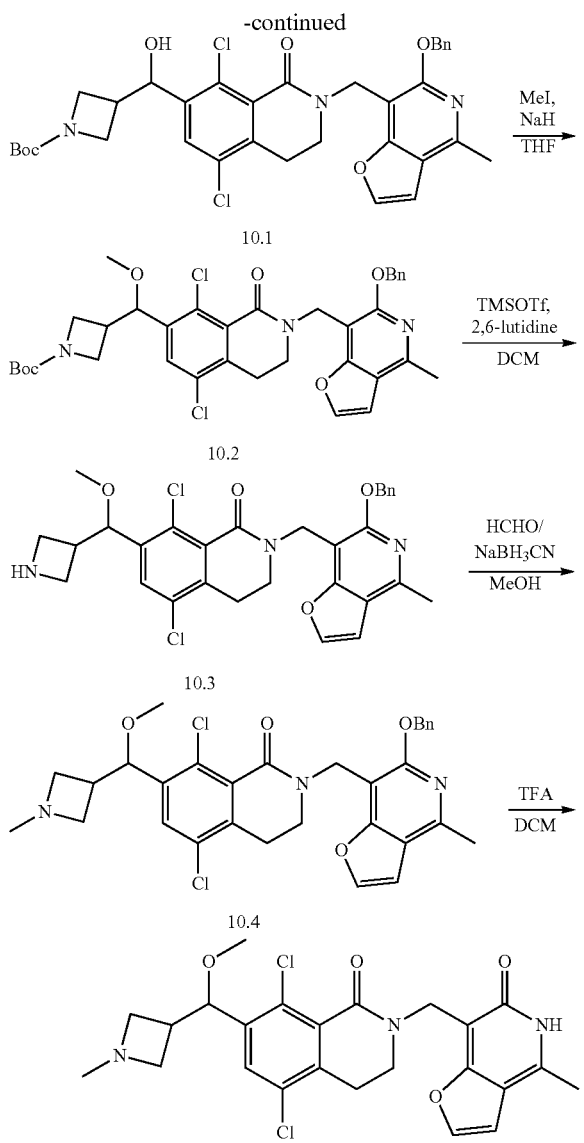

EXAMPLE 10

Compound 10.1:

To a solution of 2-[(6-benzyloxy-4-methyl-furo[3,2-c]pyridin-7-yl)methyl]-7-bromo-5,8-dichloro-3,4-dihydroisoquinolin-1-one (Intermediate A.1, 0.16 g, 293 mol, 1 equivalent) in THF (3 mL) was added isopropylmagnesium chloride (2.0 M solution in THF, 439 μL, 3 equivalents) dropwise at −65° C. over 5 minutes. After this time, the reaction mixture was warmed to −10° C. and maintained 30 minutes at this temperature, then a THF (2 mL) solution of tert-butyl 3-formylazetidine-1-carboxylate (271 mg, 1.46 mmol, 5 equivalents) was added to the mixture over 5 minutes. After the reaction was stirred for 30 minutes, it was quenched with MeOH (1 mL). The solvent was removed to give the crude product (10.1) which was purified by flash chromatography on silica gel (petroleum ether/ethyl acetate=2/1) to give tert-butyl 3-((2-((6-(benzyloxy)-4-methylfuro[3,2-c]pyridin-7-yl)methyl)-5,8-dichloro-1-oxo-1,2,3,4-tetrahydroisoquinolin-7-yl)(hydroxy)methyl)azetidine-1-carboxylate as a yellow solid (10.1, 0.10 g, yield=49.7%); LC-MS [M+1]+: 652.3.

Compound 10.2:

To a solution of tert-butyl 3-[[2-[(6-benzyloxy-4-methyl-furo[3,2-c]pyridin-7-yl)methyl]-5,8-dichloro-1-oxo-3,4-dihydroisoquinolin-7-yl]-hydroxy-methyl]azetidine-1-carboxylate (10.1, 0.15 g, 230 μmol, 1 equivalent) in THF (1 mL) was added NaH (55.2 mg, 1.38 mmol, 60% suspension in mineral oil, 6 equivalents) at 0° C. After gas evolution ceased, iodomethane (326 mg, 2.3 mmol, 143 μL, 10 equivalents) was added to the mixture and this was stirred for 1 hour. The reaction was quenched with water (10 mL), was extracted with ethyl acetate (5 mL×3), then was dried over sodium sulfate. The solvent was removed to give tert-butyl 3-((2-((6-(benzyloxy)-4-methylfuro[3,2-c]pyridin-7-yl)methyl)-5,8-dichloro-1-oxo-1,2,3,4-tetrahydroisoquinolin-7-yl)(methoxy)methyl)azetidine-1-carboxylate as a yellow solid (10.2, 120 mg, yield=78.3%). This material was carried on to the next step without further purification; LC-MS [M+H]+: 666.4.

Compound 10.3:

To a solution of tert-butyl 3-[[2-[(6-benzyloxy-4-methyl-furo[3,2-c]pyridin-7-yl)methyl]-5,8-dichloro-1-oxo-3,4-dihydroisoquinolin-7-yl]-methoxy-methyl]azetidine-1-carboxylate (10.2, 0.05 g, 75.0 μmol, 1 equivalent), 2,6-lutidine (40.2 mg, 375 μmol, 43.7 μL, 5 equivalents) in DCM (1 mL) was added TMSOTf (41.7 mg, 188 μmol, 33.9 μL, 2.5 equivalents) at 25° C. After the reaction mixture was stirred for 12 hours, the solvent was removed to afford the crude product. This material was purified by flash chromatography on silica gel (petroleum ether/ethyl acetate=1/1) to give 7-(azetidin-3-yl(methoxy)methyl)-2-((6-(benzyloxy)-4-methylfuro[3,2-c]pyridin-7-yl)methyl)-5,8-dichloro-3,4-dihydroisoquinolin-1(2H)-one as a yellow oil (10.3, 0.035 g, yield=74.9%); LC-MS [M+1]+: 566.4.

Compound 10.4:

To a solution of 7-[azetidin-3-yl(methoxy)methyl]-2-[(6-benzyloxy-4-methyl-furo[3,2-c]pyridin-7-yl)methyl]-5,8-dichloro-3,4-dihydroisoquinolin-1-one (10.3, 0.05 g, 88.3 μmol, 1 equivalent) in methanol (1 mL) was added formaldehyde (71.6 mg, 883 μmol, 65.7 μL, 37% purity, 10 equivalents) and acetic acid (5.3 mg, 88.3 μmol, 5.05 μL, 1 equivalent) at 25° C. After this mixture was stirred for 30 minutes, NaBH₃CN (16.6 mg, 265 μmol, 3 equivalents) was added in several portions and the mixture was stirred for an additional 12 hours. The reaction was quenched with water (10 mL), was extracted with ethyl acetate (10 mL×3), then was dried over sodium sulfate and the solvent was removed to give a crude product. This material was purified further by flash chromatography on silica gel (petroleum ether/ethyl acetate=3/1) to give 2-((6-(benzyloxy)-4-methylfuro[3,2-c]pyridin-7-yl)methyl)-5,8-dichloro-7-(methoxy(1-methylazetidin-3-yl)methyl)-3,4-dihydroisoquinolin-1(2H)-one as a yellow oil (10.4, 32 mg, yield=56.2%); LC-MS [M+1]+: 580.4.

EXAMPLE 10. 7-((5,8-dichloro-7-(methoxy(1-methylazetidin-3-yl)methyl)-1-oxo-3,4-dihydroisoquinolin-2(1H)-yl)methyl)-4-methylfuro[3,2-c]pyridin-6(5H)-one: To a solution of 2-[(6-benzyloxy-4-methyl-furo[3,2-c]pyridin-7-yl)methyl]-5,8-dichloro-7-[methoxy-(1-methylazetidin-3-yl)methyl]-3,4-dihydroisoquinolin-1-one (10.4, 35 mg, 60.3 μmol, 1 equivalent) in DCM (1 mL) was added trifluoroacetic acid (0.5 mL). The reaction mixture was stirred at 25° C. for 12 hours. After this time the solvent was removed to give a crude product which was purified by preparative scale HPLC (column: Phenomenex Synergi C₁₈ 150×25×10 um; mobile phase, A: water (0.1% TFA), B: ACN; B %: 8%-38%, 12 minute gradient) to give 7-((5,8-dichloro-7-(methoxy(1-methylazetidin-3-yl)methyl)-1-oxo-3,4-dihydroisoquinolin-2(1H)-yl)methyl)-4-methylfuro[3,2-c]pyridin-6(5H)-one as a white solid (EXAMPLE 10, 12 mg, yield=33.65%, purity=99.6%); LC-MS [M+H]+: 490.4.

¹H NMR (400 MHz, CDCl₃) δ=12.45 (br s, 1H), 7.72 (d, J=2.4 Hz, 1H), 7.42 (s, 1H), 6.77 (d, J=2.4 Hz, 1H), 5.03-4.84 (m, 2H), 4.77 (d, J=2.8 Hz, 1H), 4.61-4.48 (m, 1H), 4.22-4.13 (m, 1H), 3.95-3.71 (m, 4H), 3.40 (s, 3H), 3.38-3.28 (m, 1H), 3.14-3.02 (m, 2H), 2.89 (d, J=4.4 Hz, 3H), 2.75 (s, 3H).

Example 11

5,8-dichloro-7-(methoxy(1-methylazetidin-3-yl)methyl)-2-((7-methyl-5-oxo-5,6-dihydro-1H-pyrrolo[2,3-c]pyridin-4-yl)methyl)-3,4-dihydroisoquinolin-1(2H)-one

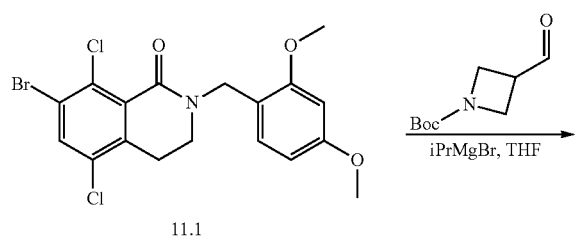

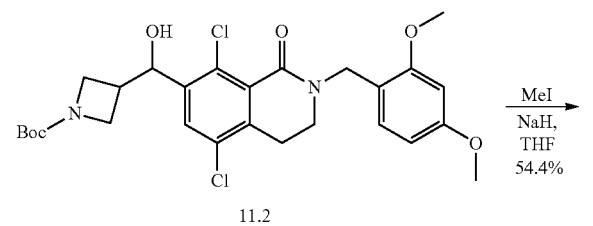

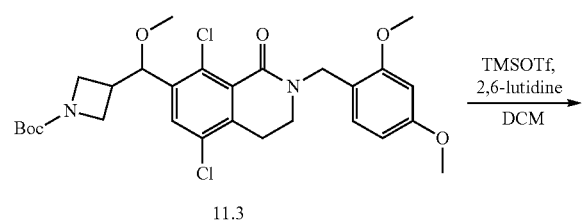

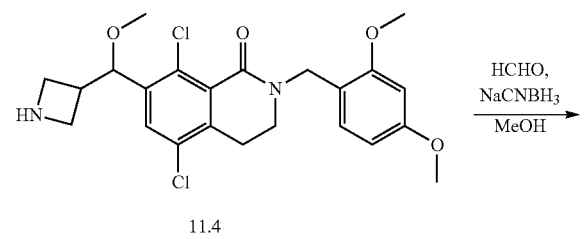

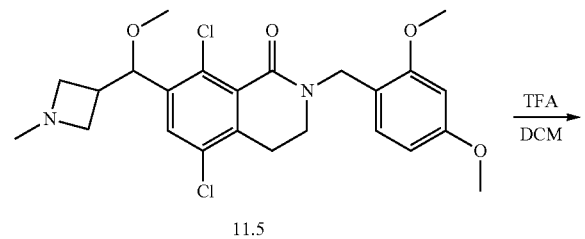

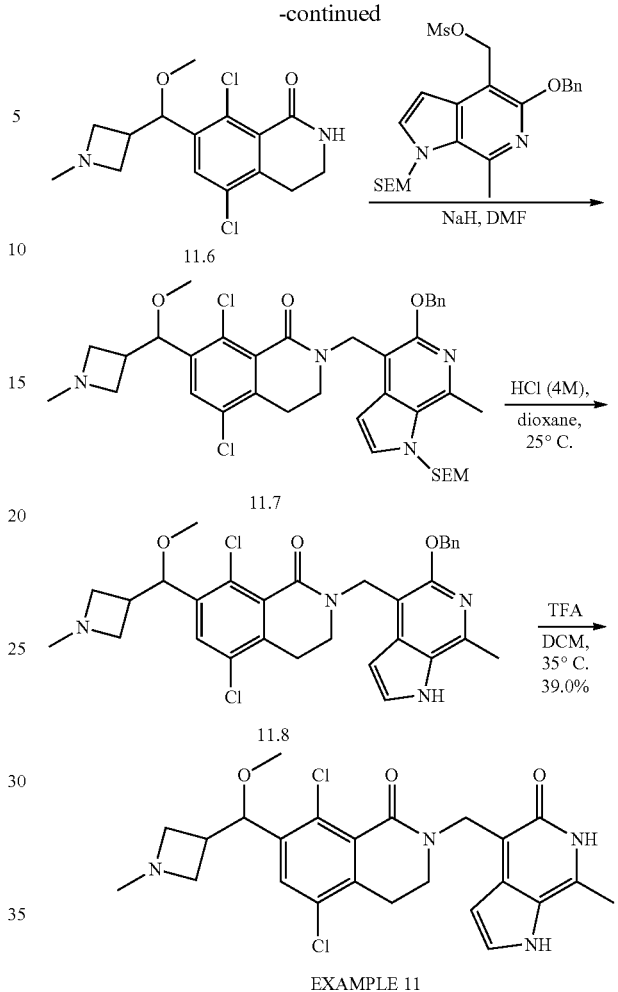

EXAMPLE 11 (Example EA, Table 2) was prepared from compound 11.1.

Compound 11.2:

To a solution of 7-bromo-5,8-dichloro-2-[(2,4-dimethoxyphenyl)methyl]-3,4-dihydroisoquinolin-1-one (11.1, 300 mg, 674 μmol, 1 equivalent) in THF (4 mL) was added i-PrMgCl (2 M, 1.01 mL, 3 equivalent) dropwise at −60° C. This reaction was stirred at −60° C. for 30 min. then the mixture was warmed to −10° C. slowly. tert-Butyl 3-formylazetidine-1-carboxylate (624 mg, 3.37 mmol, 5 equivalent) was added slowly to this cooled mixture then it was warmed to 0° C. and stirred for 1 hr. The reaction mixture was quenched by the addition of saturated aqueous NH₄Cl solution (10 mL). The resulting mixture was extracted with ethyl acetate (20 mL×3), the organic phases combined then washed with brine (30 mL×3), dried over sodium sulfate, filtered and concentrated in vacuo. The residue was purified by column chromatography (SiO₂, Petroleum ether/Ethyl acetate=10/1 to 2/1) to give tert-butyl3-[[5,8-dichloro-2-[(2,4-dimethoxyphenyl)methyl]-1-oxo-3,4-dihydroisoquinolin-7-yl]-hydroxy-methyl]azetidine-1-carboxylate (11.2, 550 mg, crude) as a light yellow oil; LCMS [M+1]: 459.1.

Compound 11.3:

To a solution of tert-butyl 3-[[5,8-dichloro-2-[(2,4-dimethoxyphenyl) methyl]-1-oxo-3,4-dihydroisoquinolin-7-yl]-hydroxy-methyl]azetidine-1-carboxylate (11.2, 800 mg, 1.45 mmol, 1 equivalent) in THF (5 mL) was added NaH (116 mg, 2.9 mmol, 60% suspension in mineral oil, 2 equivalent), the mixture was stirred at 0° C. for 0.5 hr, then MeI (515 mg, 3.63 mmol, 226 µL, 2.5 equivalent) was added dropwise. After the addition was finished, the mixture was warmed to 15° C. and stirred for 3 hrs. The reaction mixture was quenched by the addition of water (10 mL). This mixture was extracted with ethyl acetate (30 mL×2); then the organic phases were combined and washed with brine (30 mL×3), dried over sodium sulfate, filtered and concentrated in vacuo. The residue was purified by column chromatography (SiO$_2$, Petroleum ether/Ethyl acetate=8/1 to 3/1) to give tert-butyl 3-[[5,8-dichloro-2-[(2,4-dimethoxyphenyl) methyl]-1-oxo-3,4-dihydroisoquinolin-7-yl]-methoxy-methyl]azetidine-1-carboxylate (11.3, 470 mg, 790 µmol, 54.4% yield, 95% purity) as a light yellow oil.

$^1$H NMR (400 MHz, CDCl$_3$) δ=7.53 (s, 1H), 7.33 (d, J=8.8 Hz, 1H), 6.49-6.44 (m, 2H), 4.91 (d, J=5.6 Hz, 1H), 4.73 (s, 2H), 3.96 (dd, J=6.0, 8.4 Hz, 1H), 3.93-3.86 (m, 2H), 3.84 (s, 3H), 3.81 (s, 3H), 3.78-3.70 (m, 2H), 3.54-3.49 (m, 2H), 3.37 (s, 1H), 3.29 (s, 3H), 2.93 (t, J=6.4 Hz, 2H), 1.45 (s, 9H).

Compound 11.4:

To a solution of tert-butyl 3-[[5,8-dichloro-2-[(2,4-dimethoxyphenyl) methyl]-1-oxo-3,4-dihydroisoquinolin-7-yl]-methoxy-methyl]azetidine-1-carboxylate (11.3, 470 mg, 831 µmol, 1 equivalent) in DCM (5 mL) was added 2,6-lutidine (712 mg, 6.65 mmol, 774 µL, 8 equivalent) followed by TMSOTf (462 mg, 2.08 mmol, 375 µL, 2.5 equivalent) at 0° C. This mixture was stirred at 15° C. for 12 hrs, then the reaction mixture was concentrated. The residue was purified by column chromatography (SiO$_2$, DCM: MeOH=200/1 to 50/1) to give 7-[azetidin-3-yl(methoxy)methyl]-5,8-dichloro-2-[(2,4-dimethoxyphenyl) methyl]-3,4-dihydroisoquinolin-1-one (11.4, 670 mg, 605 µmol, 72.8% yield, 42% purity) as a yellow oil; LCMS [M+1]: 465.1.

Compound 11.5:

To a solution of 7-[azetidin-3-yl(methoxy)methyl]-5,8-dichloro-2-[(2,4-dimethoxyphenyl)methyl]-3,4-dihydroisoquinolin-1-one (11.4, 670 mg, 605 µmol, 1 equivalent) in MeOH (5 mL) was added formaldehyde (736 mg, 9.07 mmol, 675 µL, 37% purity, 15 equivalent) and AcOH (109 mg, 1.81 mmol, 104 µL, 3 equivalent). This mixture was stirred at 15° C. for 0.5 hr. After this time, NaBH$_3$CN (380 mg, 6.05 mmol, 10 equivalent) was added in three potions and stirred at 15° C. for 12 hrs. The reaction mixture was quenched with water (10 mL), extracted with DCM (30 mL) then was washed with brine (15 mL×3). The organic phase was dried over sodium sulfate, filtered and concentrated. The residue was purified by preparative scale TLC (SiO$_2$, DCM/MeOH=10/1) to give 5,8-dichloro-2-[(2,4-dimethoxyphenyl)methyl]-7-[methoxy-(1-methyl azetidine-3-yl) methyl]-3,4-dihydroisoquinolin-1-one (11.5, 250 mg, 519 µmol, 85.8% yield, 99.5% purity) as a yellow oil; LCMS [M+1]: 479.1.

Compound 11.6:

To a solution of 5,8-dichloro-2-[(2,4-dimethoxyphenyl) methyl]-7-[methoxy-(1-methylazetidin-3-yl)methyl]-3,4-dihydroisoquinolin-1-one (11.5, 250 mg, 519 mol, 1 equivalent) in DCM (10 mL) was added TFA (5.92 g, 51.9 mmol, 3.84 mL, 100 equivalent) and stirred at 35° C. for 12 hrs. The reaction mixture was quenched and pH adjusted to 7 with saturated aqueous sodium bicarbonate solution. The mixture was extracted with DCM (20 mL×2); the combined organic phases were dried over sodium sulfate, filtered and concentrated in vacuo. The residue was purified by preparative scale TLC (SiO$_2$, DCM/MeOH 10/1) to give 5,8-dichloro-7-[methoxy-(1-methylazetidin-3-yl)methyl]-3,4-dihydro-2H-isoquinolin-1-one (11.6, 120 mg, 365 µmol, 70.3% yield) as a light yellow solid; LCMS [M+1]: 329.0.

Compound 11.7:

To a solution of 5,8-dichloro-7-[methoxy-(1-methylazetidin-3-yl) methyl]-3,4-dihydro-2H-isoquinolin-1-one (11.6, 80 mg, 243 µmol, 1 equivalent) in DMF (2 mL) was added sodium hydride (19.4 mg, 486 µmol, 60% suspension in mineral oil, 2 equivalent) at 0° C. The reaction was stirred at 0° C. for 0.5 hour, then a solution of [5-benzyloxy-7-methyl-1-(2-trimethylsilylethoxymethyl)pyrrolo[2,3-c]pyridin-4-yl]methyl methanesulfonate (116 mg, 243 µmol, 1 equivalent) in DMF (0.2 mL) was added dropwise. The reaction was warmed to 25° C. and stirred for 1 hour. The reaction mixture was quenched by addition of water (5 mL) and was extracted with ethyl acetate (5 mL×3). The combined organic phases were washed with brine (5 mL×2), dried with anhydrous sodium sulfate, then filtered and concentrated. The crude product was purified by preparative scale TLC (Petroleum ether/Ethyl acetate=1/1) to give 2-[[5-benzyloxy-7-methyl-1-(2-trimethylsilylethoxy methyl)pyrrole[2,3-c]pyridin-4-yl]methyl]-5,8-dichloro-7-[methoxy-(1-methylazetidin-3-yl)methyl]-3,4-dihydroisoquinolin-1-one (11.7, 90 mg 42% yield) as a brown oil; LCMS: [M+1]709.0.

Compound 11.8:

To a solution of 2-[[5-benzyloxy-7-methyl-1-(2-trimethylsilylethoxy methyl)pyrrolo[2,3-c]pyridin-4-yl]methyl]-5, 8-dichloro-7-[methoxy-(1-methylazetidin-3-yl) ethyl]-3,4-dihydroisoquinolin-1-one (11.7, 70 mg, 78.9 µmol, 1 equivalent) in dioxane (1 mL) was added hydrochloric acid (1 mL, 4 M). The reaction was stirred at 40° C. for 44 hrs. The reaction pH was adjusted to 6 with aqueous saturated sodium bicarbonate solution (10 mL) then was extracted with DCM (5 mL×3). The combined organic phase was washed with brine (2 mL×2), dried with anhydrous sodium sulfate, filtered and concentrated. The residue was purified by preparative scale TLC (Dichloromethane/Methanol=10/1) to give 2-[(5-benzyloxy-7-methyl-1H-pyrrolo[2,3-c]pyridin-4-yl)methyl]-5,8-dichloro-7-[methoxy-(1-methylazetidin-3-yl)methyl]-3,4-dihydroisoquinolin-1-one (11.8, 40 mg, 56% yield) as a brown oil; LCMS: [M+1] 579.3.

EXAMPLE 11. A solution of 2-[(5-benzyloxy-7-methyl-1H-pyrrolo[2,3-c]pyridin-4-yl) methyl]-5,8-dichloro-7-[methoxy-(1-methylazetidin-3-yl)methyl]-3,4-dihydroisoquinolin-1-one (11.8, 20 mg, 34.5 µmol, 1 equivalent) in DCM (1 mL) and TFA (1 mL) was stirred at 30° C. for 12 hours. The reaction was concentrated to give the crude product; this was purified by preparative scale HPLC (TFA buffer), 5,8-dichloro-7-[methoxy-(1-methylazetidin-3-yl) methyl]-2-[(7-methyl-5-oxo-1,6-dihydropyrrolo[2,3-c]pyridin-4-yl)methyl]-3,4-dihydroisoquinolin-1-one (EXAMPLE 11, 13.2 mg, 39% yield, 99.7% purity, TFA salt) was obtained as a brown oil; LCMS: [M+1] 489.2.

$^1$H NMR (400 MHz, DMSO-d6) δ=11.52 (br s, 1H), 7.68 (br s, 1H), 7.55 (s, 1H), 6.54 (d, J=2.8 Hz, 1H), 4.98 (d, J=4.0 Hz, 1H), 4.94 (s, 2H), 4.30-3.91 (m, 4H), 3.50 (br t, J=6.4 Hz, 2H), 3.34 (s, 3H), 2.90-2.86 (m, 2H), 2.85 (s, 3H), 2.66 (s, 3H), 2.53-2.52 (m, 1H).

Example 12

4-((5,8-dichloro-7-(methoxy(1-methylazetidin-3-yl)methyl)-1-oxo-3,4-dihydroisoquinolin-2(1H)-yl)methyl)-7-methylthieno[2,3-c]pyridin-5(6H)-one

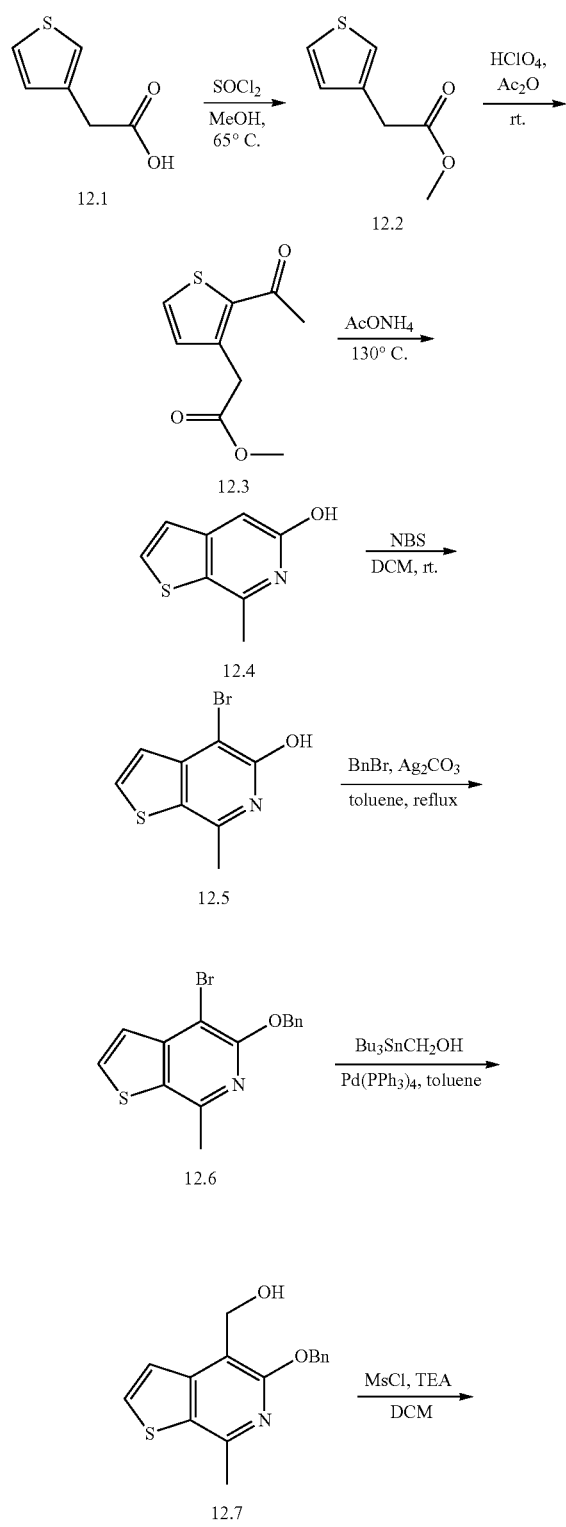

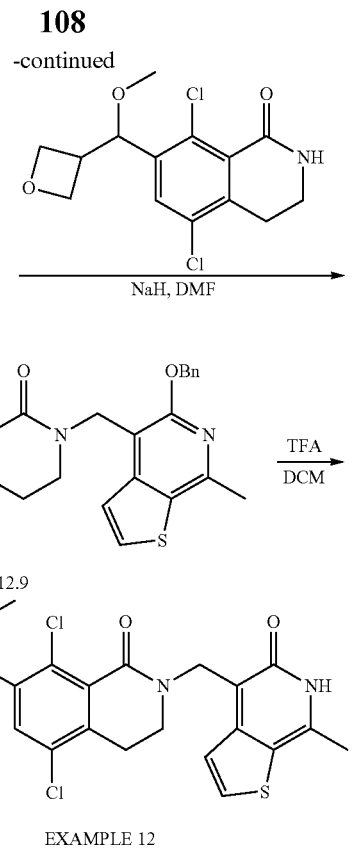

EXAMPLE 12 (Example FH, Table 2) was prepared from compound 12.1.

Compound 12.2:

To a solution of 2-(3-thienyl)acetic acid (12.1, 5.40 g, 37.9 mmol, 1 equivalent) in MeOH (50 mL) was added thionyl chloride (6.78 g, 56.9 mmol, 4.13 mL, 1.5 equivalent) at 0° C. The mixture was heated to 68° C. for 12 hours. After this time, the reaction solution was evaporated and to this residue was added saturated sodium bicarbonate solution (80 mL). The suspension was extracted with ethyl acetate (35 mL×3), then dried over sodium sulfate and the solvent was removed to afford methyl 2-(thiophen-3-yl)acetate (12.2, 5.8 g, yield=93%) as a yellow oil without further purification.

Compound 12.3

Acetic anhydride (6.07 g, 59.4 mmol, 5.56 mL, 1.6 equivalent) was added to the mixture of methyl 2-(3-thienyl)acetate (12.2, 5.80 g, 37.1 mmol, 1 equivalent) and perchloric acid (373 mg, 3.71 mmol, 225 µL, 0.1 equivalent) at 0° C. This mixture was maintained at 0° C. and stirred for 1 hour. The reaction was quenched with water (10 mL), then added saturated sodium bicarbonate solution (50 mL) was added. The suspension was extracted with ethyl acetate (40 mL×3), dried over sodium sulfate and the solvent was removed to afford methyl 2-(2-acetyl thiophen-3-yl)acetate (12.3, 7.2 g, a mixture, yield=97.8%) as a yellow oil.

Compound 12.4:

A mixture of methyl 2-(2-acetyl-3-thienyl)acetate (12.3, 7.2 g, 36.3 mmol, 1 equivalent) and ammonium acetate (70 g, 908 mmol, 25 equivalent) was heated to 140° C. for 1 hour. Water (80 mL) was added carefully to the melted mixture, a precipitate was formed. This suspension was cooled and filtered, then washed with petroleum ether/ethyl acetate (5/1, 50 mL) twice and dried under vacuum to afford 7-methylthieno[2,3-c]pyridin-5-ol (12.4, 3.1 g, yield=46.5%) as a pale solid; LC-MS: 166.1.

$^1$H NMR (400 MHz, CDCl$_3$) δ=7.59 (d, J=5.6 Hz, 1H), 7.04 (d, J=5.6 Hz, 1H), 6.76 (s, 1H), 2.68 (s, 3H).

Compound 12.5:

NBS (3.23 g, 18.2 mmol, 1 equivalent) was added to a solution of 7-methylthieno[2,3-c]pyridin-5-ol (12.4, 3 g, 18.16 mmol, 1 equivalent) in DCM (50 mL) at 25° C. and stirred for 1 hour. The resulting precipitate was filtered and washed with DCM (20.0 mL×2) to give the 4-bromo-7-methylthieno[2,3-c]pyridin-5-ol (12.5, 3.0 g, yield=64.3%) as a yellow solid; LC-MS: 246.0.

$^1$H NMR (400 MHz, DMSO-d$_6$) δ=12.02 (br s, 1H), 8.09 (d, J=5.6 Hz, 1H), 7.16 (d, J=5.6 Hz, 1H), 2.48 (br s, 3H).

Compound 12.6:

To a solution of 4-bromo-7-methyl-thieno[2,3-c]pyridin-5-ol (12.5, 0.72 g, 2.95 mmol, 1 equivalent) and benzyl bromide (605 mg, 3.54 mmol, 420 µL, 1.2 equivalent) in toluene (20 mL) was added silver oxide (752 mg, 3.24 mmol, 1.1 equivalent). This mixture was stirred at 110° C. for 8 hours. The solid was filtered and the filtrate was evaporated to give a crude product which was purified by flash chromatography on silica gel (petroleum ether/ethyl acetate=5/1). There was obtained 5-(benzyloxy)-4-bromo-7-methylthieno[2,3-c]pyridine (12.6, 0.89 g, yield=85.7%) as a white solid; LC-MS: 336.0.

Compound 12.7:

To a solution of 5-benzyloxy-4-bromo-7-methyl-thieno[2,3-c]pyridine (12.6, 140 mg, 419 µmol, 1 equivalent) tributylstannylmethanol (202 mg, 628 µmol, 1.5 equivalent) in toluene (2 mL) was added Pd(PPh$_3$)$_4$(72.6 mg, 62.8 µmol, 0.15 equivalent). The mixture was stirred at 120° C. for 12 hours, then saturated potassium fluoride solution (10 mL) was added. This mixture was extracted with ethyl acetate (10 mL×3), dried over sodium sulfate and the solvent was removed to afford crude product. The crude product was purified by flash chromatography on silica gel (Petroleum ether/ethyl acetate=5/1) to give the (5-(benzyloxy)-7-methylthieno[2,3-c]pyridin-4-yl)methanol (12.7, 56.0 mg, yield=46.8%) as a white solid; LC-MS: 286.0.

$^1$H NMR (400 MHz, CDCl$_3$) δ=7.64 (d, J=5.6 Hz, 1H), 7.49 (d, J=7.2 Hz, 2H), 7.45 (d, J=5.6 Hz, 2H), 7.39 (t, J=7.2 Hz, 2H), 7.35-7.30 (m, 1H), 7.15-7.08 (m, 1H), 5.54 (s, 2H), 4.99 (d, J=6.4 Hz, 2H), 2.72 (s, 3H).

Compound 12.8:

To a solution of (5-benzyloxy-7-methyl-thieno[2,3-c]pyridin-4-yl)methanol (12.7, 0.08 g, 280 µmol, 1 equivalent) triethylamine (85.1 mg, 841 µmol, 117 µL, 3 equivalent) in DCM (5 mL) was added methane sulfonylchloride (48.2 mg, 421 µmol, 32.6 µL, 1.5 equivalent) dropwise at 0° C. The reaction mixture was stirred at 25° C. for 3 hours, then saturated sodium bicarbonate solution (10 mL) was added; this was extracted with ethyl acetate (15 mL×3), dried over sodium sulfate and the solvent was removed to give a yellow oil. This crude product was not further purified used directly in the next step (12.8, 100 mg).

Compound 12.9:

To a solution of 5,8-dichloro-7-[methoxy(oxetan-3-yl) methyl]-3,4-dihydro-2H-isoquinolin-1-one (0.01 g, 31.6 µmol, 1 equivalent) in DMF (1 mL) was added NaH (6.32 mg, 158 µmol, 60% suspension in mineral oil, 5 equivalent) at 0° C. After gas evolution ceased (5-benzyloxy-7-methyl-thieno[2,3-c]pyridin-4-yl)methyl methanesulfonate (12.8, 17.2 mg, 47.44 µmol, 1.5 equivalent) was added and the mixture was stirred at 25° C. for 2 hours. After this time, the reaction was quenched by the addition of water (5 mL), then it was extracted with ethyl acetate (10 mL×3), dried over sodium sulfate, filtered and the solvent was removed. The residue was purified by flash chromatography on silica gel (petroleum ether/ethyl acetate=10/1) to give 2-((5-(benzyloxy)-7-methylthieno[2,3-c]pyridin-4-yl)methyl)-5,8-dichloro-7-(methoxy(oxetan-3-yl)methyl)-3,4-dihydroisoquinolin-1(2H)-one (12.9, 14.0 mg, yield=68.3%) as a yellow oil; LC-MS [M+1]: 582.9.

EXAMPLE 12. To a solution of 2-[(5-benzyloxy-7-methyl-thieno[2,3-c]pyridin-4-yl)methyl]-5,8-dichloro-7-[methoxy(oxetan-3-yl)methyl]-3,4-dihydroisoquinolin-1-one (12.9, 0.01 g, 17.14 µmol, 1 equivalent) in DCM (2 mL) was added TFA (1.54 g, 13.5 mmol, 1 mL, 788 equivalent). This mixture was stirred for 8 hours at 25° C. The solvent was removed by evaporation Evaporated to give a residue which was purified by preparative scale-HPLC (mobile phase: [water (0.1% TFA)-ACN]; B %: 31%-61%, 10 min). There was obtained 4-((5,8-dichloro-7-(methoxy(oxetan-3-yl)methyl)-1-oxo-3,4-dihydroisoquinolin-2(1H)-yl) methyl)-7-methylthieno[2,3-c]pyridin-5(6H)-one (EXAMPLE 12, 4.5 mg, yield=51.1%, purity=96.3%) as a brown solid LC-MS [M+1]: 493.2.

$^1$H NMR (400 MHz, CDCl$_3$) δ=7.77 (s, 2H), 7.50 (s, 1H), 5.04 (br d, J=6.0 Hz, 3H), 4.75-4.58 (m, 4H), 3.70 (br s, 2H), 3.41-3.32 (m, 1H), 3.29 (s, 3H), 2.87-2.83 (m, 2H), 2.72 (s, 3H).

Example 13

5,8-dichloro-7-(3,5-dimethylisoxazol-4-yl)-2-((7-methyl-5-oxo-5,6-dihydro-1H-pyrrolo[2,3-c]pyridin-4-yl)methyl)-3,4-dihydroisoquinolin-1 (2H)-one

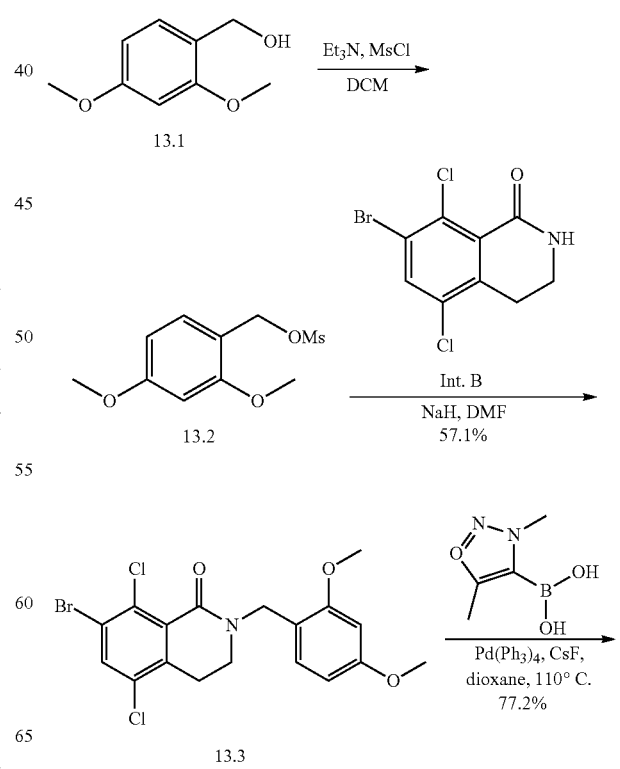

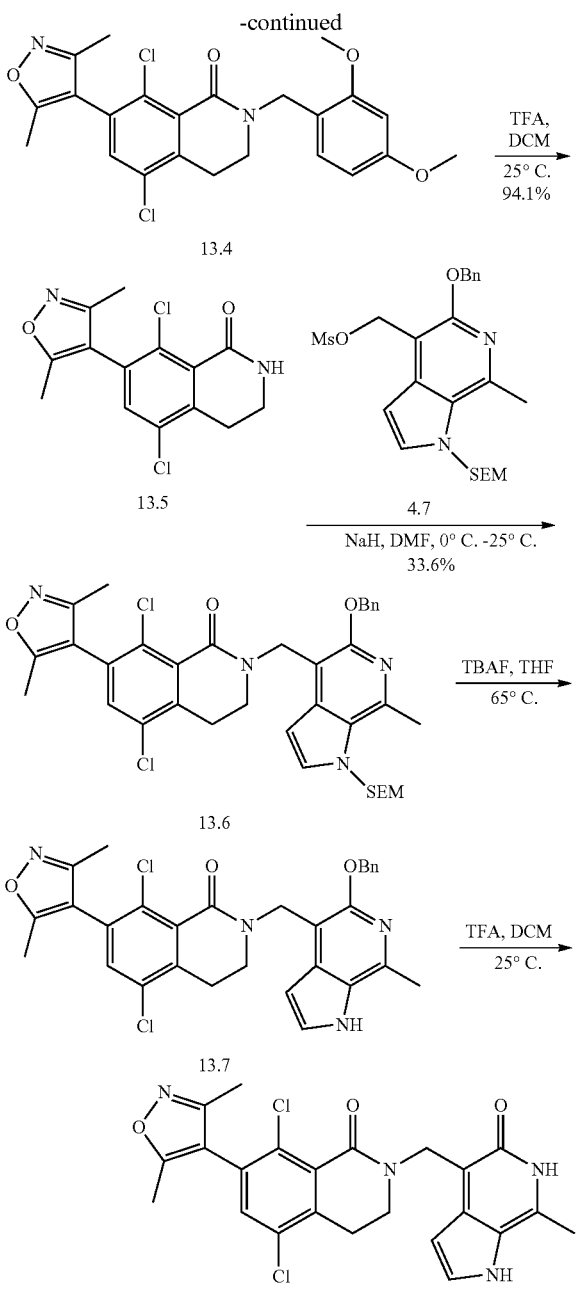

EXAMPLE 13

EXAMPLE 13 was prepared from compound 13.1.

Compound 13.2:

To a solution of (2,4-dimethoxyphenyl)methanol (13.1, 3.75 g, 22.3 mmol, 1 equivalent) and triethylamine (9.02 g, 89.2 mmol, 12.4 mL, 4 equivalent) in DCM (35 mL) was added methane sulfonylchloride (5.11 g, 44.6 mmol, 3.45 mL, 2 equivalent) dropwise at 0° C. The reaction was stirred at 0° C. for 1 hour under nitrogen then reaction was quenched by the addition of water (50 mL). The organic phase was separated and dried with anhydrous sodium sulfate then it was filtered and concentrated to give (2,4-dimethoxyphenyl)methyl methanesulfonate (13.2, 5.49 g) as brown oil which was used in the next step without further purification.

Compound 13.3:

To a solution of 7-bromo-5,8-dichloro-3,4-dihydro-2H-isoquinolin-1-one (Int. B, 1.5 g, 5.09 mmol, 1 equivalent) in DMF (15 mL) was added sodium hydride (813 mg, 20.3 mmol, 60.0% suspension in mineral oil, 4 equivalent) at 0° C. The reaction mixture was stirred at 0° C. for 0.5 hour, then (2,4-dimethoxyphenyl)methyl methanesulfonate (13.2, 3.29 g, 13.4 mmol, 2.63 equivalent) was added dropwise. This was stirred at 25° C. for 1.5 hour, then the reaction mixture was quenched with water (50 mL) and extracted with ethyl acetate (50.0 mL×3). The combined the organic phases were washed with brine (50 mL×2), dried with anhydrous sodium sulfate, filtered and concentrated in vacuo. The crude product was purified by silica gel chromatography (Petroleum ether/Ethyl acetate 10/1 to 6/1) to give 7-bromo-5,8-dichloro-2-[(2,4-dimethoxyphenyl)methyl]-3,4-dihydroisoquinolin-1-one (13.3, 1.36 g, 57.1% yield) as a white solid.

$^1$H NMR (400 MHz, CDCl$_3$) δ=7.75 (s, 1H), 7.34-7.29 (m, 1H), 6.49-6.44 (m, 2H), 4.73 (s, 2H), 3.83 (s, 3H), 3.81 (s, 3H), 3.49 (t, J=6.0 Hz, 2H), 2.89 (t, J=6.4 Hz, 2H).

Compound 13.4:

To a solution of 7-bromo-5,8-dichloro-2-[(2,4-dimethoxyphenyl)methyl]-3,4-dihydroisoquinolin-1-one (13.3, 200 mg, 449 μmol, 1 equivalent) and (3,5-dimethyl isoxazol-4-yl)boronic acid (190 mg, 1.35 mmol, 3 equivalent) in dioxane (4 mL) was added cesium fluoride (191 mg, 1.26 mmol, 46.4 μL, 2.8 equivalent) and Pd(PPh$_3$)$_4$ (104 mg, 89.9 μmol, 0.2 equivalent). The reaction mixture was stirred under nitrogen at 100° C. for 3 hours. The reaction mixture was cooled to 25° C. and water was added (5 mL), then the aqueous phase was extracted with ethyl acetate (5 mL×3). The combined organic phases were washed with brine (5 mL×2), dried over anhydrous sodium sulfate, filtered and concentrated in vacuo. The crude product was purified by silica gel chromatography (Petroleum ether/Ethyl acetate 10/1 to 3/1) to give 5,8-dichloro-2-[(2,4-dimethoxyphenyl)methyl]-7-(3,5-dimethylisoxazol-4-yl)-3,4-dihydroisoquinolin-1-one (13.4, 160 mg, 77.2% yield) as brown oil.

$^1$H NMR (400 MHz, CDCl$_3$) δ=7.36 (d, J=8.8 Hz, 1H), 7.29 (s, 1H), 6.50-6.44 (m, 2H), 4.74 (s, 2H), 3.85 (s, 3H), 3.81 (s, 3H), 3.57 (t, J=6.0 Hz, 2H), 2.99 (t, J=6.4 Hz, 2H), 2.29 (s, 3H), 2.16 (s, 3H).

Compound 13.5:

A solution of 5,8-dichloro-2-[(2,4-dimethoxyphenyl)methyl]-7-(3,5-dimethylisoxazol-4-yl)-3,4-dihydroisoquinolin-1-one (13.4, 160 mg, 347 μmol, 1 equivalent) in TFA (1 mL), DCM (1 mL) was stirred at 25° C. for 12 hours. The reaction mixture was concentrated and the pH adjusted to 6 with saturated sodium bicarbonate solution (~10 mL), then extracted with DCM (10 mL×3). The combined the organic phases were washed with brine (10 mL×2), dried with anhydrous sodium sulfate, filtered and concentrated to give 5,8-dichloro-7-(3,5-dimethylisoxazol-4-yl)-3,4-dihydro-2H-isoquinolin-1-one (13.5, 105 mg, 94.1% yield) as a brown solid; LCMS: [M+1] 310.9.

Compound 13.6:

To a solution of [5-benzyloxy-7-methyl-1-(2-trimethylsilylethoxymethyl) pyrrolo[2,3-c]pyridin-4-yl]methanol (4.7, 140 mg, 351 μmol, 1 equivalent) and triethylamine (142 mg, 1.41 mmol, 196 μL, 4 equivalent) in DCM (2 mL) was added methane sulfonylchloride (80.5 mg, 703 μmol, 54.4 μL, 2 equivalent) dropwise at 0° C. This was stirred at 0° C. for 0.5 hour, then the reaction was quenched with brine (3 mL). The organic phase was separated and dried with anhydrous sodium sulfate, filtered then concentrated under vacuum to give [5-benzyloxy-7-methyl-1-(2-trimethylsilylethoxymethyl)pyrrolo[2,3-c]pyridin-4-yl]methyl methanesulfonate (13.6, 167 mg, crude) as brown oil which was used in the next step without further manipulation.

Compound 13.7:

To a solution of 5,8-dichloro-7-(3,5-dimethylisoxazol-4-yl)-3,4-dihydro-2H-isoquinolin-1-one (13.6, 105 mg, 337 µmol, 1 equivalent) in DMF (1 mL) was added sodium hydride (27 mg, 675 µmol, 60.0% suspension in mineral oil, 2 equivalent) at 0° C. The reaction mixture was stirred at 0° C. for 0.5 hour, then a solution of [5-benzyloxy-7-methyl-1-(2-trimethylsilylethoxymethyl)pyrrolo[2,3-c] pyridin-4-yl]methyl methanesulfonate (277-7, 161 mg, 337 µmol, 1.00 equivalent) in DMF (0.2 mL) was added dropwise. The reaction mixture was allowed to warm to 25° C. then stirred for 1 hr. After this time, the reaction was quenched with water (5 mL) and extracted with ethyl acetate (5 mL×3). The combined organic phases were washed with brine (5 mL×2), dried with anhydrous sodium sulfate, filtered and concentrated to give crude 13.7 which was purified by preparative scale TLC (Petroleum ether:Ethyl acetate=2/1) to isolate 2-[[5-benzyloxy-7-methyl-1-(2-trimethylsilylethoxy methyl)pyrrolo[2,3-c]pyridin-4-yl]methyl]-5,8-dichloro-7-(3,5-dimethylisoxazol-4-yl)-3,4-dihydroisoquinolin-1-one (13.7, 80 mg, 33.6% yield) as a brown oil; LCMS: [M+1] 691.4.

Compound 13.8:

To a solution of 2-[[5-benzyloxy-7-methyl-1-(2-trimethylsilylethoxymethyl) pyrrolo[2,3-c]pyridin-4-yl]methyl]-5,8-dichloro-7-(3,5-dimethylisoxazol-4-yl)-3,4-dihydroisoquinolin-1-one (13.7, 80 mg, 116 µmol, 1 equivalent) in THF (1 mL) was added TBAF (1 M, 1.16 mL, 10.0 equivalent); the reaction mixture was stirred at 65° C. for 4.5 hrs. The reaction mixture was cooled to 25° C. and quenched with water (5.00 mL). This was extracted with ethyl acetate (5.00 mL×3) and the combined organic phases were washed with brine (5 mL×2), dried with anhydrous sodium sulfate, filtered and concentrated under vacuum. The crude product was purified by preparative scale TLC (Petroleum ether: Ethyl acetate=1/1) to give 2-[(5-benzyloxy-7-methyl-1H-pyrrolo[2,3-c]pyridin-4-yl)methyl]-5,8-dichloro-7-(3,5-dimethylisoxazol-4-yl)-3,4-dihydroisoquinolin-1-one (13.8, 40 mg, crude) as a brown oil; LCMS: [M+1] 560.9.

EXAMPLE 13. A solution of 2-[(5-benzyloxy-7-methyl-1H-pyrrolo[2,3-c] pyridine-4-yl)methyl]-5,8-dichloro-7-(3,5-dimethylisoxazol-4-yl)-3,4-dihydroisoquinolin-1-one (13.8, 40 mg, 71.2 mol, 1.00 equivalent) in TFA (1 mL) and DCM (1 mL) was stirred at 25° C. for 10 hours. The reaction was concentrated and the residue was purified by preparative scale-TLC (Dichloromethane/Methanol=10/1) to give crude EXAMPLE 13. This material was purified further by preparative scale HPLC (TFA buffer) to give 5,8-dichloro-7-(3,5-dimethylisoxazol-4-yl)-2-[(7-methyl-5-oxo-1,6-dihydropyrrolo [2,3-c] pyridin-4-yl)methyl]-3,4-dihydroisoquinolin-1-one (EXAMPLE 13, 6.43 mg, 18.7% yield, 97.5% purity) as a white solid; LCMS: [M+1]470.9.

¹H NMR (400 MHz, CD₃OD) δ=7.97 (d, J=2.8 Hz, 1H), 7.62 (s, 1H), 6.87 (d, J=3.2 Hz, 1H), 5.09 (s, 2H), 3.79 (t, J=6.4 Hz, 2H), 3.09 (t, J=6.0 Hz, 2H), 2.82 (s, 3H), 2.30 (s, 3H), 2.14 (s, 3H).

Example 14

7-((5,8-dichloro-7-(1,4-dimethyl-1H-1,2,3-triazol-5-yl)-1-oxo-3,4-dihydroisoquinolin-2(1H)-yl)methyl)-4-methylfuro[3,2-c]pyridin-6(5H)-one

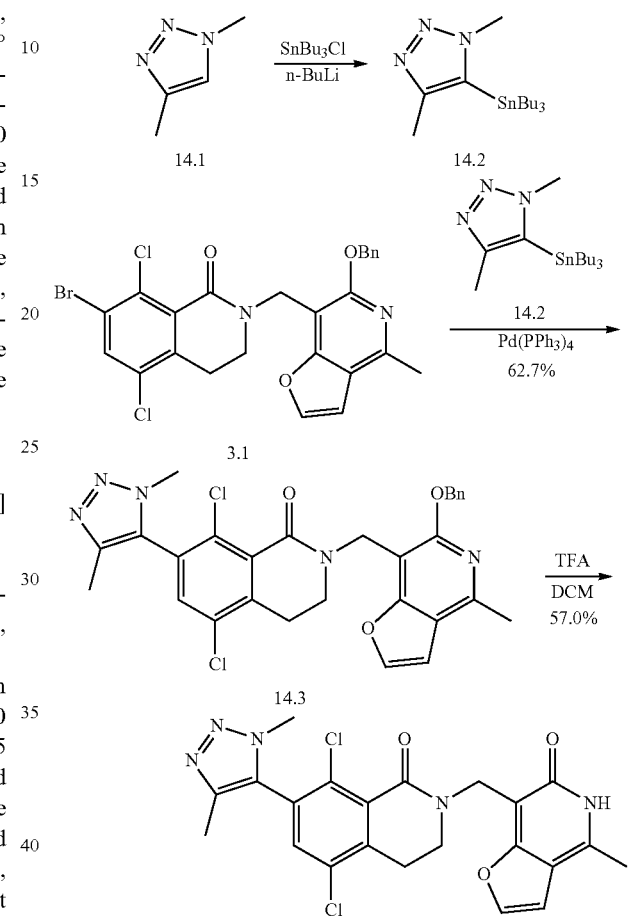

EXAMPLE 14

Example 14 was prepared from compound 14.1.

Compound 14.2:

A solution of 1,4-dimethyltriazole (14.1, 500 mg, 5.15 mmol, 1 equivalent) in THF (2 mL) was added dropwise to a solution of n-BuLi (2.5 M, 2.47 mL, 1.2 equivalent) in THF (15 mL) at −78° C. under nitrogen atmosphere. The resulting cloudy mixture was stirred at −70° C. for 1 h. After this time, tributyl tinchloride (1.84 g, 5.66 mmol, 1.52 mL, 1.1 equivalent) was added; the reaction mixture became clear and was stirred at −70° C. for 30 min, then it was allowed to warm to 20° C. The reaction mixture was poured into saturated NH₄Cl solution (10 mL) and extracted with EtOAc (50 mL×3). The combined organic layers were washed with brine (50 mL×2), were dried over sodium sulfate then filtered. The solvent was concentrated under reduced pressure to give tributyl-(3,5-dimethyltriazol-4-yl)stannane (14.2, 2.2 g) as a yellow oil; LCMS [M+1]: 388.2.

Compound 14.3:

A mixture of 2-[(6-benzyloxy-4-methyl-furo[3,2-c]pyridin-7-yl)methyl]-7-bromo-5,8-dichloro-3,4-dihydroisoquinolin-1-one (3.1, 40 mg, 73.2 µmol, 1 equivalent), tributyl- (3,5-dimethyltriazol-4-yl)stannane (14.2, 84.8 mg, 220 µmol, 3 equivalent), Pd(PPh$_3$)$_4$ (16.9 mg, 14.7 µmol, 0.2 equivalent) in toluene (2.00 mL) was degassed then purged with nitrogen 3 times. This mixture was stirred at 110° C. for 12 hours under nitrogen atmosphere. The reaction mixture was quenched by addition of a saturated solution of KF (5 mL) and extracted with EtOAc (15 mL×3). The combined organic layers were washed with brine (15 mL×2), dried over sodium sulfate, filtered and concentrated to give a crude 14.3 This was purified by column chromatography (SiO$_2$, Petroleum ether/Ethyl acetate=1/1) to afford 2-[(6-benzyloxy-4-methyl-furo[3,2-c]pyridin-7-yl)methyl]-5,8-dichloro-7-(3,5-dimethyltriazol-4-yl)-3,4-dihydroisoquinolin-1-one (14.3, 38 mg, 45.9 µmol, 62.7% yield, 68.0% purity) as a white solid; LCMS [M+1]: 562.3.

EXAMPLE 14. To a solution of 2-[(6-benzyloxy-4-methyl-furo[3,2-c]pyridin-7-yl)methyl]-5,8-dichloro-7-(3,5-dimethyltriazol-4-yl)-3,4-dihydroisoquinolin-1-one (14.3, 50 mg, 88.9 µmol, 1 equivalent) in DCM (1 mL) was added TFA (1.54 g, 13.5 mmol, 1 mL, 152 equivalent); this mixture was stirred at 25° C. for 12 hrs. The reaction mixture was filtered and concentrated under reduced pressure to give a residue which was purified by preparative scale-HPLC (column: Phenomenex Synergi C$_{18}$ 150×25×10 µm; mobile phase: [water (0.1% TFA)-ACN]; B %: 22%-52%, 12 min) to afford 7-[[5,8-dichloro-7-(3,5-dimethyltriazol-4-yl)-1-oxo-3,4-dihydroisoquinolin-2-yl]methyl]-4-methyl-5H-furo[3,2-c]pyridin-6-one (EXAMPLE 14, 24.0 mg, 50.7 µmol, 57.0% yield, 99.8% purity) as a pink solid; LCMS [M+1]: 472.1.

$^1$H NMR (400 MHz, chloroform-d) δ=7.72 (d, J=2.4 Hz, 1H), 7.36 (s, 1H), 6.79 (d, J=2.4 Hz, 1H), 4.92 (s, 2H), 3.92 (t, J=6.4 Hz, 2H), 3.86 (s, 3H), 3.21-3.18 (m, 2H), 2.76 (s, 3H), 2.24 (s, 3H).

Example 15

5,8-dichloro-7-(3,5-dimethyltriazol-4-yl)-2-[(7-methyl-5-oxo-1,6-dihydropyrrolo[2,3-c]pyridin-4-yl)methyl]-3,4-dihydroisoquinolin-1-one

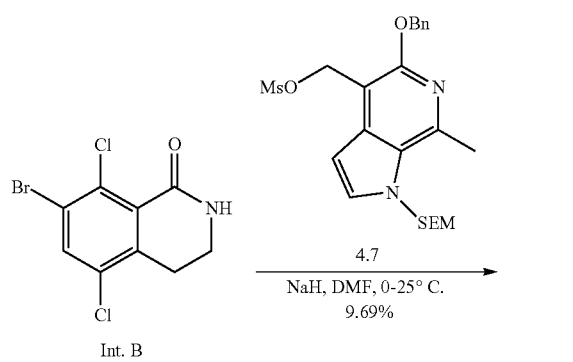

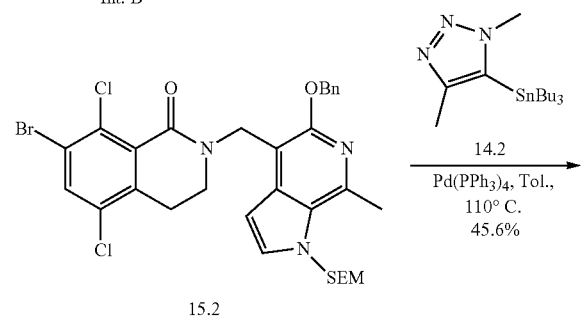

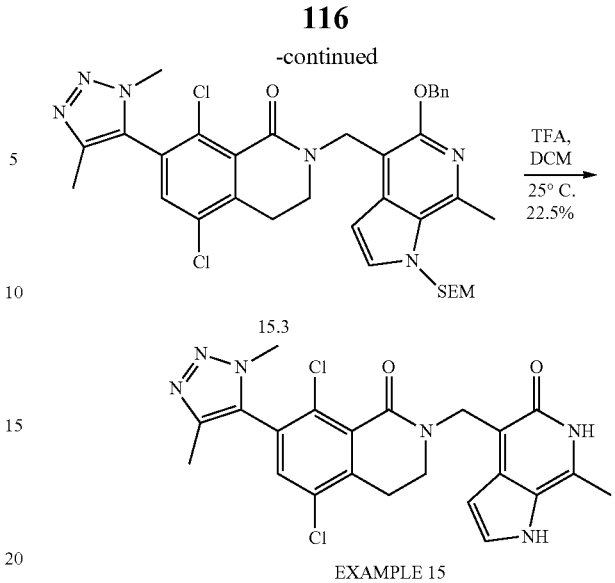

EXAMPLE 15

Example 15 (Example BM, Table 2) was prepared from compound Int. B.

Compound 15.2:

To a solution of 7-bromo-5,8-dichloro-3,4-dihydro-2H-isoquinolin-1-one (Int B, 300 mg, 1.02 mmol, 1.00 eq.) in DMF (3.00 mL) was added sodium hydride (81.4 mg, 2.03 mmol, 60.0% purity, 2.00 eq.) at 0° C. The resulting mixture was stirred at 0° C. for 0.5 hour, then a solution of [4.7, 5-benzyloxy-7-methyl-1-(2-trimethylsilylethoxymethyl)pyrrolo [2,3-c] pyridin-4-yl]methyl methanesulfonate (436 mg, 915 µmol, 0.90 eq.) in DMF (0.20 mL) was added dropwise. The resulting mixture was warmed to 25° C. and stirred for 1 hour. The reaction was quenched with water (5.00 mL) and extracted with ethyl acetate (5.00 mL×3). The combined organic phase was washed with brine (5.00 mL×2), dried with anhydrous sodium sulfate, filtered and concentrated in vacuum to give a residue which was purified by prep-TLC (Petroleum ether/Ethyl acetate 5/1) to give (15.2, 2-[[5-benzyloxy-7-methyl-1-(2-trimethylsilylethoxymethyl)pyrrolo[2,3-c]pyridin-4-yl]methyl]-7-bromo-5,8-dichloro-3,4-dihydroisoquinolin-1-one) (100 mg, 9.69% yield, 66.6% purity) as a colorless oil. LCMS: [M+1] 676.3.

Compound 15.3:

To a solution of 2-[[5-benzyloxy-7-methyl-1-(2-trimethylsilylethoxymethyl)pyrrolo[2,3-c]pyridin-4-yl]methyl]-7-bromo-5,8-dichloro-3,4-dihydroisoquinolin-1-one (15.2, 80.0 mg, 118 µmol, 1.00 eq.), tributyl-(3,5-dimethyltriazol-4-yl)stannane (14.2, 137 mg, 355 µmol, 3.00 eq.) in Tol. (2.00 mL) was added Pd(PPh$_3$)$_4$ (13.7 mg, 11.8 µmol, 0.10 eq.) under nitrogen. The reaction was stirred at 110° C. for 12 hours then cooled to 25° C., quenched with saturated potassium fluoride aqueous solution (10.0 mL), and extracted with ethyl acetate (5.00 mL×3). The combined organic phase was washed with brine (5.00 mL×2), dried with anhydrous sodium sulfate, filtered and concentrated in vacuum to give the residue which was purified by prep-TLC (Petroleum ether/Ethyl acetate 1/1) to give 2-[[5-benzyloxy-7-methyl-1-(2-trimethylsilylethoxymethyl)pyrrolo[2,3-c]pyridin-4-yl]methyl]-5,8-dichloro-7-(3,5-dimethyltriazol-4-yl)-3,4-dihydroisoquinolin-1-one (15.3, 40.0 mg, 45.6% yield, 93.4% purity) as a colorless oil. LCMS: [M+1] 691.5.

EXAMPLE 15. To a solution of 2-[[5-benzyloxy-7-methyl-1-(2-trimethylsilylethoxymethyl)pyrrolo[2,3-c]pyridin-4-yl]methyl]-5,8-dichloro-7-(3,5-dimethyltriazol-4-yl)-3,4-dihydroisoquinolin-1-one (15.3, 30.0 mg, 43.4 µmol, 1.00 eq.) in DCM (1.00 mL) was added TFA (1.00 mL). The resulting mixture was stirred at 40° C. for 12 hours then cooled to 25° C. and concentrated in vacuum. The residue was dissolved in acetonitrile (2.00 mL) and ammonium hydroxide (1.00 mL) was added. The aqueous solution was stirred at 25° C. for 10 min then purified by prep-HPLC (base buffer) to give 5,8-dichloro-7-(3,5-dimethyltriazol-4-yl)-2-[(7-methyl-5-oxo-1,6-dihydropyrrolo[2,3-c]pyridin-4-yl)methyl]-3,4-dihydroisoquinolin-1-one (EXAMPLE 15, 4.99 mg, 22.5% yield, 92.2% purity) as a white solid. LCMS: [M+1]471.3.

$^1$H NMR (400 MHz, CD$_3$OD) δ=7.66 (s, 1H), 7.59 (d, J=3.2 Hz, 1H), 6.42 (d, J=2.8 Hz, 1H), 5.04 (s, 2H), 3.89 (s, 3H), 3.57 (t, J=6.0 Hz, 2H), 2.99 (t, J=6.0 Hz, 2H), 2.63 (s, 3H), 2.20 (s, 3H).

Example 16

7-((5,8-dichloro-7-(3,5-dimethylisoxazol-4-yl)-1-oxo-3,4-dihydroisoquinolin-2(1H)-yl)methyl)-4-methylfuro[3,2-c]pyridin-6(5H)-one

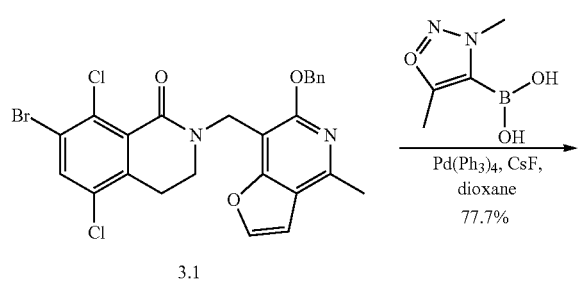

3.1

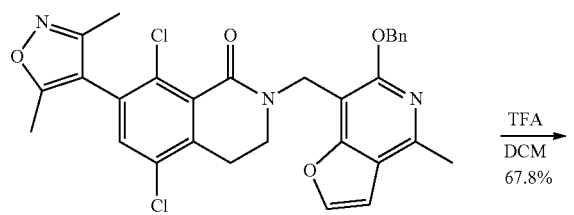

16.1

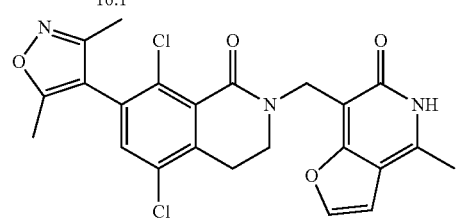

EXAMPLE 16

Example 16 was prepared from compound 3.1.
Compound 16.1:
To a solution of 2-[(6-benzyloxy-4-methyl-furo[3,2-c]pyridin-7-yl)methyl]-7-bromo-5,8-dichloro-3,4-dihydroisoquinolin-1-one (3.1, 0.045 g, 82.3 µmol, 1.00 eq.) (3,5-dimethylisoxazol-4-yl)boronic acid (34.8 mg, 247 µmol, 3.00 eq.), CsF (35.0 mg, 230.67 µmol, 8.50 µL, 2.80 eq.) in dioxane (1.00 mL) and Pd(PPh$_3$)$_4$(19.0 mg, 16.48 µmol, 0.20 eq.) were added and the mixture was stirred at 100° C. for 18 hours. The solvent was removed under reduce pressure to afford a residue which was purified by flash chromatography on silica gel (petroleum ether/ethyl acetate=3/1) to afford the desired product as a yellow solid (16.1, 40 mg, yield=77.7%). LC-MS [M+1]: 562.0.

$^1$H NMR (400 MHz, CDCl$_3$) δ=7.52 (d, J=2.4 Hz, 1H), 7.49 (br d, J=6.4 Hz, 2H), 7.37-7.30 (m, 3H), 7.28 (s, 1H), 6.72 (d, J=2.4 Hz, 1H), 5.53 (s, 2H), 5.12-5.06 (m, 2H), 3.45 (t, J=6.4 Hz, 2H), 2.82 (t, J=6.4 Hz, 2H), 2.65 (s, 3H), 2.30 (s, 3H), 2.17 (s, 3H), 2.07 (s, 3H).

EXAMPLE 16. To a solution of 2-[(6-benzyloxy-4-methyl-furo[3,2-c]pyridin-7-yl)methyl]-5,8-dichloro-7-(3,5-dimethylisoxazol-4-yl)-3,4-dihydroisoquinolin-1-one (16.1, 38.9 mg, 62.2 µmol, 1.00 eq.) in DCM (0.5 mL) was added TFA (539 mg, 4.73 mmol, 350 µL, 76.0 eq.) and the resulting mixture was stirred at 25° C. for 3 hours. After completion, the solvent was removed under reduced pressure to afford a residue which was purified by Pre-HPLC (column: UniSil 120×30×10 um; mobile phase: [water(0.1% TFA)-ACN]; B %: 35%-65%, 10 min) to give the 7-((5,8-dichloro-7-(3,5-dimethylisoxazol-4-yl)-1-oxo-3,4-dihydroisoquinolin-2(1H)-yl)methyl)-4-methylfuro[3,2-c]pyridin-6(5H)-one as a pink solid (EXAMPLE 16, 0.02 g, yield=67.8%, purity=99.7%). LC-MS [M+1]: 472.2.

$^1$H NMR (400 MHz, CDCl$_3$) δ=7.55 (d, J=2.0 Hz, 1H), 7.29 (s, 1H), 6.65 (d, J=2.4 Hz, 1H), 4.92 (s, 2H), 3.83 (br d, J=5.2 Hz, 2H), 3.08 (br t, J=6.0 Hz, 2H), 2.65 (s, 3H), 2.27 (s, 3H), 2.14 (s, 3H).

Example 17

5,8-dichloro-7-[methoxy(oxetan-3-yl)methyl]-2-[(7-methyl-5-oxo-1,6-dihydropyrrolo[2,3-c]pyridin-4-yl)methyl]-3,4-dihydroisoquinolin-1-one

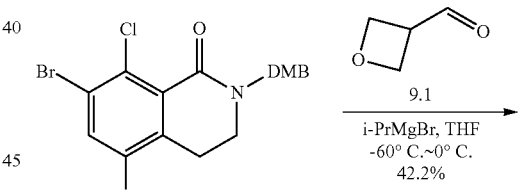

11.1

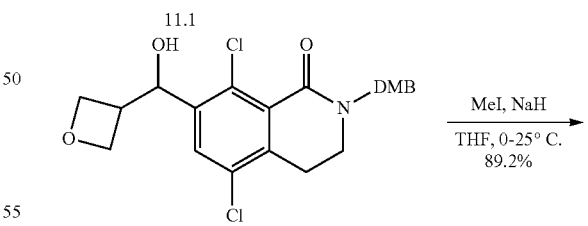

17.1

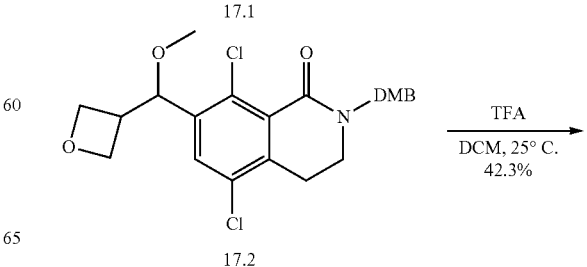

17.2

-continued

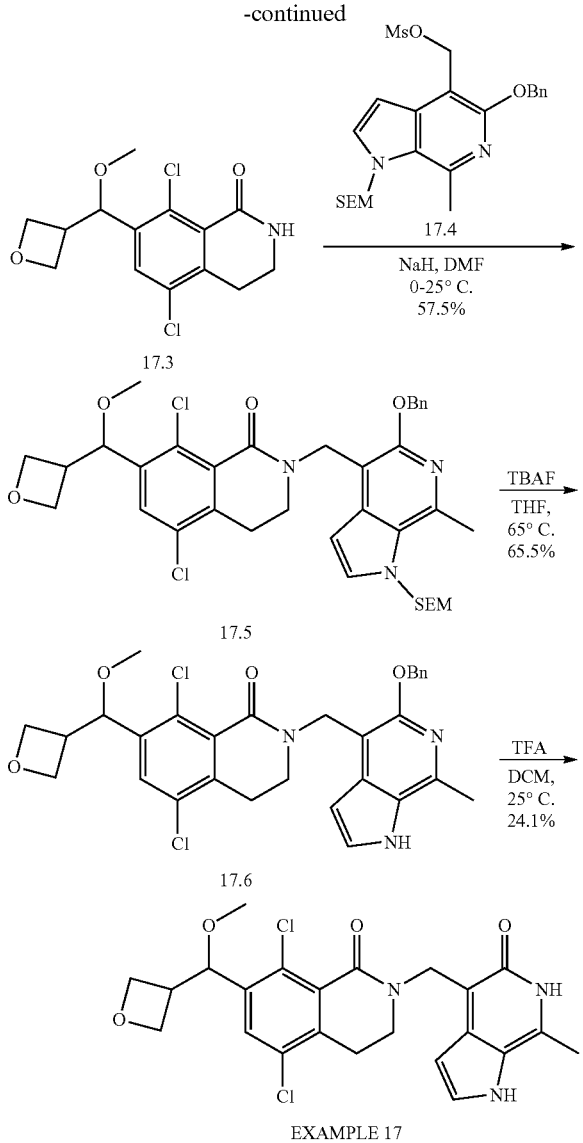

Example 17 (Example EX, Table 2) was prepared from compound 11.1.

Compound 17.1.

To a solution of 7-bromo-5,8-dichloro-2-[(2,4-dimethoxyphenyl)methyl]-3,4-dihydroisoquinolin-1-one (11.1, 130 mg, 292 μmol, 1 eq.) in THF (3.00 mL) was added isopropylmagnesium chloride (2 M, 438 μL, 3 eq.) dropwise at −65° C. over 5 min, then the mixture was warmed to −10° C. and maintained 30 min. A solution of oxetane-3-carbaldehyde (9.1, 126 mg, 1.46 mmol, 5 eq. in THF (2 mL)) was added dropwise to the mixture over 5 min, and the resulting mixture stirred at 0° C. for 30 min. The reaction was quenched by adding saturated NH₄Cl solution (4.00 mL) slowly at 0° C., then extracted with DCM (10.0 mL×3). The combined organic layers were washed with brine (10.0 mL×1), dried over sodium sulfate and concentrated to give a residue which purified by column chromatography (SiO₂, Petroleum ether/Ethyl acetate=2/1) to afford 5,8-dichloro-2-[(2,4-dimethoxyphenyl)methyl]-7-[hydroxy(oxetan-3-yl)methyl]-3,4-dihydroisoquinolin-1-one (17.1, 60.0 mg, 123 μmol, 42.2% yield, 93.0% purity) as a white solid.

¹H NMR (400 MHz, chloroform-d) δ=7.58 (s, 1H), 7.34-7.31 (m, 1H), 6.47 (qd, J=2.4, 4.4 Hz, 2H), 5.50 (br d, J=5.2 Hz, 1H), 4.83 (dd, J=6.4, 7.7 Hz, 1H), 4.79-4.73 (m, 2H), 4.72 (s, 2H), 4.71-4.66 (m, 1H), 4.63 (dd, J=6.4, 8.0 Hz, 1H), 4.49 (t, J=6.0 Hz, 1H), 3.84 (s, 3H), 3.81 (s, 3H), 3.48 (br t, J=6.4 Hz, 3H), 2.90 (t, J=6.4 Hz, 2H). LCMS [M+1]: 452.2.

Compound 17.2.

☐☐ To a solution of 5,8-dichloro-2-[(2,4-dimethoxyphenyl)methyl]-7-[hydroxy(oxetan-3-yl)methyl]-3,4-dihydroisoquinolin-1-one (17.1, 50 mg, 111 μmol, 1 eq.) in THF (2.00 mL) was added NaH (17.7 mg, 442 μmol, 60% purity, 4 eq.) at 0° C., and the resulting mixture was stirred for 15 min. MeI (62.8 mg, 442 μmol, 27.5 μL, 4 eq.) was added to the mixture and stirred at 25° C. for 1 hr. The reaction was quenched by adding water (4 mL), and the pH adjusted to 7 by addition of HCl solution (1 M). The reaction mixture was concentrated to remove the THF, then the remaining aqueous mixture was extracted with EtOAc (10.0 mL×3). The combined organic phase was washed with brine (10.0 mL×1), dried over sodium sulfate and concentrated to afford 5,8-dichloro-2-[(2,4-dimethoxyphenyl)methyl]-7 [methoxy (oxetan-3-yl)methyl]-3,4-dihydroisoquinolin-1-one (17.2, 50.0 mg, 98.6 μmol, 89.2% yield, 92.0% purity) as a white solid. LCMS [M+1]: 466.3.

Compound 17.3.

To a solution of 5,8-dichloro-2-[(2,4-dimethoxyphenyl) methyl]-7-[methoxy(oxetan-3-yl)methyl]-3,4-dihydroisoquinolin-1-one (17.2, 50.0 mg, 107 μmol, 1 eq.) in DCM (1.00 mL) was added TFA (1.54 g, 13.5 mmol, 1.00 mL, 126 eq.). The mixture was stirred at 25° C. for 5 hr. The reaction mixture was concentrated under reduced pressure to give a residue, which was purified by prep-TLC (SiO₂, DCM: MeOH=15:1) to afford 5,8-dichloro-7-[methoxy(oxetan-3-yl)methyl]-3,4-dihydro-2H-isoquinolin-1-one (17.3, 15.0 mg, 45.4 μmol, 42.3% yield, 95.6% purity) as a white solid.

¹H NMR (400 MHz, chloroform-d) δ=7.58 (s, 1H), 6.15 (br s, 1H), 5.06 (d, J=6.0 Hz, 1H), 4.75 (t, J=6.4 Hz, 1H), 4.72-4.68 (m, 1H), 4.68-4.63 (m, 5H), 4.63-4.59 (m, 3H), 3.43-3.35 (m, 1H), 3.32 (s, 4H), 3.09 (t, J=6.4 Hz, 2H). LCMS [M+1]: 316.1.

Compound 17.5.

To a solution of 5,8-dichloro-7-[methoxy(oxetan-3-yl) methyl]-3,4-dihydro-2H-isoquinolin-1-one (17.3, 20.0 mg, 44.3 μmol, 1.00 eq) in DMF (1.00 mL) was added NaH (3.54 mg, 88.6 μmol, 60.0% purity, 2.00 eq) at 0° C., and the resulting mixture was stirred at 0° C. for 0.5 hour. A solution of [5-benzyloxy-7-methyl-1-(2-trimethyl silylethoxymethyl)pyrrolo[2,3-c] pyridin-4-yl]methyl methanesulfonate (17.4, 21.1 mg, 44.3 μmol, 1.00 eq) in DMF (0.100 mL) was added dropwise, the reaction mixture was warmed to 25° C. and stirred for 1 h. The reaction was quenched with water (5.00 mL) and extracted with ethyl acetate (5.00 mL×3). The combined organic phase was washed with brine (5.00 mL×2), dried with anhydrous sodium sulfate, filtered and concentrated in vacuum to give the residue which was purified by prep-TLC (Petroleum ether/Ethyl acetate=2/1) to give 2-[[5-benzyloxy-7-methyl-1-(2-trimethylsilylethoxymethyl)pyrrolo[2,3-c]pyridin-4-yl]methyl]-5,8-dichloro-7-[methoxy(oxetan-3-yl)methyl]-3,4-dihydroisoquinolin-1-one (17.5, 20.0 mg, 57.5% yield, 88.7% purity) as a brown oil. LCMS: [M+1] 696.3.

Compound 17.6.

To a solution of 2-[[5-benzyloxy-7-methyl-1-(2-trimethylsilylethoxymethyl)pyrrolo[2,3-c]pyridin-4-yl]methyl]-5,8-dichloro-7-[methoxy(oxetan-3-yl)methyl]-3,4-dihydroisoquinolin-1-one (17.5, 16.0 mg, 23.0 μmol, 1.00 eq) in THF (0.500 mL) was added TBAF (1.00 M, 230 μL, 10.0 eq). The reaction mixture was stirred at 65° C. for 5 h. The reaction was cooled to 25° C., water (3.00 mL) was added, and the aqueous phase was extracted with ethyl acetate (3.00 mL×3). The combined organic phase was washed with brine (3.00 mL×2), dried with anhydrous sodium sulfate, filtered and concentrated in vacuum to give the residue which was purified by prep-TLC (Petroleum ether/Ethyl acetate=1/1) to give 2-[(5-benzyloxy-7-methyl-1H-pyrrolo[2,3-c]pyridin-4-yl)methyl]-5,8-dichloro-7-[methoxy(oxetan-3-yl)methyl]-3,4-dihydroisoquinolin-1-one (17.6, 10.0 mg, 65.5% yield, 85.2% purity) as brown oil. LCMS: [M+1] 566.4.

EXAMPLE 17. A solution of 2-[(5-benzyloxy-7-methyl-1H-pyrrolo[2,3-c] pyridin-4-yl)methyl]-5,8-dichloro-7-[methoxy(oxetan-3-yl)methyl]-3,4-dihydroisoquinolin-1-one (17.6, 10.0 mg, 15.0 µmol, 1.00 eq) in TFA (0.500 mL) and DCM (1.00 mL) was stirred at 25° C. for 3.5 h. The reaction mixture was concentrated in vacuum to give a residue, which was purified by prep-HPLC to give 5,8-dichloro-7-[methoxy(oxetan-3-yl)methyl]-2-[(7-methyl-5-oxo-1,6-dihydropyrrolo[2,3-c]pyridin-4-yl)methyl]-3,4-dihydroisoquinolin-1-one (EXAMPLE 17, 1.74 mg, 24.1% yield, 99.3% purity) as a brown solid.

$^1$H NMR (400 MHz, CD$_3$OD) δ=7.70 (d, J=2.4 Hz, 1H), 7.61 (s, 1H), 6.54 (d, J=2.4 Hz, 1H), 5.12 (d, J=6.0 Hz, 1H), 5.03 (s, 2H), 4.77 (t, J=6.0 Hz, 1H), 4.72-4.59 (m, 3H), 3.56 (t, J=6.0 Hz, 2H), 3.48-3.41 (m, 1H), 3.34 (s, 3H), 2.92 (t, J=6.4 Hz, 2H), 2.69 (s, 3H). LCMS: [M+1] 476.2.

Example 18

7-((5,8-dichloro-7-((1,1-dioxidothietan-3-yl)(methoxy)methyl)-1-oxo-3,4-dihydroisoquinolin-2(1H)-yl)methyl)-4-methylfuro[3,2-c]pyridin-6(5H)-one

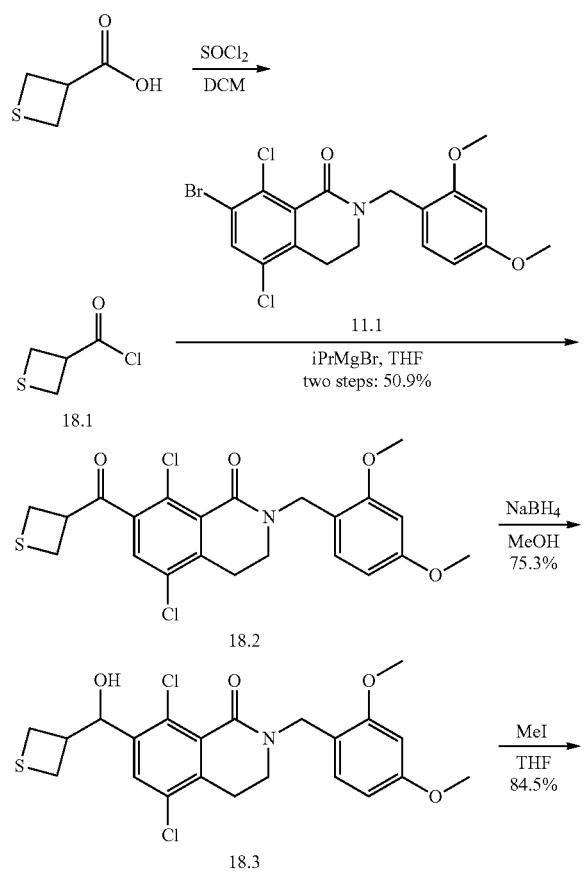

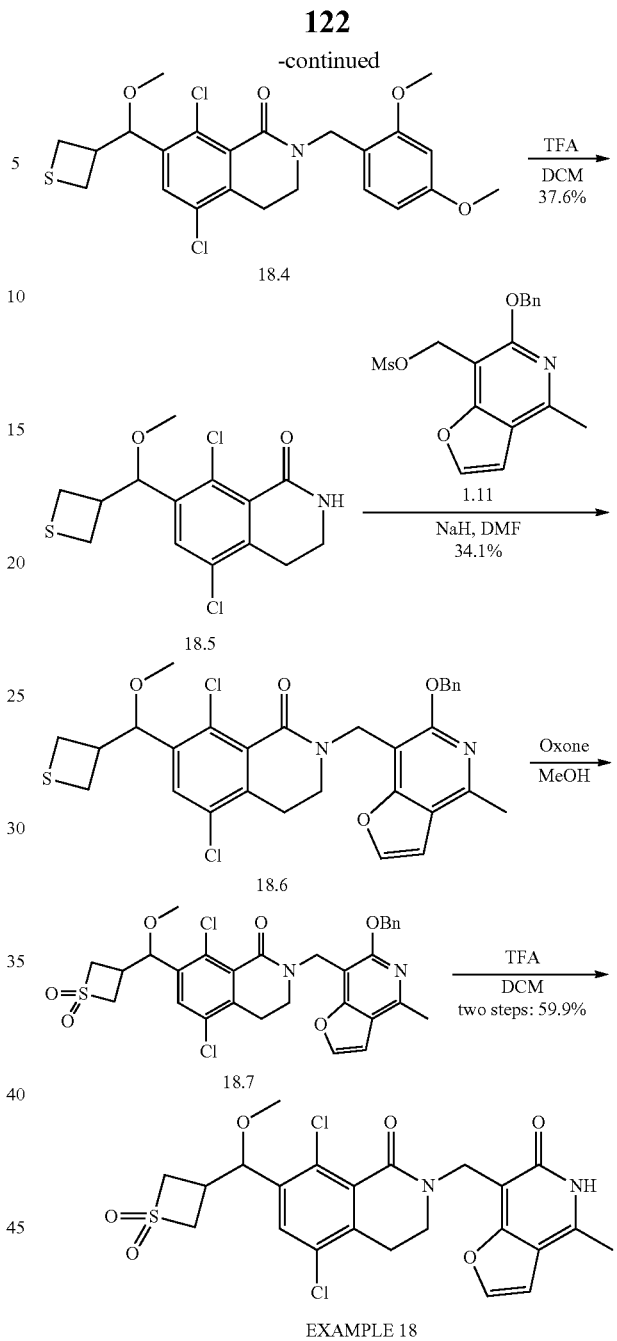

Example 18 was prepared from compound 18.1.

Compound 18.1.

To a solution of thietane-3-carboxylic acid (0.204 g, 1.73 mmol, 1.00 eq.) in DCM (1.00 mL) was added SOCl$_2$ (226 mg, 1.90 mmol, 137 µL, 1.10 eq.) at 25° C., and the resulting solution was stirred for 2 hours. The reaction mixture was concentrated under reduce pressure and then distilled as an azeotrope with toluene twice, to give the thietane-3-carbonyl chloride as a colorless oil (18.1, about 240 mg) which was used directly for the next step.

Compound 18.2.

To a solution of 7-bromo-5,8-dichloro-2-[(2,4-dimethoxyphenyl)methyl]-3,4-dihydroisoquinolin-1-one (11.1, 0.27 g, 606 µmol, 1.00 eq.) in THF (2.00 mL) was added chloro(isopropyl)magnesium (2.0 M, 0.7 mL, 2.31 eq.) dropwise at −78° C., and the resulting solution was warmed to −10° C. over 30 min, then thietane-3-carbonyl chloride (18.1, 0.2 g, 1.46 mmol, 2.41 eq.) was added. The resulting mixture was stirred at 0° C. for 30 min, quenched with MeOH (1.00 mL), diluted with water (10.0 mL), extracted with ethyl acetate (15.0 mL×3), and dried over sodium sulfate. The solvent was removed to afford a residue, which was purified by flash chromatography on silica gel (Petroleum ether/Ethyl acetate=3/1) to give the desired product 18.2 as a white solid.

Compound 18.3.

To a solution of 5,8-dichloro-2-[(2,4-dimethoxyphenyl) methyl]-7-(thietane-3-carbonyl)-3,4-dihydroisoquinolin-1-one (0.18 g, 385 μmol, 1.00 eq.) in MeOH (8.00 mL) was added $NaBH_4$ (21.9 mg, 579 μmol, 1.50 eq.) at 0° C., and the resulting mixture was stirred at 25° C. for 1 hour. The reaction was quenched with water (5.00 mL) and the solvent was evaporated to afford the crude material. Purification by flash chromatography on silica gel (Petroleum ether/Ethyl acetate=5/1 to 3/1) afforded the desired product as a white solid (0.16 g, yield=75.2%). LCMS [M+1]: 467.9.

Compound 18.4.

To a solution of 5,8-dichloro-2-[(2,4-dimethoxyphenyl) methyl]-7-[hydroxy(thietan-3-yl)methyl]-3,4-dihydroisoquinolin-1-one (18.3, 0.12 g, 256 μmol, 1.00 eq.) in THF (1.00 mL) was added NaH (20.5 mg, 512 μmol, 60% purity, 2.00 eq.) at 0° C., then MeI (72.7 mg, 512 μmol, 31.9 μL, 2.00 eq.) was added and the resulting mixture stirred at 25° C. for 1 hour. The reaction was quenched with MeOH (5.00 mL) and the solvent was evaporated to afford a residue, which was purified by flash chromatography on silica gel (Petroleum ether/Ethyl acetate=5/1) to give the desired product as a white solid (18.4, 0.11 g, yield=84.5%). LCMS [M+1]: 481.9.

Compound 18.5.

To a solution of 5,8-dichloro-2-[(2,4-dimethoxyphenyl) methyl]-7-[methoxy(thietan-3-yl)methyl]-3,4-dihydroisoquinolin-1-one (18.4, 0.11 g, 228 μmol, 1.00 eq.) in DCM (1.00 mL) was added TFA (0.50 mL). After stirring at 25° C. for 2 hours, the reaction solution was concentrated to afford a residue which was purified by flash chromatography on silica gel (Petroleum ether/ethyl acetate=3/1) to afford the desired product 18.5 as a yellow oil (0.03 g, yield=37.6%). LCMS [M+1]: 331.9.

Compound 18.6.

To a suspension of 5,8-dichloro-7-[methoxy(thietan-3-yl) methyl]-3,4-dihydro-2H-isoquinolin-1-one (18.5, 0.03 g, 90.2 μmol, 1.00 eq.) and NaH (10.8 mg, 271 mol, 60% purity, 3.00 eq.) in DMF (3 mL) at 0° C., (6-benzyloxy-4-methyl-furo[3,2-c]pyridin-7-yl)methyl methanesulfonate (1.11, 62.7 mg, 180 μmol, 2.00 eq.) was added and the resulting mixture was stirred at 25° C. for 2 hours. The reaction was quenched with water (10.0 mL), extracted with ethyl acetate (10.0 mL×3), dried over sodium sulfate and the solvent was removed to afford a residue. The crude product was purified by flash chromatography on silica gel (Petroleum ether/ethyl acetate=5/1) to give the desired product 18.6 as a yellow solid (20 mg, yield=34.16%). LCMS [M+1]: 583.0.

Compound 18.7

To a solution of 2-[(6-benzyloxy-4-methyl-furo[3,2-c] pyridin-7-yl)methyl]-5,8-dichloro-7-[methoxy(thietan-3-yl) methyl]-3,4-dihydroisoquinolin-1-one (18.6, 0.012 g, 20.6 μmol, 1.00 eq.) in MeOH (0.50 mL) and $H_2O$ (0.10 mL) was added oxone (25.3 mg, 41.1 μmol, 2.00 eq.) at 25° C. The resulting mixture was stirred for 30 min and concentrated. Water (10.0 mL) was added to the residue and extracted with ethyl acetate (10.0 mL×3). The combined organic layers were dried over sodium sulfate and the solvent was removed to afford the desired product 18.7 as a white solid, which was used without further purification (8.00 mg). LCMS [M+1]: 614.9.

EXAMPLE 18. To a solution of 2-[(6-benzyloxy-4-methyl-furo[3,2-c]pyridin-7-yl)methyl]-5,8-dichloro-7-[(1,1-dioxothietan-3-yl)-methoxy-methyl]-3,4-dihydroisoquinolin-1-one (18.7, 0.008 g, 13.0 μmol, 1.00 eq.) in DCM (1.00 mL) was added TFA (0.50 mL) at 25° C. The resulting solution was stirred at 25° C. for 12 hours and the solvent was evaporated to afford the crude product. The residue was purified by Pre-HPLC (column: Phenomenex Synergi $C_{18}$ 150×25×10 um; mobile phase: [water(0.1% TFA)-ACN]; B %: 20%-50%, 11 min) to give the desired product as a yellow solid (EXAMPLE 18, 4.4 mg, yield=59.9%, purity=93%). LCMS [M+1]: 525.2.

$^1$H NMR (400 MHz, $CD_3OD$) δ=7.64 (s, 1H), 7.59 (d, J=2.4 Hz, 1H), 6.83 (d, J=2.4 Hz, 1H), 5.04 (d, J=5.2 Hz, 1H), 4.24 (dd, J=7.6, 13.4 Hz, 1H), 4.18-4.04 (m, 2H), 3.92-3.84 (m, 1H), 3.64 (t, J=6.2 Hz, 2H), 3.05-2.99 (m, 2H), 2.99-2.91 (m, 1H), 2.54 (s, 3H).

Example 19

5,8-dichloro-2-[(7-methyl-5-oxo-1,6-dihydropyrrolo [2,3-c]pyridin-4-yl)methyl]-7-[1-(oxetan-3-yl)ethyl]-3,4-dihydroisoquinolin-1-one

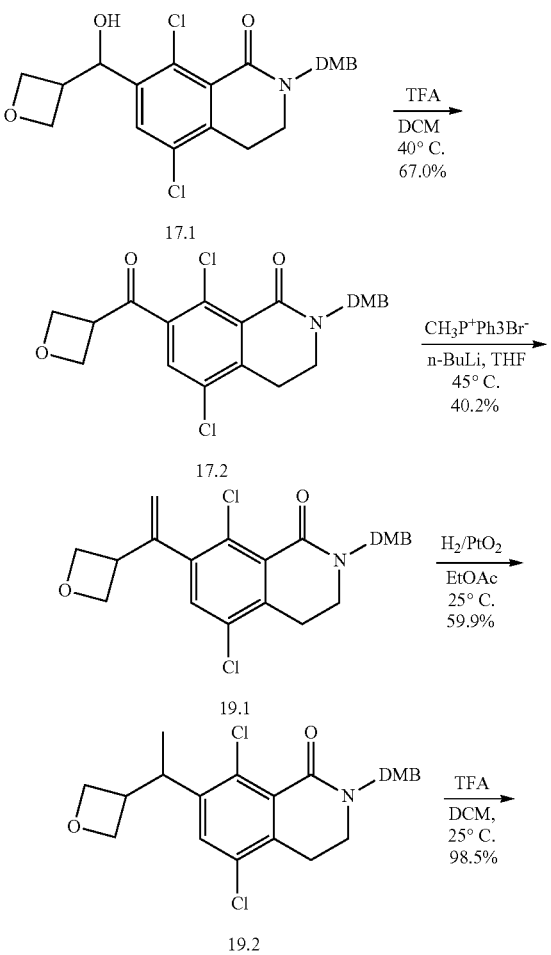

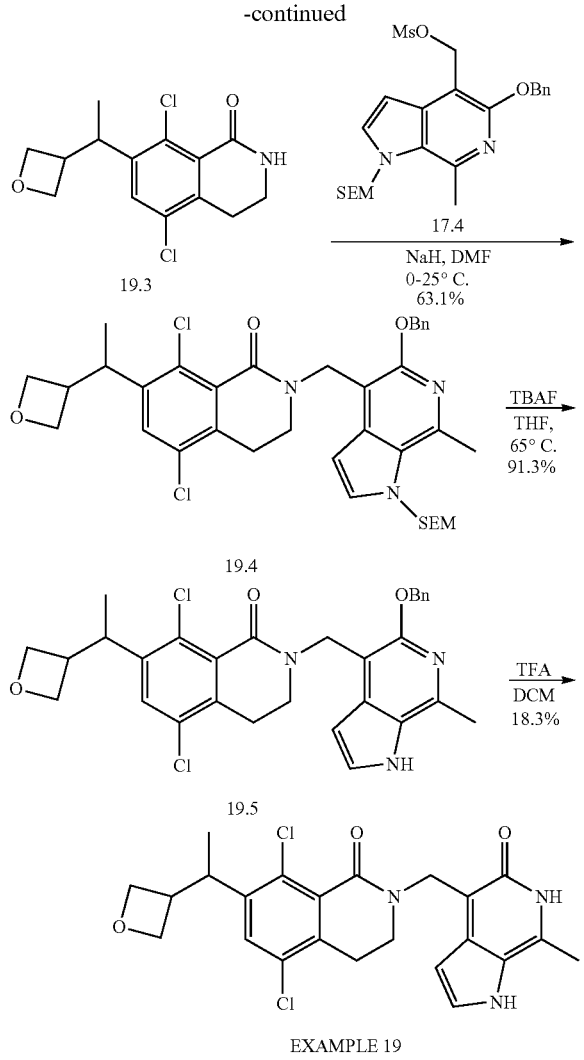

EXAMPLE 19

Example 19 (Example DE, Table 2) was prepared from compound 17.1.

Compound 17.2.

To a solution of 5,8-dichloro-2-[(2,4-dimethoxyphenyl) methyl]-7-[hydroxy(oxetan-3-yl)methyl]-3,4-dihydroisoquinolin-1-one (17.1, 441 mg, 975 μmol, 1.00 eq.) in DCM (5.00 mL) was added PDC (1.10 g, 2.92 mmol, 3.00 eq.). The resulting mixture was stirred at 40° C. for 12 h then was concentrated under reduced pressure to give a residue which purified by column chromatography (SiO₂, Petroleum ether/ Ethyl acetate=2/1) to afford 5,8-dichloro-2-[(2,4-dimethoxyphenyl)methyl]-7-(oxetane-3-carbonyl)-3,4-dihydroisoquinolin-1-one (17.2, 300 mg, 653 μmol, 67.0% yield, 98.0% purity) as a white solid. LCMS [M+1]: 449.9.

¹H NMR (400 MHz, chloroform-d) δ=7.51 (s, 1H), 7.33-7.29 (m, 1H), 6.49-6.44 (m, 2H), 4.90-4.86 (m, 4H), 4.72 (s, 2H), 4.67-4.59 (m, 1H), 4.13 (q, J=7.2 Hz, 1H), 3.83 (s, 3H), 3.81 (s, 3H), 3.52 (t, J=6.4 Hz, 2H), 2.97 (t, J=6.4 Hz, 2H).

Compound 19.1.

To a solution of Methyltriphenylphosphonium bromide (357 mg, 999 μmol, 5.0 eq.) in THF (1.00 mL) was added n-BuLi (2.5 M, 399 μL, 5.0 eq.) at 0° C. under N₂. The mixture was stirred at 0° C. for 0.5 hr, then 5,8-dichloro-2-[(2,4-dimethoxyphenyl)methyl]-7-(oxetane-3-carbonyl)-3, 4-dihydroisoquinolin-1-one (17.2, 90.0 mg, 200 μmol, 1 eq) in THF (1.0 mL) was added dropwise. The resulting mixture was warmed to 45° C. and stirred for 12 hr, then poured into saturated NH₄Cl aqeuous solution (2.0 mL) and extracted with EtOAc 5.0 mL (5.0 mL×3). The combined organic layers were washed with brine 5.0 mL (5.0 mL×2), dried over sodium sulfate, filtered and concentrated under reduced pressure to give a residue, which purified by column chromatography (SiO₂, Petroleum ether/Ethyl acetate=3/1) to afford 5,8-dichloro-2-[(2,4-dimethoxyphenyl)methyl]-7-[1-(oxetan-3-yl)vinyl]-3,4-dihydroisoquinolin-1-one (19.1, 45.0 mg, 80.3 μmol, 40.2% yield, 80.0% purity) as a light yellow oil. LCMS [M+1]: 447.9.

Compound 19.2.

To a solution of 5,8-dichloro-2-[(2,4-dimethoxyphenyl) methyl]-7-[1-(oxetan-3-yl)vinyl]-3,4-dihydroisoquinolin-1-one (43.0 mg, 93.0 μmol, 1 eq.) in EtOAc (1.00 mL) was added PtO₂ (19.1, 2.11 mg, 9.30 μmol, 0.1 eq). The suspension was degassed under vacuum and purged with H₂ (15 psi) three times. The mixture was stirred under H₂ (15 psi) at 25° C. for 15 min. The solids were removed by filtration and the filtrate concentrated under reduced pressure to give a residue, which purified by column chromatography (SiO₂, Petroleum ether/Ethyl acetate=4/1) to afford 5,8-dichloro-2-[(2,4-dimethoxyphenyl)methyl]-7-[1-(oxetan-3-yl)ethyl]-3, 4-dihydroisoquinolin-1-one (19.2, 26.0 mg, 55.7 μmol, 59.9% yield, 96.5% purity) as a white solid. LCMS [M+1]: 450.2.

Compound 19.3.

To a solution of 5,8-dichloro-2-[(2,4-dimethoxyphenyl) methyl]-7-[1-(oxetan-3-yl)ethyl]-3,4-dihydroisoquinolin-1-one (19.2, 26.0 mg, 55.4 μmol, 1 eq.) in DCM (2.00 mL) was added TFA (1.54 g, 13.51 mmol, 1 mL, 244 eq.). The mixture was stirred at 25° C. for 2 hr. The reaction mixture was quenched by addition NaHCO₃ (3.00 mL) at 0° C., and then diluted with H₂O (5.00 mL) and extracted with EtOAc (10.0 mL×3). The combined organic layers were washed with brine (10.0 mL×3), dried over NaSO₄, filtered and concentrated under reduced pressure to give a residue, which purified by column chromatography (SiO₂, DCM/ MeOH=20/1) to afford 5,8-dichloro-7-[1-(oxetan-3-yl) ethyl]-3,4-dihydro-2H-isoquinolin-1-one (19.3, 20.0 mg, 54.6 μmol, 98.5% yield, 81.9% purity) as a white solid. LCMS [M+1]: 300.0.

Compound 19.4.

To a solution of 5,8-dichloro-7-[1-(oxetan-3-yl)ethyl]-3, 4-dihydro-2H-isoquinolin-1-one (19.3, 20.0 mg, 54.0 μmol, 1.00 eq) in DMF (1.00 mL) was added NaH (4.32 mg, 108 μmol, 60.0% purity, 2.00 eq) at 0° C. The reaction mixture was stirred at 0° C. for 0.5 hour, then a solution of [5-benzyloxy-7-methyl-1-(2-trimethylsilylethoxymethyl)pyrrolo [2,3-c]pyridin-4-yl]methyl methanesulfonate (17.4, 25.7 mg, 54.0 μmol, 1.00 eq) in DMF (0.100 mL) was added dropwise. The reaction was warmed to 25° C. and stirred for 1 h. The reaction mixture was quenched with water (5.00 mL), extracted with ethyl acetate (5.00 mL×3). The combined organic phase was washed with brine (5.00 mL×2), dried with anhydrous sodium sulfate, filtered and concentrated in vacuum to give the residue which was purified by prep-TLC (Petroleum ether/Ethyl acetate=2/1) to give 2-[[5-benzyloxy-7-methyl-1-(2-trimethylsilylethoxymethyl) pyrrolo [2,3-c] pyridin-4-yl]methyl]-5,8-dichloro-7-[1-(oxetan-3-yl)ethyl]-3,4-dihydroisoquinolin-1-one (19.4, 25.0 mg, 63.1% yield, 92.7% purity) as colorless oil. LCMS: [M+1] 680.1.

Compound 19.5.

To a solution of 2-[[5-benzyloxy-7-methyl-1-(2-trimethylsilylethoxymethyl)pyrrolo[2,3-c]pyridin-4-yl]methyl]-5, 8-dichloro-7-[1-(oxetan-3-yl)ethyl]-3,4-dihydroisoquinolin-1-one (19.4, 25.0 mg, 34.0 μmol, 1.00 eq) in THF (0.500 mL) was added TBAF (1 M, 340.44 μL, 10 eq), and the resulting mixture was stirred at 65° C. for 24 h. The reaction was quenched with water (5.00 mL) and extracted with ethyl acetate (5.00 mL×3). The combined organic phase was washed with brine (5.00 mL×2), dried with anhydrous sodium sulfate, filtered and concentrated in vacuum to give the residue which was purified by prep-TLC (Petroleum ether/Ethyl acetate=2/1) to give 2-[(5-benzyloxy-7-methyl-1H-pyrrolo[2,3-c]pyridin-4-yl)methyl]-5,8-dichloro-7-[1-(oxetan-3-yl)ethyl]-3,4-dihydroisoquinolin-1-one (19.5, 18.0 mg, 91.3% yield, 95.1% purity) as colorless oil. LCMS: [M+1] 550.3.

EXAMPLE 19. A solution of 2-[(5-benzyloxy-7-methyl-1H-pyrrolo[2,3-c] pyridin-4-yl)methyl]-5,8-dichloro-7-[1-(oxetan-3-yl)ethyl]-3,4-dihydroisoquinolin-1-one (19.5, 18.0 mg, 31.1 μmol, 1.00 eq) in TFA (0.250 mL), DCM (0.500 mL) was stirred at 25° C. for 12 hours. The reaction was concentrated in vacuum to give the residue which was purified by prep-HPLC (TFA buffer, column: Phenomenex Synergi C18 150*25*10 um; mobile phase: [water(0.1% TFA)-ACN]; B %: 25%-55%, 13 min) and lyophilization to give 5,8-dichloro-2-[(7-methyl-5-oxo-1,6-dihydropyrrolo[2,3-c]pyridin-4-yl)methyl]-7-[1-(oxetan-3-yl)ethyl]-3,4-dihydroisoquinolin-1-one (EXAMPLE 19, 2.72 mg, 18.3% yield, 96.5% purity) as a purple solid. LCMS: [M+1]460.2.

$^1$H NMR (400 MHz, CD$_3$OD) δ=7.94 (d, J=2.4 Hz, 1H), 7.46 (s, 1H), 6.82 (d, J=2.4 Hz, 1H), 5.06 (s, 2H), 4.94-4.93 (m, 1H), 4.64 (t, J=6.4 Hz, 1H), 4.59 (t, J=6.0 Hz, 1H), 4.22 (t, J=6.4 Hz, 1H), 4.03-3.95 (m, 1H), 3.71 (t, J=6.0 Hz, 2H), 3.46-3.38 (m, 1H), 2.97 (t, J=5.2 Hz, 2H), 2.80 (s, 3H), 1.18 (d, J=6.8 Hz, 3H).

Exemplary compounds of formula (I) shown in Table 2 may be prepared using INTERMEDIATES A-T according to the teachings and methods provided in the General Reaction Schemes, Procedure A, Schemes 1-4 and the EXAMPLES described herein.

Table 2

Exemplary Compounds of Formula (I)

TABLE 2

Exemplary Compounds of Formula (I)

| Cmpd | Structure | Expected [M + 1]$^+$ |
|---|---|---|
| A | 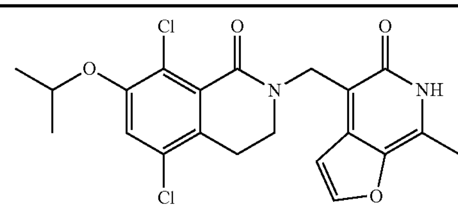 | 435.0 |
| B | 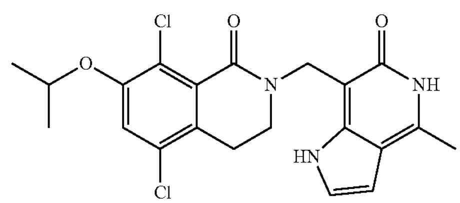 | 434.1 |
| C | 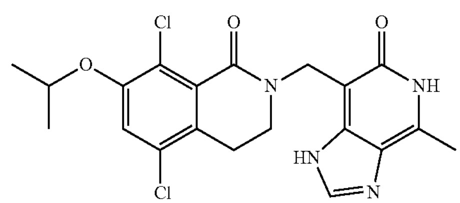 [SMILES: Cc1[nH]c(=O)c(CN2CCc3c(Cl)cc(OC(C)C)c(Cl)c3C2=O)c2[nH]cnc12] | 435.0 |
| D | 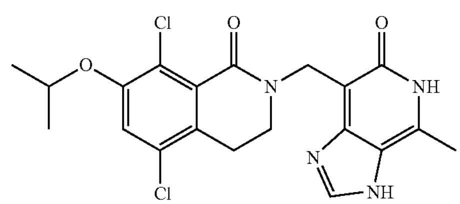 [SMILES: Cc1[nH]c(=O)c(CN2CCc3c(Cl)cc(OC(C)C)c(Cl)c3C2=O)c2nc[nH]c12] | 435.0 |
| E | 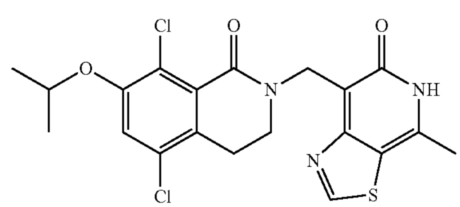 [SMILES: Cc1[nH]c(=O)c(CN2CCc3c(Cl)cc(OC(C)C)c(Cl)c3C2=O)c2ncsc12] | 452.0 |

TABLE 2-continued

Exemplary Compounds of Formula (I)

| Cmpd | Structure | Expected [M + 1]+ |
|---|---|---|
| F | 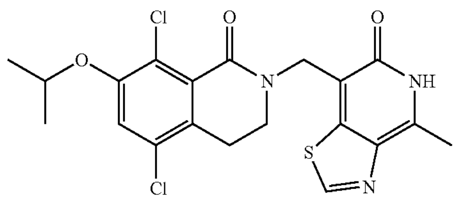 | 452.0 |
| G | 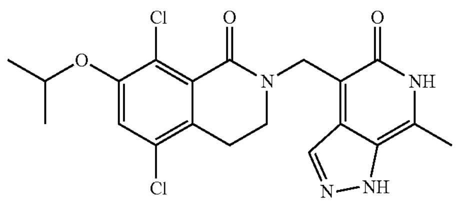 | 435.0 |
| H | 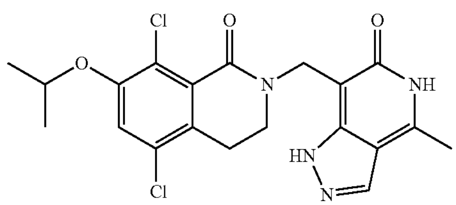 | 435.0 |
| I | 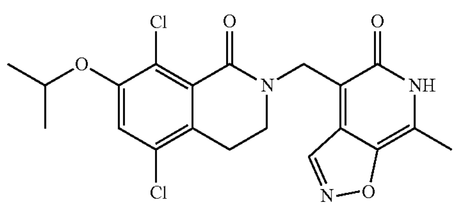 | 436.0 |
| J | 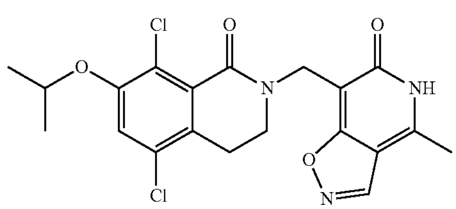 [SMILES: Cc1[nH]c(=O)c(CN2CCc3c(Cl)cc(OC(C)C)c(Cl)c3C2=O)c2oncc12] | 436.0 |
| K | 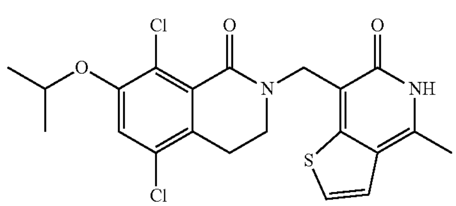 [SMILES: Cc1[nH]c(=O)c(CN2CCc3c(Cl)cc(OC(C)C)c(Cl)c3C2=O)c2sccc12] | 451.0 |
| L | 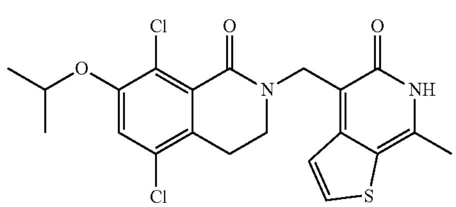 [SMILES: Cc1[nH]c(=O)c(CN2CCc3c(Cl)cc(OC(C)C)c(Cl)c3C2=O)c2ccsc12] | 451.0 |

TABLE 2-continued

| Cmpd | Structure | Expected [M + 1]+ |
|---|---|---|
| M | 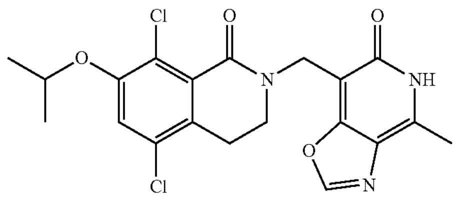 [SMILES: Cc1[nH]c(=O)c(CN2CCc3c(Cl)cc(OC(C)C)c(Cl)c3C2=O)c2ocnc12] | 436.0 |
| O | 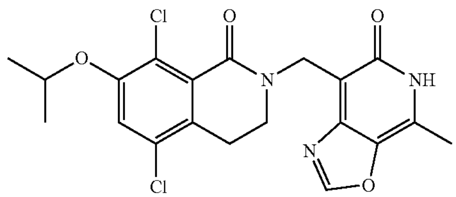 [SMILES: Cc1[nH]c(=O)c(CN2CCc3c(Cl)cc(OC(C)C)c(Cl)c3C2=O)c2ncoc12] | 436.0 |
| P | 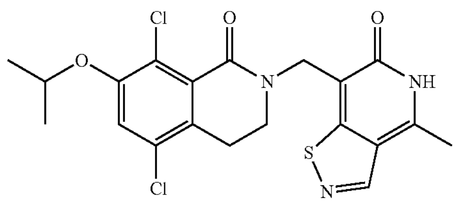 [SMILES: Cc1[nH]c(=O)c(CN2CCc3c(Cl)cc(OC(C)C)c(Cl)c3C2=O)c2sncc12] | 452.0 |
| Q | 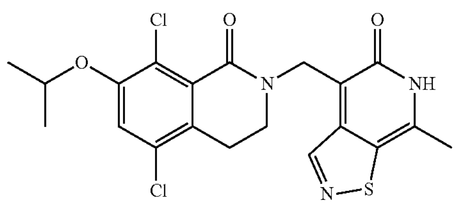 [SMILES: Cc1[nH]c(=O)c(CN2CCc3c(Cl)cc(OC(C)C)c(Cl)c3C2=O)c2cnsc12] | 452.0 |
| R | 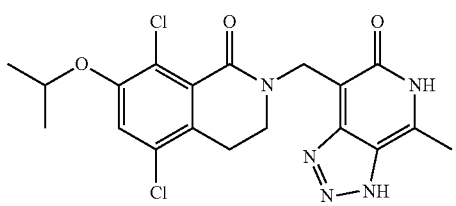 | 436.0 |
| S | 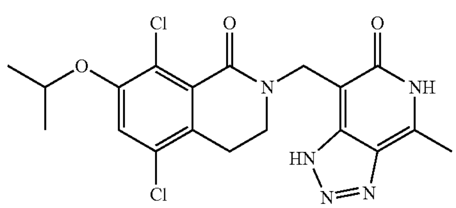 [SMILES: Cc1[nH]c(=O)c(CN2CCc3c(Cl)cc(OC(C)C)c(Cl)c3C2=O)c2[nH]nnc12] | 436.0 |
| T | 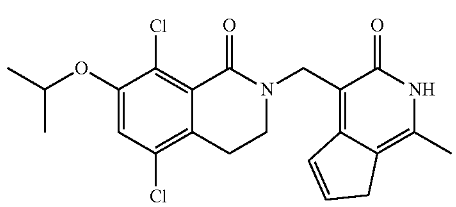 [SMILES: Cc1[nH]c(=O)c(CN2CCc3c(Cl)cc(OC(C)C)c(Cl)c3C2=O)c2c1CC=C2] | 433.1 |

TABLE 2-continued

Exemplary Compounds of Formula (I)

| Cmpd | Structure | Expected [M + 1]+ |
|---|---|---|
| U | 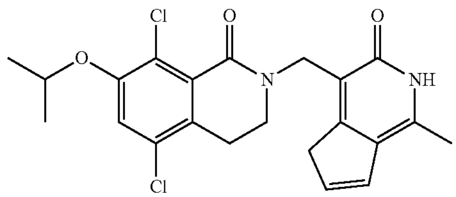 [SMILES: Cc1[nH]c(=O)c(CN2CCc3c(Cl)cc(OC(C)C)c(Cl)c3C2=O)c2c1C=CC2] | 433.1 |
| V | 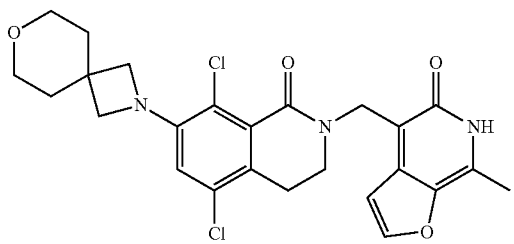 [SMILES: Cc1[nH]c(=O)c(CN2CCc3c(Cl)cc(N4CC5(CCOCC5)C4)c(Cl)c3C2=O)c2ccoc12] | 502.1 |
| W | | 501.1 |
| X | 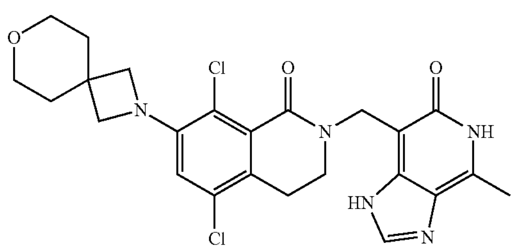 [SMILES: Cc1[nH]c(=O)c(CN2CCc3c(Cl)cc(N4CC5(CCOCC5)C4)c(Cl)c3C2=O)c2[nH]cnc12] | 502.1 |
| W | | 502.1 |
| Z | 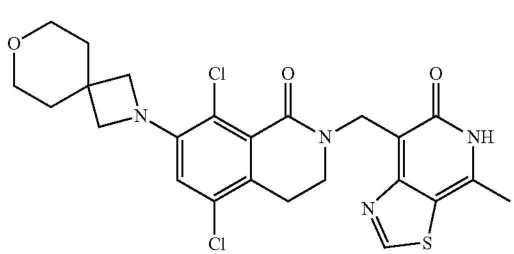 [SMILES: Cc1[nH]c(=O)c(CN2CCc3c(Cl)cc(N4CC5(CCOCC5)C4)c(Cl)c3C2=O)c2ncsc12] | 519.1 |

TABLE 2-continued

Exemplary Compounds of Formula (I)

| Cmpd | Structure | Expected [M + 1]+ |
|---|---|---|
| AA | 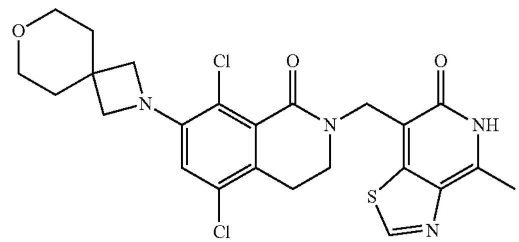 | 519.1 |
| AB | 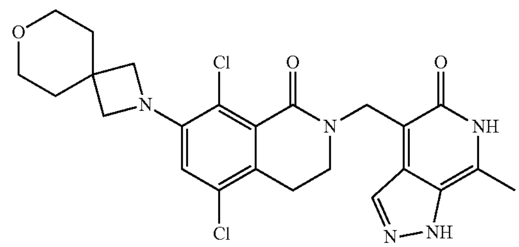 [SMILES: Cc1[nH]c(=O)c(CN2CCc3c(Cl)cc(N4CC5(CCOCC5)C4)c(Cl)c3C2=O)c2cn[nH]c12] | 502.1 |
| AC | 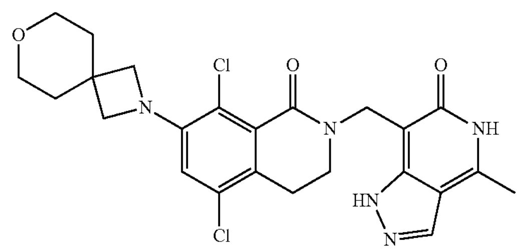 [SMILES: Cc1[nH]c(=O)c(CN2CCc3c(Cl)cc(N4CC5(CCOCC5)C4)c(Cl)c3C2=O)c2[nH]ncc12] | 502.1 |
| AD | 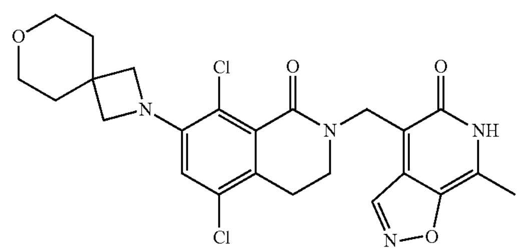 [SMILES: Cc1[nH]c(=O)c(CN2CCc3c(Cl)cc(N4CC5(CCOCC5)C4)c(Cl)c3C2=O)c2cnoc12] | 503.1 |
| AE | 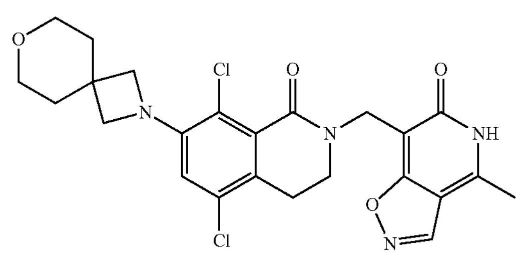 [SMILES: Cc1[nH]c(=O)c(CN2CCc3c(Cl)cc(N4CC5(CCOCC5)C4)c(Cl)c3C2=O)c2oncc12] | 503.1 |
| AF | 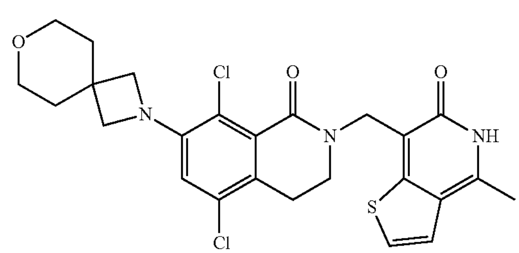 [SMILES: Cc1[nH]c(=O)c(CN2CCc3c(Cl)cc(N4CC5(CCOCC5)C4)c(Cl)c3C2=O)c2sccc12] | 518.1 |

TABLE 2-continued

Exemplary Compounds of Formula (I)

| Cmpd | Structure | Expected [M + 1]+ |
|---|---|---|
| AG | 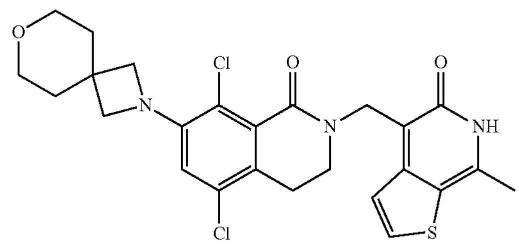 [SMILES: Cc1[nH]c(=O)c(CN2CCc3c(Cl)cc(N4CC5(CCOCC5)C4)c(Cl)c3C2=O)c2ccsc12] | 518.1 |
| AH | 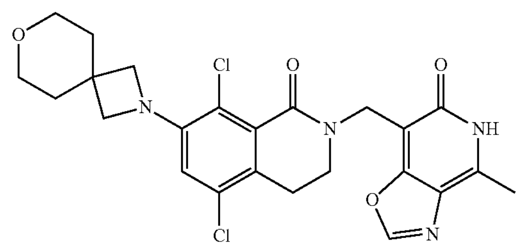 [SMILES: Cc1[nH]c(=O)c(CN2CCc3c(Cl)cc(N4CC5(CCOCC5)C4)c(Cl)c3C2=O)c2ocnc12] | 503.1 |
| AI | 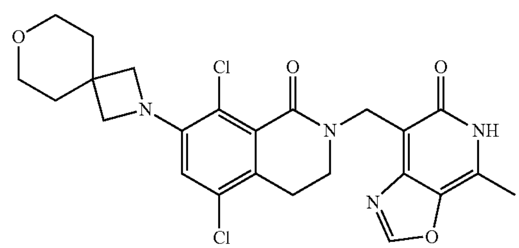 [SMILES: Cc1[nH]c(=O)c(CN2CCc3c(Cl)cc(N4CC5(CCOCC5)C4)c(Cl)c3C2=O)c2ncoc12] | 503.1 |
| AJ | 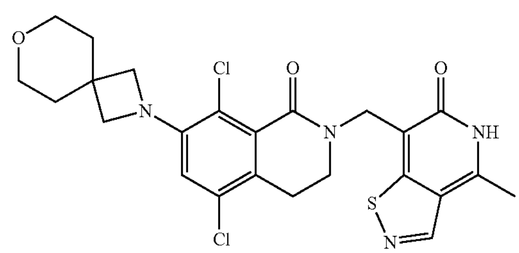 | 519.1 |
| AK | 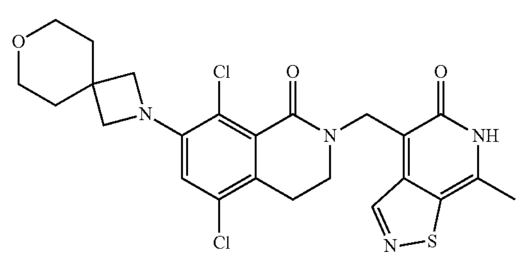 | 519.1 |
| AL | 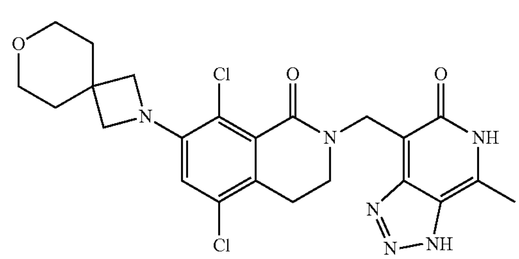 [SMILES: Cc1[nH]c(=O)c(CN2CCc3c(Cl)cc(N4CC5(CCOCC5)C4)c(Cl)c3C2=O)c2nn[nH]c12] | 503.1 |

TABLE 2-continued

Exemplary Compounds of Formula (I)

| Cmpd | Structure | Expected [M + 1]+ |
|---|---|---|
| AM | 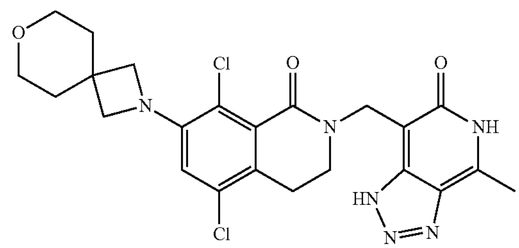 [SMILES: Cc1[nH]c(=O)c(CN2CCc3c(Cl)cc(N4CC5(CCOCC5)C4)c(Cl)c3C2=O)c2[nH]nnc12] | 503.1 |
| AN | 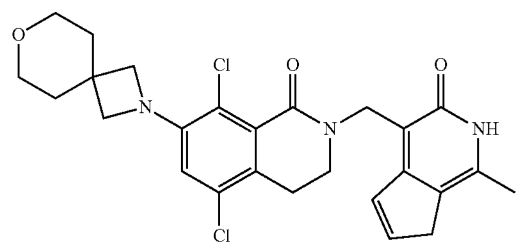 [SMILES: Cc1[nH]c(=O)c(CN2CCc3c(Cl)cc(N4CC5(CCOCC5)C4)c(Cl)c3C2=O)c2c1CC=C2] | 500.1 |
| AO | 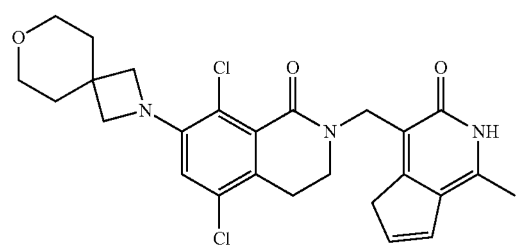 [SMILES: Cc1[nH]c(=O)c(CN2CCc3c(Cl)cc(N4CC5(CCOCC5)C4)c(Cl)c3C2=O)c2c1C=CC2] | 500.1 |
| AP | 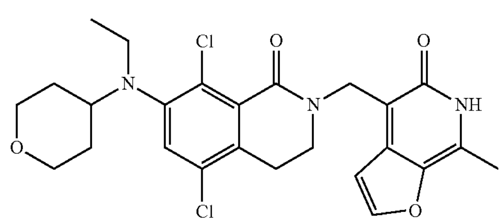 | 504.1 |
| AQ | 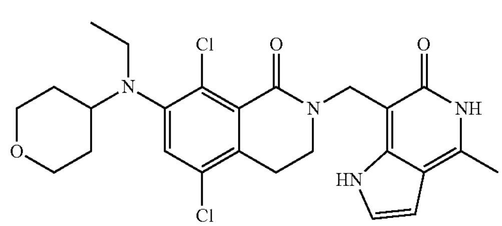 [SMILES: CCN(c1cc(Cl)c2c(c1Cl)C(=O)N(Cc1c(=O)[nH]c(C)c3cc[nH]c13)CC2)C1CCOCC1] | 503.1 |
| AR | 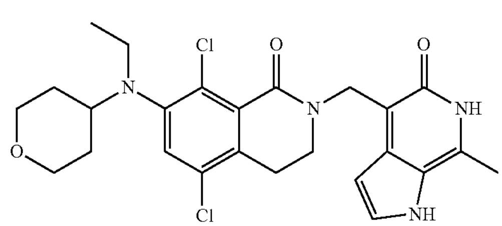 [SMILES: CCN(c1cc(Cl)c2c(c1Cl)C(=O)N(Cc1c(=O)[nH]c(C)c3[nH]ccc13)CC2)C1CCOCC1] | 503.1 |

TABLE 2-continued

Exemplary Compounds of Formula (I)

| Cmpd | Structure | Expected [M + 1]+ |
|---|---|---|
| AS | 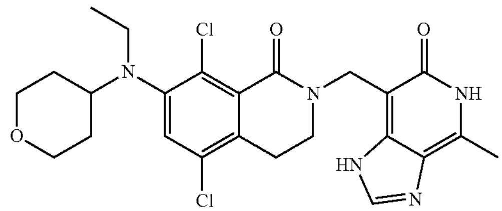 [SMILES: CCN(c1cc(Cl)c2c(c1Cl)C(=O)N(Cc1c(=O)[nH]c(C)c3nc[nH]c13)CC2)C1CCOCC1] | 504.1 |
| AT | 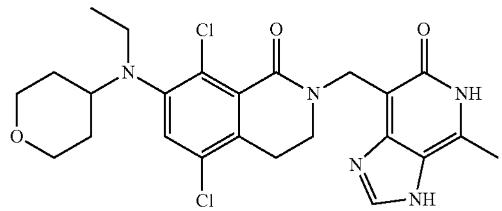 [SMILES: CCN(c1cc(Cl)c2c(c1Cl)C(=O)N(Cc1c(=O)[nH]c(C)c3[nH]cnc13)CC2)C1CCOCC1] | 504.1 |
| AU | 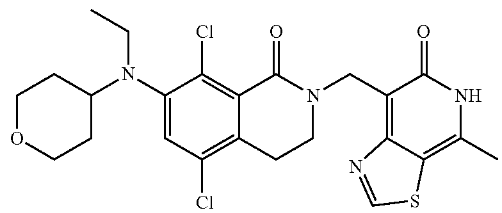 | 521.1 |
| AV | 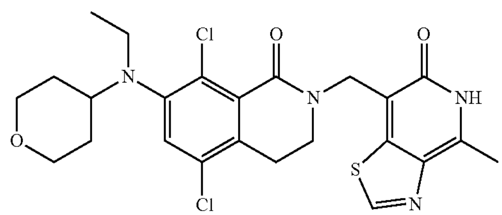 | 521.1 |
| AW | 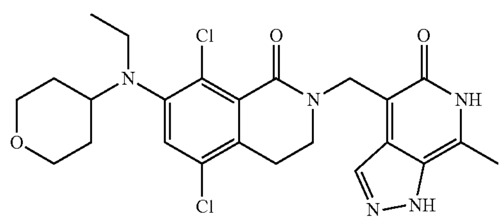 [SMILES: CCN(c1cc(Cl)c2c(c1Cl)C(=O)N(Cc1c(=O)[nH]c(C)c3[nH]ncc13)CC2)C1CCOCC1] | 504.1 |
| AX | 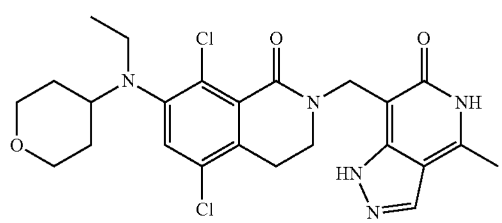 [SMILES: CCN(c1cc(Cl)c2c(c1Cl)C(=O)N(Cc1c(=O)[nH]c(C)c3cn[nH]c13)CC2)C1CCOCC1] | 504.1 |
| AY | 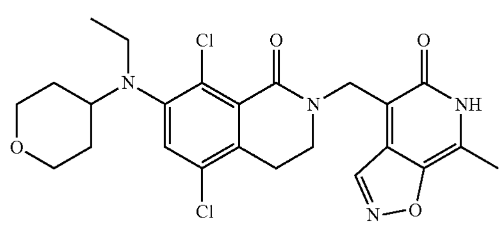 [SMILES: CCN(c1cc(Cl)c2c(c1Cl)C(=O)N(Cc1c(=O)[nH]c(C)c3oncc13)CC2)C1CCOCC1] | 505.1 |

TABLE 2-continued

Exemplary Compounds of Formula (I)

| Cmpd | Structure | Expected [M + 1]+ |
|---|---|---|
| AZ | 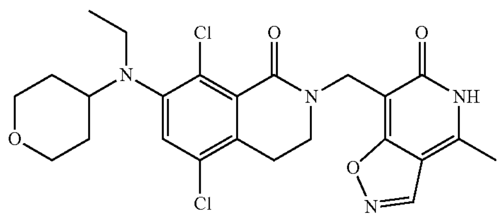 [SMILES: CCN(c1cc(Cl)c2c(c1Cl)C(=O)N(Cc1c(=O)[nH]c(C)c3cnoc13)CC2)C1CCOCC1] | 505.1 |
| BA | 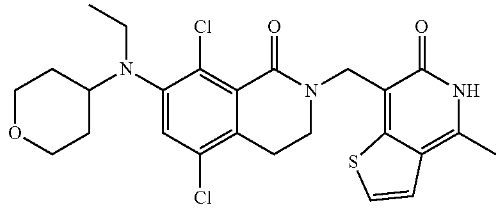 [SMILES: CCN(c1cc(Cl)c2c(c1Cl)C(=O)N(Cc1c(=O)[nH]c(C)c3ccsc13)CC2)C1CCOCC1] | 520.1 |
| BB | 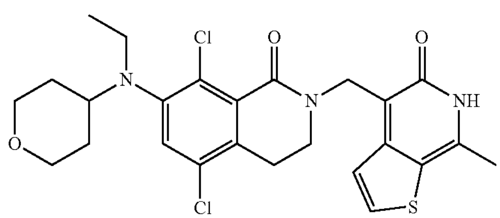 [SMILES: CCN(c1cc(Cl)c2c(c1Cl)C(=O)N(Cc1c(=O)[nH]c(C)c3sccc13)CC2)C1CCOCC1] | 520.1 |
| BC | 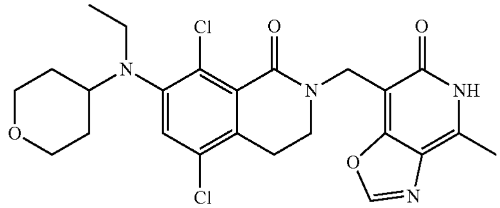 [SMILES: CCN(c1cc(Cl)c2c(c1Cl)C(=O)N(Cc1c(=O)[nH]c(C)c3ncoc13)CC2)C1CCOCC1] | 505.1 |
| BD | 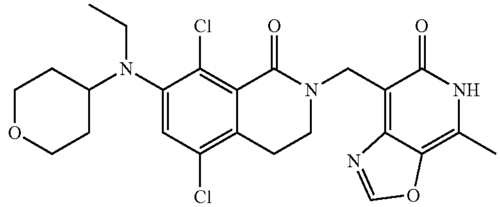 [SMILES: CCN(c1cc(Cl)c2c(c1Cl)C(=O)N(Cc1c(=O)[nH]c(C)c3ocnc13)CC2)C1CCOCC1] | 505.1 |
| BE | 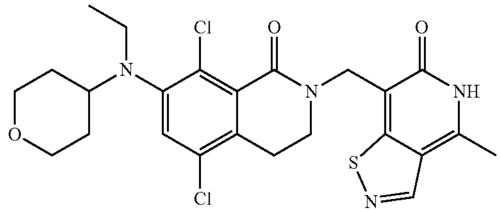 [SMILES: CCN(c1cc(Cl)c2c(c1Cl)C(=O)N(Cc1c(=O)[nH]c(C)c3cnsc13)CC2)C1CCOCC1] | 521.1 |

TABLE 2-continued

Exemplary Compounds of Formula (I)

| Cmpd | Structure | Expected [M + 1]+ |
|---|---|---|
| BF | 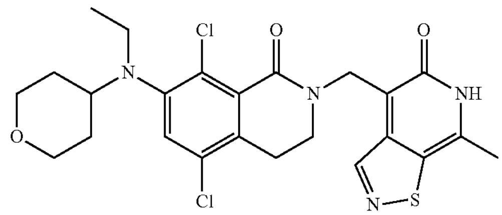 | 521.1 |
| BG | 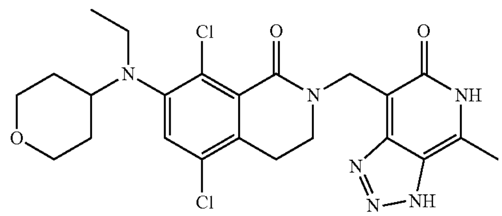 [SMILES: CCN(c1cc(Cl)c2c(c1Cl)C(=O)N(Cc1c(=O)[nH]c(C)c3[nH]nnc13)CC2)C1CCOCC1] | 505.1 |
| BH | 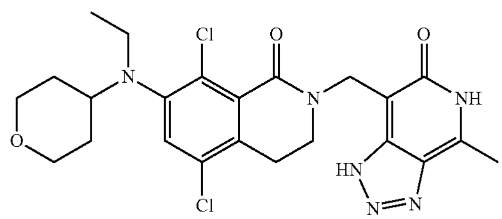 [SMILES: CCN(c1cc(Cl)c2c(c1Cl)C(=O)N(Cc1c(=O)[nH]c(C)c3nn[nH]c13)CC2)C1CCOCC1] | 505.1 |
| BI | 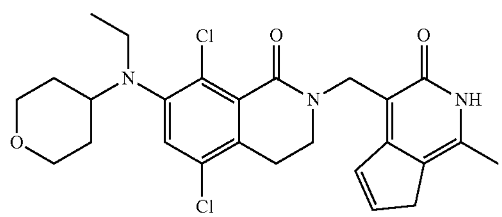 [SMILES: CCN(c1cc(Cl)c2c(c1Cl)C(=O)N(Cc1c3c(c(C)[nH]c1=O)CC=C3)CC2)C1CCOCC1] | 502.1 |
| BJ | 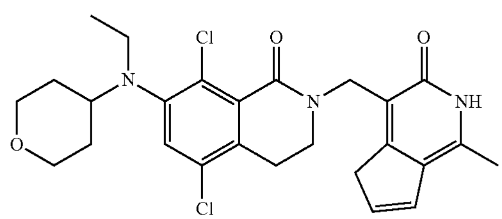 [SMILES: CCN(c1cc(Cl)c2c(c1Cl)C(=O)N(Cc1c3c(c(C)[nH]c1=O)C=CC3)CC2)C1CCOCC1] | 502.1 |
| BK | 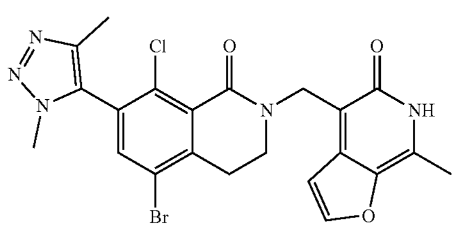 [SMILES: Cc1nnn(C)c1-c1cc(Br)c2c(c1Cl)C(=O)N(Cc1c(=O)[nH]c(C)c3occc13)CC2] | 516.0 |
| BL | 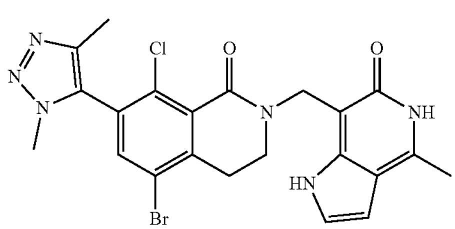 [SMILES: Cc1nnn(C)c1-c1cc(Br)c2c(c1Cl)C(=O)N(Cc1c(=O)[nH]c(C)c3cc[nH]c13)CC2] | 515.0 |

TABLE 2-continued

Exemplary Compounds of Formula (I)

| Cmpd | Structure | Expected [M + 1]+ |
|---|---|---|
| BM | 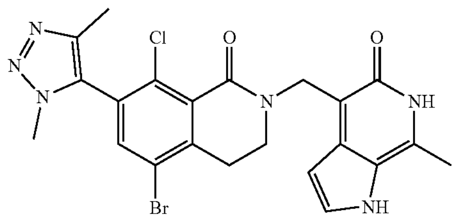 | 515.0 |
| BN | 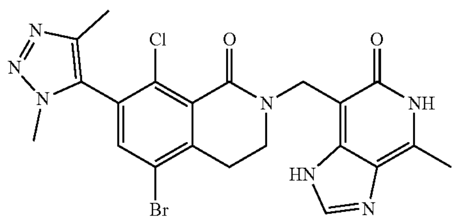 [SMILES: Cc1nnn(C)c1-c1cc(Br)c2c(c1Cl)C(=O)N(Cc1c(=O)[nH]c(C)c3nc[nH]c13)CC2] | 516.0 |
| BO | 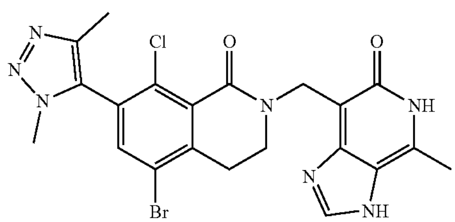 | 516.0 |
| BP | 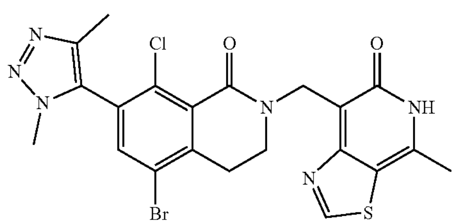 | 533.0 |
| BQ | 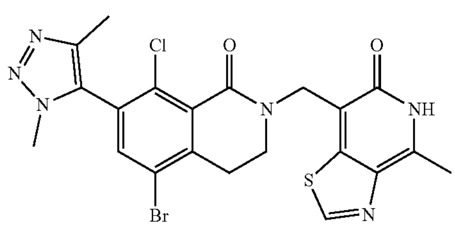 [SMILES: Cc1nnn(C)c1-c1cc(Br)c2c(c1Cl)C(=O)N(Cc1c(=O)[nH]c(C)c3ncsc13)CC2] | 533.0 |
| BR | 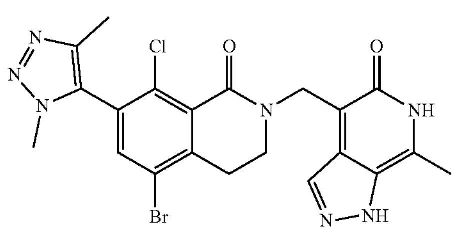 [SMILES: Cc1nnn(C)c1-c1cc(Br)c2c(c1Cl)C(=O)N(Cc1c(=O)[nH]c(C)c3[nH]ncc13)CC2] | 516.0 |

TABLE 2-continued

Exemplary Compounds of Formula (I)

| Cmpd | Structure | Expected [M + 1]+ |
|---|---|---|
| BS | 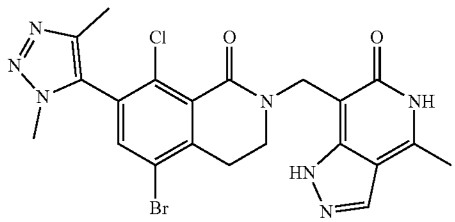 [SMILES: Cc1nnn(C)c1-c1cc(Br)c2c(c1Cl)C(=O)N(Cc1c(=O)[nH]c(C)c3cn[nH]c13)CC2] | 516.0 |
| BT | 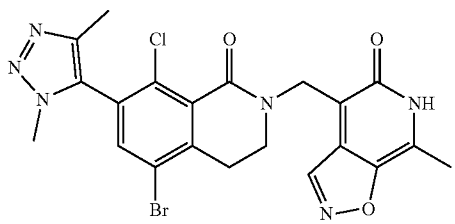 [SMILES: Cc1nnn(C)c1-c1cc(Br)c2c(c1Cl)C(=O)N(Cc1c(=O)[nH]c(C)c3oncc13)CC2] | 517.0 |
| BU | 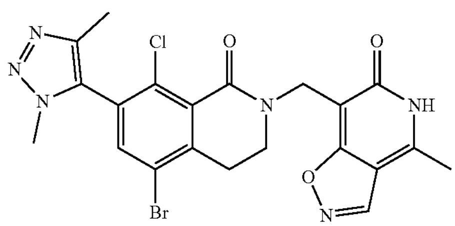 [SMILES: Cc1nnn(C)c1-c1cc(Br)c2c(c1Cl)C(=O)N(Cc1c(=O)[nH]c(C)c3cnoc13)CC2] | 517.0 |
| BV | 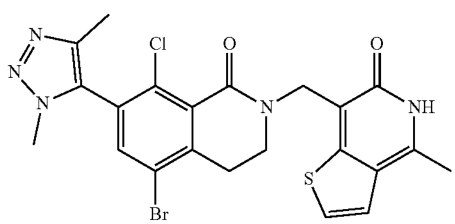 [SMILES: Cc1nnn(C)c1-c1cc(Br)c2c(c1Cl)C(=O)N(Cc1c(=O)[nH]c(C)c3ccsc13)CC2] | 532.0 |
| BW | 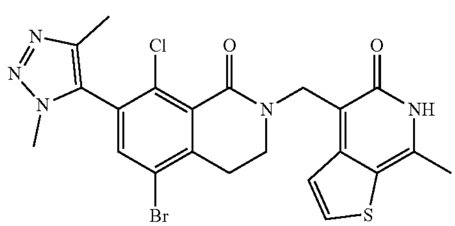 | 532.0 |
| BX | 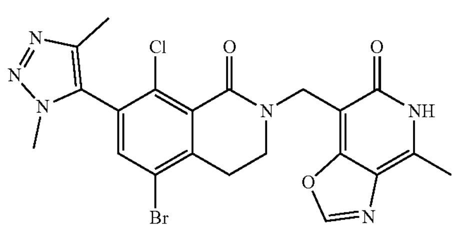 [SMILES: Cc1nnn(C)c1-c1cc(Br)c2c(c1Cl)C(=O)N(Cc1c(=O)[nH]c(C)c3ncoc13)CC2] | 517.0 |

TABLE 2-continued
Exemplary Compounds of Formula (I)
| Cmpd | Structure | Expected [M + 1]+ |
|---|---|---|
| BY | 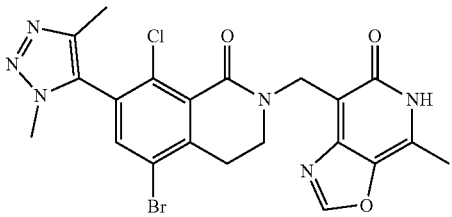 | 517.0 |
| BZ | 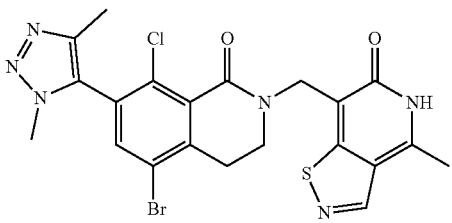 | 533.0 |
| CA | 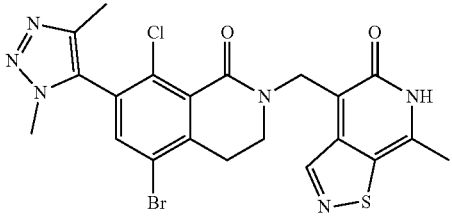 | 533.0 |
| CB | 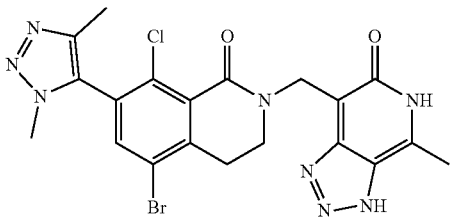 | 512.1 |
| CC | 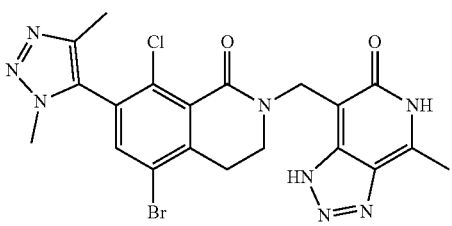 | 512.1 |
| CD | 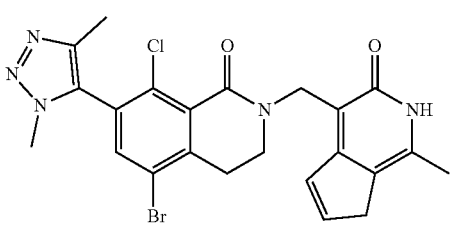 | 514.0 |

TABLE 2-continued

| Cmpd | Structure | Expected [M + 1]+ |
|---|---|---|
| CE | 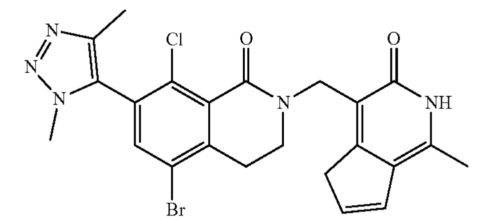 [SMILES: Cc1nnn(C)c1-c1cc(Br)c2c(c1Cl)C(=O)N(Cc1c3c(c(C)[nH]c1=O)C=CC3)CC2] | 514.0 |
| CF | 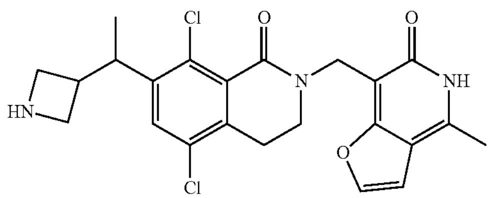 [SMILES: Cc1[nH]c(=O)c(CN2CCc3c(Cl)cc(C(C)C4CNC4)c(Cl)c3C2=O)c2occc12] | 460.1 |
| CG | 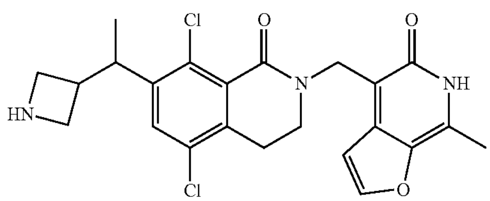 [SMILES: Cc1[nH]c(=O)c(CN2CCc3c(Cl)cc(C(C)C4CNC4)c(Cl)c3C2=O)c2ccoc12] | 460.1 |
| CH | 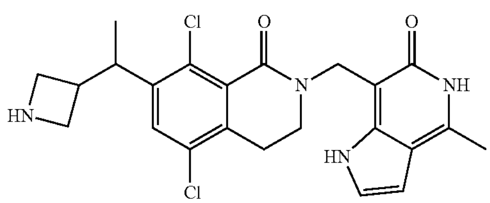 [SMILES: Cc1[nH]c(=O)c(CN2CCc3c(Cl)cc(C(C)C4CNC4)c(Cl)c3C2=O)c2[nH]ccc12] | 459.1 |
| CI | 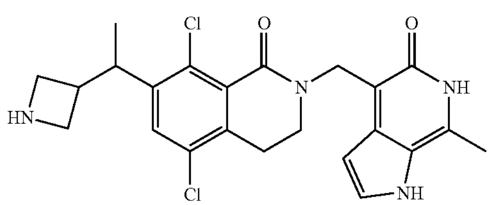 | 459.1 |
| CJ | 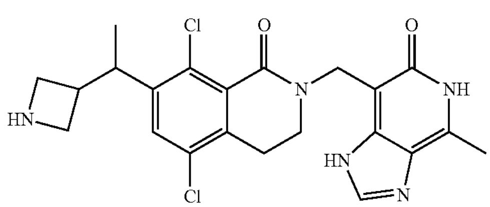 [SMILES: Cc1[nH]c(=O)c(CN2CCc3c(Cl)cc(C(C)C4CNC4)c(Cl)c3C2=O)c2[nH]cnc12] | 460.1 |
| CK | 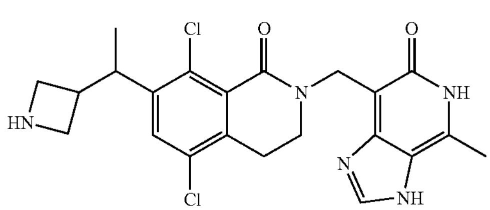 [SMILES: Cc1[nH]c(=O)c(CN2CCc3c(Cl)cc(C(C)C4CNC4)c(Cl)c3C2=O)c2nc[nH]c12] | 460.1 |

TABLE 2-continued

| Cmpd | Structure | Expected [M + 1]+ |
|---|---|---|
| CL | 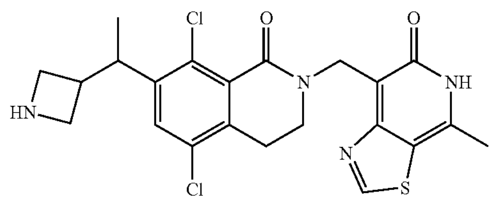 [SMILES: Cc1[nH]c(=O)c(CN2CCc3c(Cl)cc(C(C)C4CNC4)c(Cl)c3C2=O)c2ncsc12] | 477.0 |
| CM | 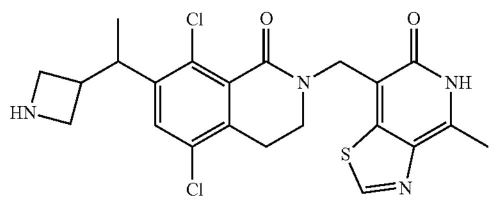 [SMILES: Cc1[nH]c(=O)c(CN2CCc3c(Cl)cc(C(C)C4CNC4)c(Cl)c3C2=O)c2scnc12] | 477.0 |
| CN | 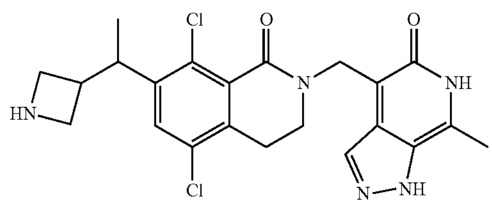 [SMILES: Cc1[nH]c(=O)c(CN2CCc3c(Cl)cc(C(C)C4CNC4)c(Cl)c3C2=O)c2cn[nH]c12] | 460.1 |
| CO | 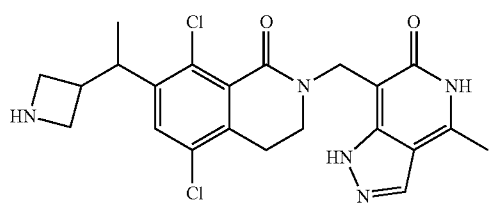 [SMILES: Cc1[nH]c(=O)c(CN2CCc3c(Cl)cc(C(C)C4CNC4)c(Cl)c3C2=O)c2[nH]ncc12] | 460.1 |
| CP | 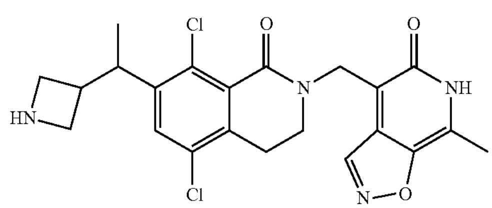 [SMILES: Cc1[nH]c(=O)c(CN2CCc3c(Cl)cc(C(C)C4CNC4)c(Cl)c3C2=O)c2cnoc12] | 461.1 |
| CQ | 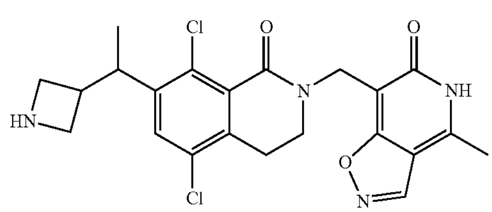 [SMILES: Cc1[nH]c(=O)c(CN2CCc3c(Cl)cc(C(C)C4CNC4)c(Cl)c3C2=O)c2oncc12] | 461.1 |
| CR | 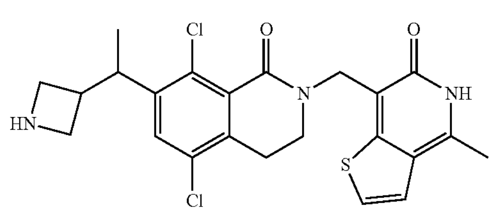 [SMILES: Cc1[nH]c(=O)c(CN2CCc3c(Cl)cc(C(C)C4CNC4)c(Cl)c3C2=O)c2sccc12] | 476.0 |

TABLE 2-continued

Exemplary Compounds of Formula (I)

| Cmpd | Structure | Expected [M + 1]+ |
|---|---|---|
| CS | 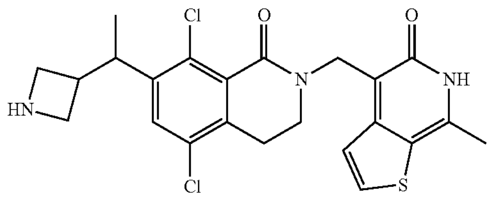 [SMILES: Cc1[nH]c(=O)c(CN2CCc3c(Cl)cc(C(C)C4CNC4)c(Cl)c3C2=O)c2ccsc12] | 476.0 |
| CT | 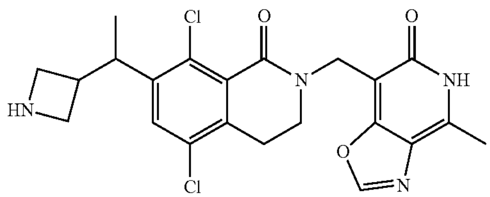 [SMILES: Cc1[nH]c(=O)c(CN2CCc3c(Cl)cc(C(C)C4CNC4)c(Cl)c3C2=O)c2ocnc12] | 461.0 |
| CU | 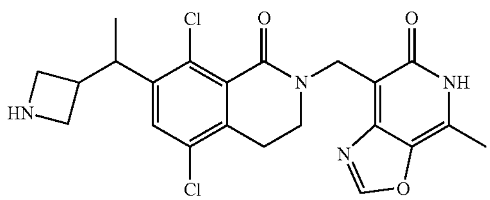 [SMILES: Cc1[nH]c(=O)c(CN2CCc3c(Cl)cc(C(C)C4CNC4)c(Cl)c3C2=O)c2ncoc12] | 461.0 |
| CV | 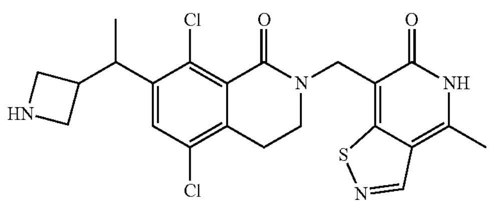 [SMILES: Cc1[nH]c(=O)c(CN2CCc3c(Cl)cc(C(C)C4CNC4)c(Cl)c3C2=O)c2sncc12] | 477.0 |
| CW | 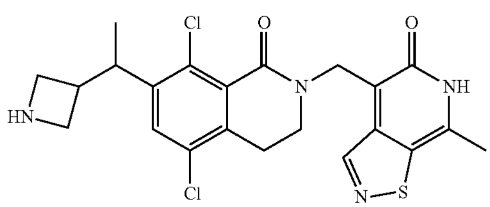 [SMILES: Cc1[nH]c(=O)c(CN2CCc3c(Cl)cc(C(C)C4CNC4)c(Cl)c3C2=O)c2cnsc12] | 477.0 |
| CX | 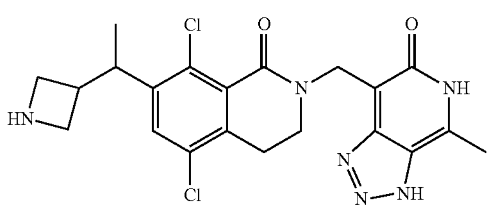 [SMILES: Cc1[nH]c(=O)c(CN2CCc3c(Cl)cc(C(C)C4CNC4)c(Cl)c3C2=O)c2nn[nH]c12] | 461.1 |
| CY | 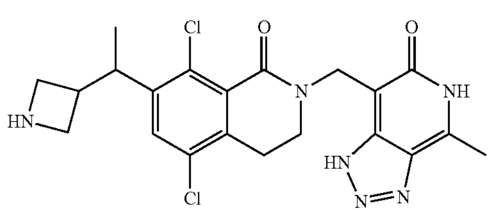 [SMILES: Cc1[nH]c(=O)c(CN2CCc3c(Cl)cc(C(C)C4CNC4)c(Cl)c3C2=O)c2[nH]nnc12] | 461.1 |

TABLE 2-continued

| Cmpd | Structure | Expected [M + 1]+ |
|---|---|---|
| CZ | 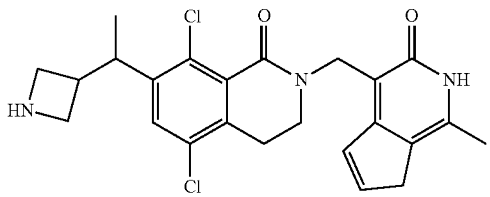 [SMILES: Cc1[nH]c(=O)c(CN2CCc3c(Cl)cc(C(C)C4CNC4)c(Cl)c3C2=O)c2c1CC=C2] | 457.1 |
| DA | 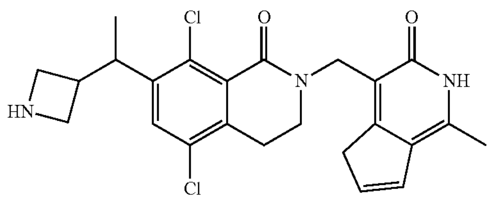 [SMILES: Cc1[nH]c(=O)c(CN2CCc3c(Cl)cc(C(C)C4CNC4)c(Cl)c3C2=O)c2c1C=CC2] | 457.1 |
| DB | 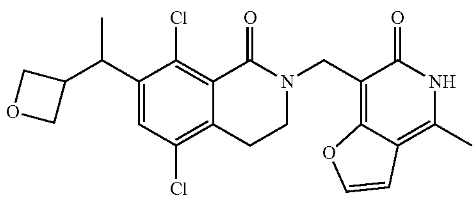 | 461.1 |
| DC | 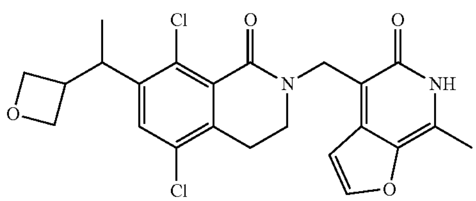 [SMILES: Cc1[nH]c(=O)c(CN2CCc3c(Cl)cc(C(C)C4COC4)c(Cl)c3C2=O)c2ccoc12] | 461.1 |
| DD | 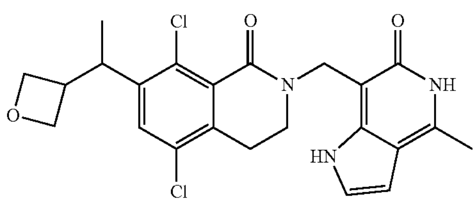 [SMILES: Cc1[nH]c(=O)c(CN2CCc3c(Cl)cc(C(C)C4COC4)c(Cl)c3C2=O)c2[nH]ccc12] | 460.1 |
| DE | 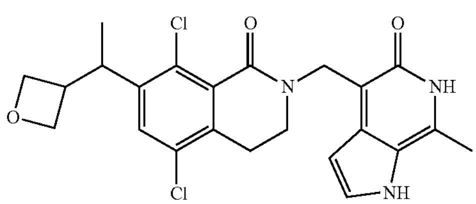 [SMILES: Cc1[nH]c(=O)c(CN2CCc3c(Cl)cc(C(C)C4COC4)c(Cl)c3C2=O)c2cc[nH]c12] | 460.1 |
| DF | 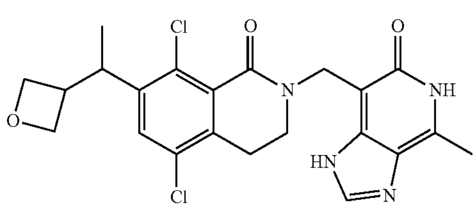 [SMILES: Cc1[nH]c(=O)c(CN2CCc3c(Cl)cc(C(C)C4COC4)c(Cl)c3C2=O)c2[nH]cnc12] | 461.1 |

TABLE 2-continued

Exemplary Compounds of Formula (I)

| Cmpd | Structure | Expected [M + 1]+ |
|---|---|---|
| DG | 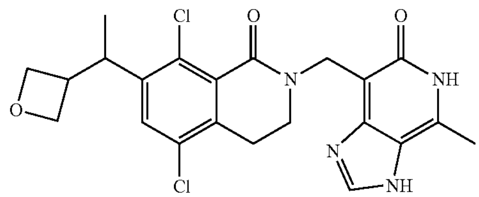 [SMILES: Cc1[nH]c(=O)c(CN2CCc3c(Cl)cc(C(C)C4COC4)c(Cl)c3C2=O)c2nc[nH]c12] | 461.1 |
| DH | 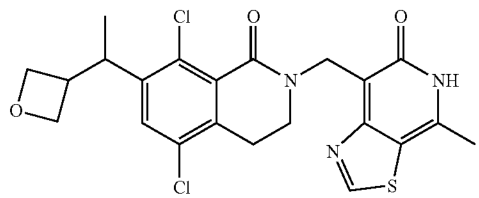 | 478.0 |
| DJ | 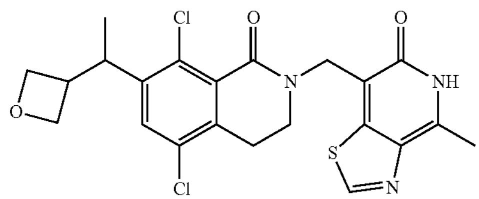 | 478.0 |
| DI | 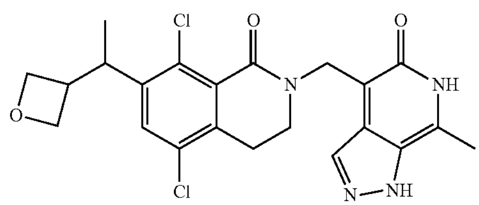 [SMILES: Cc1[nH]c(=O)c(CN2CCc3c(Cl)cc(C(C)C4COC4)c(Cl)c3C2=O)c2cn[nH]c12] | 461.1 |
| DK | 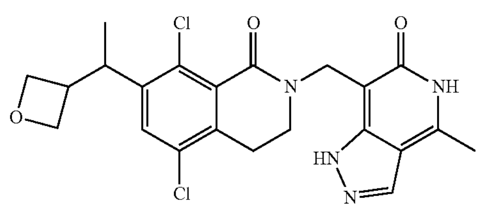 [SMILES: Cc1[nH]c(=O)c(CN2CCc3c(Cl)cc(C(C)C4COC4)c(Cl)c3C2=O)c2[nH]ncc12] | 461.1 |
| DL | 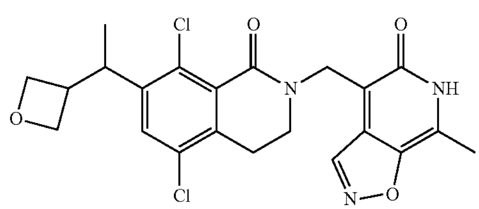 [SMILES: Cc1[nH]c(=O)c(CN2CCc3c(Cl)cc(C(C)C4COC4)c(Cl)c3C2=O)c2cnoc12] | 462.0 |
| DM | 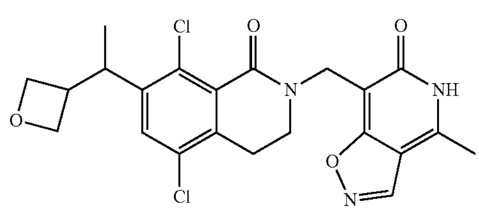 [SMILES: Cc1[nH]c(=O)c(CN2CCc3c(Cl)cc(C(C)C4COC4)c(Cl)c3C2=O)c2oncc12] | 462.0 |

TABLE 2-continued

Exemplary Compounds of Formula (I)

| Cmpd | Structure | Expected [M + 1]+ |
|---|---|---|
| DN | 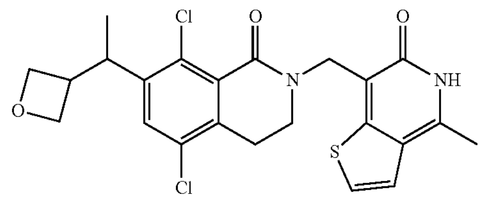 | 477.0 |
| DO | 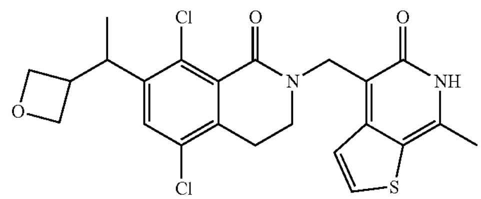 | 477.0 |
| DP | 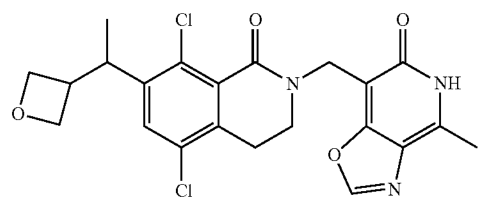 [SMILES: Cc1[nH]c(=O)c(CN2CCc3c(Cl)cc(C(C)C4COC4)c(Cl)c3C2=O)c2ocnc12] | 462.0 |
| DQ | 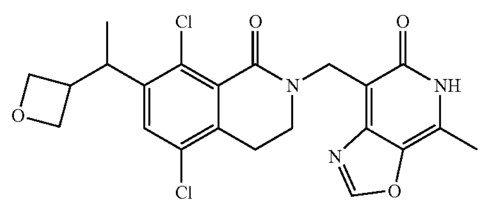 [SMILES: Cc1[nH]c(=O)c(CN2CCc3c(Cl)cc(C(C)C4COC4)c(Cl)c3C2=O)c2ncoc12] | 462.0 |
| DR | 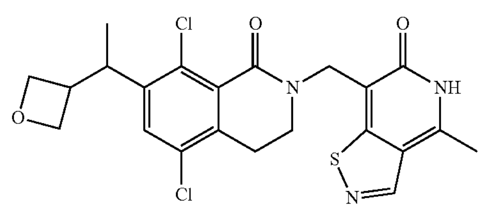 [SMILES: Cc1[nH]c(=O)c(CN2CCc3c(Cl)cc(C(C)C4COC4)c(Cl)c3C2=O)c2sncc12] | 478.0 |
| DS | 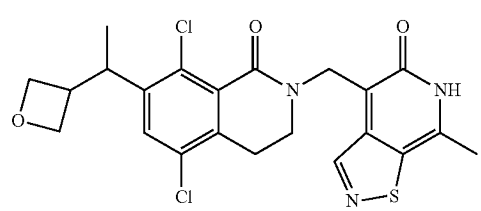 [SMILES: Cc1[nH]c(=O)c(CN2CCc3c(Cl)cc(C(C)C4COC4)c(Cl)c3C2=O)c2cnsc12] | 478.0 |
| DT | 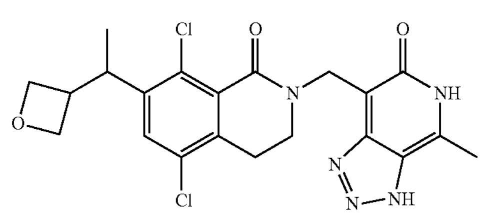 [SMILES: Cc1[nH]c(=O)c(CN2CCc3c(Cl)cc(C(C)C4COC4)c(Cl)c3C2=O)c2nn[nH]c12] | 462.1 |

TABLE 2-continued

Exemplary Compounds of Formula (I)

| Cmpd | Structure | Expected [M + 1]+ |
|---|---|---|
| DU | 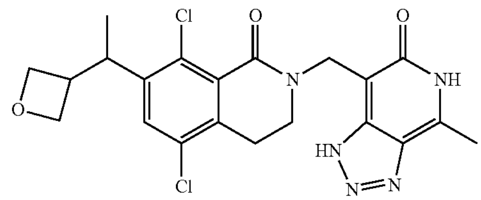 [SMILES: Cc1[nH]c(=O)c(CN2CCc3c(Cl)cc(C(C)C4COC4)c(Cl)c3C2=O)c2[nH]nnc12] | 462.1 |
| DV | 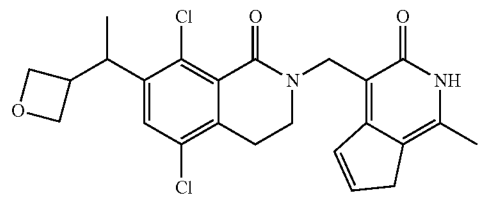 [SMILES: Cc1[nH]c(=O)c(CN2CCc3c(Cl)cc(C(C)C4COC4)c(Cl)c3C2=O)c2c1CC=C2] | 459.1 |
| DW | 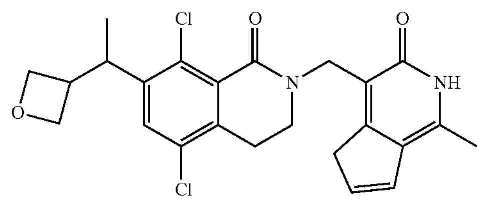 [SMILES: Cc1[nH]c(=O)c(CN2CCc3c(Cl)cc(C(C)C4COC4)c(Cl)c3C2=O)c2c1C=CC2] | 459.1 |
| DX | 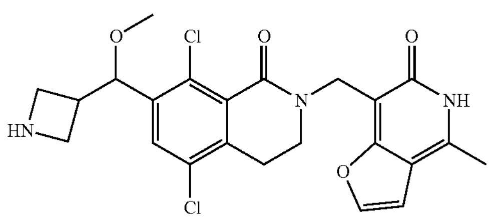 | 476.1 |
| DY | 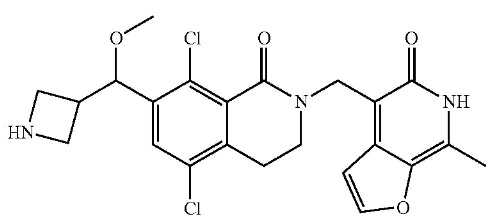 | 476.1 |
| DZ | 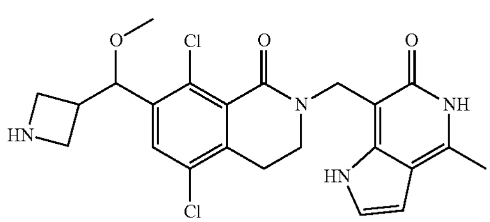 | 475.1 |
| EA | 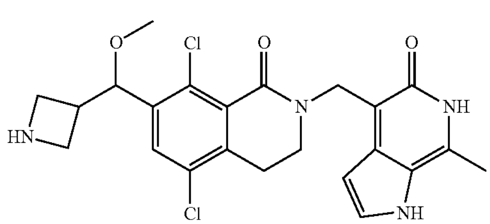 [SMILES: COC(c1cc(Cl)c2c(c1Cl)C(=O)N(Cc1c(=O)[nH]c(C)c3[nH]ccc13)CC2)C1CNC1] | 475.1 |

TABLE 2-continued
Exemplary Compounds of Formula (I)
| Cmpd | Structure | Expected [M + 1]+ |
|---|---|---|
| EB | 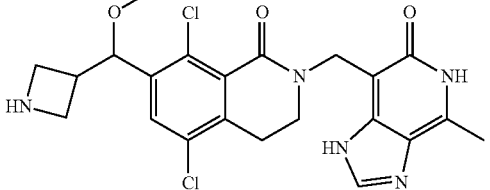 | 476.1 |
| EC | 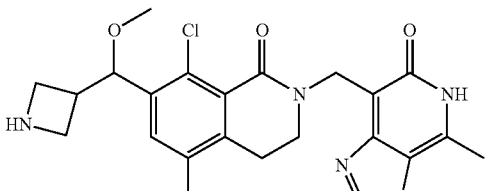 | 476.1 |
| ED | 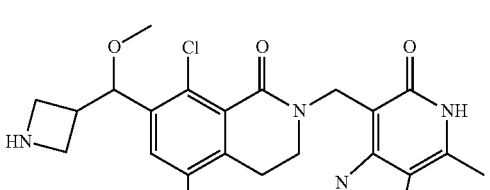 | 493.0 |
| EE | 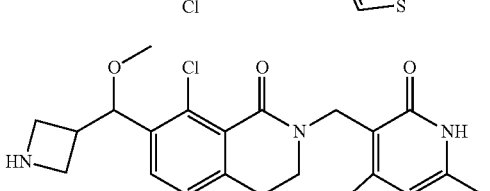 | 493.0 |
| EF | 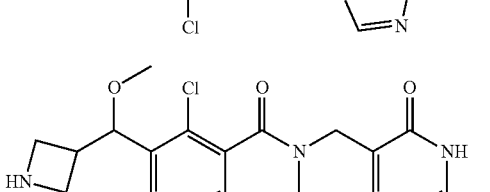 | 476.1 |
| EG | 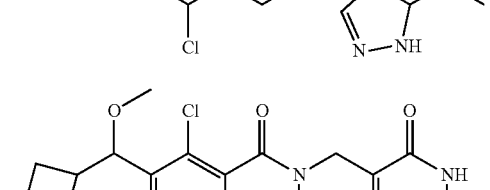 | 476.1 |
| EH | 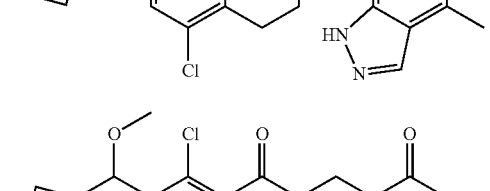 | 492.0 |

TABLE 2-continued

| Cmpd | Structure | Expected [M + 1]+ |
|---|---|---|
| EI | 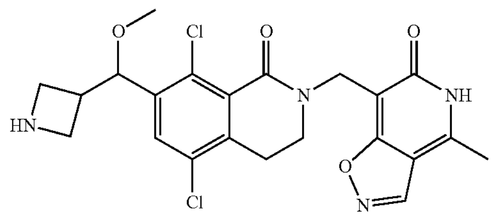 [SMILES: COC(c1cc(Cl)c2c(c1Cl)C(=O)N(Cc1c(=O)[nH]c(C)c3cnoc13)CC2)C1CNC1] | 492.0 |
| EJ | 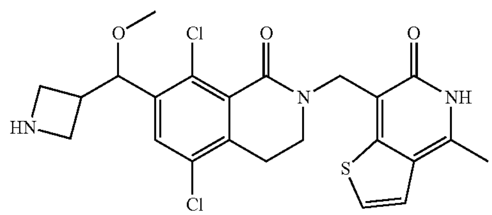 [SMILES: COC(c1cc(Cl)c2c(c1Cl)C(=O)N(Cc1c(=O)[nH]c(C)c3ccsc13)CC2)C1CNC1] | 477.1 |
| EK | 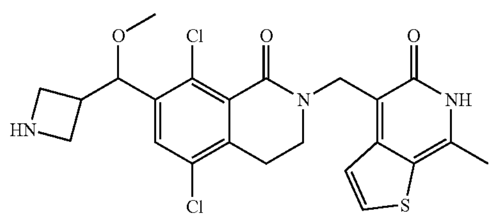 [SMILES: COC(c1cc(Cl)c2c(c1Cl)C(=O)N(Cc1c(=O)[nH]c(C)c3sccc13)CC2)C1CNC1] | 477.1 |
| EL | 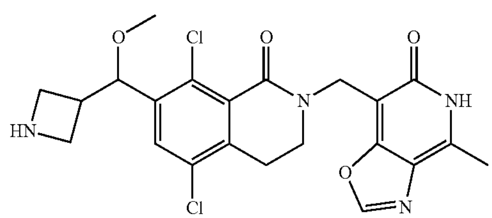 [SMILES: COC(c1cc(Cl)c2c(c1Cl)C(=O)N(Cc1c(=O)[nH]c(C)c3ncoc13)CC2)C1CNC1] | 492.0 |
| EM | 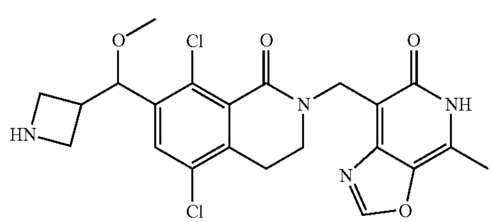 [SMILES: COC(c1cc(Cl)c2c(c1Cl)C(=O)N(Cc1c(=O)[nH]c(C)c3ocnc13)CC2)C1CNC1] | 493.0 |
| EN | 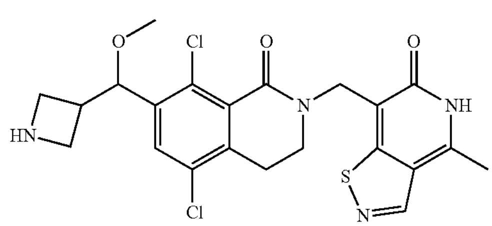 [SMILES: COC(c1cc(Cl)c2c(c1Cl)C(=O)N(Cc1c(=O)[nH]c(C)c3cnsc13)CC2)C1CNC1] | 493.0 |

TABLE 2-continued

Exemplary Compounds of Formula (I)

| Cmpd | Structure | Expected [M + 1]+ |
|------|-----------|-------------------|
| EO | 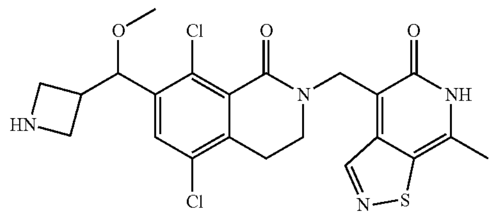 | 493.0 |
| EP | 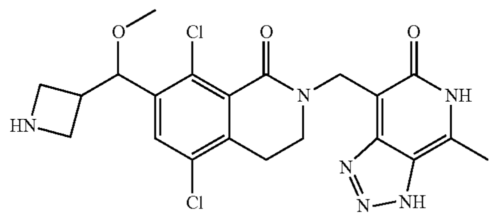 [SMILES: COC(c1cc(Cl)c2c(c1Cl)C(=O)N(Cc1c(=O)[nH]c(C)c3[nH]nnc13)CC2)C1CNC1] | 477.1 |
| EQ | 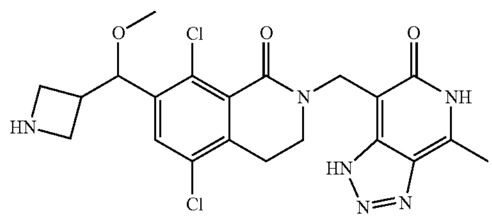 [SMILES: COC(c1cc(Cl)c2c(c1Cl)C(=O)N(Cc1c(=O)[nH]c(C)c3nn[nH]c13)CC2)C1CNC1] | 477.1 |
| ER | 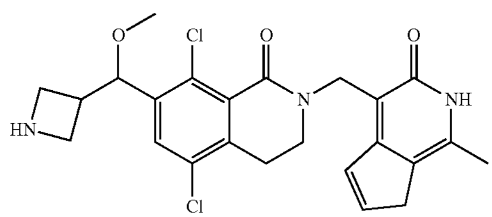 [SMILES: COC(c1cc(Cl)c2c(c1Cl)C(=O)N(Cc1c3c(c(C)[nH]c1=O)CC=C3)CC2)C1CNC1] | 474.1 |
| ES | 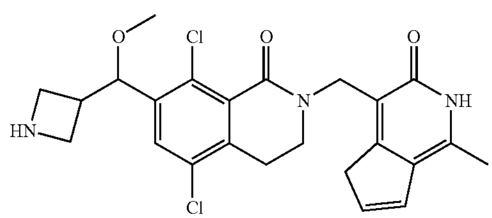 [SMILES: COC(c1cc(Cl)c2c(c1Cl)C(=O)N(Cc1c3c(c(C)[nH]c1=O)C=CC3)CC2)C1CNC1] | 474.1 |
| ET | 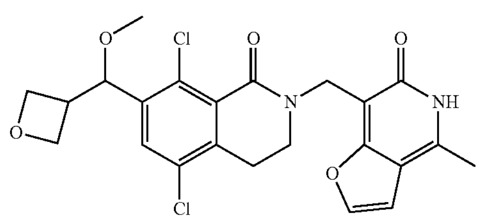 [SMILES: COC(c1cc(Cl)c2c(c1Cl)C(=O)N(Cc1c(=O)[nH]c(C)c3ccoc13)CC2)C1COC1] | 477.0 |
| EU | 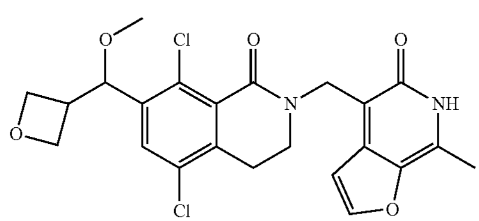 [SMILES: COC(c1cc(Cl)c2c(c1Cl)C(=O)N(Cc1c(=O)[nH]c(C)c3occc13)CC2)C1COC1] | 477.0 |

TABLE 2-continued

Exemplary Compounds of Formula (I)

| Cmpd | Structure | Expected [M + 1]+ |
|---|---|---|
| EV | 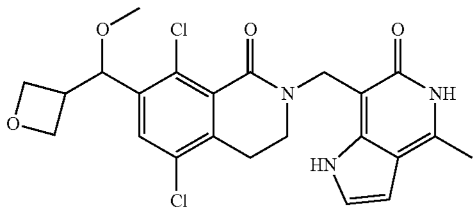 [SMILES: COC(c1cc(Cl)c2c(c1Cl)C(=O)N(Cc1c(=O)[nH]c(C)c3cc[nH]c13)CC2)C1COC1] | 476.1 |
| EX | 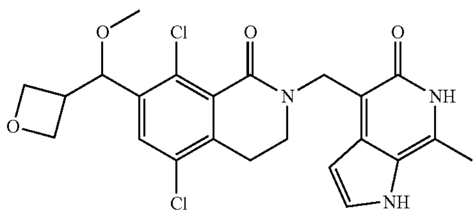 [SMILES: COC(c1cc(Cl)c2c(c1Cl)C(=O)N(Cc1c(=O)[nH]c(C)c3[nH]ccc13)CC2)C1COC1] | 476.1 |
| EY | 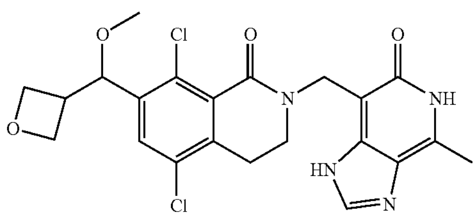 [SMILES: COC(c1cc(Cl)c2c(c1Cl)C(=O)N(Cc1c(=O)[nH]c(C)c3nc[nH]c13)CC2)C1COC1] | 477.1 |
| EZ | 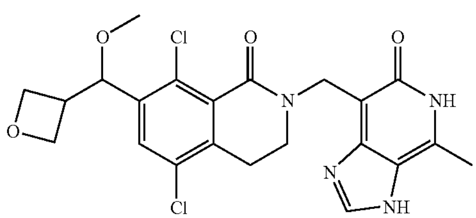 [SMILES: COC(c1cc(Cl)c2c(c1Cl)C(=O)N(Cc1c(=O)[nH]c(C)c3[nH]cnc13)CC2)C1COC1] | 477.1' |
| FA | 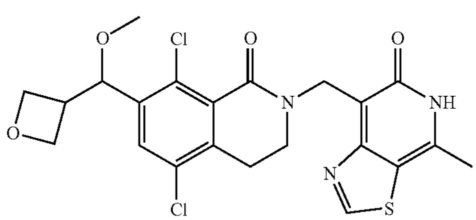 | 494.0 |
| FB | 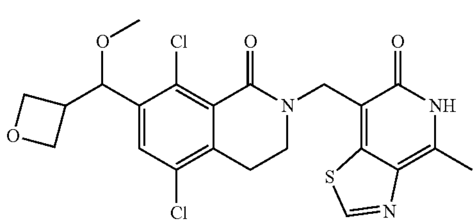 | 494.0 |

TABLE 2-continued

Exemplary Compounds of Formula (I)

| Cmpd | Structure | Expected [M + 1]+ |
|---|---|---|
| FC | 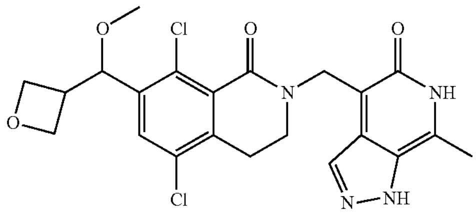 [SMILES: COC(c1cc(Cl)c2c(c1Cl)C(=O)N(Cc1c(=O)[nH]c(C)c3[nH]ncc13)CC2)C1COC1] | 477.1 |
| FD | 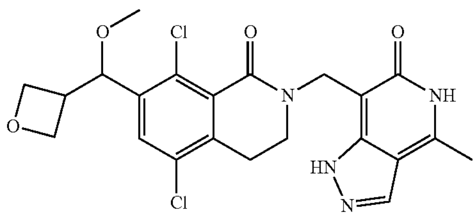 [SMILES: COC(c1cc(Cl)c2c(c1Cl)C(=O)N(Cc1c(=O)[nH]c(C)c3cn[nH]c13)CC2)C1COC1] | 477.1 |
| FE | 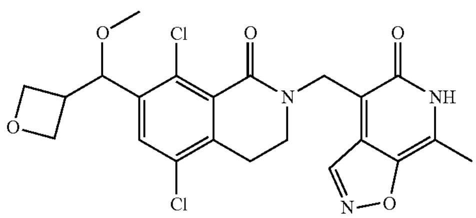 [SMILES: COC(c1cc(Cl)c2c(c1Cl)C(=O)N(Cc1c(=O)[nH]c(C)c3oncc13)CC2)C1COC1] | 478.0 |
| FF | 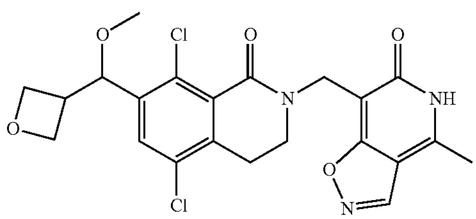 [SMILES: COC(c1cc(Cl)c2c(c1Cl)C(=O)N(Cc1c(=O)[nH]c(C)c3cnoc13)CC2)C1COC1] | 478.0 |
| FG | 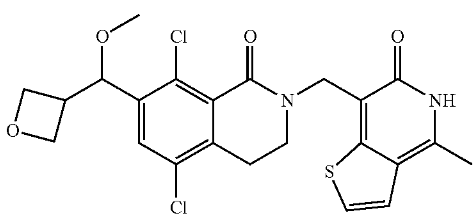 | 493.0 |
| FH | 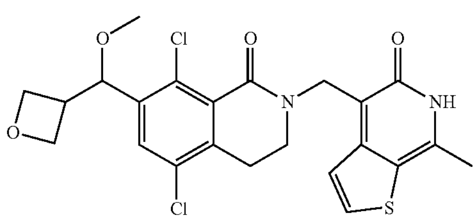 | 493.0 |
| FI | 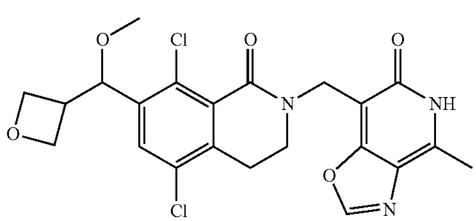 [SMILES: COC(c1cc(Cl)c2c(c1Cl)C(=O)N(Cc1c(=O)[nH]c(C)c3ncoc13)CC2)C1COC1] | 478.0 |

TABLE 2-continued

Exemplary Compounds of Formula (I)

| Cmpd | Structure | Expected [M + 1]+ |
|---|---|---|
| FJ | 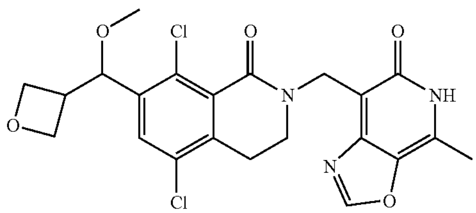 [SMILES: COC(c1cc(Cl)c2c(c1Cl)C(=O)N(Cc1c(=O)[nH]c(C)c3ocnc13)CC2)C1COC1] | 478.0 |
| FK | 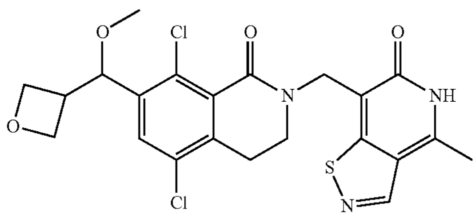 [SMILES: COC(c1cc(Cl)c2c(c1Cl)C(=O)N(Cc1c(=O)[nH]c(C)c3cnsc13)CC2)C1COC1] | 494.0 |
| FL | 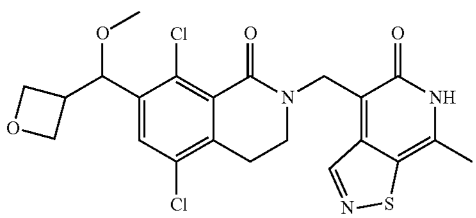 | 494.0 |
| FM | 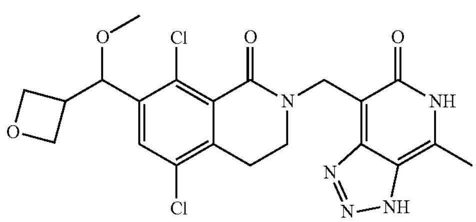 [SMILES: COC(c1cc(Cl)c2c(c1Cl)C(=O)N(Cc1c(=O)[nH]c(C)c3[nH]nnc13)CC2)C1COC1] | 478.1 |
| FN | 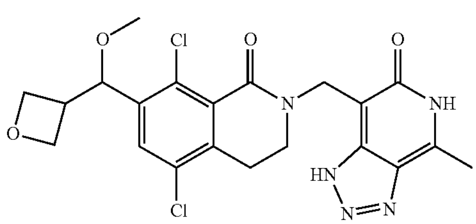 [SMILES: COC(c1cc(Cl)c2c(c1Cl)C(=O)N(Cc1c(=O)[nH]c(C)c3nn[nH]c13)CC2)C1COC1] | 478.1 |
| FO | 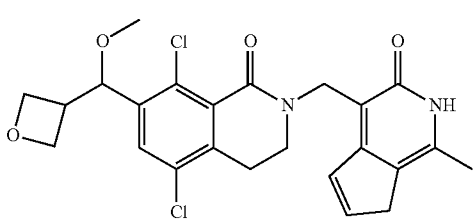 [SMILES: COC(c1cc(Cl)c2c(c1Cl)C(=O)N(Cc1c3c(c(C)[nH]c1=O)CC=C3)CC2)C1COC1] | 475.1 |

TABLE 2-continued

Exemplary Compounds of Formula (I)

| Cmpd | Structure | Expected [M + 1]+ |
|---|---|---|
| FP | (structure drawing) | 475.1 |

The compounds of the present invention may have one or more chiral center and, if so, are synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g, using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or entantiomers. Unless otherwise indicated, all chiral (enantiomeric and diastereomeric) and racemic forms are within the scope of the invention.

Example A

This Example illustrates that exemplary compounds of the present invention inhibit EZH2 enzymatic activity.

Ten-point dose-response curves for a subset of compounds shown in Table 1 were determined using a Transcreener® EPIGEN Methyltransferase HTS assay using purified EZH2 enzyme (BellBrook Labs). In this assay, the S-adenosylhomocysteine (SAH) generated by the transfer of the methyl group from S-adenosyl methionine (SAM) to purified histone 3.3 protein by EZH2 is enzymatically converted to AMP, which is detected using a fluorescence polarization readout.

Briefly, compounds of the present invention were solubilized in DMSO and a series of 10, three-fold serial dilutions were made for each compound in 15% DMSO. The initial starting concentration for the serial dilutions of each compound was 1.0 µM. Control samples lacking compound, EZH2 enzyme or various reaction components also were prepared and processed in parallel with compound test samples. A panel of dilutions of SAH/SAM also was prepared as a standard curve to ensure the linearity of the assay.

An aliquot of each serial dilution of test compound was added to deep 384 well plate containing 5 mg/ml purified EZH2 enzyme (Reaction Biology) in a 15 microliter reaction volume. The plate was pre-incubated at room temperature for 15 min to which 4 µM SAM and 6 mg/ml of full length histone 3.3 protein were added to initiate the enzymatic reaction. The reaction mixture was incubated at 30° C. for three hours during which the SAH produced from the methylation reaction is enzymatically converted to AMP. The reaction was stopped by quenching and a detector buffer containing the coupling enzymes, fluorescent indicator and AMP antibody was added to each well. After 1 hr, the resulting fluorescent output of the assay was read on Tecan Safire2 instrument according to the manufacturer's instructions. The $IC_{50}$ value for each compound was determined from each 10-point dose-response curve and the results for exemplary compounds of Formula (I) are shown in Table 3.

TABLE 3

Inhibition of EZH2-mediated Cell Proliferation by Exemplary Compounds of Formula (I)

| Example No. | $IC_{50}$ (nM) |
|---|---|
| 1 | 6 |
| 2 | 5 |
| 3 | 5 |
| 4 | 202 |
| 5 | <0.5 |
| 6 | 7 |
| 7 | 3 |
| 8 | 95 |
| 9 | 4 |
| 10 | 12 |
| 11 | 10 |
| 12 | 37 |
| 13 | 2 |
| 14 | 10 |
| 15 | 2 |
| 16 | 3 |
| 17 | 1 |
| 18 | 2 |
| 19 | 2 |

Example B

This Example illustrates that exemplary compounds of the present invention inhibit tumor cells harboring activating mutations of EZH2.

The Pfeiffer cell line was established from a pleural infusion from a patient having metastatic diffuse large B-cell lymphoma (DLBCL). This cell line expresses a mutant form of the EZH2 enzyme (A677G) that results in enhanced EZH2 activity leading to increased methylation of histone H3 Lys27. Increased trimethylation of histone H3 Lys27 is believed to be implicated in tumorgenesis and poor clinical prognosis in lymphomas (McCabe et al, (2012) Nature 492:108-112).

Inhibition of EZH2-mediated histone H3 methylation by compounds of Formula (I) was measured by ELISA using a Tri-Methyl Histone H3 (Lys 27) Sandwich ELISA Kit (Cell Signaling Tech) #7866C in accordance with the manufacturer's instructions. Briefly, Pfeiffer cells were cultured in RPMI medium supplemented with 10% fetal bovine serum and 1% penicillin and 1% streptomycin in 96 well culture plates at 37° C. to a density of 8000 cells/90 µl/well and the cells were harvested. A series of 3-fold serial dilutions of each test compound of Formula (I) were prepared in RPMI medium and added to the cells at final concentrations ranging from 1 µM to 0.15 nM. The plates were incubated at 37° C. for 96 hours.

After incubation, the cells were pelleted by centrifugation in a pre-cooled 4° C. rotor at 1,100 rpm for 10 min and the supernatant was removed by aspiration. The cell pellet was resuspended in 55 µl of Lysis Buffer (0.4M HCl) and incubated on ice with periodic shaking for 30 minutes. The lysed cells were subjected to centrifugation at 4,200 rpm for 10 min at 4° C. and the supernatant containing acid-soluble proteins was collected and the remainder discarded. The acid-soluble proteins were brought to a neutral pH by the addition of 20 µl of Neutralization Buffer (1 M Sodium phosphate, dibasic (pH 12.5), 2.5 mM DTT and 1 mM PMSF) and the neutralized lysates were analyzed by ELISA.

A 65 µl aliquot of each cell lysate was added to a well of a microwell strip, the microwells were sealed using tape and incubated either at 37° C. for two hours or at 4° C. overnight. After incubation, the tape was removed at the microwells were washed four times using 200 µl of 1× Wash Buffer. To each washed microwell, a 100 µl aliquot of an anti-trimethyl histone H3 Lys27 Detection Antibody solution was added and the microwells were incubated at 37° C. for one hour. The Detection Antibody solution was removed by aspiration and the wells were washed four times each using 200 µl of 1× Wash Buffer.

A 100 µl aliquot of an HRP-linked secondary antibody was added to each well, the wells were sealed with tape and incubated at 37° C. for 30 min. The HRP-linked secondary antibody solution was removed by aspiration and the wells were washed four times using 200 µl of 1× Wash Buffer. A 100 µl aliquot of a TMB substrate was added to each well, the wells were sealed with tape and incubated at 37° C. for 10 min or 25° C. for 30 min. The reaction was stopped by the addition of 100 µl aliquot of a STOP solution and the plate was shaken briefly. The degree of histone H3 trimethylation was determined using a spectrophotometric readout by measuring the absorbance at 450 nm and then calculating the amount of trimethylated histone H3. The results are shown in Table 4. Key: N.D.=not determined.

TABLE 4

Inhibition of EZH2-mediated Cell Proliferation by Exemplary Compounds of Formula (I)

| Example No. | IC$_{50}$ (nM) |
|---|---|
| 1 | 759 |
| 2 | 273 |
| 3 | 31 |
| 4 | 1045 |
| 5 | 17 |
| 6 | 44 |
| 7 | 30 |
| 8 | N.D. |
| 9 | 126 |
| 10 | 336 |
| 11 | 12 |
| 12 | 330 |
| 13 | 2 |
| 14 | 26 |
| 15 | 6 |
| 16 | 7 |
| 17 | N.D. |
| 18 | 78 |
| 19 | 78 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:
1. A compound of formula (I):

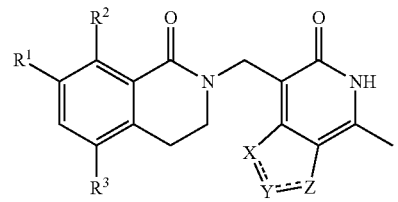

Formula (I)

or a pharmaceutically acceptable salt thereof:
wherein:
each ===== represents a single or a double bond, wherein only one of the bonds between X—Y and Y—Z is a double bond;

X, Y and Z are each independently O, N, NR$^4$, S, or CR$^5$, wherein when one of X, Y or Z is other than N or NR$^4$, at least one of X, Y or Z is CR$^5$ and only one of X, Y or Z can be O or S;

R$^1$ is C1-C6 alkyl, C1-C6 alkoxy, heterocyclyl, aryl, heteroaryl, —OR$^6$; —NR$^4$R$^6$ or —W—R$^7$; wherein each of the heterocyclyl, aryl, or heteroaryl is optionally substituted with one or more R$^6$;

W is —(CH$_2$)$_p$—CR$^8$R$^9$—(CHR$^{10}$)$_q$—;

R$^2$ is hydrogen, halogen, haloalkyl, or C1-C3 alkyl;

R$^3$ is hydrogen, cyano, halogen, haloalkyl, C1-C4 alkyl, C1-C4 alkoxy, cycloalkyl, heterocyclyl, aryl, heteroaryl or R$^{12}$-L-R$^{13}$, wherein the cycloalkyl, heterocyclyl, aryl, heteroaryl is optionally substituted with one or more C1-C3 alkyl, heteroalkyl, or —NR$^4$R$^{11}$.

each R$^4$ is independently hydrogen or C1-C3 alkyl;

each R$^5$ is independently hydrogen, halogen, C1-C3 alkoxy, cyano, C1-C3 alkyl;

each R$^6$ is independently C1-C3 alkyl, cycloalkyl or heterocyclyl, wherein the heterocyclyl is optionally substituted with one or more C1-C3 alkyl or C1-C3 alkylsulfonyl and the cycloalkyl is optionally substituted with —NR$^4$R$^{11}$;

each R$^7$ is independently cycloalkyl, heterocyclyl, aryl or heteroaryl, wherein each of the cycloalkyl, heterocyclyl, aryl or heteroaryl is optionally substituted with one or more R$^{14}$;

R$^8$ is hydrogen, halogen or C1-C4 alkyl;

each R$^9$ is independently hydrogen, —N(R$^4$)$_2$, hydroxyl, halogen, cyano, hydroxyalkyl, C1-C4 alkyl, or C1-C4 alkoxy;

R$^{10}$ is absent or hydrogen;

each R$^{11}$ is independently hydrogen, acyl, C1-C3 alkyl or C1-C4 alkoxy;

R$^{12}$ is C2-C4 alkynylene, arylene or heteroarylene;

L is a bond or C1-C3 alkylene;

$R^{13}$ is heterocyclyl optionally substituted with one or more acyl or C1-C3 alkyl;

each $R^{14}$ is independently oxo, hydroxyl, halogen, cyano, acetyl, hydroxyacetyl, alkyl, sulfonylalkyl, hydroxyalkyl, carbonylalkyl or heterocyclyl; and p and q are each independently zero or one.

2. The compound of claim 1, wherein X is O and Y and Z are each $CR^5$.

3. The compound of claim 1, wherein Z is O and X and Y are each $CR^5$.

4. The compound of claim 1, wherein X and Y are each $CR^5$ and Z is $NR^4$.

5. The compound of claim 1, wherein X is $NR^4$ and Y and Z are each $CR^5$.

6. The compound of claim 1, wherein $R^1$ is $-OR^6$.

7. The compound of claim 6, wherein $R^6$ is C1-C4 alkyl, hydroxyalkyl or heterocyclyl.

8. The compound of claim 1, wherein $R^1$ is heterocyclyl optionally substituted with one or more $R^6$.

9. The compound of claim 8, wherein the heterocyclyl is an 8-10 membered spirocycle comprising 1-4 heteroatoms selected from O, N or S.

10. The compound of claim 1, wherein $R^1$ is heteroaryl optionally substituted with one or more $R^6$.

11. The compound of claim 10, wherein the heteroaryl is oxazolyl, 1,4-dimethyl-oxazolyl, triazinyl or 1,4-dimethyl-1H-1,2,3-triazinyl.

12. The compound of claim 1, wherein $R^1$ is $-NR^4R^6$.

13. The compound of claim 12, wherein $R^4$ is C1-C3 alkyl and $R^6$ is heterocyclyl optionally substituted with one or more $R^{14}$.

14. The compound of claim 13, wherein the heterocyclyl is tetrahydropyranyl, piperidinyl or methylsulfonylpiperdinyl.

15. The compound of claim 12, wherein $R^4$ is C1-C3 alkyl and $R^6$ is cycloalkyl optionally substituted with $-NR^4R^{10}$.

16. The compound of claim 15, wherein the cycloalkyl is substituted with $-NR^4R^{10}$, and $R^{10}$ is hydrogen, acyl, C1-C3 alkyl or C1-C4 alkoxy.

17. The compound of claim 1, wherein $R^1$ is $-W-R^7$.

18. The compound of claim 17, wherein:
p and q are each zero;
$R^7$ is heterocyclyl optionally substituted with acyl, or one or more oxo or C1-C3 alkyl;
$R^8$ is hydrogen; and
$R^9$ is C1-C4 alkoxy.

19. The compound of claim 18, wherein the heterocyclyl is azetidinyl, 1-methyl-azetidinyl, oxetanyl, thietane 1,1-dioxide, furanyl, tetrahydrofuranyl, tetrahydropyranyl, pyrrolidinyl, piperdinyl, 4-methyl-piperdinyl, 4-acyl-piperdinyl, piperazinyl, 4-methyl-piperazinyl, 4-acyl-piperazinyl, dioxidothiopyranyl, or morpholinyl.

20. The compound of claim 1, wherein $R^2$ is halogen.

21. The compound of claim 20, wherein the halogen is chlorine.

22. The compound of claim 1, wherein $R^3$ is halogen.

23. The compound of claim 22, wherein the halogen is chlorine or bromine.

24. The compound of claim 1, wherein $R^3$ is $R^{12}$-L-$R^{13}$.

25. The compound of claim 24, wherein $R^{12}$ is heteroarylene.

26. The compound of claim 25, wherein the heteroarylene is pyrazolylene, pyrimidinylene or triazolylene.

27. The compound of claim 24, wherein L is a bond and $R^{13}$ is azetidinyl, 1-methylazetidinyl, piperidinyl, 1-methyl-piperdinyl, 4-acyl-piperdinyl, piperazinyl, 4-methylpiperazinyl, 4-acyl-piperazinyl, oxetanyl or morpholinyl.

28. The compound of claim 24, wherein $R^{12}$ is arylene.

29. The compound of claim 28, wherein the aryl is phenylene.

30. The compound of claim 28, wherein L is C1 alkylene and $R^{13}$ is morpholinyl.

31. The compound of claim 24, wherein $R^{12}$ is C2-C4 alkynylene.

32. The compound of claim 31, wherein the C2-C4 alkynylene is ethynylene.

33. The compound of claim 31, wherein L is a bond and $R^{13}$ is morpholinyl or oxetanyl.

34. The compound of claim 1, wherein the compound is:

185
-continued
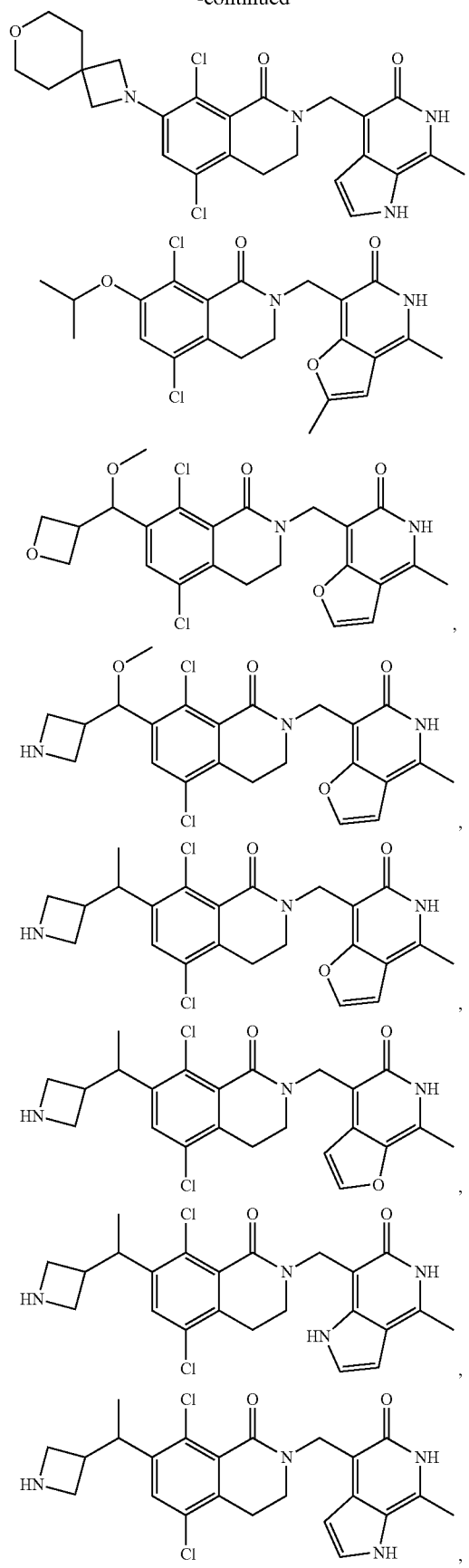
186
-continued
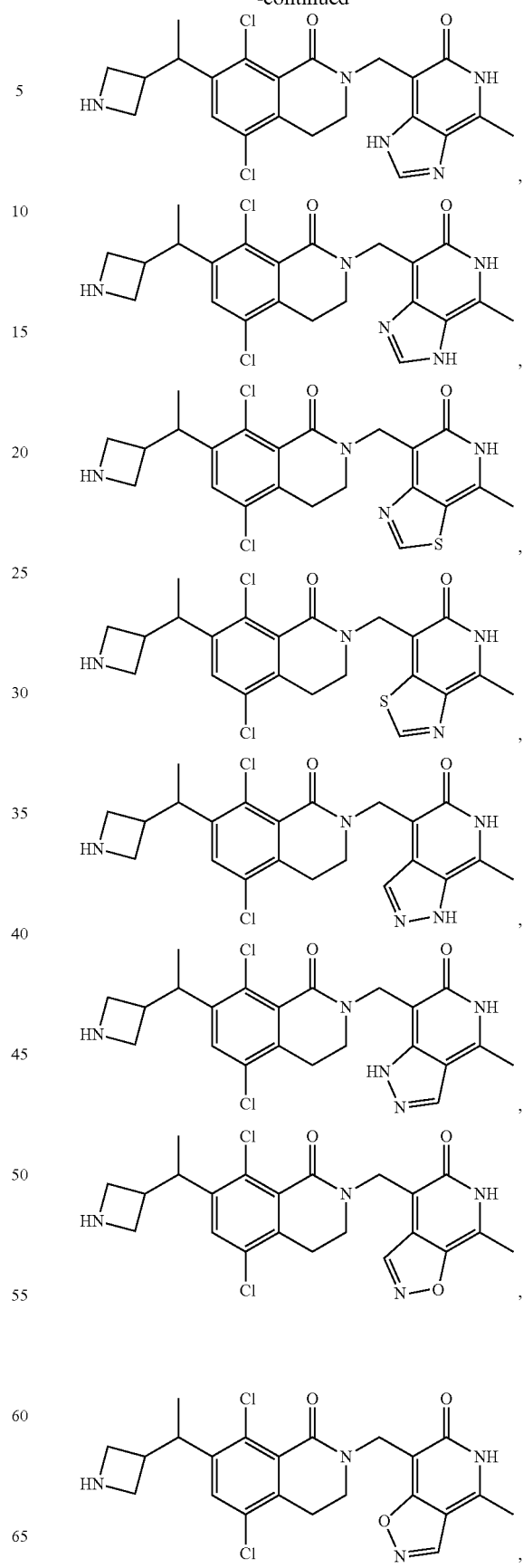

187
-continued
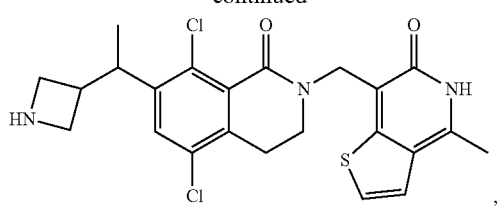
,
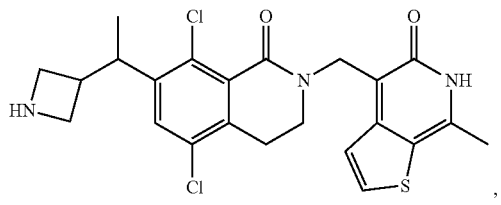
,
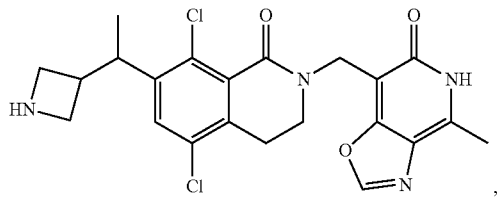
,
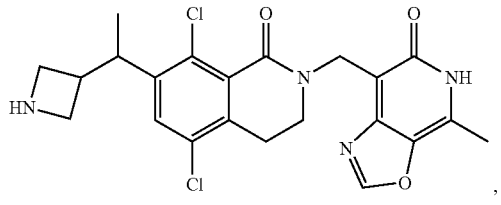
,
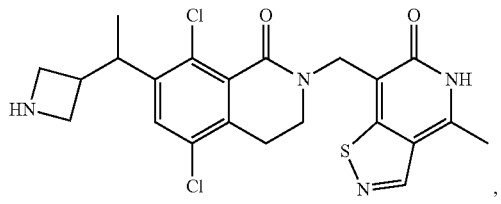
,
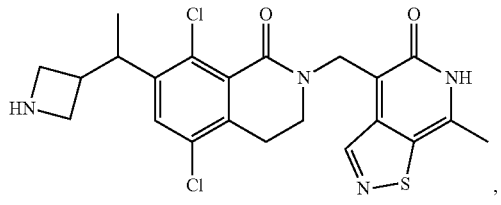
,
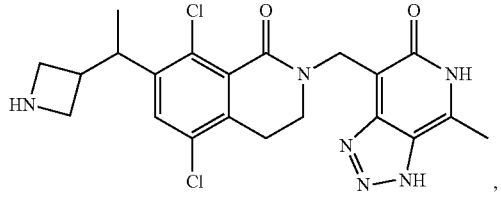
,
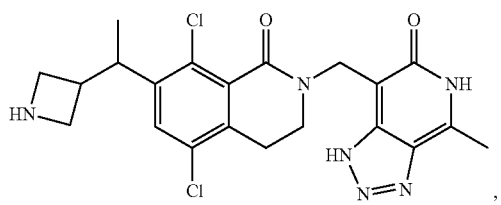
,
188
-continued
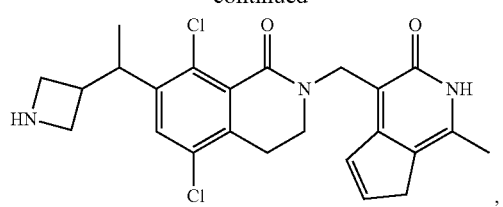
,
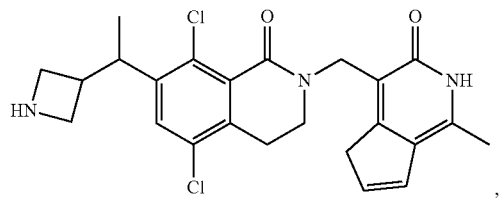
,
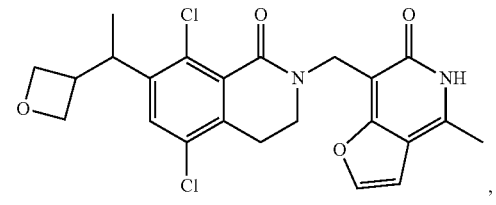
,
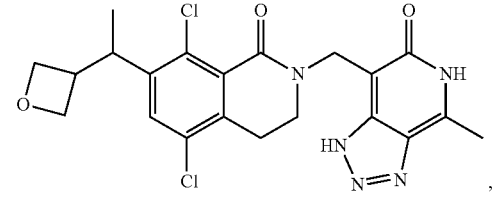
,
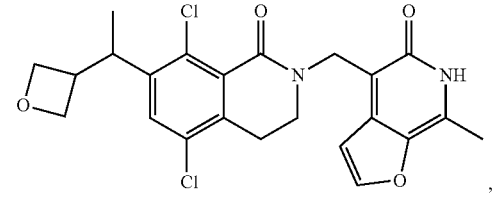
,
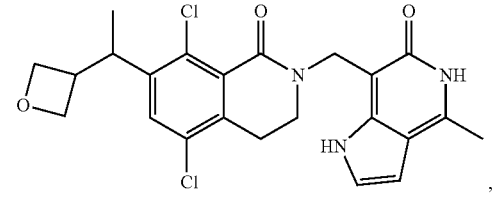
,
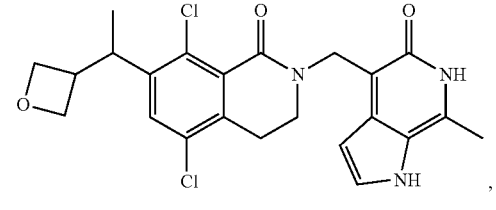
,
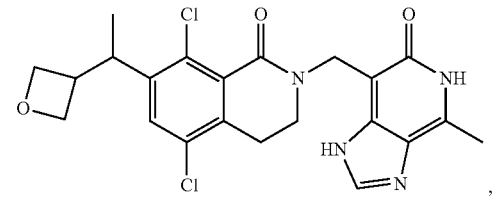
,

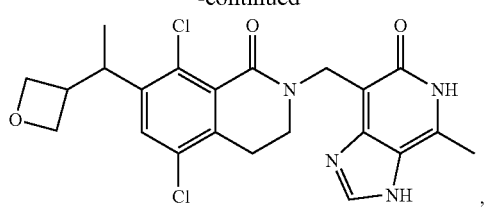,
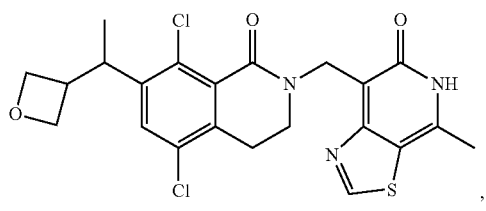,
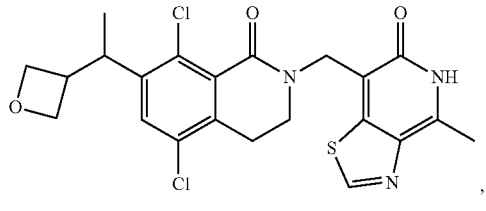,
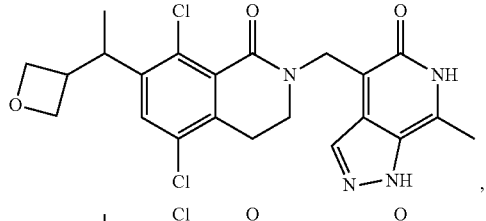,
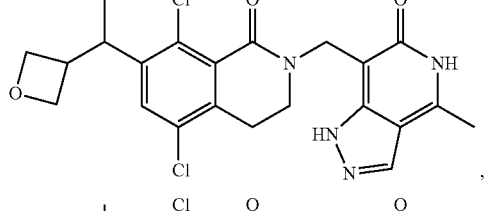,
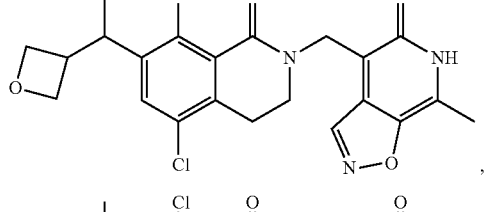,
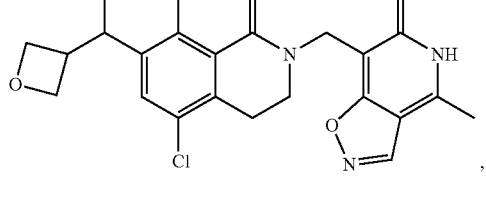,
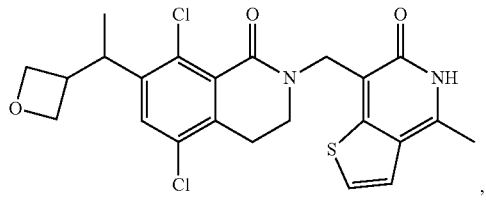,
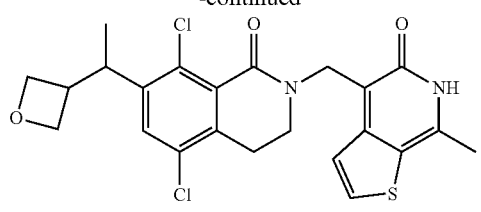,
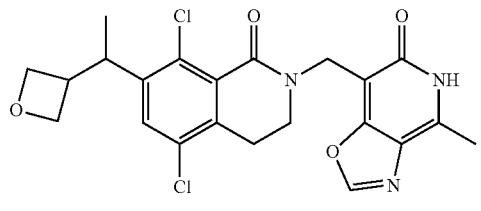,
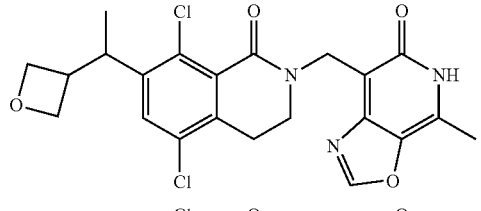,
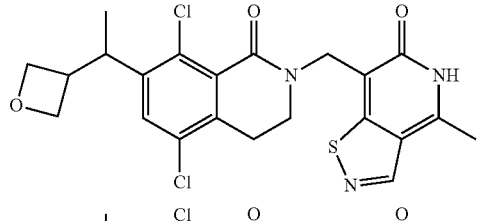,
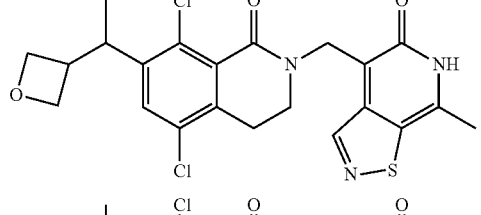,
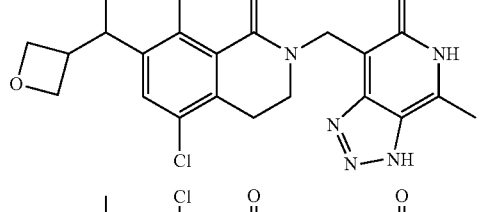,
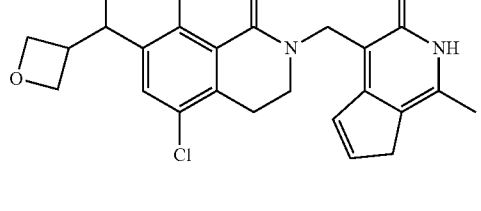,
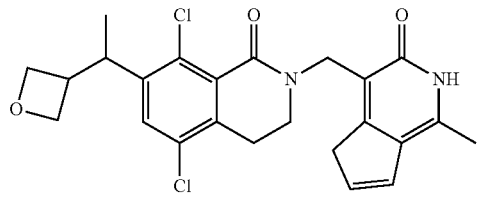, 191
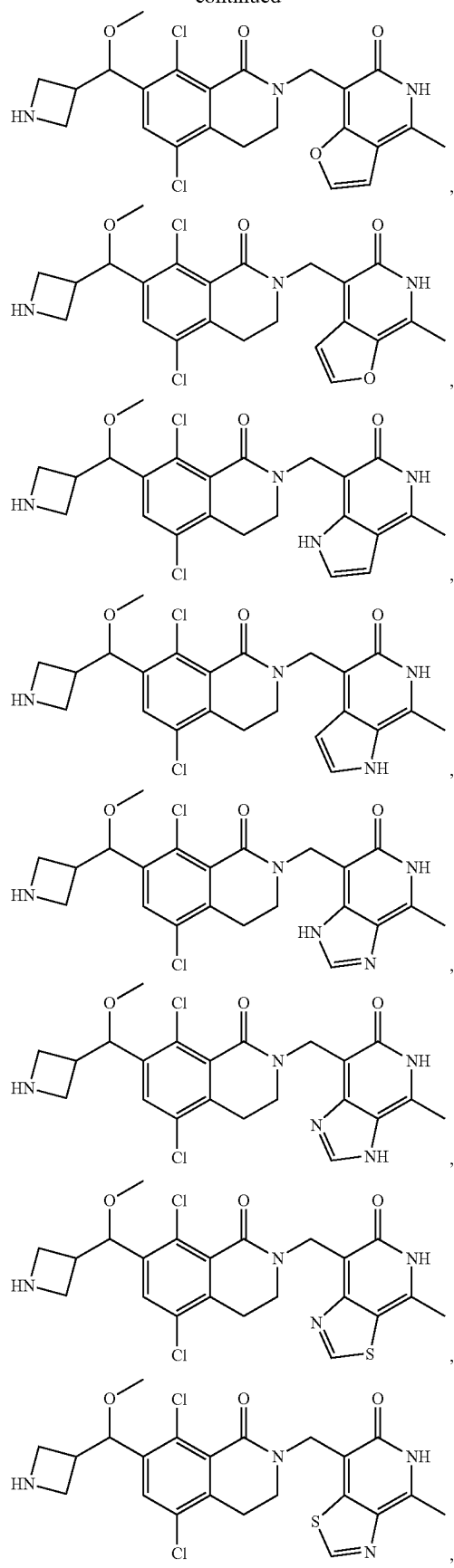
192
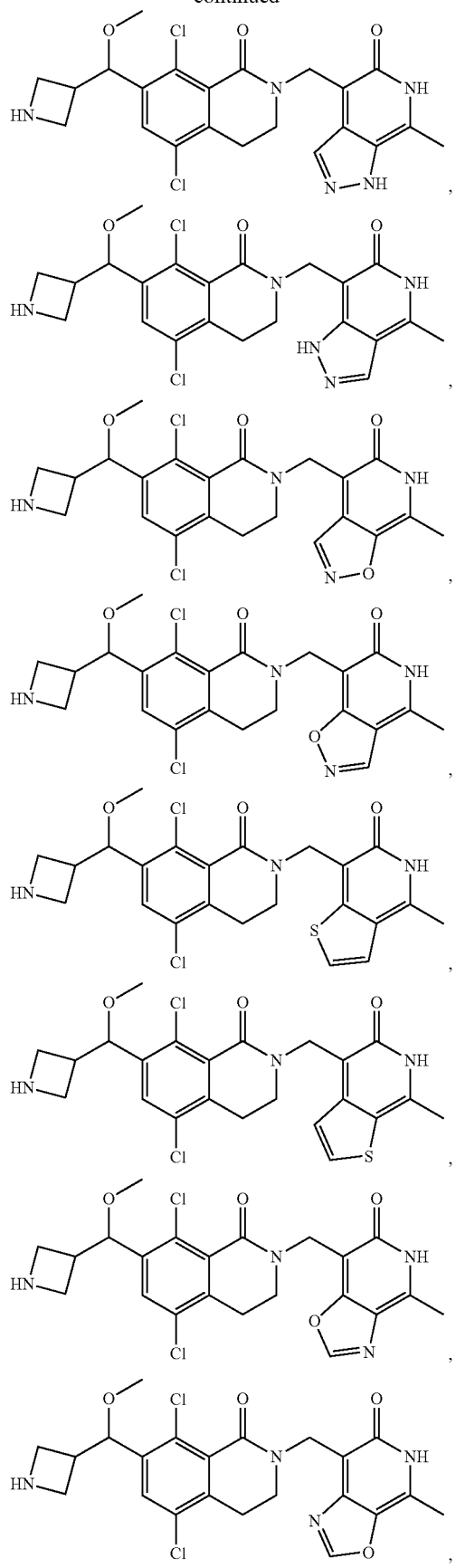

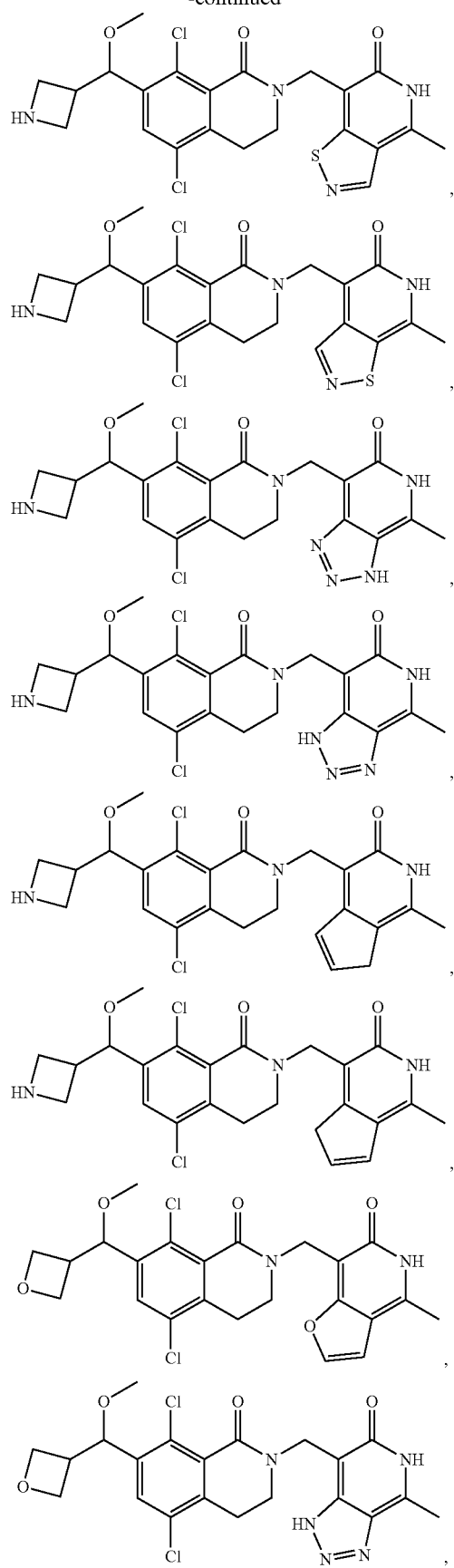
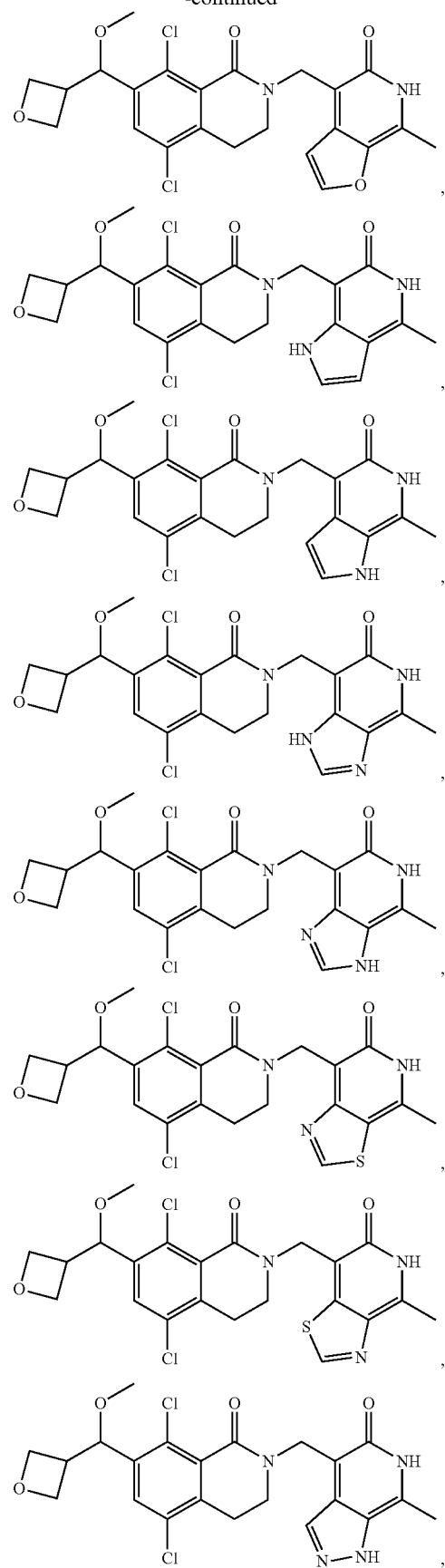

195
-continued
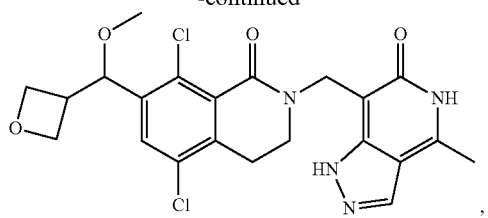,
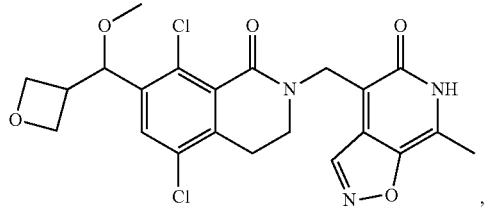,
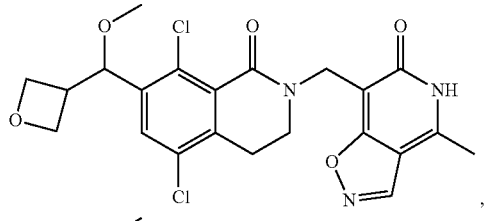,
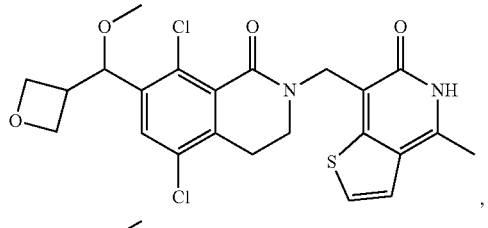,
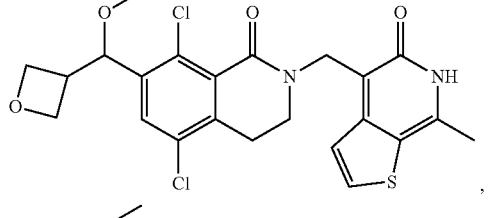,
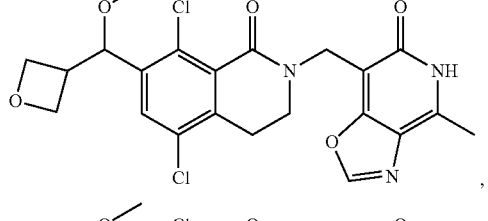,
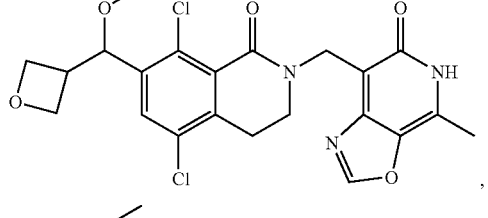,
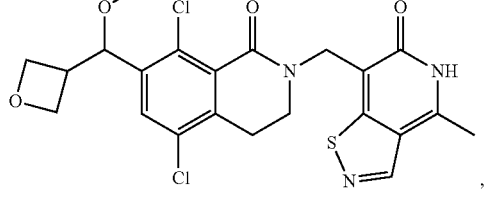,
196
-continued
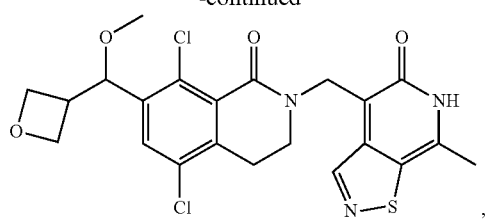,
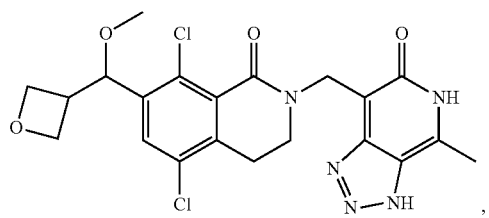,
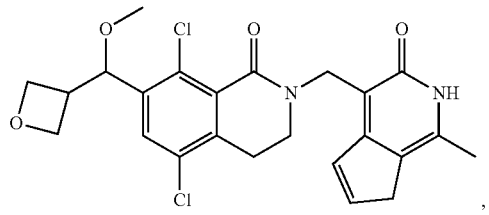,
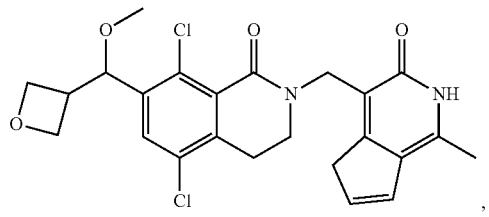,
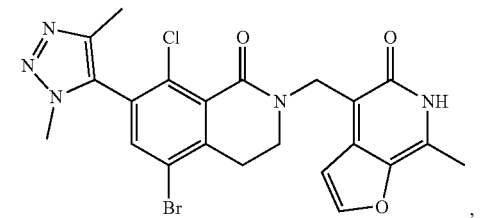,
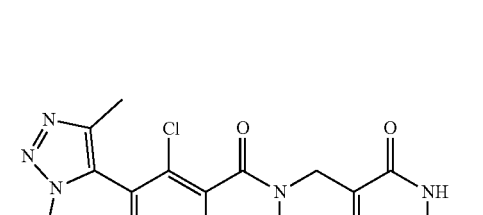,
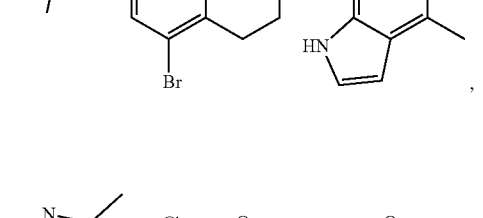,
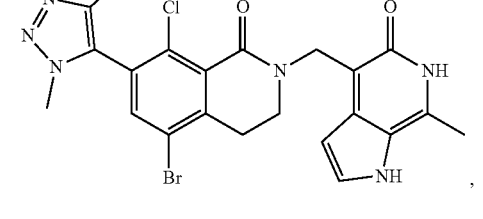, 197
-continued
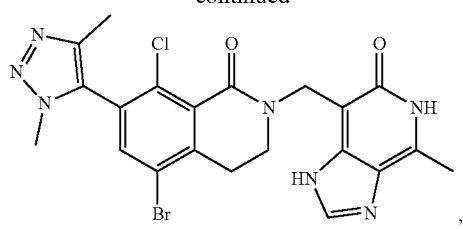
,
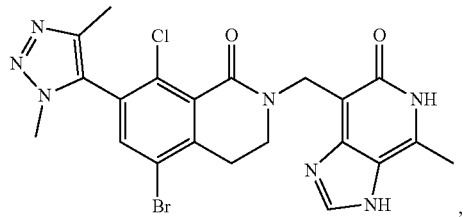
,
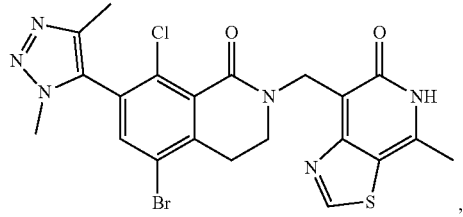
,
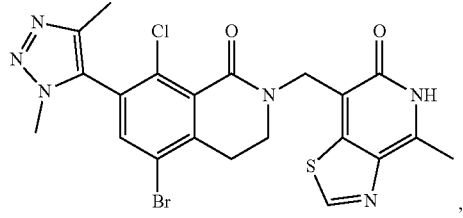
,
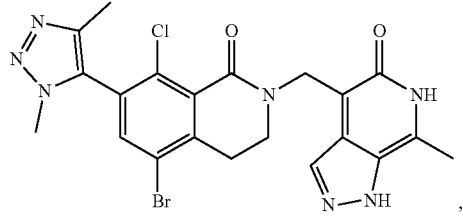
,
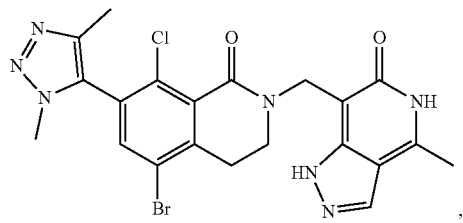
,
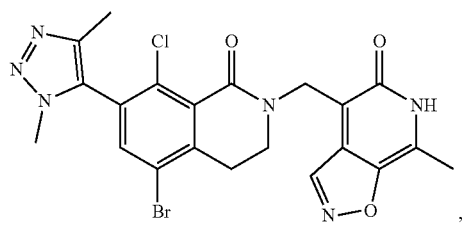
,
198
-continued
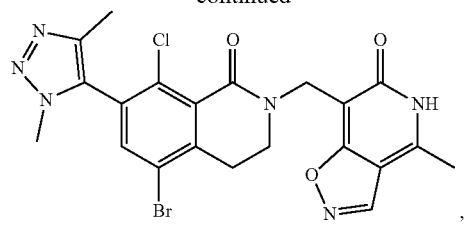
,
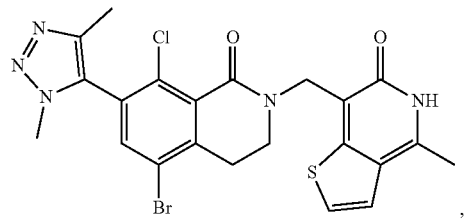
,
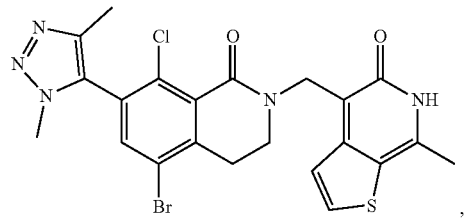
,
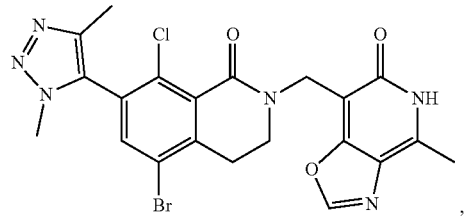
,
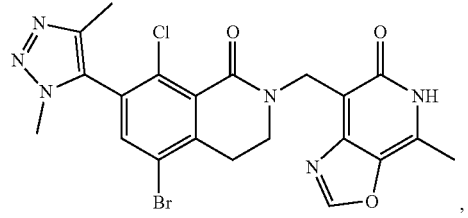
,
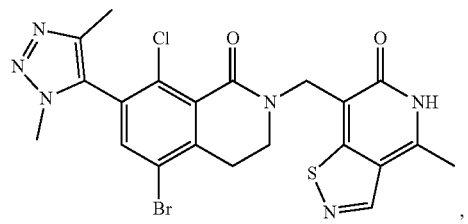
,
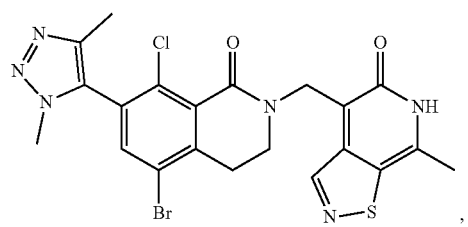
, 199
-continued
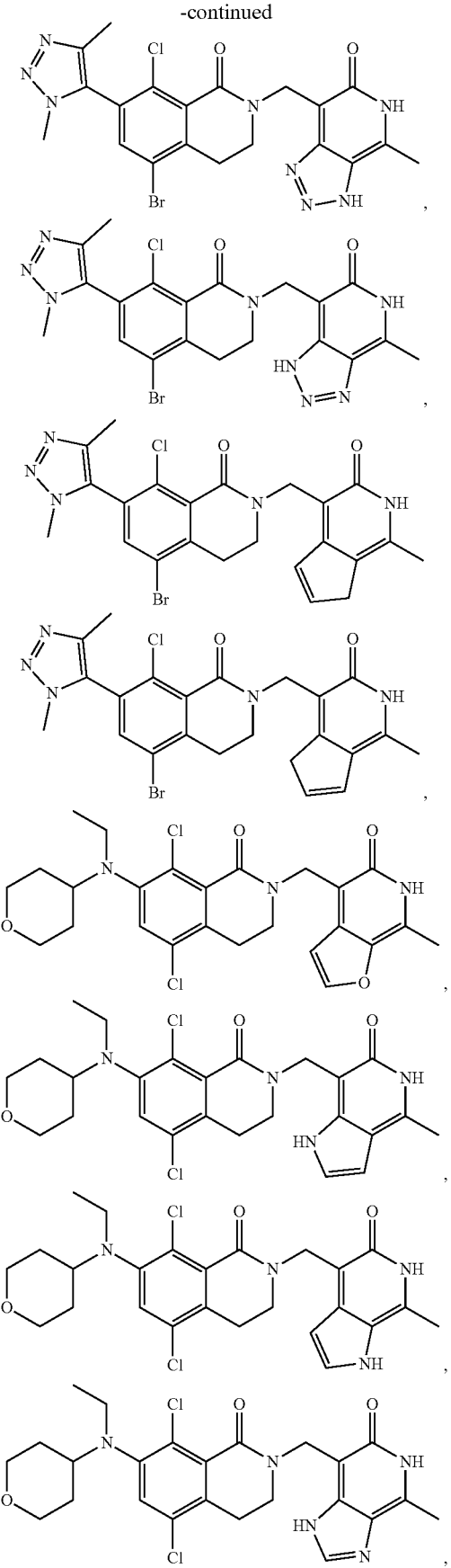
200
-continued
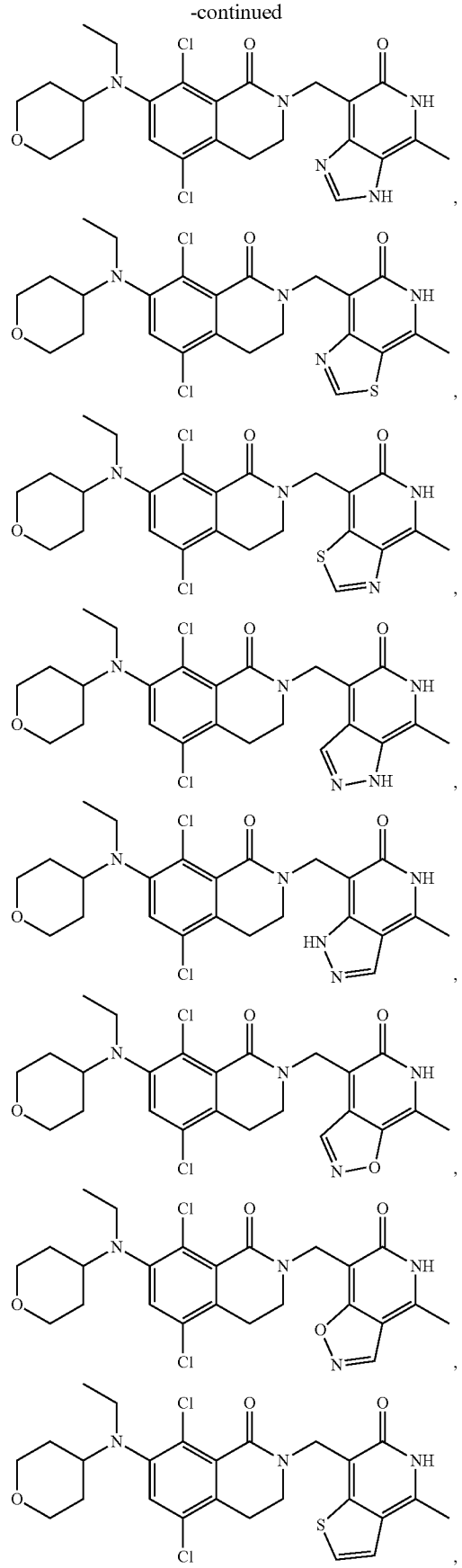

201
-continued
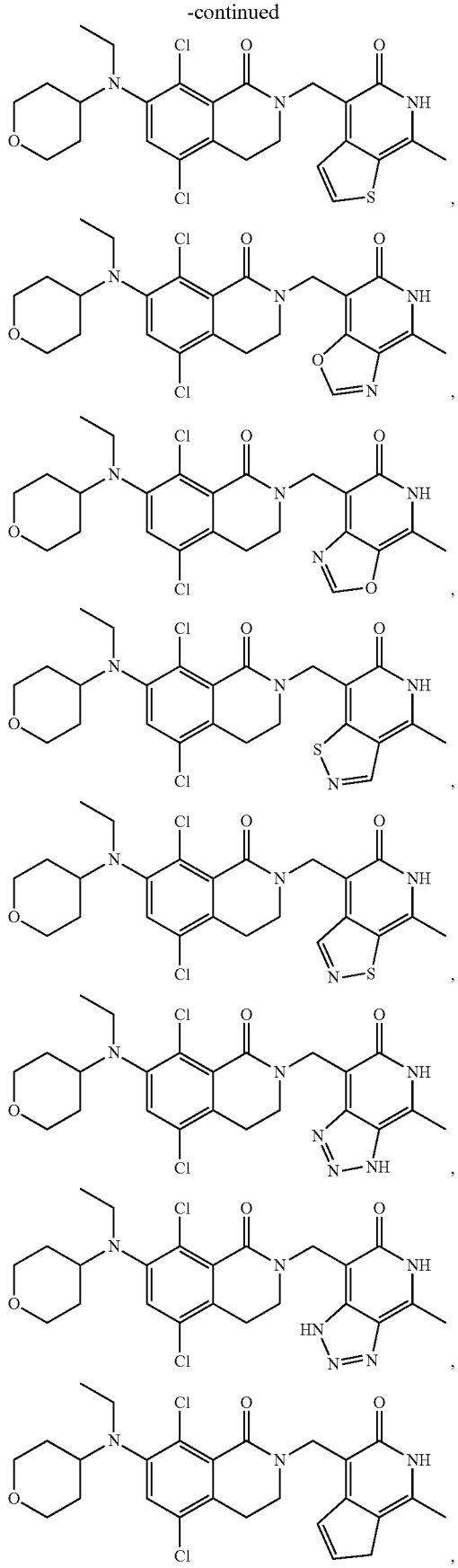
202
-continued
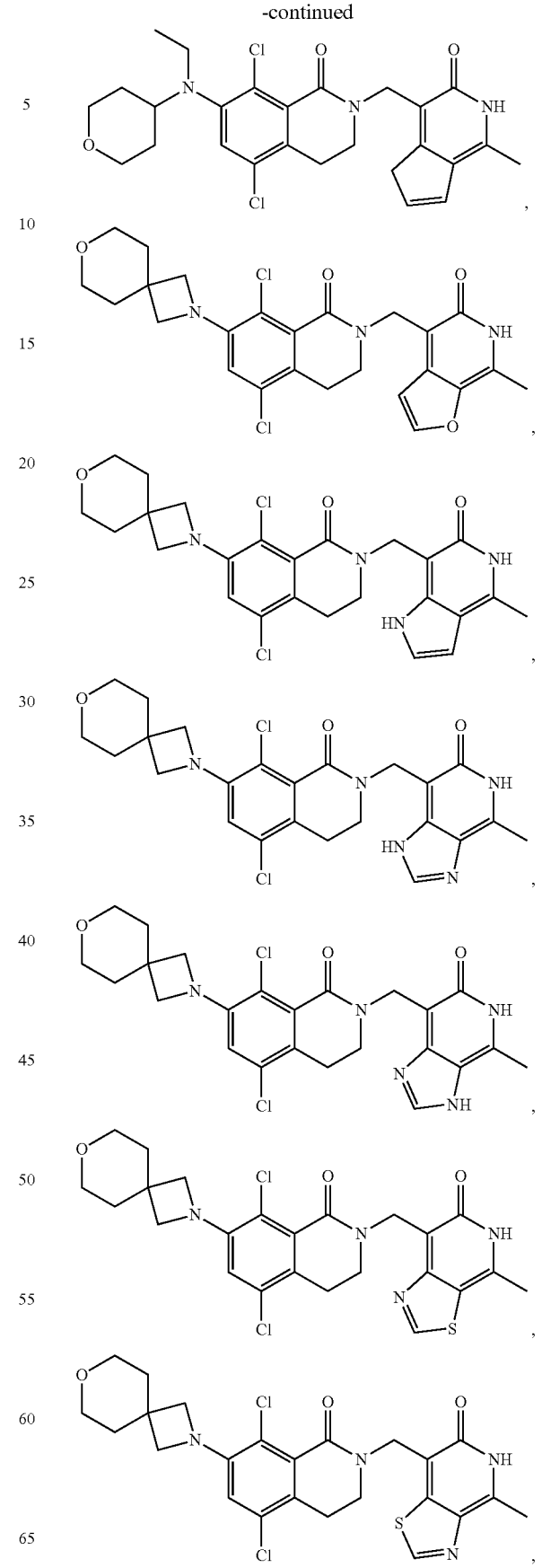

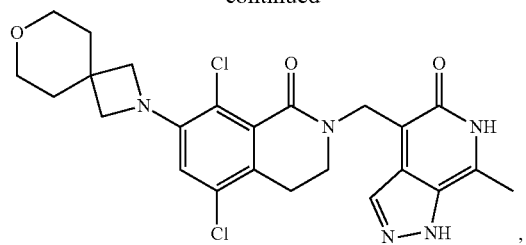
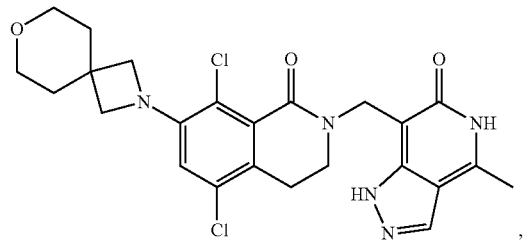
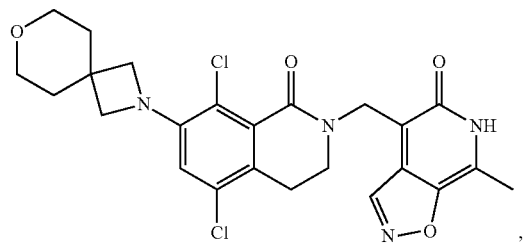
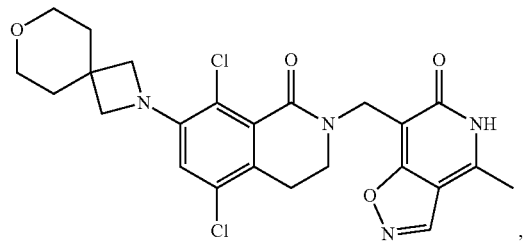
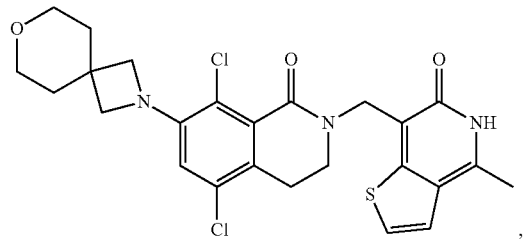
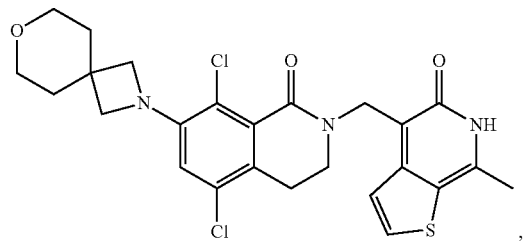
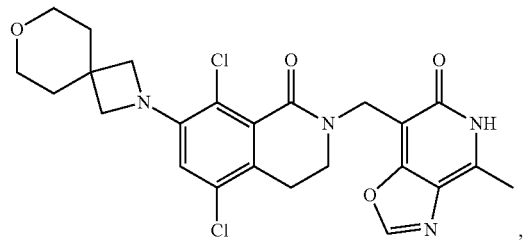
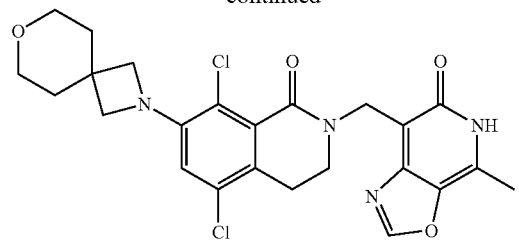
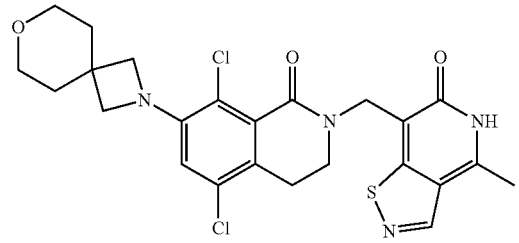
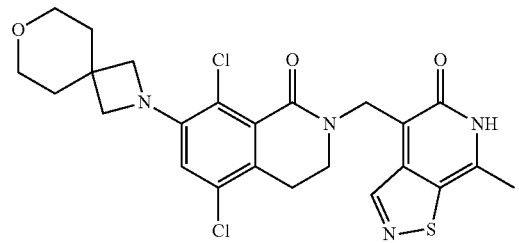
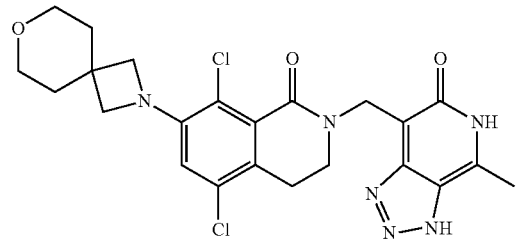
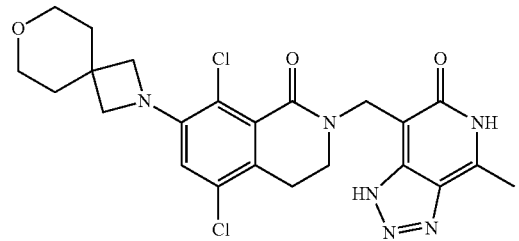
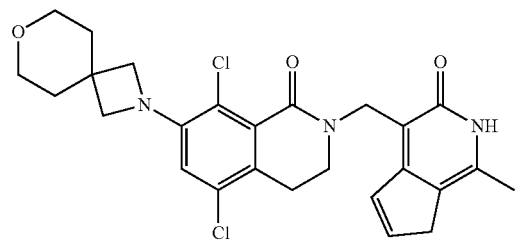
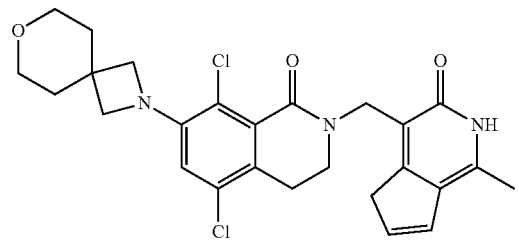

205
-continued
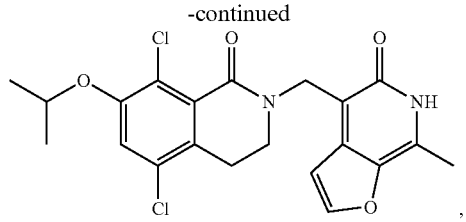,
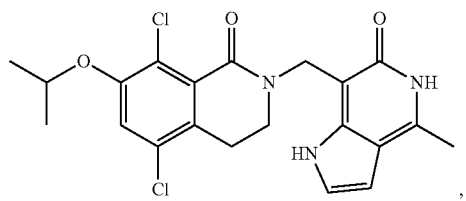,
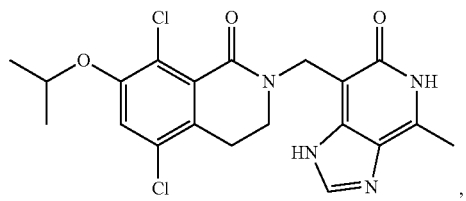,
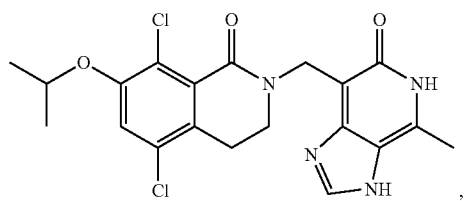,
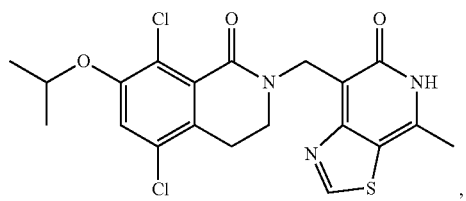,
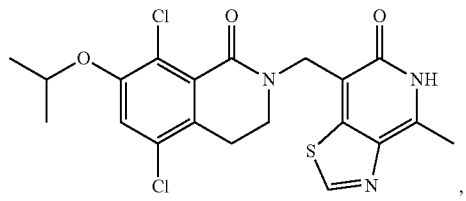,
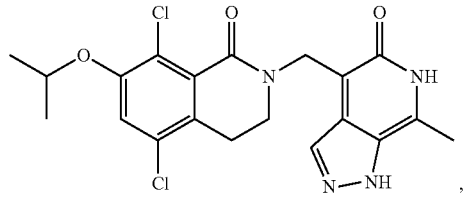,
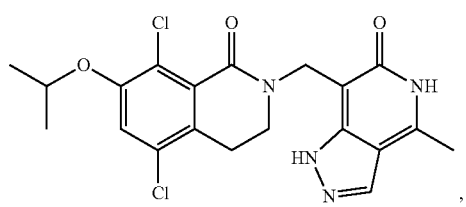,
206
-continued
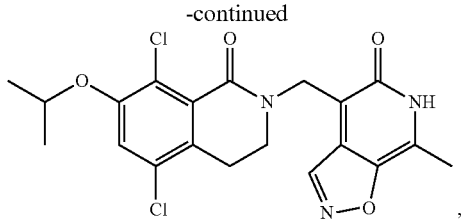,
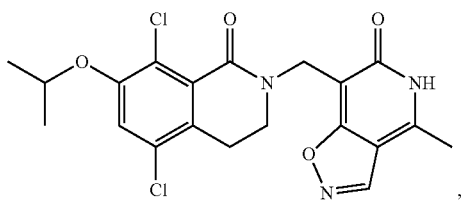,
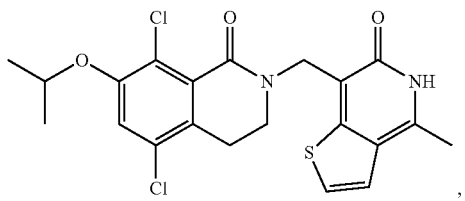,
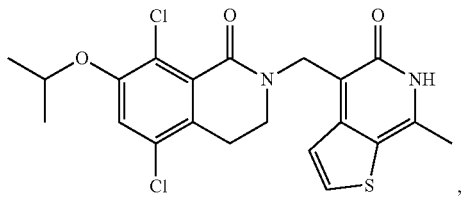,
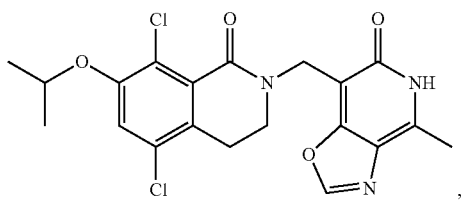,
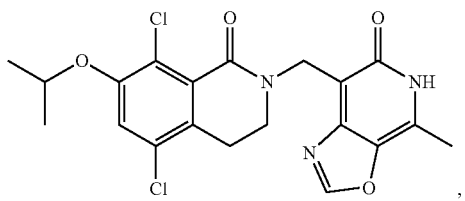,
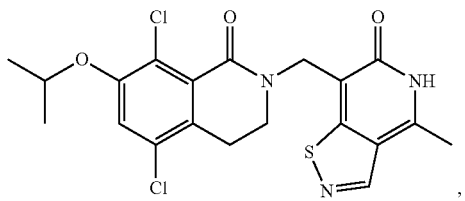,
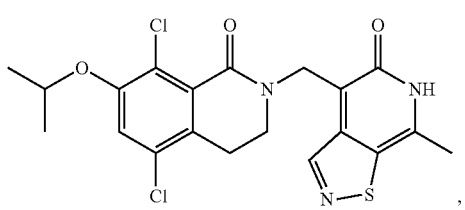,

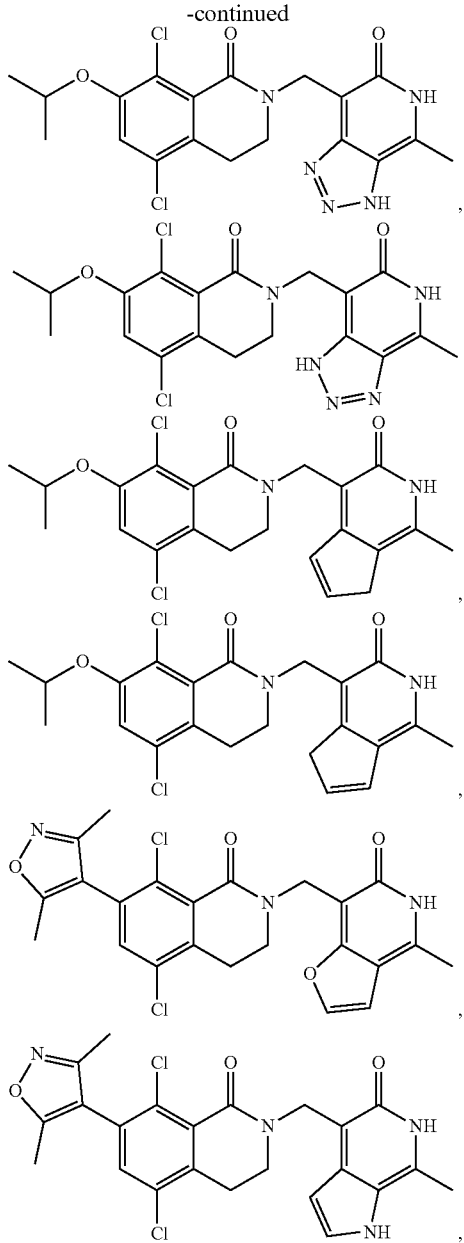

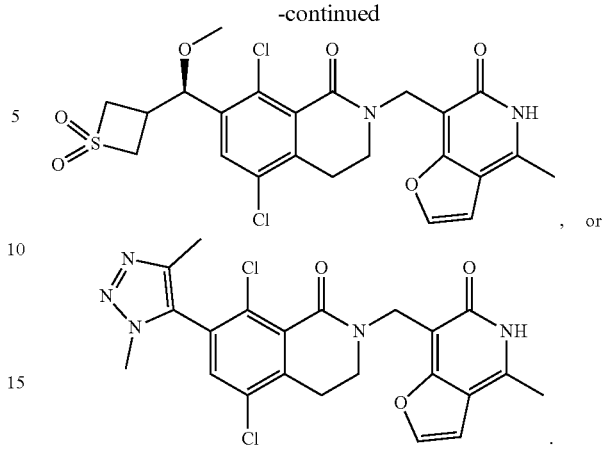

, or

35. A pharmaceutical composition, comprising a therapeutically effective amount of a compound of claim 1, and a pharmaceutically acceptable excipient.

36. A method for inhibiting EZH2 activity in a cell, comprising contacting the cell in which inhibition of EZH2 activity is desired with an effective amount of a compound of claim 1 pharmaceutically acceptable salts thereof or pharmaceutical compositions containing the compound of claim 1 or pharmaceutically acceptable salt thereof.

37. A method for treating an EZH2-associated cancer comprising administering to a patient having cancer a therapeutically effective amount of a compound of claim 1 or a pharmaceutically acceptable salt thereof, alone or combined with a pharmaceutically acceptable carrier, exicipient or diluents.

38. The method of claim 37, wherein the therapeutically effective amount of the compound is between about 0.01 to 300 mg/kg per day.

39. The method of claim 38, wherein the therapeutically effective amount of the compound is between about 0.1 to 100 mg/kg per day.

40. The method of claim 39, wherein the cancer is selected from the group consisting of leukemia, lymphoma, breast cancer, prostate cancer, pancreatic cancer, brain cancer, bladder cancer, lung cancer, head and neck cancer, liver cancer, kidney cancer, cervical cancer, uterine cancer, ovarian cancer and bone cancer.

* * * * *